US00RE39247E

(19) United States
(12) Reissued Patent
Barry et al.

(10) Patent Number: US RE39,247 E
(45) Date of Reissued Patent: Aug. 22, 2006

(54) GLYPHOSATE-TOLERANT 5-ENOLPYRUVYLSHIKIMATE-3-PHOSPHATE SYNTHASES

(75) Inventors: Gerard F. Barry, St. Louis, MO (US); Ganesh M. Kishore, Creve Coeur, MO (US); Stephen R. Padgette, Wildwood, MO (US); William C. Stallings, Wildwood, MO (US)

(73) Assignee: Monsanto Technology LLC, St. Louis, MO (US)

(21) Appl. No.: 10/622,201

(22) Filed: Jul. 18, 2003

Related U.S. Patent Documents

Reissue of:
(64) Patent No.: 5,633,435
Issued: May 27, 1997
Appl. No.: 08/306,063
Filed: Sep. 13, 1994

U.S. Applications:
(63) Continuation-in-part of application No. 07/749,611, filed on Aug. 28, 1991, now abandoned, which is a continuation-in-part of application No. 07/576,537, filed on Aug. 31, 1990, now abandoned.

(51) Int. Cl.
*A01H 5/00* (2006.01)
*A01H 5/10* (2006.01)
*C12N 15/82* (2006.01)

(52) U.S. Cl. ..... 800/300; 435/419; 435/320.1; 536/23.2; 536/23.4; 536/23.7; 800/278; 800/288

(58) Field of Classification Search ..... 800/300, 800/278, 288, 312, 298; 536/23.2, 23.7; 435/419, 435/320.1
See application file for complete search history.

(56) References Cited

U.S. PATENT DOCUMENTS

| | | | | | |
|---|---|---|---|---|---|
| 4,769,061 | A | * | 9/1988 | Comai | 504/206 |
| 4,971,908 | A | * | 11/1990 | Kishore et al. | 435/172.1 |
| 5,004,863 | A | | 4/1991 | Umbeck | 800/205 |
| 5,094,945 | A | * | 3/1992 | Comai | 435/172.3 |
| 5,159,135 | A | | 10/1992 | Umbeck | 800/205 |
| 5,164,316 | A | | 11/1992 | McPherson et al. | 435/240.4 |
| 5,196,525 | A | | 3/1993 | McPherson et al. | 536/24.1 |
| 5,310,667 | A | * | 5/1994 | Eichholtz et al. | 435/172.3 |
| 5,312,910 | A | | 5/1994 | Kishore et al. | 536/23.2 |
| 5,322,938 | A | | 6/1994 | McPherson et al. | 536/24.1 |
| 5,352,605 | A | | 10/1994 | Fraley et al. | 435/240.4 |
| 5,416,011 | A | | 5/1995 | Hinchee et al. | 435/172.3 |
| 5,463,174 | A | | 10/1995 | Moloney et al. | 800/205 |
| 5,512,466 | A | | 4/1996 | Klee et al. | 800/283 |
| 5,518,908 | A | | 5/1996 | Corbin et al. | 435/172.3 |
| 5,569,834 | A | | 10/1996 | Hinchee et al. | 800/205 |
| 5,627,061 | A | | 5/1997 | Barry et al. | 800/288 |
| 5,633,435 | A | | 5/1997 | Barry et al. | 800/205 |
| 5,804,425 | A | | 9/1998 | Barry et al. | 435/193 |
| 6,204,436 | B1 | | 3/2001 | Mannerloef et al. | 800/300 |
| 6,248,876 | B1 | | 6/2001 | Barry et al. | 536/24.3 |

FOREIGN PATENT DOCUMENTS

| | | | | |
|---|---|---|---|---|
| EP | 0 193 259 | * | 9/1986 | 800/205 |
| EP | 0 218 571 | | 4/1987 | |
| EP | 0 293 358 | | 11/1988 | |
| EP | 0 426 641 | | 5/1991 | |
| EP | 0 546 090 | | 6/1996 | |
| WO | WO 91/04323 | | 4/1991 | |
| WO | WO 92/04449 | | 3/1992 | |

OTHER PUBLICATIONS

Comai et. al. (1988) *Journal of Biological Chemistry* 263:15104–15109.*
Fillatti et al. (Jul. 1987) *Bio/Technology* 5:726–730.*
Fitzgibbon (Dec. 1988) Ph.D. Thesis University Microfilms International, (1989).*
Griffin and Gasson (1995) *Mol. Gen. Genet.* 246:119–127.*
Henner et al. (1986) *Gene* 49:147–152.*
Potrykus (Jun. 1990) *Bio/Technology* 8:535–542.*
Comai, et al (1988) Journal of Biological Chemistry 263:15104–15109.*
Fitzgibbon (Dec. 1988) Ph.D. Thesis University Microfilms International, 1989, pp. viii–ix, 18, 22–29, 32, 93, 96–108.*
Henner, et al. (1984) *Gene, 34*:169–177.
Eichholtz, et al. (1989) *Plant Physiology, 89*: 47.
Fitzgibbon, et al (1990) *Chemical Abstracts,* vol. 112, abstract No. 92785.
Schulz, et al. (1985) *FEMS Microbiol Lett., 28*:297–301.
Schulz, et al. (1985) *Chemical Abstracts,* vol. 103, abstract No. 119839.
Larson–Kelly et al. (1988) *SAAS Bulletin, 1*: 37–40.
Barlow, et al. (1989) *Biochemistry, 28*: 7985–7991.
Shuttleworth et al. (1992) *Protein Engineering, 5*: 461–466, 1992.
Selvapandiyan, et al. (1995) *FEBS Letters, 374*: 253–256.
Alberg, et al. (1989) *Journal of The American Chemical Society, 111*: 2337–2338.
Lanzetta, et al. (1979) *Analytical Biochemistry, 100*: 95–97.
Majumder, et al. (1995) *Eur. J. Biochem., 229*: 99–106.
Steinrücken, et al. (1984) *Eur. J. Biochem., 143*: 341–349.
Steinrücken, et al. (1986) *Archives of Biochemistry and Biophysics, 244*: 169–178.
Kane, et al. (1971) *Journal of Biological Chemistry, 246*: 4308–4316.
Fischer, et al. (1987) *Archives of Biochemistry and Biophysics, 256*: 325–334.
Chiesa, et al., *Gene,* (1994) 144: 145–146.

(Continued)

*Primary Examiner*—David H Kruse
(74) *Attorney, Agent, or Firm*—Howrey LLP

(57) ABSTRACT

Genes encoding Class II EPSPS enzymes are disclosed. The genes are useful in producing transformed bacteria and plants which are tolerant to glyphosate herbicide. Class II EPSPS genes share little homology with known, Class I EPSPS genes, and do not hybridize to probes from Class I EPSPS's. The Class II EPSPS enzymes are characterized by being more kinetically efficient than Class I EPSPS's in the presence of glyphosate. Plants transformed with Class II EPSPS genes are also disclosed as well as a method for selectively controlling weeds in a planted transgenic crop field.

127 Claims, 70 Drawing Sheets

OTHER PUBLICATIONS

Kishore, et al., 1988 *From Biochemistry to Genetic Engineering of Glyphosate Tolerance,* American Chemical Society, Chapter 3, pp. 37–48.
Schulz, et al. (1985) *FEMS Microbiology Letters, 28*: 297–301.
Padgette, et al. (1996) *Herbicide–Resistant Crops,* Chapter 4, pp. 53–84.
Padgette, et al. (1987) *Archives of Biochemistry and Biophysics, 258*: 564–573.
Lorz, et al. (1985) *Mol. Gen. Gene, 199*:178–182.
Gasser, et al., (1989), *Science, 244*: 1293–1299.
Fromm, et al. (1990) *Bio/Technology, 8*: 833–839.
Gordon–Kamm, et al. (1990) *Plant Cell, 2*: 603–618.
Armstrong, et al. (1995) *Crop Sci., 35*:550–557.
Christou, et al. (1991) *Bio/Technology, 9*: 957–962.
Vasil, et al. (1992) *Bio/Technology, 10*: 667–674.
Flavell, et al. (1987) *Nature, 307*: 108–109.
Goodman, et al. (1987) *Science, 236*: 48–54.
Paszkowski, et al. (1984) *EMBO Journal, 3*: 2717–2722.
Potrykus, et al. (1985) *Mol. Gen. Genet., 199*: 183–188.
Shimamoto, et al. (1989) *Nature, 338*: 274–276.
Rhodes, et al. (1988) *Science, 240*: 204–207.
Horn, et al. (1988) *Plant Cell Reports, 7*: 469–472.
Jahne, et al. (1995), *Euphytica, 85*: 35–44.
McCabe, et al. (1988) *Bio/Technology, 6*: 923–926.
Klein, et al. (1988) *Proc. Natl. Acad. Sci. USA, 85*: 8502–8505.
Christou, et al. (1988) *Plant Physiol., 87*: 671–674.
Cheng, et al. (1996) *Plant Cell Reports, 15*: 653–657.
McKently, et al. (1995) *Plant Cell Reports, 14*: 699–703.
Yang, et al. (1996) *Plant Cell Reports, 15*: 459–464.
Grant, et al. (1995) *Plant Cell Reports, 15*: 254–258.
De Kathen, et al. (1990) *Plant Cell Reports, 9*: 276–279.
Zhang, et al. (1988) *Plant Cell Reports, 7*: 379–384.
Weeks, et al. (1988) *Plant Physiol., 102*: 1077–1084.
Schroeder, et al. (1993) *Plant Physiol., 101*: 751–757.
Wan, et al. (1994) *Plant Physiol., 104*: 37–48.
Bytebier, et al. (1987) *Proc. Natl. Acad. Sci. USA, 84*: 5345–5349.
Koziel, et al. (1993) *Bio/Technology, 11*: 194–200.
Somers, et al. (1992) *Bio/Technology, 10*: 1589–1594.
Wang, et al. (1992) *Bio/Technology, 10*: 691–696.
Toryama, et al. (1990) *Bio/Technology, 6*: 1072–1074.
Zhang, et al. (1988) *Theor. Appl. Genet., 76*: 835–840.
Battraw, et al. (1990) *Plant Mol. Biol., 15*: 527–538.
Davey, et al. (1989) *Plant Mol. Biol., 13*: 273–285.
Park, et al. (1996) *Plant Mol. Biol., 32*: 1135–1148.
De la Pena, et al. (1987) *Nature, 325*: 274–276.
Bower, et al. (1992) *Plant Journal, 2*: 409–416.
Davey, et al. (1986) "Transformation of the Genomic Expression of Plant Cells," in *Plasticity in Plants, Symposia of the Society for Experimental Biology,* pp. 85–120.
Fitzgibbon and Braymer (1990) *Appl. Envir. Microbiol.* 56:3382–3388.
Schultz, et al. (1984) *Arch. Microbiol.,* 137:121–123.
English language translation of excerpt, *Chemistry and Biology, Bioscience and Biotechnology,* (1991) 29:734.
English language translation of excerpt, Okada (ed.) "Gene Expression and Regulation in Higher Plants," in *Developments of Molecular Biology,* No. 13, Maruzen Co., Japan., 1990.
English language translation of excerpt, Nagata (1993), *Plant Protoplast and Cell Engineering,* p. 104, Kodansha Co., Ltd.
English language translation of excerpt, Uozumi (1993) *Plant Engineering,* p. 111, Maruzen Co., Ltd.
Minutes of the Public Oral Proceedings before the EPO Technical Board of Appeal, on Apr. 6, 2005, for European Patent No. 0 546,090.
"Monsanto Holds Right to Patent Herbicide–Resistant Seeds, European Patent Office Says," Associated Press, Apr. 9, 2005.
"*Efficient Transfer Of A Glyphosate Tolerance Gene Into Tomato Using A Binary Agrobacterium Tumefaciens Vector,"* L. Fillati, J. Kiser, R. Rose, and L. Comai, *Bio/Technology* 5:726–730 (1987).
"*Chloroplast Transport Of A Ribulose Biphosphate Carboxylase Small Subunit–5–Enolpyruvyl 3–Phosphoshikimate Synthase Chimeric Protein Requires Part Of The Mature Small Subunit In Addition To The Transit Peptide,"* L. Comai, N. Larson–Kelly, J. Kiser, C. Mau, A. Pokalsky, C. Shewmaker, K. McBride, A. Jones, and D. Stalker, *J. Biol. Chem.* 263:15104–15109 (1988).
"*The Organization And Nucleotide Sequence Of the Bacillus Subtilis hisH, tyrA and AroE Genes,"* D. Henner, L. Band, G. Glaggs, and E. Chen, *Gene* 49:147–152 (1986).
"*Pseudomonas sp. Strain PG2082: Uptake Of Glyphosate And Cloning Of A Gene Which Confers Increased Resistance To Glyphosate,"* J. Fitzgibbon, Ph.D. (Dec. 1998).
"*Gene Transfer To Cereal: An Assessment,"* I. Potrykus, *Bio/Technology* 1:535–542 (1990).
"*Genetic Aspects Of Aromatic Amino Acid Biosynthesis In Lactococcus Lactis,"* H. Griffin, and M. Gasson, *Mol. Gen. Genet.* 246:119–127 (1995).
"*Targeting A Herbicide–Resistant Enzyme From Escherichia Coli To Chloroplasts Of Higher Plants,"* G. della–Cioppa, S. Bauer, M. Taylor, D. Rochester, B. Klein, D. Shah, R. Fraley, and G. Kishore, *Bio/Technology* 5:579–584 (1987).
"*Production Of Transgenic Soybean Plants Using Agrobacterium–Mediated DNA Transfer,"* M. Hinchee, D. Connor–Ward, C. Newell, R. McDonnell, S. Sato, C. Gasser, D. Fischhoff, D. Re, R. Fraley, and R. Horsch, *Bio/Technology* 6:915–926 (1988).
"*Chloroplast Delivery Of A Bacterial EPSPS Synthase In Transgenic Plants And Tolerance To Glyphosate,"* N. Larson–Kelly, L. Comai, J. Kiser, C. Mau, A. Pokalsky, K. McBride, A. Jones, C. Shewmaker, and D. Stalker, *Biochem. Biotech.* 1:37–40 (1998).
"*Glyphosate Tolerant Flax Plants From Agrobacterium Mediated Gene Transfer,"* M. Jordan and A. McHughen, *Plant Cell Reports* 7:281–284 (1988).
"*Agrobacterium–Mediated Gene Transfer To Plants; Engineering Tolerance To Glyphosate,"* R. Horsch, R. Fraley, S. Rogers, H. Klee, J. Fry, M. Hinchee, and D. Shah, *Iowa State Journal of Research* 62:487–502 (1988).
"*The Use Of Bacterial Genes Encoding Herbicide Tolerance In Constructing Transgenic Plants,"* E. Piruzian, V. Mett, N. Kobets, and F. Urmeeva, *Microbiological Sciences* 5:242–248 (1988).
"*Cloning Of An Arabidopsis Thaliana Gene Encoding 5–Enolpyruvylshikimate–3–Phosphate Synthase: Sequence Analysis And Manipulation To Obtain Glyphosae–Tolerant Plants,"* H. Klee, Y. Muskopf, and C. Gasser, *Mol. Gen. Gene.* 210:437–442 (1987).

"*Genetically–Engineered Herbicide Tolerance—Technical And Commercial Considerations,*" R. Fraley, G. Kishore, C. Gasser, S. Padgette, R. Horsch, S. Rogers, G. Della–Cioppa, and D. Shah, *British Crop Protection Conference—Weeds* 2:463–471 (1987).

"*Engineering Herbicide Tolerance In Transgenic Plants,*" D. Shah, R. Horsch, H. Klee, G. Kishore, J. Winter, N. Tumer, C. Hironaka, P. Sanders, C. Gasser, S. Aykent, N. Siegel, S. Rogers, and R. Fraley, *Science* 233:478–481 (1986).

"*An Altered aroA Gene Product Confers Resistance to the Herbicide Glyphosate,*" L. Comai, L. Sen, and D. Stalker, *Science* 221:370–371 (1983).

"*A Single Amino Acid Substitution In The Enzyme 5–Enolpyruvylshikimate–3–Phosphate Synthase Confers Resistance To The Herbicide Glyphosate,*" D. Stalker, W. Hiatt, and L., Comai, *J. Biol. Chem.* 260:4724–4728 (1985).

"*Engineering Herbicide Resistance In Plants,*" J. Botterman and J. Leemans, *Trends In Genetics* 4:219–222 (1988).

"*Glyphosate Tolerant Variants Of Petunia EPSP Synthase,*" D. Eichholtz, C. Gasser, D. Re, S. Padgette, G. Kishore, D. Shah, and R. Fraley, American Society of Plant Physiologists, Sup. To Plant Physiology (1989).

"*EPSP Synthase—From Biochemistry To Genetic Engineering Of Herbicide Tolerance,*" G. Kishore, S. Padgette, G. Della–Cioppa, D. Biest Re, L. Brundage, D. Shah, C. Gasser, P. Sanders, H. Klee, R. Horsch, N. Hoffmann, and R. Fraley, American Society of Biological Chemists, 78$^{th}$ Annual Meeting, Abstract # 754 (1987).

"*Genetic Engineering Of Plants For Herbicide Resistance Expression Of An RuBP Carboxylase Small Subunit–EPSP Synthase Chimeric Gene, Chlorophast Transport Of The Hybrid Protein, And Tolerance Phenotype In Transgenic Plants,*" L. Comai, N. Larson–Kelly, J. Kiser, A. Jones, D. Stalker, P. Moran, K. Kiehne, and A. Koning, *Vortr. Pflanzenzüchtg* 16:441–454 (1989).

"*Biocontrol Of Plant Diseases vol. II*" K. Mukerji and K. Garg, Editors, CRC Press Inc. (1988).

"*The Development Of Herbicide Resistant Crops,*" B. Mazur and S. Falco, *Annu. Rev. Plant Physiol. Plant Mol. Biol.* 40:441–470 (1989).

"*Producing Herbicide–Resistant Plants By Gene Transfer Technology*". D. Stalker, in "Target Sites of Herbicide Action", P. Boger and G. Sandmann Editors, 1989.

"*Genetic Engineering Of Tobacco For Resistance To The Herbicide Glyphosate,*" L. Comai, D. Stalker, W. Hiatt, G. Thompson, and D. Facciotti, (abstract, 1985).

"*Performance Assessment Under Field Conditions Of A Rapid Immunological Test For Transgenic Soybeans,*" J. Fagan, B. Schoel, A. Haegert, J. Moore, and J. Beeby, *International Journal of Food Science and Technology* 36:357–367 (2001).

"*Expression In Plants of a Mutant aroA Gene from Salmonella Typhimurium Confers Tolerance to Glyphosate,*" L. Comai, D. Facciotti, W.R. Hiatt, G. Thompson, R.E. Rose & D. M. Stalker, *Nature* 317:741–744 (1985).

Defendant's Second Supplemental Answers to Plaintiff's Third Set of Interrogatories to Mitchell Scruggs, as filed May 30, 2004, in *Monsanto Company* v. *Scruggs,* 3:00CV161–P–D, U.S. District Court, Northern District of Mississippi, Western Division.

Defendants' Motion for Summary Judgmnt on Plaintiff's Patent Infringement Claim, Count One, Third Amended Complaint, dated Aug. 8, 2003, as filed in *Monsanto Company* v. *Scruggs,* 3:00CV161–B–A, U.S. District Court, Northern District of Mississippi, Western Division.

Memorandum in Support of Defendants' Motion for Summary Judgment on Plaintiff's Patent Infringement Claim, Count One, Third Amended Complaint (with exhibits), dated Aug. 8, 2003, as filed in *Monsanto Company* v. *Scruggs,* 3:00CV161–B–A, U.S. District Court, Northern District of Mississippi, Western Division.

Defendants' Response to Plaintiff's Notice of Dismissal of Count One (and Rebuttal to Monsanto's Response to Defendant's Motion for Summary Judgment on Count One (with exhibits), dated Jan. 12, 2004, as filed in *Monsanto Company* v. *Scruggs,* 3:00CV161–B–A, U.S. District Court, Northern District of Mississippi, Western Division.

Defendants' Motion for Establishment of Certain Facts, Invalidation of Patent Claims and Expenses, as a Sanction, and Defendants' Opposition to Monsanto's Notice of Dismissal of Count One, Third Amended Complaint with Prejudice and Motion to Dismiss Defendants' Counterclaim Alleging Invalidity of the '435 Patent for Lack of Subject Matter Jurisdiction Filed Dec. 8, 2003, dated Dec. 31, 2003, as filed in *Monsanto Company* v. *Scruggs,* 3:00CV161–B–A, U.S. District Court, Northern District of Mississippi, Western Division.

Memorandum Brief in Support of Defendants' Motion for Establishment of Certain Facts, Invalidation of Patent Claims and Expenses, as a Sanction and in Opposition to Monsanto's Motion to Dismiss Counterclaim (with exhibits), dated Dec. 31, 2003, as filed in *Monsanto Company* v. *Scruggs,* 3:00CV161–B–A, U.S. District Court, Northern District of Mississippi, Western Division.

Amended Answer, Affirmative Defenses and Counterclaims, as filed Jun. 30, 2000, in *Monsanto Co.* v. *Roush,* 1:00CV0208, U.S. District Court for the Norther District of Indiana, Fort Wayne Division.

Amended Answer, Affirmative Defenses and Counterclaims, as filed Dec. 21, 2000, in *Monsanto Co.* v. *Roush,* 1:00CV0208, U.S. District Court for the Northern District of Indiana, Fort Wayne Division.

Defendants' Supplemental Answers to Monsanto's Third Set of Interrogatories to Defendants, dated Sep. 28, 2001, in *Monsanto Co.* v. *Roush,* 1:00CV0208, U.S. District Court for the Northern District of Indiana, Fort Wayne Division.

* cited by examiner

```
          SspI
     TCATCAAAATATTTAGCAGCATTCCAGATTGGGTTCAATCAACAAGGTACGAGCCATATC
6358                                                              6417
     AGTAGTTTTATAAATCGTCGTAAGGTCTAACCCAAGTTAGTTGTTCCATGCTCGGTATAG

     ACTTTATTCAAATTGGTATCGCCAAAACCAAGAAGGAACTCCCATCCTCAAAGGTTTGTA
6418                                                              6477
     TGAAATAAGTTTAACCATAGCGGTTTTGGTTCTTCCTTGAGGGTAGGAGTTTCCAAACAT

     AGGAAGAATTCTCAGTCCAAAGCCTCAACAAGGTCAGGGTACAGAGTCTCCAAACCATTA
6478                                                              6537
     TCCTTCTTAAGAGTCAGGTTTCGGAGTTGTTCCAGTCCCATGTCTCAGAGGTTTGGTAAT

     GCCAAAAGCTACAGGAGATCAATGAAGAATCTTCAATCAAAGTAAACTACTGTTCCAGCA
6538                                                              6597
     CGGTTTTCGATGTCCTCTAGTTACTTCTTAGAAGTTAGTTTCATTTGATGACAAGGTCGT

     CATGCATCATGGTCAGTAAGTTTCAGAAAAAGACATCCACCGAAGACTTAAAGTTAGTGG
6598                                                              6657
     GTACGTAGTACCAGTCATTCAAAGTCTTTTTCTGTAGGTGGCTTCTGAATTTCAATCACC
```

Figure 1A

```
      GCATCTTTGAAAGTAATCTTGTCAACATCGAGCAGCTGGCTTGTGGGGACCAGACAAAAA
6658                                                                6717
      CGTAGAAACTTTCATTAGAACAGTTGTAGCTCGTCGACCGAACACCCCTGGTCTGTTTTT

      AGGAATGGTGCAGAATTGTTAGGCGCACCTACCAAAAGCATCTTTGCCTTTATTGCAAAG
6718                                                                6777
      TCCTTACCACGTCTTAACAATCCGCGTGGATGGTTTTCGTAGAAACGGAAATAACGTTTC

      ATAAAGCAGATTCCTCTAGTACAAGTGGGGAACAAAATAACGTGGAAAAGAGCTGTCCTG
6778                                                                6837
      TATTTCGTCTAAGGAGATCATGTTCACCCCTTGTTTTATTGCACCTTTTCTCGACAGGAC

      ACAGCCCACTCACTAATGCGTATGACGAACGCAGTGACGACCACAAAAGAATTCCCTCTA
6838                                                                6897
      TGTCGGGTGAGTGATTACGCATACTGCTTGCGTCACTGCTGGTGTTTTCTTAAGGGAGAT

                                                  SspI
      TATAAGAAGGCATTCATTCCCATTTGAAGGATCATCAGATACTAACCAATATTTCTC
6898                                                                6954
      ATATTCTTCCGTAAGTAAGGGTAAACTTCCTAGTAGTCTATGATTGGTTATAAAGAG
```

Figure 1B

```
AAGCCCGCGT TCTCTCCGGC GCTCCGCCCG GAGAGCCGTG GATAGATTAA GGAAGACGCC      60

C   ATG TCG CAC GGT GCA AGC AGC CGG CCC GCA ACC GCC CGC AAA TCC      106
    Met Ser His Gly Ala Ser Ser Arg Pro Ala Thr Ala Arg Lys Ser
     1               5                  10                  15

TCT GGC CTT TCC GGA ACC GTC CGC ATT CCC GGC GAC AAG TCG ATC TCC      154
Ser Gly Leu Ser Gly Thr Val Arg Ile Pro Gly Asp Lys Ser Ile Ser
                20                  25                  30

CAC CGG TCC TTC ATG TTC GGC GGT CTC GCG AGC GGT GAA ACG CGC ATC      202
His Arg Ser Phe Met Phe Gly Gly Leu Ala Ser Gly Glu Thr Arg Ile
            35                  40                  45

ACC GGC CTT CTG GAA GGC GAG GAC GTC ATC AAT ACG GGC AAG GCC ATG      250
Thr Gly Leu Leu Glu Gly Glu Asp Val Ile Asn Thr Gly Lys Ala Met
        50                  55                  60

CAG GCC ATG GGC GCC AGG ATC CGT AAG GAA GGC GAC ACC TGG ATC ATC      298
Gln Ala Met Gly Ala Arg Ile Arg Lys Glu Gly Asp Thr Trp Ile Ile
    65                  70                  75

GAT GGC GTC GGC AAT GGC GGC CTC CTG GCG CCT GAG GCG CCG CTC GAT      346
Asp Gly Val Gly Asn Gly Gly Leu Leu Ala Pro Glu Ala Pro Leu Asp
80                  85                  90                  95
```

Figure 3A

```
TTC GGC AAT GCC GCC ACG GGC TGC CGC CTG ACC ATG GGC CTC GTC GGG      394
Phe Gly Asn Ala Ala Thr Gly Cys Arg Leu Thr Met Gly Leu Val Gly
                100                 105                 110

GTC TAC GAT TTC GAC AGC ACC TTC ATC GGC GAC GCC TCG CTC ACA AAG      442
Val Tyr Asp Phe Asp Ser Thr Phe Ile Gly Asp Ala Ser Leu Thr Lys
            115                 120                 125

CGC CCG ATG GGC CGC GTG TTG AAC CCG CTG CGC GAA ATG GGC GTG CAG      490
Arg Pro Met Gly Arg Val Leu Asn Pro Leu Arg Glu Met Gly Val Gln
        130                 135                 140

GTG AAA TCG GAA GAC GGT GAC CGT CTT CCC GTT ACC TTG CGC GGG CCG      538
Val Lys Ser Glu Asp Gly Asp Arg Leu Pro Val Thr Leu Arg Gly Pro
    145                 150                 155

AAG ACG CCG ACG CCG ATC ACC TAC CGC GTG CCG ATG GCC TCC GCA CAG      586
Lys Thr Pro Thr Pro Ile Thr Tyr Arg Val Pro Met Ala Ser Ala Gln
160                 165                 170                 175

GTG AAG TCC GCC GTG CTG CTC GCC GGC CTC AAC ACG CCC GGC ATC ACG      634
Val Lys Ser Ala Val Leu Leu Ala Gly Leu Asn Thr Pro Gly Ile Thr
                180                 185                 190

ACG GTC ATC GAG CCG ATC ATG ACG CGC GAT CAT ACG GAA AAG ATG CTG      682
Thr Val Ile Glu Pro Ile Met Thr Arg Asp His Thr Glu Lys Met Leu
            195                 200                 205
```

Figure 3B

```
CAG GGC TTT GGC GCC AAC CTT ACC GTC GAG ACG GAT GCG GAC GGC GTG      730
Gln Gly Phe Gly Ala Asn Leu Thr Val Glu Thr Asp Ala Asp Gly Val
        210                 215                 220
CGC ACC ATC CGC CTG GAA GGC CGC GGC AAG CTC ACC GGC CAA GTC ATC      778
Arg Thr Ile Arg Leu Glu Gly Arg Gly Lys Leu Thr Gly Gln Val Ile
    225                 230                 235

GAC GTG CCG GGC GAC CCG TCC TCG ACG GCC TTC CCG CTG GTT GCG GCC      826
Asp Val Pro Gly Asp Pro Ser Ser Thr Ala Phe Pro Leu Val Ala Ala
240                 245                 250                 255

CTG CTT GTT CCG GGC TCC GAC GTC ACC ATC CTC AAC GTG CTG ATG AAC      874
Leu Leu Val Pro Gly Ser Asp Val Thr Ile Leu Asn Val Leu Met Asn
                260                 265                 270

CCC ACC CGC ACC GGC CTC ATC CTG ACG CTG CAG GAA ATG GGC GCC GAC      922
Pro Thr Arg Thr Gly Leu Ile Leu Thr Leu Gln Glu Met Gly Ala Asp
            275                 280                 285

ATC GAA GTC ATC AAC CCG CGC CTT GCC GGC GGC GAA GAC GTG GCG GAC      970
Ile Glu Val Ile Asn Pro Arg Leu Ala Gly Gly Glu Asp Val Ala Asp
        290                 295                 300

CTG CGC GTT CGC TCC TCC ACG CTG AAG GGC GTC ACG GTG CCG GAA GAC     1018
Leu Arg Val Arg Ser Ser Thr Leu Lys Gly Val Thr Val Pro Glu Asp
    305                 310                 315
```

Figure 3C

```
CGC GCG CCT TCG ATG ATC GAC GAA TAT CCG ATT CTC GCT GTC GCC GCC      1066
Arg Ala Pro Ser Met Ile Asp Glu Tyr Pro Ile Leu Ala Val Ala Ala
320                 325                 330                 335

GCC TTC GCG GAA GGG GCG ACC GTG ATG AAC GGT CTG GAA GAA CTC CGC      1114
Ala Phe Ala Glu Gly Ala Thr Val Met Asn Gly Leu Glu Glu Leu Arg
                340                 345                 350

GTC AAG GAA AGC GAC CGC CTC TCG GCC GTC GCC AAT GGC CTC AAG CTC      1162
Val Lys Glu Ser Asp Arg Leu Ser Ala Val Ala Asn Gly Leu Lys Leu
            355                 360                 365

AAT GGC GTG GAT TGC GAT GAG GGC GAG ACG TCG CTC GTC GTG CGC GGC      1210
Asn Gly Val Asp Cys Asp Glu Gly Glu Thr Ser Leu Val Val Arg Gly
        370                 375                 380

CGC CCT GAC GGC AAG GGG CTC GGC AAC GCC TCG GGC GCC GCC GTC GCC      1258
Arg Pro Asp Gly Lys Gly Leu Gly Asn Ala Ser Gly Ala Ala Val Ala
    385                 390                 395

ACC CAT CTC GAT CAC CGC ATC GCC ATG AGC TTC CTC GTC ATG GGC CTC      1306
Thr His Leu Asp His Arg Ile Ala Met Ser Phe Leu Val Met Gly Leu
400                 405                 410                 415

GTG TCG GAA AAC CCT GTC ACG GTG GAC GAT GCC ACG ATG ATC GCC ACG      1354
Val Ser Glu Asn Pro Val Thr Val Asp Asp Ala Thr Met Ile Ala Thr
                420                 425                 430
```

Figure 3D

```
AGC TTC CCG GAG TTC ATG GAC CTG ATG GCC GGG CTG GGC GCG AAG ATC      1402
Ser Phe Pro Glu Phe Met Asp Leu Met Ala Gly Leu Gly Ala Lys Ile
            435                 440                 445

GAA CTC TCC GAT ACG AAG GCT GCC TGATGACCTT CACAATCGCC ATCGATGGTC     1456
Glu Leu Ser Asp Thr Lys Ala Ala
        450                 455

CCGCTGCGGC CGGCAAGGGG ACGCTCTCGC GCCGTATCGC GGAGGTCTAT GGCTTTCATC    1516

ATCTCGATAC GGGCCTGACC TATCGCGCCA CGGCCAAAGC GCTGCTCGAT CGCGGCCTGT    1576

CGCTTGATGA CGAGGCGGTT GCGGCCGATG TCGCCCGCAA TCTCGATCTT GCCGGGCTCG    1636

ACCGGTCGGT GCTGTCGGCC CATGCCATCG GCGAGGCGGC TTCGAAGATC GCGGTCATGC    1696

CCTCGGTGCG GCGGGCGCTG GTCGAGGCGC AGCGCAGCTT TGCGGCGCGT GAGCCGGGCA    1756

CGGTGCTGGA TGGACGCGAT ATCGGCACGG TGGTCTGCCC GGATGCGCCG GTGAAGCTCT    1816

ATGTCACCGC GTCACCGGAA GTGCGCGCGA AACGCCGCTA TGACGAAATC CTCGGCAATG    1876

GCGGGTTGGC CGATTACGGG ACGATCCTCG AGGATATCCG CCGCCGCGAC GAGCGGGACA    1936

TGGGTCGGGC GGACAGTCCT TTGAAGCCCG CCGACGATGC GCACTT                   1982
```

Figure 3E

```
GTAGCCACAC ATAATTACTA TAGCTAGGAA GCCCGCTATC TCTCAATCCC GCGTGATCGC      60

GCCAAAATGT GACTGTGAAA AATCC ATG TCC CAT TCT GCA TCC CCG AAA CCA      112
                            Met Ser His Ser Ala Ser Pro Lys Pro
                             1               5

GCA ACC GCC CGC CGC TCG GAG GCA CTC ACG GGC GAA ATC CGC ATT CCG      160
Ala Thr Ala Arg Arg Ser Glu Ala Leu Thr Gly Glu Ile Arg Ile Pro
 10                  15                  20                  25

GGC GAC AAG TCC ATC TCG CAT CGC TCC TTC ATG TTT GGC GGT CTC GCA      208
Gly Asp Lys Ser Ile Ser His Arg Ser Phe Met Phe Gly Gly Leu Ala
                 30                  35                  40

TCG GGC GAA ACC CGC ATC ACC GGC CTT CTG GAA GGC GAG GAC GTC ATC      256
Ser Gly Glu Thr Arg Ile Thr Gly Leu Leu Glu Gly Glu Asp Val Ile
             45                  50                  55

AAT ACA GGC CGC GCC ATG CAG GCC ATG GGC GCG AAA ATC CGT AAA GAG      304
Asn Thr Gly Arg Ala Met Gln Ala Met Gly Ala Lys Ile Arg Lys Glu
         60                  65                  70

GGC GAT GTC TGG ATC ATC AAC GGC GTC GGC AAT GGC TGC CTG TTG CAG      352
Gly Asp Val Trp Ile Ile Asn Gly Val Gly Asn Gly Cys Leu Leu Gln
     75                  80                  85
```

Figure 4A

```
CCC GAA GCT GCG CTC GAT TTC GGC AAT GCC GGA ACC GGC GCG CGC CTC      400
Pro Glu Ala Ala Leu Asp Phe Gly Asn Ala Gly Thr Gly Ala Arg Leu
 90                  95                  100                 105

ACC ATG GGC CTT GTC GGC ACC TAT GAC ATG AAG ACC TCC TTT ATC GGC      448
Thr Met Gly Leu Val Gly Thr Tyr Asp Met Lys Thr Ser Phe Ile Gly
                110                 115                 120

GAC GCC TCG CTG TCG AAG CGC CCG ATG GGC CGC GTG CTG AAC CCG TTG      496
Asp Ala Ser Leu Ser Lys Arg Pro Met Gly Arg Val Leu Asn Pro Leu
            125                 130                 135

CGC GAA ATG GGC GTT CAG GTG GAA GCA GCC GAT GGC GAC CGC ATG CCG      544
Arg Glu Met Gly Val Gln Val Glu Ala Ala Asp Gly Asp Arg Met Pro
        140                 145                 150

CTG ACG CTG ATC GGC CCG AAG ACG GCC AAT CCG ATC ACC TAT CGC GTG      592
Leu Thr Leu Ile Gly Pro Lys Thr Ala Asn Pro Ile Thr Tyr Arg Val
    155                 160                 165

CCG ATG GCC TCC GCG CAG GTA AAA TCC GCC GTG CTG CTC GCC GGT CTC      640
Pro Met Ala Ser Ala Gln Val Lys Ser Ala Val Leu Leu Ala Gly Leu
170                 175                 180                 185

AAC ACG CCG GGC GTC ACC ACC GTC ATC GAG CCG GTC ATG ACC CGC GAC      688
Asn Thr Pro Gly Val Thr Thr Val Ile Glu Pro Val Met Thr Arg Asp
                190                 195                 200
```

Figure 4B

```
CAC ACC GAA AAG ATG CTG CAG GGC TTT GGC GCC GAC CTC ACG GTC GAG      736
His Thr Glu Lys Met Leu Gln Gly Phe Gly Ala Asp Leu Thr Val Glu
            205                 210                 215

ACC GAC AAG GAT GGC GTG CGC CAT ATC CGC ATC ACC GGC CAG GGC AAG      784
Thr Asp Lys Asp Gly Val Arg His Ile Arg Ile Thr Gly Gln Gly Lys
        220                 225                 230

CTT GTC GGC CAG ACC ATC GAC GTG CCG GGC GAT CCG TCA TCG ACC GCC      832
Leu Val Gly Gln Thr Ile Asp Val Pro Gly Asp Pro Ser Ser Thr Ala
    235                 240                 245

TTC CCG CTC GTT GCC GCC CTT CTG GTG GAA GGT TCC GAC GTC ACC ATC      880
Phe Pro Leu Val Ala Ala Leu Leu Val Glu Gly Ser Asp Val Thr Ile
250                 255                 260                 265

CGC AAC GTG CTG ATG AAC CCG ACC CGT ACC GGC CTC ATC CTC ACC TTG      928
Arg Asn Val Leu Met Asn Pro Thr Arg Thr Gly Leu Ile Leu Thr Leu
                270                 275                 280

CAG GAA ATG GGC GCC GAT ATC GAA GTG CTC AAT GCC CGT CTT GCA GGC      976
Gln Glu Met Gly Ala Asp Ile Glu Val Leu Asn Ala Arg Leu Ala Gly
            285                 290                 295

GGC GAA GAC GTC GCC GAT CTG CGC GTC AGG GCT TCG AAG CTC AAG GGC     1024
Gly Glu Asp Val Ala Asp Leu Arg Val Arg Ala Ser Lys Leu Lys Gly
        300                 305                 310
```

Figure 4C

```
GTC GTC GTT CCG CCG GAA CGT GCG CCG TCG ATG ATC GAC GAA TAT CCG      1072
Val Val Val Pro Pro Glu Arg Ala Pro Ser Met Ile Asp Glu Tyr Pro
    315                 320                 325

GTC CTG GCG ATT GCC GCC TCC TTC GCG GAA GGC GAA ACC GTG ATG GAC      1120
Val Leu Ala Ile Ala Ala Ser Phe Ala Glu Gly Glu Thr Val Met Asp
330                 335                 340                 345

GGG CTC GAC GAA CTG CGC GTC AAG GAA TCG GAT CGT CTG GCA GCG GTC      1168
Gly Leu Asp Glu Leu Arg Val Lys Glu Ser Asp Arg Leu Ala Ala Val
                350                 355                 360

GCA CGC GGC CTT GAA GCC AAC GGC GTC GAT TGC ACC GAA GGC GAG ATG      1216
Ala Arg Gly Leu Glu Ala Asn Gly Val Asp Cys Thr Glu Gly Glu Met
            365                 370                 375

TCG CTG ACG GTT CGC GGC CGC CCC GAC GGC AAG GGA CTG GGC GGC GGC      1264
Ser Leu Thr Val Arg Gly Arg Pro Asp Gly Lys Gly Leu Gly Gly Gly
        380                 385                 390

ACG GTT GCA ACC CAT CTC GAT CAT CGT ATC GCG ATG AGC TTC CTC GTG      1312
Thr Val Ala Thr His Leu Asp His Arg Ile Ala Met Ser Phe Leu Val
    395                 400                 405

ATG GGC CTT GCG GCG GAA AAG CCG GTG ACG GTT GAC GAC AGT AAC ATG      1360
Met Gly Leu Ala Ala Glu Lys Pro Val Thr Val Asp Asp Ser Asn Met
410                 415                 420                 425
```

Figure 4D

```
ATC GCC ACG TCC TTC CCC GAA TTC ATG GAC ATG ATG CCG GGA TTG GGC      1408
Ile Ala Thr Ser Phe Pro Glu Phe Met Asp Met Met Pro Gly Leu Gly
                430                 435                 440

GCA AAG ATC GAG TTG AGC ATA CTC TAGTCACTCG ACAGCGAAAA TATTATTTGC     1462
Ala Lys Ile Glu Leu Ser Ile Leu
            445

GAGATTGGGC ATTATTACCG GTTGGTCTCA GCGGGGGTTT AATGTCCAAT CTTCCATACG    1522

TAACAGCATC AGGAAATATC AAAAAAGCTT TAGAAGGAAT TGCTAGAGCA GCGACGCCGC    1582

CTAAGCTTTC TCAAGACTTC GTTAAAACTG TACTGAAATC CCGGGGGGTC CGGGGATCAA    1642

ATGACTTCAT TTCTGAGAAA TTGGCCTCGC A                                   1673
```

Figure 4E

```
GTGATCGCGC CAAAATGTGA CTGTGAAAAA TCC ATG TCC CAT TCT GCA TCC CCG      54
                                     Met Ser His Ser Ala Ser Pro
                                      1               5

AAA CCA GCA ACC GCC CGC CGC TCG GAG GCA CTC ACG GGC GAA ATC CGC      102
Lys Pro Ala Thr Ala Arg Arg Ser Glu Ala Leu Thr Gly Glu Ile Arg
        10                  15                  20

ATT CCG GGC GAC AAG TCC ATC TCG CAT CGC TCC TTC ATG TTT GGC GGT      150
Ile Pro Gly Asp Lys Ser Ile Ser His Arg Ser Phe Met Phe Gly Gly
    25                  30                  35

CTC GCA TCG GGC GAA ACC CGC ATC ACC GGC CTT CTG GAA GGC GAG GAC      198
Leu Ala Ser Gly Glu Thr Arg Ile Thr Gly Leu Leu Glu Gly Glu Asp
40                  45                  50                  55

GTC ATC AAT ACA GGC CGC GCC ATG CAG GCC ATG GGC GCG AAA ATC CGT      246
Val Ile Asn Thr Gly Arg Ala Met Gln Ala Met Gly Ala Lys Ile Arg
                60                  65                  70

AAA GAG GGC GAT GTC TGG ATC ATC AAC GGC GTC GGC AAT GGC TGC CTG      294
Lys Glu Gly Asp Val Trp Ile Ile Asn Gly Val Gly Asn Gly Cys Leu
            75                  80                  85

TTG CAG CCC GAA GCT GCG CTC GAT TTC GGC AAT GCC GGA ACC GGC GCG      342
Leu Gln Pro Glu Ala Ala Leu Asp Phe Gly Asn Ala Gly Thr Gly Ala
        90                  95                  100
```

Figure 5A

```
CGC CTC ACC ATG GGC CTT GTC GGC ACC TAT GAC ATG AAG ACC TCC TTT      390
Arg Leu Thr Met Gly Leu Val Gly Thr Tyr Asp Met Lys Thr Ser Phe
    105                 110                 115

ATC GGC GAC GCC TCG CTG TCG AAG CGC CCG ATG GGC CGC GTG CTG AAC      438
Ile Gly Asp Ala Ser Leu Ser Lys Arg Pro Met Gly Arg Val Leu Asn
120                 125                 130                 135

CCG TTG CGC GAA ATG GGC GTT CAG GTG GAA GCA GCC GAT GGC GAC CGC      486
Pro Leu Arg Glu Met Gly Val Gln Val Glu Ala Ala Asp Gly Asp Arg
                140                 145                 150

ATG CCG CTG ACG CTG ATC GGC CCG AAG ACG GCC AAT CCG ATC ACC TAT      534
Met Pro Leu Thr Leu Ile Gly Pro Lys Thr Ala Asn Pro Ile Thr Tyr
            155                 160                 165

CGC GTG CCG ATG GCC TCC GCG CAG GTA AAA TCC GCC GTG CTG CTC GCC      582
Arg Val Pro Met Ala Ser Ala Gln Val Lys Ser Ala Val Leu Leu Ala
        170                 175                 180

GGT CTC AAC ACG CCG GGC GTC ACC ACC GTC ATC GAG CCG GTC ATG ACC      630
Gly Leu Asn Thr Pro Gly Val Thr Thr Val Ile Glu Pro Val Met Thr
    185                 190                 195

CGC GAC CAC ACC GAA AAG ATG CTG CAG GGC TTT GGC GCC GAC CTC ACG      678
Arg Asp His Thr Glu Lys Met Leu Gln Gly Phe Gly Ala Asp Leu Thr
200                 205                 210                 215
```

Figure 5B

```
GTC GAG ACC GAC AAG GAT GGC GTG CGC CAT ATC CGC ATC ACC GGC CAG      726
Val Glu Thr Asp Lys Asp Gly Val Arg His Ile Arg Ile Thr Gly Gln
                220                 225                 230

GGC AAG CTT GTC GGC CAG ACC ATC GAC GTG CCG GGC GAT CCG TCA TCG      774
Gly Lys Leu Val Gly Gln Thr Ile Asp Val Pro Gly Asp Pro Ser Ser
            235                 240                 245

ACC GCC TTC CCG CTC GTT GCC GCC CTT CTG GTG GAA GGT TCC GAC GTC      822
Thr Ala Phe Pro Leu Val Ala Ala Leu Leu Val Glu Gly Ser Asp Val
        250                 255                 260

ACC ATC CGC AAC GTG CTG ATG AAC CCG ACC CGT ACC GGC CTC ATC CTC      870
Thr Ile Arg Asn Val Leu Met Asn Pro Thr Arg Thr Gly Leu Ile Leu
    265                 270                 275

ACC TTG CAG GAA ATG GGC GCC GAT ATC GAA GTG CTC AAT GCC CGT CTT      918
Thr Leu Gln Glu Met Gly Ala Asp Ile Glu Val Leu Asn Ala Arg Leu
280                 285                 290                 295

GCA GGC GGC GAA GAC GTC GCC GAT CTG CGC GTC AGG GCT TCG AAG CTC      966
Ala Gly Gly Glu Asp Val Ala Asp Leu Arg Val Arg Ala Ser Lys Leu
                300                 305                 310

AAG GGC GTC GTC GTT CCG CCG GAA CGT GCG CCG TCG ATG ATC GAC GAA     1014
Lys Gly Val Val Val Pro Pro Glu Arg Ala Pro Ser Met Ile Asp Glu
            315                 320                 325
```

Figure 5C

```
TAT CCG GTC CTG GCG ATT GCC GCC TCC TTC GCG GAA GGC GAA ACC GTG      1062
Tyr Pro Val Leu Ala Ile Ala Ala Ser Phe Ala Glu Gly Glu Thr Val
        330                 335                 340

ATG GAC GGG CTC GAC GAA CTG CGC GTC AAG GAA TCG GAT CGT CTG GCA      1110
Met Asp Gly Leu Asp Glu Leu Arg Val Lys Glu Ser Asp Arg Leu Ala
    345                 350                 355

GCG GTC GCA CGC GGC CTT GAA GCC AAC GGC GTC GAT TGC ACC GAA GGC      1158
Ala Val Ala Arg Gly Leu Glu Ala Asn Gly Val Asp Cys Thr Glu Gly
360                 365                 370                 375

GAG ATG TCG CTG ACG GTT CGC GGC CGC CCC GAC GGC AAG GGA CTG GGC      1206
Glu Met Ser Leu Thr Val Arg Gly Arg Pro Asp Gly Lys Gly Leu Gly
                380                 385                 390

GGC GGC ACG GTT GCA ACC CAT CTC GAT CAT CGT ATC GCG ATG AGC TTC      1254
Gly Gly Thr Val Ala Thr His Leu Asp His Arg Ile Ala Met Ser Phe
            395                 400                 405

CTC GTG ATG GGC CTT GCG GCG GAA AAG CCG GTG ACG GTT GAC GAC AGT      1302
Leu Val Met Gly Leu Ala Ala Glu Lys Pro Val Thr Val Asp Asp Ser
        410                 415                 420

AAC ATG ATC GCC ACG TCC TTC CCC GAA TTC ATG GAC ATG ATG CCG GGA      1350
Asn Met Ile Ala Thr Ser Phe Pro Glu Phe Met Asp Met Met Pro Gly
    425                 430                 435
```

Figure 5D

```
TTG GGC GCA AAG ATC GAG TTG AGC ATA CTC TAGTCACTCG ACAGCGAAAA      1400
Leu Gly Ala Lys Ile Glu Leu Ser Ile Leu
440                 445

TATTATTTGC GAGATTGGGC ATTATTACCG GTTGGTCTCA GCGGGGGTTT AATGTCCAAT  1460

CTTCCATACG TAACAGCATC AGGAAATATC AAAAAAGCTT                        1500
```

Figure 5E

```
  1 MSHGASSRPATARKSSGLSGTVRIPGDKSISHRSFMFGGLASGETRITGL 50
            . | .. . :.||:.:||.|.:|:|.::::::|| |.| :|.|
  1 ......MESLTLQPIARVDGTINLPGSKTVSNRALLLAALAHGKTVLTNL 44
            .         .         .         .         .
 51 LEGEDVINTGKAMQAMGARIRKEGDTWIIDGVGNGGLLAPEAPLD..FGN 98
    |:::|| :  .|: |:|...  .:|   .: :|||| | :|::|:  :||
 45 LDSDDVRHMLNALTALGVSYTLSADRTRCEIIGNGGPLHAEGALELFLGN 94
            .         .         .         .         .
 99 AATGCRLTMGLVGVYDFDSTFIGDASLTKRPMGRVLNPLREMGVQVK.SE 147
    |:|: |   : :.: . | .:.|::.:..||:|:::::||  |..:.  |
 95 AGTAMRPLAAALCLGSNDIVLTGEPRMKERPIGHLVDALRLGGAKITYLE 144
            .         .         .         .         ..
148 DGDRLPVTLRGPKTPTPITYRVPMASAQVKSAVLLAGLNTPGITTVIEPI 197
    :::  |: |.|. |.. :.  ..:.|. :.. :: |.|...:... |..
145 QENYPPLRLQGGFTGGNVDVDGSVSSQFLTALLMTAPLAPEDTVIRIKGD 194
            .         .         .         .         .
198 MTRDHTEKMLQGFGANLTVETDADGVRTIRLEGRGKLTGQVIDVPGDPSS 247
    :....  .:  .:  .:.||.:.:  . : :.| ... :... :.::..|
195 LVSKPYIDITLNLMKTFGVEIENQHYQQFVVKGGQSYQSPGTYLVEGDAS 244
```

Figure 6A

```
                .         .         .         .         .
248 TAFPLVAALLVPGSDVTILNVLMNPTRTGLILT..LQEMGADIEVINPRL 295
    .|  ::||  :.|:.|.: .: .|. ..:: :.  |:.|||.|
245 SASYFLAAAAIKGGTVKVTGIGRNSMQGDIRFADVLEKMGATI....... 287
                .         .         .         .         .
296 AGGEDVADLRVRSSTLKGVTVPEDRAPSMIDEYPILAVAAAFAEGATVMN 345
    . |:|   :.. .:.|.::.:. :: |   |.  .:|.|| ||.|.| :.
288 CWGDDY..ISCTRGELNAIDMDMNHIP...DAAMTIATAALFAKGTTRLR 332
                .         .         .         .         .
346 GLEELRVKESDRLSAVANGLKLNGVDCDEGETSLVVRGRPDGKGLGNASG 395
    .: ::||||.||| |:|.:|:  |.:.:||.. : : ..|:  .:
333 NIYNWRVKETDRLFAMATELRKVGAEVEEGHDYIRI.TPPEKLNF..... 376
                .         .         .         .         .
396 AAVATHLDHRIAMSFLVMGLVSENPVTVDDATMIATSFPEFMDLMAGLGA 445
    |.:||. |||:||:| :::| |:.|||: |:. .|..||:::: :| ::.
377 AEIATYNDHRMAMCFSLVAL.SDTPVTILDPKCTAKTFPDYFEQLARISQ 425
                .
446 KIELSDTKAA* 456

426 AA*........ 428
```

Figure 6B

```
  1 MSHGASSRPATARKSSGLSGTVRIPGDKSISHRSFMFGGLASGETRITGL 50
    |||:||.:|||||:|.:|.|.:||||||||||||||||||||||||||||
  1 MSHSASPKPATARRSEALTGEIRIPGDKSISHRSFMFGGLASGETRITGL 50
                .         .         .         .         .
 51 LEGEDVINTGKAMQAMGARIRKEGDTWIIDGVGNGGLLAPEAPLDFGNAA 100
    ||||||||||:|||||||:||||||.|||:|||||.||.|||:||||||:
 51 LEGEDVINTGRAMQAMGAKIRKEGDVWIINGVGNGCLLQPEAALDFGNAG 100
                .         .         .         .         .
101 TGCRLTMGLVGVYDFDSTFIGDASLTKRPMGRVLNPLREMGVQVKSEDGD 150
    ||.||||||||.||:...|||||||.||||||||||||||||||...|||
101 TGARLTMGLVGTYDMKTSFIGDASLSKRPMGRVLNPLREMGVQVEAADGD 150
                .         .         .         .         .
151 RLPVTLRGPKTPTPITYRVPMASAQVKSAVLLAGLNTPGITTVIEPIMTR 200
    |:|:|| ||||:.||||||||||||||||||||||||:||||||:||||
151 RMPLTLIGPKTANPITYRVPMASAQVKSAVLLAGLNTPGVTTVIEPVMTR 200
                .         .         .         .         .
201 DHTEKMLQGFGANLTVETDADGVRTIRLEGRGKLTGQVIDVPGDPSSTAF 250
    ||||||||||||:|||||| |||| ||:.|.|||.||.||||||||||||
201 DHTEKMLQGFGADLTVETDKDGVRHIRITGQGKLVGQTIDVPGDPSSTAF 250
                .         .         .         .         .
251 PLVAALLVPGSDVTILNVLMNPTRTGLILTLQEMGADIEVINPRLAGGED 300
    ||||||||.|||||| ||||||||||||||||||||||:|:|||||||
251 PLVAALLVEGSDVTIRNVLMNPTRTGLILTLQEMGADIEVLNARLAGGED 300
```

Figure 7A

```
                .         .         .         .         .
301 VADLRVRSSTLKGVTVPEDRAPSMIDEYPILAVAAAFAEGATVMNGLEEL 350
    |||||||.|.||||.||.:||||||||||:||:||.||||.|||:||:||
301 VADLRVRASKLKGVVVPPERAPSMIDEYPVLAIAASFAEGETVMDGLDEL 350
                .         .         .         .         .
351 RVKESDRLSAVANGLKLNGVDCDEGETSLVVRGRPDGKGLGNASGAAVAT 400
    ||||||||.|||.||. |||||.||| ||.||||||||||||   |:.|||
351 RVKESDRLAAVARGLEANGVDCTEGEMSLTVRGRPDGKGLG...GGTVAT 397
                .         .         .         .         .
401 HLDHRIAMSFLVMGLVSENPVTVDDATMIATSFPEFMDLMAGLGAKIELS 450
    ||||||||||||||||..|.||||||..||||||||||||:|:||||||||
398 HLDHRIAMSFLVMGLAAEKPVTVDDSNMIATSFPEFMDMMPGLGAKIELS 447

451 DTKAA* 456

448 IL.... 449
```

Figure 7B

```
CCATGGCTCA CGGTGCAAGC AGCCGTCCAG CAACTGCTCG TAAGTCCTCT GGTCTTTCTG    60
GAACCGTCCG TATTCCAGGT GACAAGTCTA TCTCCCACAG GTCCTTCATG TTTGGAGGTC   120
TCGCTAGCGG TGAAACTCGT ATCACCGGTC TTTTGGAAGG TGAAGATGTT ATCAACACTG   180
GTAAGGCTAT GCAAGCTATG GGTGCCAGAA TCCGTAAGGA AGGTGATACT TGGATCATTG   240
ATGGTGTTGG TAACGGTGGA CTCCTTGCTC CTGAGGCTCC TCTCGATTTC GGTAACGCTG   300
CAACTGGTTG CCGTTTGACT ATGGGTCTTG TTGGTGTTTA CGATTTCGAT AGCACTTTCA   360
TTGGTGACGC TTCTCTCACT AAGCGTCCAA TGGGTCGTGT GTTGAACCCA CTTCGCGAAA   420
TGGGTGTGCA GGTGAAGTCT GAAGACGGTG ATCGTCTTCC AGTTACCTTG CGTGGACCAA   480
AGACTCCAAC GCCAATCACC TACAGGGTAC CTATGGCTTC CGCTCAAGTG AAGTCCGCTG   540
TTCTGCTTGC TGGTCTCAAC ACCCCAGGTA TCACCACTGT TATCGAGCCA ATCATGACTC   600
GTGACCACAC TGAAAAGATG CTTCAAGGTT TTGGTGCTAA CCTTACCGTT GAGACTGATG   660
CTGACGGTGT GCGTACCATC CGTCTTGAAG GTCGTGGTAA GCTCACCGGT CAAGTGATTG   720
ATGTTCCAGG TGATCCATCC TCTACTGCTT TCCCATTGGT TGCTGCCTTG CTTGTTCCAG   780
GTTCCGACGT CACCATCCTT AACGTTTTGA TGAACCCAAC CCGTACTGGT CTCATCTTGA   840
```

Figure 8A

CTCTGCAGGA AATGGGTGCC GACATCGAAG TGATCAACCC ACGTCTTGCT GGTGGAGAAG 900

ACGTGGCTGA CTTGCGTGTT CGTTCTTCTA CTTTGAAGGG TGTTACTGTT CCAGAAGACC 960

GTGCTCCTTC TATGATCGAC GAGTATCCAA TTCTCGCTGT TGCAGCTGCA TTCGCTGAAG 1020

GTGCTACCGT TATGAACGGT TTGGAAGAAC TCCGTGTTAA GGAAAGCGAC CGTCTTTCTG 1080

CTGTCGCAAA CGGTCTCAAG CTCAACGGTG TTGATTGCGA TGAAGGTGAG ACTTCTCTCG 1140

TCGTGCGTGG TCGTCCTGAC GGTAAGGGTC TCGGTAACGC TTCTGGAGCA GCTGTCGCTA 1200

CCCACCTCGA TCACCGTATC GCTATGAGCT TCCTCGTTAT GGGTCTCGTT TCTGAAAACC 1260

CTGTTACTGT TGATGATGCT ACTATGATCG CTACTAGCTT CCCAGAGTTC ATGGATTTGA 1320

TGGCTGGTCT TGGAGCTAAG ATCGAACTCT CCGACACTAA GGCTGCTTGA TGAGCTC 1377

Figure 8B

```
AGATCTATCG ATAAGCTTGA TGTAATTGGA GGAAGATCAA AATTTTCAAT CCCCATTCTT      60

CGATTGCTTC AATTGAAGTT TCTCCG ATG GCG CAA GTT AGC AGA ATC TGC AAT      113
                             Met Ala Gln Val Ser Arg Ile Cys Asn
                              1               5

GGT GTG CAG AAC CCA TCT CTT ATC TCC AAT CTC TCG AAA TCC AGT CAA       161
Gly Val Gln Asn Pro Ser Leu Ile Ser Asn Leu Ser Lys Ser Ser Gln
 10                  15                  20                  25

CGC AAA TCT CCC TTA TCG GTT TCT CTG AAG ACG CAG CAG CAT CCA CGA       209
Arg Lys Ser Pro Leu Ser Val Ser Leu Lys Thr Gln Gln His Pro Arg
                 30                  35                  40

GCT TAT CCG ATT TCG TCG TCG TGG GGA TTG AAG AAG AGT GGG ATG ACG       257
Ala Tyr Pro Ile Ser Ser Ser Trp Gly Leu Lys Lys Ser Gly Met Thr
             45                  50                  55

TTA ATT GGC TCT GAG CTT CGT CCT CTT AAG GTC ATG TCT TCT GTT TCC       305
Leu Ile Gly Ser Glu Leu Arg Pro Leu Lys Val Met Ser Ser Val Ser
         60                  65                  70

ACG GCG TGC ATG C                                                     318
Thr Ala Cys Met
     75
```

Figure 9

```
AGATCTATCG ATAAGCTTGA TGTAATTGGA GGAAGATCAA AATTTTCAAT CCCCATTCTT      60

CGATTGCTTC AATTGAAGTT TCTCCG ATG GCG CAA GTT AGC AGA ATC TGC AAT      113
                             Met Ala Gln Val Ser Arg Ile Cys Asn
                              1               5

GGT GTG CAG AAC CCA TCT CTT ATC TCC AAT CTC TCG AAA TCC AGT CAA       161
Gly Val Gln Asn Pro Ser Leu Ile Ser Asn Leu Ser Lys Ser Ser Gln
 10                  15                  20                  25

CGC AAA TCT CCC TTA TCG GTT TCT CTG AAG ACG CAG CAG CAT CCA CGA       209
Arg Lys Ser Pro Leu Ser Val Ser Leu Lys Thr Gln Gln His Pro Arg
                 30                  35                  40

GCT TAT CCG ATT TCG TCG TCG TGG GGA TTG AAG AAG AGT GGG ATG ACG       257
Ala Tyr Pro Ile Ser Ser Ser Trp Gly Leu Lys Lys Ser Gly Met Thr
             45                  50                  55
```

Figure 10A

```
TTA ATT GGC TCT GAG CTT CGT CCT CTT AAG GTC ATG TCT TCT GTT TCC      305
Leu Ile Gly Ser Glu Leu Arg Pro Leu Lys Val Met Ser Ser Val Ser
        60                  65                  70

ACG GCG GAG AAA GCG TCG GAG ATT GTA CTT CAA CCC ATT AGA GAA ATC      353
Thr Ala Glu Lys Ala Ser Glu Ile Val Leu Gln Pro Ile Arg Glu Ile
    75                  80                  85

TCC GGT CTT ATT AAG TTG CCT GGC TCC AAG TCT CTA TCA AAT AGA ATT      401
Ser Gly Leu Ile Lys Leu Pro Gly Ser Lys Ser Leu Ser Asn Arg Ile
 90                  95                 100                 105

C                                                                    402
```

Figure 10B

```
AGATCTTTCA AGA ATG GCA CAA ATT AAC AAC ATG GCT CAA GGG ATA CAA      49
               Met Ala Gln Ile Asn Asn Met Ala Gln Gly Ile Gln
                 1               5                  10

ACC CTT AAT CCC AAT TCC AAT TTC CAT AAA CCC CAA GTT CCT AAA TCT     97
Thr Leu Asn Pro Asn Ser Asn Phe His Lys Pro Gln Val Pro Lys Ser
         15                  20                  25

TCA AGT TTT CTT GTT TTT GGA TCT AAA AAA CTG AAA AAT TCA GCA AAT    145
Ser Ser Phe Leu Val Phe Gly Ser Lys Lys Leu Lys Asn Ser Ala Asn
     30                  35                  40

TCT ATG TTG GTT TTG AAA AAA GAT TCA ATT TTT ATG CAA AAG TTT TGT    193
Ser Met Leu Val Leu Lys Lys Asp Ser Ile Phe Met Gln Lys Phe Cys
 45                  50                  55                  60

TCC TTT AGG ATT TCA GCA TCA GTG GCT ACA GCC TGC ATG C              233
Ser Phe Arg Ile Ser Ala Ser Val Ala Thr Ala Cys Met
                 65                  70
```

Figure 11

```
AGATCTGCTA GAAATAATTT TGTTTAACTT TAAGAAGGAG ATATATCC ATG GCA CAA      57
                                                     Met Ala Gln
                                                       1

ATT AAC AAC ATG GCT CAA GGG ATA CAA ACC CTT AAT CCC AAT TCC AAT      105
Ile Asn Asn Met Ala Gln Gly Ile Gln Thr Leu Asn Pro Asn Ser Asn
      5                  10                  15

TTC CAT AAA CCC CAA GTT CCT AAA TCT TCA AGT TTT CTT GTT TTT GGA      153
Phe His Lys Pro Gln Val Pro Lys Ser Ser Ser Phe Leu Val Phe Gly
 20                  25                  30                  35

TCT AAA AAA CTG AAA AAT TCA GCA AAT TCT ATG TTG GTT TTG AAA AAA      201
Ser Lys Lys Leu Lys Asn Ser Ala Asn Ser Met Leu Val Leu Lys Lys
                 40                  45                  50
```

Figure 12A

```
GAT TCA ATT TTT ATG CAA AAG TTT TGT TCC TTT AGG ATT TCA GCA TCA      249
Asp Ser Ile Phe Met Gln Lys Phe Cys Ser Phe Arg Ile Ser Ala Ser
            55                  60                  65

GTG GCT ACA GCA CAG AAG CCT TCT GAG ATA GTG TTG CAA CCC ATT AAA      297
Val Ala Thr Ala Gln Lys Pro Ser Glu Ile Val Leu Gln Pro Ile Lys
        70                  75                  80

GAG ATT TCA GGC ACT GTT AAA TTG CCT GGC TCT AAA TCA TTA TCT AAT      345
Glu Ile Ser Gly Thr Val Lys Leu Pro Gly Ser Lys Ser Leu Ser Asn
    85                  90                  95

AGA ATT C                                                            352
Arg Ile
100
```

Figure 12B

```
ATG AAA CGA GAT AAG GTG CAG ACC TTA CAT GGA GAA ATA CAT ATT CCC      48
Met Lys Arg Asp Lys Val Gln Thr Leu His Gly Glu Ile His Ile Pro
 1               5                  10                  15

GGT GAT AAA TCC ATT TCT CAC CGC TCT GTT ATG TTT GGC GCG CTA GCG      96
Gly Asp Lys Ser Ile Ser His Arg Ser Val Met Phe Gly Ala Leu Ala
            20                  25                  30

GCA GGC ACA ACA ACA GTT AAA AAC TTT CTG CCG GGA GCA GAT TGT CTG     144
Ala Gly Thr Thr Thr Val Lys Asn Phe Leu Pro Gly Ala Asp Cys Leu
        35                  40                  45

AGC ACG ATC GAT TGC TTT AGA AAA ATG GGT GTT CAC ATT GAG CAA AGC     192
Ser Thr Ile Asp Cys Phe Arg Lys Met Gly Val His Ile Glu Gln Ser
    50                  55                  60

AGC AGC GAT GTC GTG ATT CAC GGA AAA GGA ATC GAT GCC CTG AAA GAG     240
Ser Ser Asp Val Val Ile His Gly Lys Gly Ile Asp Ala Leu Lys Glu
65                  70                  75                  80

CCA GAA AGC CTT TTA GAT GTC GGA AAT TCA GGT ACA ACG ATT CGC CTG     288
Pro Glu Ser Leu Leu Asp Val Gly Asn Ser Gly Thr Thr Ile Arg Leu
                85                  90                  95

ATG CTC GGA ATA TTG GCG GGC CGT CCT TTT TAC AGC GCG GTA GCC GGA     336
Met Leu Gly Ile Leu Ala Gly Arg Pro Phe Tyr Ser Ala Val Ala Gly
            100                 105                 110
```

Figure 18A

```
GAT GAG AGC ATT GCG AAA CGC CCA ATG AAG CGT GTG ACT GAG CCT TTG      384
Asp Glu Ser Ile Ala Lys Arg Pro Met Lys Arg Val Thr Glu Pro Leu
        115                 120                 125

AAA AAA ATG GGG GCT AAA ATC GAC GGC AGA GCC GGC GGA GAG TTT ACA      432
Lys Lys Met Gly Ala Lys Ile Asp Gly Arg Ala Gly Gly Glu Phe Thr
    130                 135                 140

CCG CTG TCA GTG AGC GGC GCT TCA TTA AAA GGA ATT GAT TAT GTA TCA      480
Pro Leu Ser Val Ser Gly Ala Ser Leu Lys Gly Ile Asp Tyr Val Ser
145                 150                 155                 160

CCT GTT GCA AGC GCG CAA ATT AAA TCT GCT GTT TTG CTG GCC GGA TTA      528
Pro Val Ala Ser Ala Gln Ile Lys Ser Ala Val Leu Leu Ala Gly Leu
                165                 170                 175

CAG GCT GAG GGC ACA ACA ACT GTA ACA GAG CCC CAT AAA TCT CGG GAC      576
Gln Ala Glu Gly Thr Thr Thr Val Thr Glu Pro His Lys Ser Arg Asp
            180                 185                 190

CAC ACT GAG CGG ATG CTT TCT GCT TTT GGC GTT AAG CTT TCT GAA GAT      624
His Thr Glu Arg Met Leu Ser Ala Phe Gly Val Lys Leu Ser Glu Asp
        195                 200                 205

CAA ACG AGT GTT TCC ATT GCT GGT GGC CAG AAA CTG ACA GCT GCT GAT      672
Gln Thr Ser Val Ser Ile Ala Gly Gly Gln Lys Leu Thr Ala Ala Asp
    210                 215                 220
```

Figure 18B

```
ATT TTT GTT CCT GGA GAC ATT TCT TCA GCC GCG TTT TTC CTT GCT GCT      720
Ile Phe Val Pro Gly Asp Ile Ser Ser Ala Ala Phe Phe Leu Ala Ala
225                 230                 235                 240

GGC GCG ATG GTT CCA AAC AGC AGA ATT GTA TTG AAA AAC GTA GGT TTA      768
Gly Ala Met Val Pro Asn Ser Arg Ile Val Leu Lys Asn Val Gly Leu
                245                 250                 255

AAT CCG ACT CGG ACA GGT ATT ATT GAT GTC CTT CAA AAC ATG GGG GCA      816
Asn Pro Thr Arg Thr Gly Ile Ile Asp Val Leu Gln Asn Met Gly Ala
            260                 265                 270

AAA CTT GAA ATC AAA CCA TCT GCT GAT AGC GGT GCA GAG CCT TAT GGA      864
Lys Leu Glu Ile Lys Pro Ser Ala Asp Ser Gly Ala Glu Pro Tyr Gly
        275                 280                 285

GAT TTG ATT ATA GAA ACG TCA TCT CTA AAG GCA GTT GAA ATC GGA GGA      912
Asp Leu Ile Ile Glu Thr Ser Ser Leu Lys Ala Val Glu Ile Gly Gly
    290                 295                 300

GAT ATC ATT CCG CGT TTA ATT GAT GAG ATC CCT ATC ATC GCG CTT CTT      960
Asp Ile Ile Pro Arg Leu Ile Asp Glu Ile Pro Ile Ile Ala Leu Leu
305                 310                 315                 320

GCG ACT CAG GCG GAA GGA ACC ACC GTT ATT AAG GAC GCG GCA GAG CTA     1008
Ala Thr Gln Ala Glu Gly Thr Thr Val Ile Lys Asp Ala Ala Glu Leu
                325                 330                 335
```

Figure 18C

```
AAA GTG AAA GAA ACA AAC CGT ATT GAT ACT GTT GTT TCT GAG CTT CGC      1056
Lys Val Lys Glu Thr Asn Arg Ile Asp Thr Val Val Ser Glu Leu Arg
            340                 345                 350

AAG CTG GGT GCT GAA ATT GAA CCG ACA GCA GAT GGA ATG AAG GTT TAT      1104
Lys Leu Gly Ala Glu Ile Glu Pro Thr Ala Asp Gly Met Lys Val Tyr
        355                 360                 365

GGC AAA CAA ACG TTG AAA GGC GGC GCT GCA GTG TCC AGC CAC GGA GAT      1152
Gly Lys Gln Thr Leu Lys Gly Gly Ala Ala Val Ser Ser His Gly Asp
    370                 375                 380

CAT CGA ATC GGA ATG ATG CTT GGT ATT GCT TCC TGT ATA ACG GAG GAG      1200
His Arg Ile Gly Met Met Leu Gly Ile Ala Ser Cys Ile Thr Glu Glu
385                 390                 395                 400

CCG ATT GAA ATC GAG CAC ACG GAT GCC ATT CAC GTT TCT TAT CCA ACC      1248
Pro Ile Glu Ile Glu His Thr Asp Ala Ile His Val Ser Tyr Pro Thr
                405                 410                 415

TTC TTC GAG CAT TTA AAT AAG CTT TCG AAA AAA TCC TGA                  1287
Phe Phe Glu His Leu Asn Lys Leu Ser Lys Lys Ser
            420                 425
```

Figure 18D

```
ATG GTA AAT GAA CAA ATC ATT GAT ATT TCA GGT CCG TTA AAG GGC GAA      48
Met Val Asn Glu Gln Ile Ile Asp Ile Ser Gly Pro Leu Lys Gly Glu
 1               5                  10                  15

ATA GAA GTG CCG GGC GAT AAG TCA ATG ACA CAC CGT GCA ATC ATG TTG      96
Ile Glu Val Pro Gly Asp Lys Ser Met Thr His Arg Ala Ile Met Leu
            20                  25                  30

GCG TCG CTA GCT GAA GGT GTA TCT ACT ATA TAT AAG CCA CTA CTT GGC     144
Ala Ser Leu Ala Glu Gly Val Ser Thr Ile Tyr Lys Pro Leu Leu Gly
        35                  40                  45

GAA GAT TGT CGT CGT ACG ATG GAC ATT TTC CGA CAC TTA GGT GTA GAA     192
Glu Asp Cys Arg Arg Thr Met Asp Ile Phe Arg His Leu Gly Val Glu
    50                  55                  60

ATC AAA GAA GAT GAT GAA AAA TTA GTT GTG ACT TCC CCA GGA TAT CAA     240
Ile Lys Glu Asp Asp Glu Lys Leu Val Val Thr Ser Pro Gly Tyr Gln
65                  70                  75                  80

GTT AAC ACG CCA CAT CAA GTA TTG TAT ACA GGT AAT TCT GGT ACG ACA     288
Val Asn Thr Pro His Gln Val Leu Tyr Thr Gly Asn Ser Gly Thr Thr
                85                  90                  95

ACA CGA TTA TTG GCA GGT TTG TTA AGT GGT TTA GGT AAT GAA AGT GTT     336
Thr Arg Leu Leu Ala Gly Leu Leu Ser Gly Leu Gly Asn Glu Ser Val
            100                 105                 110
```

Figure 19A

```
TTG TCT GGC GAT GTT TCA ATT GGT AAA AGG CCA ATG GAT CGT GTC TTG      384
Leu Ser Gly Asp Val Ser Ile Gly Lys Arg Pro Met Asp Arg Val Leu
        115                 120                 125

AGA CCA TTG AAA CTT ATG GAT GCG AAT ATT GAA GGT ATT GAA GAT AAT      432
Arg Pro Leu Lys Leu Met Asp Ala Asn Ile Glu Gly Ile Glu Asp Asn
    130                 135                 140

TAT ACA CCA TTA ATT ATT AAG CCA TCT GTC ATA AAA GGT ATA AAT TAT      480
Tyr Thr Pro Leu Ile Ile Lys Pro Ser Val Ile Lys Gly Ile Asn Tyr
145                 150                 155                 160

CAA ATG GAA GTT GCA AGT GCA CAA GTA AAA AGT GCC ATT TTA TTT GCA      528
Gln Met Glu Val Ala Ser Ala Gln Val Lys Ser Ala Ile Leu Phe Ala
                165                 170                 175

AGT TTG TTT TCT AAG GAA CCG ACC ATC ATT AAA GAA TTA GAT GTA AGT      576
Ser Leu Phe Ser Lys Glu Pro Thr Ile Ile Lys Glu Leu Asp Val Ser
            180                 185                 190

CGA AAT CAT ACT GAG ACG ATG TTC AAA CAT TTT AAT ATT CCA ATT GAA      624
Arg Asn His Thr Glu Thr Met Phe Lys His Phe Asn Ile Pro Ile Glu
        195                 200                 205

GCA GAA GGG TTA TCA ATT AAT ACA ACC CCT GAA GCA ATT CGA TAC ATT      672
Ala Glu Gly Leu Ser Ile Asn Thr Thr Pro Glu Ala Ile Arg Tyr Ile
    210                 215                 220
```

Figure 19B

```
AAA CCT GCA GAT TTT CAT GTT CCT GGC GAT ATT TCA TCT GCA GCG TTC      720
Lys Pro Ala Asp Phe His Val Pro Gly Asp Ile Ser Ser Ala Ala Phe
225                 230                 235                 240

TTT ATT GTT GCA GCA CTT ATC ACA CCA GGA AGT GAT GTA ACA ATT CAT      768
Phe Ile Val Ala Ala Leu Ile Thr Pro Gly Ser Asp Val Thr Ile His
                245                 250                 255

AAT GTT GGA ATC AAT CAA ACA CGT TCA GGT ATT ATT GAT ATT GTT GAA      816
Asn Val Gly Ile Asn Gln Thr Arg Ser Gly Ile Ile Asp Ile Val Glu
            260                 265                 270

AAA ATG GGC GGT AAT ATC CAA CTT TTC AAT CAA ACA ACT GGT GCT GAA      864
Lys Met Gly Gly Asn Ile Gln Leu Phe Asn Gln Thr Thr Gly Ala Glu
        275                 280                 285

CCT ACT GCT TCT ATT CGT ATT CAA TAC ACA CCA ATG CTT CAA CCA ATA      912
Pro Thr Ala Ser Ile Arg Ile Gln Tyr Thr Pro Met Leu Gln Pro Ile
    290                 295                 300

ACA ATC GAA GGA GAA TTA GTT CCA AAA GCA ATT GAT GAA CTG CCT GTA      960
Thr Ile Glu Gly Glu Leu Val Pro Lys Ala Ile Asp Glu Leu Pro Val
305                 310                 315                 320

ATA GCA TTA CTT TGT ACA CAA GCA GTT GGC ACG AGT ACA ATT AAA GAT     1008
Ile Ala Leu Leu Cys Thr Gln Ala Val Gly Thr Ser Thr Ile Lys Asp
                325                 330                 335
```

Figure 19C

```
GCC GAG GAA TTA AAA GTA AAA GAA ACA AAT AGA ATT GAT ACA ACG GCT      1056
Ala Glu Glu Leu Lys Val Lys Glu Thr Asn Arg Ile Asp Thr Thr Ala
            340                 345                 350

GAT ATG TTA AAC TTG TTA GGG TTT GAA TTA CAA CCA ACT AAT GAT GGA      1104
Asp Met Leu Asn Leu Leu Gly Phe Glu Leu Gln Pro Thr Asn Asp Gly
        355                 360                 365

TTG ATT ATT CAT CCG TCA GAA TTT AAA ACA AAT GCA ACA GAT ATT TTA      1152
Leu Ile Ile His Pro Ser Glu Phe Lys Thr Asn Ala Thr Asp Ile Leu
    370                 375                 380

ACT GAT CAT CGA ATA GGA ATG ATG CTT GCA GTT GCT TGT GTA CTT TCA      1200
Thr Asp His Arg Ile Gly Met Met Leu Ala Val Ala Cys Val Leu Ser
385                 390                 395                 400

AGC GAG CCT GTC AAA ATC AAA CAA TTT GAT GCT GTA AAT GTA TCA TTT      1248
Ser Glu Pro Val Lys Ile Lys Gln Phe Asp Ala Val Asn Val Ser Phe
                405                 410                 415

CCA GGA TTT TTA CCA AAA CTA AAG CTT TTA CAA AAT GAG GGA TAA          1293
Pro Gly Phe Leu Pro Lys Leu Lys Leu Leu Gln Asn Glu Gly
            420                 425                 430
```

Figure 19D

```
                    1                                                  50
PG2982              .......... .......... .......... MSHSASPKPA TARRSEALTG
LBAA                .......... .......... .......... MSHSASPKPA TARRSEALTG
Agrobacterium CP4   .......... .......... .......... MSHGASSRPA TARKSSGLSG
B. subtilis         .......... .......... .......... .........M KRDKVQTLHG
S. aureus           .......... .......... .......... .....MVNEQ IIDISGPLKG
S. cerevisiae       .......... .......... .......... ......LVYP FKDIPADQQK
A. nidulans         .......... .......... .......... .......VHP ..GVAHSSNV
B. napus            .......... .......... .......... .K....ASEI VLQPIREISG
A. thaliana         .......... .......... .......... .K....ASEI VLQPIREISG
N. tabacum          .......... .......... .......... .K....PNEI VLQPIKDISG
L. esculentum       .......... .......... .......... .K....PHEI VLXPIKDISG
P. hybrida          .......... .......... .......... .K....PSEI VLQPIKEISG
Z. mays             .......... .......... .......... ....AGAEEI VLQPIKEISG
S. gallinarum       .......... .......... .......... ......MESL TLQPIARVDG
S. typhimurium      .......... .......... .......... ......MESL TLQPIARVDG
S. typhi            .......... .......... .......... ......MESL TLQPIARVDG
E. coli             .......... .......... .......... ......MESL TLQPIARVDG
K. pneumoniae       .......... .......... .......... ......MESL TLQPIARVDG
Y. entoercolitica   .......... .......... .......... .....MLESL TLHPIALING
H. influenzae       .......... .......... .......... ......MEKI TLAPISAVEG
P. multocida        .......... .......... .......... ..MIKDATAI TLNPISYIEG
A. salmonicida      .......... .......... .......... .......NSL RLEPISRVAG
B. pertussis        .......... .......... .......... ...MSGLAYL DLPAARLARG
Consensus           ---------- ---------- ---------- ---------- ----------
```

Figure 20A

```
                  51                                                  100
PG2982            EIRIPGDKSI SHRSFMFGGL ASGETRITGL LEGEDVINTG RAMQAM.GAK
LBAA              EIRIPGDKSI SHRSFMFGGL ASGETRITGL LEGEDVINTG RAMQAM.GAK
Agrobacterium CP4 TVRIPGDKSI SHRSFMFGGL ASGETRITGL LEGEDVINTG KAMQAM.GAR
B. subtilis       EIHIPGDKSI SHRSVMFGAL AAGTTTVKNF LPGADCLSTI DCFRKM.GVH
S. aureus         EIEVPGDKSM THRAIMLASL AEGVSTIYKP LLGEDCRRTM DIFRHL.GVE
S. cerevisiae     VVIPPGSKSI SNRALILAAL GEGQCKIKNL LHSDDTKHML TAVHELKGAT
A. nidulans       ICAPPGSKSI SNRALVLAAL GSGTCRIKNL LHSDDTEVML NALERLGAAT
B. napus          LIKLPGSKSL SNRILLLAAL SEGTTVVDNL LNSDDINYML DALKKL.GLN
A. thaliana       LIKLPGSKSL SNRILLLAAL SEGTTVVDNL LNSDDINYML DALKRL.GLN
N. tabacum        TVKLPGSKSL SNRILLLAAL SKGRTVVDNL LSSDDIHYML GALKTL.GLH
L. esculentum     TVKLPGSKSL SNRILLLAAL SEGRTVVDNL LSSDDIHYML GALKTL.GLH
P. hybrida        TVKLPGSKSL SNRILLLAAL SEGTTVVDNL LSSDDIHYML GALKTL.GLH
Z. mays           TVKLPGSKSL SNRILLLAAL SEGTTVVDNL LNSEDVHYML GALRTL.GLS
S. gallinarum     AINLPGSKSV SNRALLLAAL ACGKTVLTNL LDSDDVRHML NALSAL.GIN
S. typhimurium    AINLPGSKSV SNRALLLAAL PCGKTALTNL LDSDDVRHML NALSAL.GIN
S. typhi          AINLPGSKSV SNRALLLAAL ACGKTVLTNL LDSDDVRHML NALSAL.GIN
E. coli           TINLPGSKTV SNRALLLAAL AHGKTVLTNL LDSDDVRHML NALTAL.GVS
K. pneumoniae     TVNLPGSKSV SNRALLLAAL ARGTTVLTNL LDSDDVRHML NALSAL.GVH
Y. entoercolitica TVNLPGSKSV SNRALLLAAL AEGTTQLNNL LDSDDIRHML NALQAL.GVK
H. influenzae     TINLPGSKSL SNRALLLAAL AKGTTKVTNL LDSDDIRHML NALKAL.GVR
P. multocida      EVRLPGSKSL SNRALLLSAL AKGKTTLTNL LDSDDVRHML NALKEL.GVT
A. salmonicida    EVNLPGSKSV SNRALLLAAL ARGTTRLTNL LDSDDIRHML AALTQL.GVK
B. pertussis      EVALPGSKSI SNRVLLLAAL AEGSTEITGL LDSDDTRVML AALRQL.GVS
Consensus         ----PG-K-- --R------L --G------- L---D----- ----------
```

Figure 20B

```
                    101                                                150
PG2982              IRKEGDVWII NGVGNGCLLQ P......EAA LDFGNAGTGA RLTMGLVGTY
LBAA                IRKEGDVWII NGVGNGCLLQ P......EAA LDFGNAGTGA RLTMGLVGTY
Agrobacterium CP4   IRKEGDTWII DGVGNGGLLA P......EAP LDFGNAATGC RLTMGLVGVY
B. subtilis         IEQSSSDVVI HGKGIDALKE P......ESL LDVGNSGTTI RLMLGILAGR
S. aureus           IKEDDEKLVV TSPGYQ.VNT P......HQV LYTGNSGTTT RLLAGLLSGL
S. cerevisiae       ISWEDNGETV VVEGHGG... .STLSACADP LYLGNAGTAS RFLTSLAALV
A. nidulans         FSWEEEGEVL VVNGKGG... ..NLQASSSP LYLGNAGTAS RFLTTVATLA
B. napus            VERDSVNNRA VVEGCGGIFP ASLDSKSDIE LYLGNAGTAM RPLTAAVTAA
A. thaliana         VETDSENNRA VVEGCGGIFP ASIDSKSDIE LYLGNAGTAM RPLTAAVTAA
N. tabacum          VEDDNENQRA IVEGCGGQFP VGKKSEEEIQ LFLGNAGTAM RPLTAAVTVA
L. esculentum       VEDDNENQRA IVEGCGGQFP VGKKSEEEIQ LFLGNAGTAM RPLTAAVTVA
P. hybrida          VEEDSANQRA VVEGCGGLFP VGKESKEEIQ LFLGNAGTAM RPLTAAVTVA
Z. mays             VEADKAAKRA VVVGCGGKFP VE.DAKEEVQ LFLGNAGTAM RPLTAAVTAA
S. gallinarum       YTLSADRTRC DITGNGGPLR AP....GALE LFLGNAGTAM RPLAAALCL.
S. typhimurium      YTLSADRTRC DITGNGGALR AP....GALE LFLGNAGTAM RPLAAALCL.
S. typhi            YTLSADRTRC DITGNGGPLR AS....GTLE LFLGNAGTAM RPLAAALCL.
E. coli             YTLSADRTRC EIIGNGGPLH AE....GALE LFLGNAGTAM RPLAAALCL.
K. pneumoniae       YVLSSDRTRC EVTGTGGPLQ AG....SALE LFLGNAGTAM RPLAAALCL.
Y. entoercolitica   YRLSADRTRC EVDGLGGKLV AE....QPLE LFLGNAGTAM RPLAAALCL.
H. influenzae       YQLSDDKTIC EIEGLGGAFN IQ....DNLS LFLGNAGTAM RPLTAALCLK
P. multocida        YQLSEDKSVC EIEGLGRAFE WQ....SGLA LFLGNAGTAM RPLTAALCLS
A. salmonicida      YKLSADKTEC TVHGLGRSFA VS....APVN LFLGNAGTAM RPLCAALCL.
B. pertussis        VGEVAD..GC VTIEGVARFP TE.....QAE LFLGNAGTAF RPLTAALALM
Consensus           ---------- ---------- ---------- L--GN--T-- R---------
```

Figure 20C

```
                    151                                                  200
PG2982              DM......KT SFIGDASLSK RPMGRVLNPL REMGVQVEAA DGDRMPLT..
LBAA                DM......KT SFIGDASLSK RPMGRVLNPL REMGVQVEAA DGDRMPLT..
Agrobacterium CP4   DF......DS TFIGDASLTK RPMGRVLNPL REMGVQVKSE DGDRLPVT..
B. subtilis         PF......YS AVAGDESIAK RPMKRVTEPL KKMGAKIDGR AGGEFTPL..
S. aureus           GN......ES VLSGDVSIGK RPMDRVLRPL KLMDANIEG. IEDNYTPL..
S. cerevisiae       NST.SSQKYI VLTGNARMQQ RPIAPLVDSL RANGTKIEYL NNEGSLPIKV
A. nidulans         NS..STVDSS VLTGNNRMKQ RPIGDLVDAL TANVLPLNTS KGRASLPLKI
B. napus            G....GNASY VLDGVPRMRE RPIGDLVVGL KQLGADVECT LGTNCPPVRV
A. thaliana         G....GNASY VLDGVPRMRE RPIGDLVVGL KQLGADVECT LGTNCPPVRV
N. tabacum          G....GHSRY VLDGVPRMRE RPIGDLVDGL KQLGAEVDCF LGTNCPPVRI
L. esculentum       G....GHSRY VLDGVPRMRE RPIGDLVDGL KQLGAEVDCS LGTNCPPVRI
P. hybrida          G....GNSRY VLDGVPRMRE RPISDLVDGL KQLGAEVDCF LGTKCPPVRI
Z. mays             G....GNATY VLDGVPRMRE RPIGDLVVGL KQLGADVDCF LGTDCPPVRV
S. gallinarum       .....GQNEI VLTGEPRMKE RPIGHLVDSL RQGGANIDYL EQENYPPLRL
S. typhimurium      .....GQNEI VLTGEPRMKE RPIGHLVDSL RQGGANIDYL EQENYPPLRL
S. typhi            .....GQNEI VLTGEPRMKE RPIGHLVDSL RQGGANIDYL EQENYPPLRL
E. coli             .....GSNDI VLTGEPRMKE RPIGHLVDAL RLGGAKITYL EQENYPPLRL
K. pneumoniae       .....GSNDI VLTGEPRMKE RPIGHLVDAL RQGGAQIDYL EQENYPPLRL
Y. entoercolitica   .....GKNDI VLTGEPRMKE RPIGHLVDAL RQGGAQIDYL EQENYRR.CI
H. influenzae       G.NHEV..EI ILTGEPRMKE RPILHLVDAL RQAGADIRYL ENEGYPPLAI
P. multocida        TPNREGKNEI VLTGEPRMKE RPIQHLVDAL CQAGAEIQYL EQEGYPPIAI
A. salmonicida      .....GSGEY MLGGEPRMEE RPIGHLVDCL ALKGAHIQYL KKDGYPPLVV
B. pertussis        G......GDY RLSGVPRMHE RPIGDLVDAL RQFGAGIEYL GQAGYPPLRI
Consensus           ---------- ---G------ RP-------L ---------- ----------
```

Figure 20D

```
                    201                                                  250
PG2982              .....LIGPK TANPITYRVP MASAQVKSAV LLAGLN.... ....TPGVTT
LBAA                .....LIGPK TANPITYRVP MASAQVKSAV LLAGLN.... ....TPGVTT
Agrobacterium CP4   .....LRGPK TPTPITYRVP MASAQVKSAV LLAGLN.... ....TPGITT
B. subtilis         .....SVSGA SLKGIDYVSP VASAQIKSAV LLAGLQ.... ....AEGTTT
S. aureus           .....IIKPS VIKGINYQME VASAQVKSAI LFASLF.... ....SKEPTI
S. cerevisiae       YTDSVFKG.. ...GRIELAA TVSSQYVSSI LMCAPYAE.. .EPVTLALVG
A. nidulans         AASGGFAG.. ...GNINLAA KVSSQYVSSL LMCAPYAK.. .EPVTLRLVG
B. napus            NANGGLPG.. ...GKVKLSG SISSQYLTAL LMAAP.LA.. .LGDVEIEII
A. thaliana         NANGGLPG.. ...GKVKLSG SISSQYLTAL LMSAP.LA.. .LGDVEIEIV
N. tabacum          VSKGGLPG.. ...GKVKLSG SISSQYLTAL LMAAP.LA.. .LGDVEIEII
L. esculentum       VSKGGLPG.. ...GKVKLSG SISSQYLTAL LMAAP.LA.. .LGDVEIEII
P. hybrida          VSKGGLPG.. ...GKVKLSG SISSQYLTAL LMAAP.LA.. .LGDVEIEII
Z. mays             NGIGGLPG.. ...GKVKLSG SISSQYLSAL LMAAP.LP.. .LGDVEIEII
S. gallinarum       RG..GFIG.. ...GDIEVDG SVSSQFLTAL LMTAP.LA.. .PKDTIIRVK
S. typhimurium      RG..GFTG.. ...GDIEVDG SVSSQFLTAL LMTAP.LA.. .PKDTIIRVK
S. typhi            RG..GFIG.. ...GDIEVDG SVSSQFLTAL LMTAP.LA.. .PEDTIIRVK
E. coli             QG..GFTG.. ...GNVDVDG SVSSQFLTAL LMTAP.LA.. .PEDTVIRIK
K. pneumoniae       RG..GFTG.. ...GDVEVDG SVSSQFLTAL LMASP.LA.. .PQDTVIAIK
Y. entoercolitica   AG..GFRG.. ...GKLTVDG SVSSQFLTAL LMTAP.LA.. .EQDTEIQIQ
H. influenzae       RNK.GIKG.. ...GKVKIDG SISSQFLTAL LMSAP.LA.. .ENDTEIEII
P. multocida        RNT.GLKG.. ...GRIQIDG SVSSQFLTAL LMAAP.MA.. .EADTEIEII
A. salmonicida      DAK.GLWG.. ...GDVHVDG SVSSQFLTAF LMAAPAMA.. .PVIPRIHIK
B. pertussis        GGGSIRVD.. ...GPVRVEG SVSSQFLTAL LMAAPVLARR SGQDITIEVV
Consensus           ---------- ---------- --S-Q----- L--------- ----------
```

Figure 20E

```
                    251                                                  300
PG2982              VIEPVMTRDH TEKMLQGFGA DLTVETDKDG VRHIRITGQG KLVGQ.TIDV
LBAA                VIEPVMTRDH TEKMLQGFGA DLTVETDKDG VRHIRITGQG KLVGQ.TIDV
Agrobacterium CP4   VIEPIMTRDH TEKMLQGFGA NLTVETDADG VRTIRLEGRG KLTGQ.VIDV
B. subtilis         VTEPHKSRDH TERMLSAFGV KLSEDQTS.. ...VSIAGGQ KLTAA.DIFV
S. aureus           IKELDVSRNH TETMFKHFNI PIEAEGLS.. ..INTTPEAI RYIKPADFHV
S. cerevisiae       GKPISKLYVD MTIKMMEKFG IN.VET.STT EPYTYYIPKG HYINPSEYVI
A. nidulans         GKPISQPYID MTTAMMRSFG ID..VQKSTT EEHTYHIPQG RYVNPAEYVI
B. napus            DKLISVPYVE MTLKLMERFG VS..AEHSDS WDRFFVKGGQ KYKSPGNAYV
A. thaliana         DKLISVPYVE MTLKLMERFG VS..VEHSDS WDRFFVKGGQ KYKSPGNAYV
N. tabacum          DKLISVPYVE MTLKLMERFG VS..VEHTSS WDKFLVRGGQ KYKSPGKAYV
L. esculentum       DKLISVPYVE MTLKLMERFG VF..VEHSSG WDRFLVKGGQ KYKSPGKAFV
P. hybrida          DKLISVPYVE MTLKLMERFG IS..VEHSSS WDRFFVRGGQ KYKSPGKAFV
Z. mays             DKLISIPYVE MTLRLMERFG VK..AEHSDS WDRFYIKGGQ KYKSPKNAYV
S. gallinarum       GELVSKPYID ITLNLMKTFG VE..IAN.HH YQQFVVKGGQ QYHSPGRYLV
S. typhimurium      GELVSKPYID ITLNLMKTFG VE..IAN.HH YQQFVVKGGQ QYHSPGRYLV
S. typhi            GELVSKPYID ITLNLMKTFG VE..IAN.HH YQQFVVKGGQ QYHSPGRYLV
E. coli             GDLVSKPYID ITLNLMKTFG VE..IEN.QH YQQFVVKGGQ SYQSPGTYLV
K. pneumoniae       GELVSRPYID ITLHLMKTFG VE..VEN.QA YQRFIVRGNQ QYQSPGDYLV
Y. entoercolitica   GELVSKPYID ITLHLMKAFG VD..VVH.EN YQIFHIKGGQ TYRSPGIYLV
H. influenzae       GELVSKPYID ITLAMMRDFG VK..VEN.HH YQKFQVKGNQ SYISPNKYLV
P. multocida        GELVSKPYID ITLKMMQTFG VE..VEN.QA YQRFLVKGHQ QYQSPHRFLV
A. salmonicida      GELVSKPYID ITLHIMNSSG VV..IEH.DN YKLFYIKGNQ SIVSPGDFLV
B. pertussis        GELISKPYIE ITLNLMARFG VS..V.RRDG WRAFTIARDA VYRGPGRMAI
Consensus           ---------- ---------- ---------- ---------- ----------
```

Figure 20F

```
                 301                                                  350
PG2982           PGDPSSTAFP LVAALLVEGS DVTIRNVLMN PTRTGL...I LTLQEMGADI
LBAA             PGDPSSTAFP LVAALLVEGS DVTIRNVLMN PTRTGL...I LTLQEMGADI
Agrobacterium CP4 PGDPSSTAFP LVAALLVPGS DVTILNVLMN PTRTGL...I LTLQEMGADI
B. subtilis      PGDISSAAFF LAAGAMVPNS RIVLKNVGLN PTRTGI...I DVLQNMGAKL
S. aureus        PGDISSAAFF IVAALITPGS DVTIHNVGIN QTRSGI...I DIVEKMGGNI
S. cerevisiae    ESDASSATYP LAFAA.MTGT TVTVPNIGFE SLQGDARFAR DVLKPMGCKI
A. nidulans      ESDASCATYP LAVAA.VTGT TCTVPNIGSA SLQGDARFAV EVLRPMGCTV
B. napus         EGDASSASYF LAGAA.ITGE TVTVEGCGTT SLQGDVKFA. EVLEKMGCKV
A. thaliana      EGDASSASYF LAGAA.ITGE TVTVEGCGTT SLQGDVKFA. EVLEKMGCKV
N. tabacum       EGDASSASYF LAGAA.VTGG TVTVEGCGTS SLQGDVKFA. EVLEKMGAEV
L. esculentum    EGDASSASYF LAGAA.VTGG TVTVEGCGTS SLQGDVKFA. EVLEKMGAEV
P. hybrida       EGDASSASYF LAGAA.VTGG TITVEGCGTN SLQGDVKFA. EVLEKMGAEV
Z. mays          EGDASSASYF LAGAA.ITGG TVTVEGCGTT SLQGDVKFA. EVLEMMGAKV
S. gallinarum    EGDASSASYF LAAGA.IKGG TVKVTGIGRK SMQGDIRFA. DVLEKMGATI
S. typhimurium   EGDASSASYF LAAGA.IKGG TVKVTGIGRK SMQGDIRFA. DVLEKMGATI
S. typhi         EGDASSASYF LAAGG.IKGG TVKVTGIGGK SMQGDIRFA. DVLHKMGATI
E. coli          EGDASSASYF LAAAA.IKGG TVKVTGIGRN SMQGDIRFA. DVLEKMGATI
K. pneumoniae    EGDASSASYF LAAGA.IKGG TVKVTGIGRN SVQGDIRFA. DVLEKMGATV
Y. entoercolitica EGDASSASYF LAAAA.IKGG TVRVTGIGKQ SVQGDTKFA. DVLEKMGAKI
H. influenzae    EGDASSASYF LAAGA.IK.G KVKVTGIGKN SIQGDRLFA. DVLEKMGAKI
P. multocida     EGDASSASYF LAAAA.IK.G KVKVTGVGKN SIQGDRLFA. DVLEKMGAHI
A. salmonicida   EGDASSASYF LAAGA.IK.G KVRVTGIGKH SI.GDIHFA. DVLERMGARI
B. pertussis     EGDASTASYF LALGA.IGGG PVRVTGVGED SIQGDVAFA. ATLAAMGADV
Consensus        --D-S----- ---------- ---------- ---------- -----MG---
```

Figure 20G

```
                    351                                                  400
PG2982              EVLNARLAGG EDVADLRVR. ASKLKGVVVP PERAPSMIDE YPVLAIAASF
LBAA                EVLNARLAGG EDVADLRVR. ASKLKGVVVP PERAPSMIDE YPVLAIAASF
Agrobacterium CP4   EVINPRLAGG EDVADLRVR. SSTLKGVTVP EDRAPSMIDE YPILAVAAAF
B. subtilis         EIKPSADSGA EPYGDLIIE. TSSLKAVEIG GDIIPRLIDE IPIIALLATQ
S. aureus           QL.FNQTTGA EPTASIRIQY TPMLQPITIE GELVPKAIDE LPVIALLCTQ
S. cerevisiae       ....TQTATS TTVSGPPV.. ...GTLKPLK HVDMEPMTDA FLTACVVAAI
A. nidulans         ....EQTETS TTVTGPSD.. ...GILRATS KRGYGT.NDR CVPRCFRTGS
B. napus            ....SWTENS VTVTGPSRDA FGMRHLRAV. DVNMNKMPDV AMTLAVVALF
A. thaliana         ....SWTENS VTVTGPPRDA FGMRHLRAI. DVNMNKMPDV AMTLAVVALF
N. tabacum          ....TWTENS VTVKGPPRNS SGMKHLRAV. DVNMNKMPDV AMTLAVVALF
L. esculentum       ....TWTENS VTVKGPPRNS SGMKHLRAI. DVNMNKMPDV AMTLAVVALF
P. hybrida          ....TWTENS VTVKGPPRSS SGRKHLRAI. DVNMNKMPDV AMTLAVVALY
Z. mays             ....TWTETS VTVTGPPREP FGRKHLKAI. DVNMNKMPDV AMTLAVVALF
S. gallinarum       ....TWGDDF I........A CTRGELHAI. DMDMNHIPDA AMTIATTALF
S. typhimurium      ....TWGDDF I........A CTRGELHAI. DMDMNHIPDA AMTIATTALF
S. typhi            ....TWGDDF I........A CTRGELHAI. DMDMNHIPDA AMTIATTALF
E. coli             ....CWGDDY I........S CTRGELNAI. DMDMNHIPDA AMTIATAALF
K. pneumoniae       ....TWGEDY I........A CTRGELNAI. DMDMNHIPDA AMTIATAALF
Y. entoercolitica   ....SWGDDY I........E CSRGELQGI. DMDMNHIPDA AMTIATTALF
H. influenzae       ....TWGEDF I........Q AEHAELNGI. DMDMNHIPDA AMTIATTALF
P. multocida        ....TWGDDF I........Q VEKGNLKGI. DMDMNHIPDA AMTIATTALF
A. salmonicida      ....TWGDDF I........E AEQGPLHGV. DMDMNHIPDV GHDHSGQSHC
B. pertussis        ....RYGPGW IETRGVRVAE GGR..LKAF. DADFNLIPDA AMTAATLALY
Consensus           ---------- ---------- ---------- --------D- ----------
```

Figure 20H

```
                    401                                                  450
PG2982              AEG....... ETVMDGLDEL RVKESDRLAA VARGLEANGV DCTEGEMSLT
LBAA                AEG....... ETVMDGLDEL RVKESDRLAA VARGLEANGV DCTEGEMSLT
Agrobacterium CP4   AEG....... ATVMNGLEEL RVKESDRLSA VANGLKLNGV DCDEGETSLV
B. subtilis         AEG....... TTVIKDAAEL KVKETNRIDT VVSELRKLGA EIEPTADGMK
S. aureus           AVG....... TSTIKDAEEL KVKETNRIDT TADMLNLLGF ELQPTNDGLI
S. cerevisiae       SHDSDPNSAN TTTIEGIANQ RVKECNRILA MATELAKFGV KTTELPDGIQ
A. nidulans         HRPMEKSQTT PPVSSGIANQ RVKECNRIKA MKDELAKFGV ICREHDDGLE
B. napus            ADG....... PTTIRDVASW RVKETERMIA ICTELRKLGA TV.EEGSDYC
A. thaliana         ADG....... PTTIRDVASW RVKETERMIA ICTELRKLGA TV.EEGSDYC
N. tabacum          ADG....... PTAIRDVASW RVKETERMIA ICTELRKLGA TV.VEGSDYC
L. esculentum       ADG....... PTTIRDVASW RVKETERMIA ICTELRKLGA TV.VEGSDYC
P. hybrida          ADG....... PTAIRDVASW RVKETERMIA ICTELRKLGA TV.EEGPDYC
Z. mays             ADG....... PTAIRDVASW RVKETERMVA IRTELTKLGA SV.EEGPDYC
S. gallinarum       AKG....... TTTLRNIYNW RVKETDRLFA MATELRKVGA EV.EEGHDYI
S. typhimurium      AKG....... TTTLRNIYNW RVKETDRLFA MATELRKVGA EV.EEGHDYI
S. typhi            AKG....... TTTLRNIYNW RVKETDRLFA MATELRKVGA EV.EEGHDYI
E. coli             AKG....... TTRLRNIYNW RVKETDRLFA MATELRKVGA EV.EEGHDYI
K. pneumoniae       ARG....... TTTLRNIYNW RVKETDRLFA MATELRKVGA EV.EEGEDYI
Y. entoercolitica   ADG....... PTVIRNIYNW RVKETDRLSA MATELRKVGA EV.EEGQDYI
H. influenzae       SNG....... ETVIRNIYNW RVKETDRLTA MATELRKVGA EV.EEGEDFI
P. multocida        AEG....... ETVIRNIYNW RVKETDRLTA MATELRKVGA EV.EEGEDFI
A. salmonicida      LPR....... VPPHSQHLQL AVRD.DRCTP CTHGHRRAQA GVSEEGTTFI
B. pertussis        ADG....... PCRLRNIGSW RVKETDRIHA MHTELEKLGA GV.QSGADWL
Consensus           ---------- ---------- -V----R--- ---------- ----------
```

Figure 20I

```
                    451                                                  500
PG2982              VRGRPDGKGL G...GG.... TVATHLDHRI AMSFLVMGLA .........A
LBAA                VRGRPDGKGL G...GG.... TVATHLDHRI AMSFLVMGLA .........A
Agrobacterium CP4   VRGRPDGKGL GNASGA.... AVATHLDHRI AMSFLVMGLV .........S
B. subtilis         VYGKQTLKG. ....GA.... AVSSHGDHRI GMMLGIASCI .........T
S. aureus           IHPSEFKTN. ....AT.... DI..LTDHRI GMMLAVACVL .........S
S. cerevisiae       VHGLNSIKDL KVPSDSSGPV GVCTYDDHRV AMSFSLLAGM VNSQNERDEV
A. nidulans         IDGIDR.SNL RQPVG..... GVFCYDDHRV AFSFSVL.SL VTPQ......
B. napus            VITP..PAKV KPA....... EIDTYDDHRM AMAFSLAAC. .........A
A. thaliana         VITP..PKKV KTA....... EIDTYDDHRM AMAFSLAAC. .........A
N. tabacum          IITP..PEKL NVT....... EIDTYDDHRM AMAFSLAAC. .........A
L. esculentum       IITP..PEKL NVT....... EIDTYDDHRM AMAFSLAAC. .........A
P. hybrida          IITP..PEKL NVT....... DIDTYDDHRM AMAFSLAAC. .........A
Z. mays             IITP..PEKL NVT....... AIDTYDDHRM AMAFSLAAC. .........A
S. gallinarum       RITP..PAKL QHA....... DIGTYNDHRM AMCFSLVAL. .........S
S. typhimurium      RITP..PAKL QHA....... DIGTYNDHRM AMCFSLVAL. .........S
S. typhi            RITP..PAKL QHA....... DIGTYNDHRM AMCFSLVAL. .........S
E. coli             RITP..PEKL NFA....... EIATYNDHRM AMCFSLVAL. .........S
K. pneumoniae       RITP..PLTL QFA....... EIGTYNDHRM AMCFSLVAL. .........S
Y. entoercolitica   RVVP..PAQL IAA....... EIGTYNDHRM AMCFSLVAL. .........S
H. influenzae       RIQPLALNQF KHA....... NIETYNDHRM AMCFSLIAL. .........S
P. multocida        RIQPLNLAQF QHA....... ELNI.HDHRM AMCFALIAL. .........S
A. salmonicida      TRDAADPAQA RRD....... R..HLQRSRI AMCFSLVAL. .........S
B. pertussis        EVAPPEPGGW RDA....... HIGTWDDHRM AMCFLLAAF. .........G
Consensus           ---------- ---------- --------R- ---------- ----------
```

Figure 20J

```
                    501                                          538
PG2982              EKPVTVDDSN MIATSFPEFM DMMPGLGAKI ELSIL...
LBAA                EKPVTVDDSN MIATSFPEFM DMMPGLGAKI ELSIL...
Agrobacterium CP4   ENPVTVDDAT MIATSFPEFM DLMAGLGAKI ELSDTKAA
B. subtilis         EEPIEIEHTD AIHVSYPTFF EHLNKLSKKS ........
S. aureus           SEPVKIKQFD AVNVSFPGFL PKLKLLQNEG ........
S. cerevisiae       ANPVRILERH CTGKTWPGWW DVLH...... ........
A. nidulans         ..PTLILEKE CVGKTWPGWW DTLRQLFKV. ........
B. napus            DVPVTIKDPG CTRKTFPDYF QVLESITKH. ........
A. thaliana         DVPITINDSG CTRKTFPDYF QVLERITKH. ........
N. tabacum          DVPVTIKDPG CTRKTFPNYF DVLQQYSKH. ........
L. esculentum       DVPVTIKNPG CTRKTFPDYF EVLQKYSKH. ........
P. hybrida          DVPVTINDPG CTRKTFPNYF DVLQQYSKH. ........
Z. mays             EVPVTIRDPG CTRKTFPDYF DVLSTFVKN. ........
S. gallinarum       DTPVTILDPK CTAKTFPDYF EQLARMSTPA ........
S. typhimurium      DTPVTILDPK CTAKTFPDYF EQLARMSTPA ........
S. typhi            DTPVTILDPK CTAKTFPDYF EQLARMSTPA ........
E. coli             DTPVTILDPK CTAKTFPDYF EQLARISQAA ........
K. pneumoniae       DTPVTILDPK CTAKTFPDYF GQLARISTLA ........
Y. entoercolitica   DTPVTILDPK CTAKTFPDYF EQLARLSQIA ........
H. influenzae       NTPVTILDPK CTAKTFPTFF NEFE....KI CLKN....
P. multocida        KTSVTILDPS CTAKTFPTFL ILFTLNTREV AYR.....
A. salmonicida      DIAVTINDPG CTSKTFPDYF DKLASVSQAV ........
B. pertussis        PAAVRILDPG CVSKTFPDYF DVYAGLLAAR D.......
Consensus           ---------- ------P--- ---------- --------
```

Figure 20K

```
ACGGGCTGTA ACGGTAGTAG GGGTCCCGAG CACAAAAGCG GTGCCGGCAA GCAGAACTAA      60

TTTCCATGGG GAATAATGGT ATTTCATTGG TTTGGCCTCT GGTCTGGCAA TGGTTGCTAG     120

GCGATCGCCT GTTGAAATTA ACAAACTGTC GCCCTTCCAC TGACCATGGT AACGATGTTT     180

TTTACTTCCT TGACTAACCG AGGAAAATTT GGCGGGGGGC AGAAATGCCA ATACAATTTA     240

GCTTGGTCTT CCCTGCCCCT AATTTGTCCC CTCC ATG GCC TTG CTT TCC CTC         292
                                      Met Ala Leu Leu Ser Leu
                                        1               5

AAC AAT CAT CAA TCC CAT CAA CGC TTA ACT GTT AAT CCC CCT GCC CAA       340
Asn Asn His Gln Ser His Gln Arg Leu Thr Val Asn Pro Pro Ala Gln
            10                  15                  20

GGG GTC GCT TTG ACT GGC CGC CTA AGG GTG CCG GGG GAT AAA TCC ATT       388
Gly Val Ala Leu Thr Gly Arg Leu Arg Val Pro Gly Asp Lys Ser Ile
        25                  30                  35

TCC CAT CGG GCC TTG ATG TTG GGG GCG ATC GCC ACC GGG GAA ACC ATT       436
Ser His Arg Ala Leu Met Leu Gly Ala Ile Ala Thr Gly Glu Thr Ile
    40                  45                  50

ATC GAA GGG CTA CTG TTG GGG GAA GAT CCC CGT AGT ACG GCC CAT TGC       484
Ile Glu Gly Leu Leu Leu Gly Glu Asp Pro Arg Ser Thr Ala His Cys
55                  60                  65                  70
```

Figure 21A

```
TTT CGG GCC ATG GGA GCA GAA ATC AGC GAA CTA AAT TCA GAA AAA ATC      532
Phe Arg Ala Met Gly Ala Glu Ile Ser Glu Leu Asn Ser Glu Lys Ile
                 75                  80                  85

ATC GTT CAG GGT CGG GGT CTG GGA CAG TTG CAG GAA CCC AGT ACC GTT      580
Ile Val Gln Gly Arg Gly Leu Gly Gln Leu Gln Glu Pro Ser Thr Val
            90                  95                 100

TTG GAT GCG GGG AAC TCT GGC ACC ACC ATG CGC TTA ATG TTG GGC TTG      628
Leu Asp Ala Gly Asn Ser Gly Thr Thr Met Arg Leu Met Leu Gly Leu
        105                 110                 115

CTA GCC GGG CAA AAA GAT TGT TTA TTC ACC GTC ACC GGC GAT GAT TCC      676
Leu Ala Gly Gln Lys Asp Cys Leu Phe Thr Val Thr Gly Asp Asp Ser
    120                 125                 130

CTC CGT CAC CGC CCC ATG TCC CGG GTA ATT CAA CCC TTG CAA CAA ATG      724
Leu Arg His Arg Pro Met Ser Arg Val Ile Gln Pro Leu Gln Gln Met
135                 140                 145                 150

GGG GCA AAA ATT TGG GCC CGG AGT AAC GGC AAG TTT GCG CCG CTG GCA      772
Gly Ala Lys Ile Trp Ala Arg Ser Asn Gly Lys Phe Ala Pro Leu Ala
                155                 160                 165

GTC CAG GGT AGC CAA TTA AAA CCG ATC CAT TAC CAT TCC CCC ATT GCT      820
Val Gln Gly Ser Gln Leu Lys Pro Ile His Tyr His Ser Pro Ile Ala
            170                 175                 180
```

Figure 21B

```
TCA GCC CAG GTA AAG TCC TGC CTG TTG CTA GCG GGG TTA ACC ACC GAG      868
Ser Ala Gln Val Lys Ser Cys Leu Leu Leu Ala Gly Leu Thr Thr Glu
        185                 190                 195

GGG GAC ACC ACG GTT ACA GAA CCA GCT CTA TCC CGG GAT CAT AGC GAA      916
Gly Asp Thr Thr Val Thr Glu Pro Ala Leu Ser Arg Asp His Ser Glu
    200                 205                 210

CGC ATG TTG CAG GCC TTT GGA GCC AAA TTA ACC ATT GAT CCA GTA ACC      964
Arg Met Leu Gln Ala Phe Gly Ala Lys Leu Thr Ile Asp Pro Val Thr
215                 220                 225                 230

CAT AGC GTC ACT GTC CAT GGC CCG GCC CAT TTA ACG GGG CAA CGG GTG     1012
His Ser Val Thr Val His Gly Pro Ala His Leu Thr Gly Gln Arg Val
                235                 240                 245

GTG GTG CCA GGG GAC ATC AGC TCG GCG GCC TTT TGG TTA GTG GCG GCA     1060
Val Val Pro Gly Asp Ile Ser Ser Ala Ala Phe Trp Leu Val Ala Ala
            250                 255                 260

TCC ATT TTG CCT GGA TCA GAA TTG TTG GTG GAA AAT GTA GGC ATT AAC     1108
Ser Ile Leu Pro Gly Ser Glu Leu Leu Val Glu Asn Val Gly Ile Asn
        265                 270                 275

CCC ACC AGG ACA GGG GTG TTG GAA GTG TTG GCC CAG ATG GGG GCG GAC     1156
Pro Thr Arg Thr Gly Val Leu Glu Val Leu Ala Gln Met Gly Ala Asp
    280                 285                 290
```

Figure 21C

```
ATT ACC CCG GAG AAT GAA CGA TTG GTA ACG GGG GAA CCG GTA GCA GAT      1204
Ile Thr Pro Glu Asn Glu Arg Leu Val Thr Gly Glu Pro Val Ala Asp
295                 300                 305                 310

CTG CGG GTT AGG GCA AGC CAT CTC CAG GGT TGC ACC TTC GGC GGC GAA      1252
Leu Arg Val Arg Ala Ser His Leu Gln Gly Cys Thr Phe Gly Gly Glu
                315                 320                 325

ATT ATT CCC CGA CTG ATT GAT GAA ATT CCC ATT TTG GCA GTG GCG GCG      1300
Ile Ile Pro Arg Leu Ile Asp Glu Ile Pro Ile Leu Ala Val Ala Ala
            330                 335                 340

GCC TTT GCA GAG GGC ACT ACC CGC ATT GAA GAT GCC GCA GAA CTG AGG      1348
Ala Phe Ala Glu Gly Thr Thr Arg Ile Glu Asp Ala Ala Glu Leu Arg
        345                 350                 355

GTT AAA GAA AGC GAT CGC CTG GCG GCC ATT GCT TCG GAG TTG GGC AAA      1396
Val Lys Glu Ser Asp Arg Leu Ala Ala Ile Ala Ser Glu Leu Gly Lys
    360                 365                 370

ATG GGG GCC AAA GTC ACC GAA TTT GAT GAT GGC CTG GAA ATT CAA GGG      1444
Met Gly Ala Lys Val Thr Glu Phe Asp Asp Gly Leu Glu Ile Gln Gly
375                 380                 385                 390

GGA AGC CCG TTA CAA GGG GCC GAG GTG GAT AGC TTG ACG GAT CAT CGC      1492
Gly Ser Pro Leu Gln Gly Ala Glu Val Asp Ser Leu Thr Asp His Arg
                395                 400                 405
```

Figure 21D

```
ATT GCC ATG GCG TTG GCG ATC GCC GCT TTA GGT AGT GGG GGG CAA ACA      1540
Ile Ala Met Ala Leu Ala Ile Ala Ala Leu Gly Ser Gly Gly Gln Thr
            410                 415                 420

ATT ATT AAC CGG GCG GAA GCG GCC GCC ATT TCC TAT CCA GAA TTT TTT      1588
Ile Ile Asn Arg Ala Glu Ala Ala Ala Ile Ser Tyr Pro Glu Phe Phe
        425                 430                 435

GGC ACG CTA GGG CAA GTT GCC CAA GGA TAAAGTTAGA AAAACTCCTG            1635
Gly Thr Leu Gly Gln Val Ala Gln Gly
    440                 445

GGCGGTTTGT AAATGTTTTA CCAAGGTAGT TTGGGGTAAA GGCCCCAGCA AGTGCTGCCA    1695

GGGTAATTTA TCCGCAATTG ACCAATCGGC ATGGACCGTA TCGTTCAAAC TGGGTAATTC    1755

TCCCTTTAAT TCCTTAAAAG CTCGCTTAAA ACTGCCCAAC GTATCTCCGT AATGGCGAGT    1815

GAGTAGAAGT AATGGGGCCA AACGGCGATC GCCACGGGAA ATTAAAGCCT GCATCACTGA    1875

CCACTTATAA CTTTCGGGA                                                 1894
```

Figure 21E

```
TTTAAAAACA ATGAGTTAAA AAATTATTTT TCTGGCACAC GCGCTTTTTT TGCATTTTTT      60

CTCCCATTTT TCCGGCACAA TAACGTTGGT TTTATAAAAG GAAATG ATG ATG ACG        115
                                                   Met Met Thr
                                                     1

AAT ATA TGG CAC ACC GCG CCC GTC TCT GCG CTT TCC GGC GAA ATA ACG        163
Asn Ile Trp His Thr Ala Pro Val Ser Ala Leu Ser Gly Glu Ile Thr
     5                  10                  15

ATA TGC GGC GAT AAA TCA ATG TCG CAT CGC GCC TTA TTA TTA GCA GCG        211
Ile Cys Gly Asp Lys Ser Met Ser His Arg Ala Leu Leu Leu Ala Ala
 20                  25                  30                  35

TTA GCA GAA GGA CAA ACG GAA ATC CGC GGC TTT TTA GCG TGC GCG GAT        259
Leu Ala Glu Gly Gln Thr Glu Ile Arg Gly Phe Leu Ala Cys Ala Asp
                 40                  45                  50

TGT TTG GCG ACG CGG CAA GCA TTG CGC GCA TTA GGC GTT GAT ATT CAA        307
Cys Leu Ala Thr Arg Gln Ala Leu Arg Ala Leu Gly Val Asp Ile Gln
             55                  60                  65

AGA GAA AAA GAA ATA GTG ACG ATT CGC GGT GTG GGA TTT CTG GGT TTG        355
Arg Glu Lys Glu Ile Val Thr Ile Arg Gly Val Gly Phe Leu Gly Leu
         70                  75                  80
```

Figure 22A

```
CAG CCG CCG AAA GCA CCG TTA AAT ATG CAA AAC AGT GGC ACT AGC ATG      403
Gln Pro Pro Lys Ala Pro Leu Asn Met Gln Asn Ser Gly Thr Ser Met
     85                  90                  95

CGT TTA TTG GCA GGA ATT TTG GCA GCG CAG CGC TTT GAG AGC GTG TTA      451
Arg Leu Leu Ala Gly Ile Leu Ala Ala Gln Arg Phe Glu Ser Val Leu
100                 105                 110                 115

TGC GGC GAT GAA TCA TTA GAA AAA CGT CCG ATG CAG CGC ATT ATT ACG      499
Cys Gly Asp Glu Ser Leu Glu Lys Arg Pro Met Gln Arg Ile Ile Thr
                120                 125                 130

CCG CTT GTG CAA ATG GGG GCA AAA ATT GTC AGT CAC AGC AAT TTT ACG      547
Pro Leu Val Gln Met Gly Ala Lys Ile Val Ser His Ser Asn Phe Thr
            135                 140                 145

GCG CCG TTA CAT ATT TCA GGA CGC CCG CTG ACC GGC ATT GAT TAC GCG      595
Ala Pro Leu His Ile Ser Gly Arg Pro Leu Thr Gly Ile Asp Tyr Ala
        150                 155                 160

TTA CCG CTT CCC AGC GCG CAA TTA AAA AGT TGC CTT ATT TTG GCA GGA      643
Leu Pro Leu Pro Ser Ala Gln Leu Lys Ser Cys Leu Ile Leu Ala Gly
    165                 170                 175

TTA TTG GCT GAC GGT ACC ACG CGG CTG CAT ACT TGC GGC ATC AGT CGC      691
Leu Leu Ala Asp Gly Thr Thr Arg Leu His Thr Cys Gly Ile Ser Arg
180                 185                 190                 195
```

Figure 22B

```
GAC CAC ACG GAA CGC ATG TTG CCG CTT TTT GGT GGC GCA CTT GAG ATC      739
Asp His Thr Glu Arg Met Leu Pro Leu Phe Gly Gly Ala Leu Glu Ile
                200                 205                 210

AAG AAA GAG CAA ATA ATC GTC ACC GGT GGA CAA AAA TTG CAC GGT TGC      787
Lys Lys Glu Gln Ile Ile Val Thr Gly Gly Gln Lys Leu His Gly Cys
            215                 220                 225

GTG CTT GAT ATT GTC GGC GAT TTG TCG GCG GCG GCG TTT TTT ATG GTT      835
Val Leu Asp Ile Val Gly Asp Leu Ser Ala Ala Ala Phe Phe Met Val
        230                 235                 240

GCG GCT TTG ATT GCG CCG CGC GCG GAA GTC GTT ATT CGT AAT GTC GGC      883
Ala Ala Leu Ile Ala Pro Arg Ala Glu Val Val Ile Arg Asn Val Gly
    245                 250                 255

ATT AAT CCG ACG CGG GCG GCA ATC ATT ACT TTG TTG CAA AAA ATG GGC      931
Ile Asn Pro Thr Arg Ala Ala Ile Ile Thr Leu Leu Gln Lys Met Gly
260                 265                 270                 275

GGA CGG ATT GAA TTG CAT CAT CAG CGC TTT TGG GGC GCC GAA CCG GTG      979
Gly Arg Ile Glu Leu His His Gln Arg Phe Trp Gly Ala Glu Pro Val
                280                 285                 290

GCA GAT ATT GTT GTT TAT CAT TCA AAA TTG CGC GGC ATT ACG GTG GCG     1027
Ala Asp Ile Val Val Tyr His Ser Lys Leu Arg Gly Ile Thr Val Ala
            295                 300                 305
```

Figure 22C

```
CCG GAA TGG ATT GCC AAC GCG ATT GAT GAA TTG CCG ATT TTT TTT ATT      1075
Pro Glu Trp Ile Ala Asn Ala Ile Asp Glu Leu Pro Ile Phe Phe Ile
        310                 315                 320

GCG GCA GCT TGC GCG GAA GGG ACG ACT TTT GTG GGC AAT TTG TCA GAA      1123
Ala Ala Ala Cys Ala Glu Gly Thr Thr Phe Val Gly Asn Leu Ser Glu
    325                 330                 335

TTG CGT GTG AAA GAA TCG GAT CGT TTA GCG GCG ATG GCG CAA AAT TTA      1171
Leu Arg Val Lys Glu Ser Asp Arg Leu Ala Ala Met Ala Gln Asn Leu
340                 345                 350                 355

CAA ACT TTG GGC GTG GCG TGC GAC GTT GGC GCC GAT TTT ATT CAT ATA      1219
Gln Thr Leu Gly Val Ala Cys Asp Val Gly Ala Asp Phe Ile His Ile
                360                 365                 370

TAT GGA AGA AGC GAT CGG CAA TTT TTA CCG GCG CGG GTG AAC AGT TTT      1267
Tyr Gly Arg Ser Asp Arg Gln Phe Leu Pro Ala Arg Val Asn Ser Phe
            375                 380                 385

GGC GAT CAT CGG ATT GCG ATG AGT TTG GCG GTG GCA GGT GTG CGC GCG      1315
Gly Asp His Arg Ile Ala Met Ser Leu Ala Val Ala Gly Val Arg Ala
        390                 395                 400

GCA GGT GAA TTA TTG ATT GAT GAC GGC GCG GTG GCG GCG GTT TCT ATG      1363
Ala Gly Glu Leu Leu Ile Asp Asp Gly Ala Val Ala Ala Val Ser Met
    405                 410                 415
```

Figure 22D

```
CCG CAA TTT CGC GAT TTT GCC GCC GCA ATT GGT ATG AAT GTA GGA GAA      1411
Pro Gln Phe Arg Asp Phe Ala Ala Ala Ile Gly Met Asn Val Gly Glu
420                 425                 430                 435

AAA GAT GCG AAA AAT TGT CAC GAT TGATGGTCCT AGCGGTGTTG GAAAAGGCAC    1465
Lys Asp Ala Lys Asn Cys His Asp
                440

GGTGGCGCAA GCTT                                                      1479
```

Figure 22E

```
                          1                                        40
PG2982                    ........MS HSASPKPATA RRSEALTGEI RIPGDKSISH
LBAA                      ........MS HSASPKPATA RRSEALTGEI RIPGDKSISH
Agrobacterium CP4         ........MS HGASSRPATA RKSSGLSGTV RIPGDKSISH
Synechocystis sp. PCC6803 MALLSLNNHQ SHQRLTVNPP AQGVALTGRL RVPGDKSISH
B. subtilis               .......... .......MKR DKVQTLHGEI HIPGDKSISH
D. nodosus                .......... ..MMTNIWHT APVSALSGEI TICGDKSMSH
S. aureus                 .......... ...MVNEQII DISGPLKGEI EVPGDKSMTH
Consensus                 ---------- ---------- -----L-G-- -I-GDKS--H
                          41                                       80
PG2982                    RSFMFGGLAS GETRITGLLE GEDVINTGRA MQAMGAKI.R
LBAA                      RSFMFGGLAS GETRITGLLE GEDVINTGRA MQAMGAKI.R
Agrobacterium CP4         RSFMFGGLAS GETRITGLLE GEDVINTGKA MQAMGARI.R
Synechocystis sp. PCC6803 RALMLGAIAT GETIIEGLLL GEDPRSTAHC FRAMGAEISE
B. subtilis               RSVMFGALAA GTTTVKNFLP GADCLSTIDC FRKMGVHI.E
D. nodosus                RALLLAALAE GQTEIRGFLA CADCLATRQA LRALGVDI.Q
S. aureus                 RAIMLASLAE GVSTIYKPLL GEDCRRTMDI FRHLGVEI.K
Consensus                 R--MF---A- G---I---L- --D---T--- ---MG--I--
                          81                                      120
PG2982                    KEGDVWIING VGNGCLLQPE AALDFGNAGT GARLTMGLVG
LBAA                      KEGDVWIING VGNGCLLQPE AALDFGNAGT GARLTMGLVG
Agrobacterium CP4         KEGDTWIIDG VGNGGLLAPE APLDFGNAAT GCRLTMGLVG
Synechocystis sp. PCC6803 LNSEKIIVQG RGLGQLQEPS TVLDAGNSGT TMRLMLGLLA
B. subtilis               QSSSDVVIHG KGIDALKEPE SLLDVGNSGT TIRLMLGILA
D. nodosus                REKEIVTIRG VGFLGLQPPK APLNMQNSGT SMRLLAGILA
S. aureus                 EDDEKLVVTS PGYQ.VNTPH QVLYTGNSGT TTRLLAGLLS
Consensus                 -------I-- -G------P- --L---N--T --RL--G---
```

Figure 23A

```
                          121                                        160
                PG2982    TY.DMKTSFI GDASLSKRPM GRVLNPLREM GVQVEAADGD
                  LBAA    TY.DMKTSFI GDASLSKRPM GRVLNPLREM GVQVEAADGD
     Agrobacterium CP4    VY.DFDSTFI GDASLTKRPM GRVLNPLREM GVQVKSEDGD
Synechocystis sp. PCC6803 GQKDCLFTVT GDDSLRHRPM SRVIQPLQQM GAKIWARSNG
           B. subtilis    G.RPFYSAVA GDESIAKRPM KRVTEPLKKM GAKIDGRAGG
            D. nodosus    AQR.FESVLC GDESLEKRPM QRIITPLVQM GAKIVSHSNF
             S. aureus    GLGN.ESVLS GDVSIGKRPM DRVLRPLKLM DANIEGIEDN
             Consensus    ---------- GD-S---RPM -RV--PL--M ---I------
                          161                                        200
                PG2982    RMPLTLIGPK TANPITYRVP MASAQVKSAV LLAGLNTPGV
                  LBAA    RMPLTLIGPK TANPITYRVP MASAQVKSAV LLAGLNTPGV
     Agrobacterium CP4    RLPVTLRGPK TPTPITYRVP MASAQVKSAV LLAGLNTPGI
Synechocystis sp. PCC6803 KFAPLAVQGS QLKPIHYHSP IASAQVKSCL LLAGLTTEGD
           B. subtilis    EFTPLSVSGA SLKGIDYVSP VASAQIKSAV LLAGLQAEGT
            D. nodosus    T.APLHISGR PLTGIDYALP LPSAQLKSCL ILAGLLADGT
             S. aureus    .YTPLIIKPS VIKGINYQME VASAQVKSAI LFASLFSKEP
             Consensus    ---------- ----I-Y--- --SAQ-KS-- -LA-L-----
                          201                                        240
                PG2982    TTVIEPVMTR DHTEKMLQGF .....GADLT VETDKDGVRH
                  LBAA    TTVIEPVMTR DHTEKMLQGF .....GADLT VETDKDGVRH
     Agrobacterium CP4    TTVIEPIMTR DHTEKMLQGF .....GANLT VETDADGVRT
Synechocystis sp. PCC6803 TTVTEPALSR DHSERMLQAF .....GAKLT IDPVTHSV..
           B. subtilis    TTVTEPHKSR DHTERMLSAF .....GVKLS EDQT..SV..
            D. nodosus    TRLHTCGISR DHTERMLPLF .....GGALE IKK..EQI..
             S. aureus    TIIKELDVSR NHTETMFKHF NIPIEAEGLS INTTPEAIRY
             Consensus    T--------R -H-E-ML--F --------L- -------V--
```

Figure 23B

```
                          241                                       280
                PG2982    IRITGQGKLV GQTIDVPGDP SSTAFPLVAA LLVEGSDVTI
                  LBAA    IRITGQGKLV GQTIDVPGDP SSTAFPLVAA LLVEGSDVTI
     Agrobacterium CP4    IRLEGRGKLT GQVIDVPGDP SSTAFPLVAA LLVPGSDVTI
Synechocystis sp. PCC6803 .TVHGPAHLT GQRVVVPGDI SSAAFWLVAA SILPGSELLV
            B. subtilis   .SIAGGQKLT AADIFVPGDI SSAAFFLAAG AMVPNSRIVL
             D. nodosus   .IVTGGQKLH GCVLDIVGDL SAAAFFMVAA LIAPRAEVVI
              S. aureus   IKPAD..... ...FHVPGDI SSAAFFIVAA LITPGSDVTI
              Consensus   ---------- -----V-GD- S--AF---A- ----------
                          281                                       320
                PG2982    RNVLMNPTRT GLILTLQEMG ADIEVLNARL AGGEDVADLR
                  LBAA    RNVLMNPTRT GLILTLQEMG ADIEVLNARL AGGEDVADLR
     Agrobacterium CP4    LNVLMNPTRT GLILTLQEMG ADIEVINPRL AGGEDVADLR
Synechocystis sp. PCC6803 ENVGINPTRT GVLEVLAQMG ADITPENERL VTGEPVADLR
            B. subtilis   KNVGLNPTRT GIIDVLQNMG AKLEIKPSAD SGAEPYGDLI
             D. nodosus   RNVGINPTRA AIITLLQKMG GRIELHHQRF WGAEPVADIV
              S. aureus   HNVGINQTRS GIIDIVEKMG GNIQLFNQT. TGAEPTASIR
              Consensus   -NV--N-TR- --------MG ---------- ---E------
                          321                                       360
                PG2982    VR.ASKLKGV VVPPERAPSM IDEYPVLAIA ASFAEGETVM
                  LBAA    VR.ASKLKGV VVPPERAPSM IDEYPVLAIA ASFAEGETVM
     Agrobacterium CP4    VR.SSTLKGV TVPEDRAPSM IDEYPILAVA AAFAEGATVM
Synechocystis sp. PCC6803 VR.ASHLQGC TFGGEIIPRL IDEIPILAVA AAFAEGTTRI
            B. subtilis   IE.TSSLKAV EIGGDIIPRL IDEIPIIALL ATQAEGTTVI
             D. nodosus   VY.HSKLRGI TVAPEWIANA IDELPIFFIA AACAEGTTFV
              S. aureus   IQYTPMLQPI TIEGELVPKA IDELPVIALL CTQAVGTSTI
              Consensus   V-----L--- ----E----- IDE-PI---- ---A-G----
```

Figure 23C

```
                          361                                        400
PG2982                    DGLDELRVKE SDRLAAVARG LEANGVDCTE GEMSLTVRGR
LBAA                      DGLDELRVKE SDRLAAVARG LEANGVDCTE GEMSLTVRGR
Agrobacterium CP4         NGLEELRVKE SDRLSAVANG LKLNGVDCDE GETSLVVRGR
Synechocystis sp. PCC6803 EDAAELRVKE SDRLAAIASE LGKMGAKVTE FDDGLEIQGG
B. subtilis               KDAAELKVKE TNRIDTVVSE LRKLGAEIEP TADGMKVYGK
D. nodosus                GNLSELRVKE SDRLAAMAQN LQTLGVACDV GADFIHIYGR
S. aureus                 KDAEELKVKE TNRIDTTADM LNLLGFELQP TNDGLIIHPS
Consensus                 ----EL-VKE --R------- L---G----- ------V---
                          401                                        440
PG2982                    PDGKGLG... GGTVATHLDH RIAMSFLVMG LAAEKPVTVD
LBAA                      PDGKGLG... GGTVATHLDH RIAMSFLVMG LAAEKPVTVD
Agrobacterium CP4         PDGKGLGNAS GAAVATHLDH RIAMSFLVMG LVSENPVTVD
Synechocystis sp. PCC6803 SPLQ...... GAEVDSLTDH RIAMALAIAA LGSGGQTIIN
B. subtilis               QTLK.G.... GAAVSSHGDH RIGMMLGIAS CITEEPIEIE
D. nodosus                SDRQFL.... PARVNSFGDH RIAMSLAVAG VRAAGELLID
S. aureus                 E.......FK TNATDILTDH RIGMMLAVAC VLSSEPVKIK
Consensus                 ---------- --------DH RI-M-L-V-- --------I-
                          441                                 473
PG2982                    DSNMIATSFP EFMDMMPGLG AKIELSIL.. ...
LBAA                      DSNMIATSFP EFMDMMPGLG AKIELSIL.. ...
Agrobacterium CP4         DATMIATSFP EFMDLMAGLG AKIELSDTKA A..
Synechocystis sp. PCC6803 RAEAAAISYP EFFGTLGQVA QG*....... ...
B. subtilis               HTDAIHVSYP TFFEHLNKLS KKS....... ...
D. nodosus                DGAVAAVSMP QFRDFAAAIG MNVGEKDAKN CHD
S. aureus                 QFDAVNVSFP GFLPKLKLLQ NEG....... ...
Consensus                 -------S-P -F-------- ---------- ---
```

Figure 23D

GLYPHOSATE-TOLERANT 5-ENOLPYRUVYLSHIKIMATE-3-PHOSPHATE SYNTHASES

Matter enclosed in heavy brackets [ ] appears in the original patent but forms no part of this reissue specification; matter printed in italics indicates the additions made by reissue.

This is a continuation-in-part of a U.S. patent application Ser. No. 07/749,611, filed Aug. 28, 1991 now abandoned, which is a continuation-in-part of U.S. patent application Ser. No. 07/576,537, filed Aug. 31, 1990, now abandoned.

BACKGROUND OF THE INVENTION

This invention relates in general to plant molecular biology and, more particularly, to a new class of glyphosate-tolerant 5-enolpyruvylshikimate-3-phosphate synthases.

Recent advances in genetic engineering have provided the requisite tools to transform plants to contain foreign genes. It is now possible to produce plants which have unique characteristics of agronomic importance. Certainly, one such advantageous trait is more cost effective, environmentally compatible weed control via herbicide tolerance. Herbicide-tolerant plants may reduce the need for tillage to control weeds thereby effectively reducing soil erosion.

One herbicide which is the subject of much investigation in this regard is N-phosphonomethylglycine commonly referred to as glyphosate. Glyphosate inhibits the shikimic acid pathway which leads to the biosynthesis of aromatic compounds including amino acids, plant hormones and vitamins. Specifically, glyphosate curbs the conversion of phosphoenolpyruvic acid (PEP) and 3-phosphoshikimic acid to 5-enolpyruvyl-3-phosphoshikimic acid by inhibiting the enzyme 5-enolpyruvylshikimate-3-phosphate synthase (hereinafter referred to as EPSP synthase or EPSPS). For purposes of the present invention, the term "glyphosate" should be considered to include any herbicidally effective form of N-phosphonomethylglycine (including any salt thereof) and other forms which result in the production of the glyphosate anion in plants.

It has been shown that glyphosate-tolerant plants can be produced by inserting into the genome of the plant the capacity to produce a higher level of EPSP synthase in the chloroplast of the cell (Shah et al., 1986) which enzyme is preferably glyphosate-tolerant (Kishore et al. 1988). Variants of the wild-type EPSPS enzyme have been isolated which are glyphosate-tolerant as a result of alterations in the EPSPS amino acid coding sequence (Kishore and Shah, 1988; Schulz et al., 1984; Sost et al., 1984; Kishore et al., 1986). These variants typically have a higher $K_i$ for glyphosate than the wild-type EPSPS enzyme which confers the glyphosate-tolerant phenotype, but these variants are also characterized by a high $K_m$ for PEP which makes the enzyme kinetically less efficient (Kishore and Shah, 1988; Sost et al., 1984; Schulz et al., 1984; Kishore et al., 1986; Sost and Amrhein, 1990). For example, the apparent $K_m$ for PEP and the apparent $K_i$ for glyphosate for the native EPSPS from E. coli are 10 μM and 0.5 μM while for a glyphosate-tolerant isolate having a single amino acid substitution of an alanine for the glycine at position 96 these values are 220 μM and 4.0 mM, respectively. A number of glyphosate-tolerant plant variant EPSPS genes have been constructed by mutagenesis. Again, the glyphosate-tolerant EPSPS was impaired due to an increase in the $K_m$ for PEP and a slight reduction of the $V_{max}$ of the native plant enzyme (Kishore and Shah, 1988) thereby lowering the catalytic efficiency ($V_{max}/K_m$) of the enzyme. Since the kinetic constants of the variant enzymes are impaired with respect to PEP, it has been proposed that high levels of overproduction of the variant enzyme, 40–80 fold, would be required to maintain normal catalytic activity in plants in the presence of glyphosate (Kishore et al., 1988).

While such variant EPSP synthases have proved useful in obtaining transgenic plants tolerant to glyphospate, it would be increasingly beneficial to obtain an EPSP synthase that is highly glyphosate-tolerant while still kinetically efficient such that the amount of the glyphosate-tolerant EPSPS needed to be produced to maintain normal catalytic activity in the plant is reduced or that improved tolerance be obtained with the same expression level.

Previous studies have shown that EPSPS enzymes from different sources vary widely with respect to their degree of sensitivity to inhibition by glyphosate. A study of plant and bacterial EPSPS enzyme activity as a function of glyphosate concentration showed that there was a very wide range in the degree of sensitivity to glyphosate. The degree of sensitivity showed no correlation with any genus or species tested (Schulz et al., 1985). Insensitivity to glyphosate inhibition of the activity of the EPSPS from the Pseudomonas sp. PG2982 has also been reported but with no details of the studies (Fitzgibbon, 1988). In general, while such natural tolerance has been reported, there is no report suggesting the kinetic superiority of the naturally occurring bacterial phosphosate-tolerant EPSPS enzymes over those of mutated EPSPS enzymes nor have any of the genes been characterized. Similarly, there are no reports on the expression of naturally glyphosate-tolerant EPSPS enzymes in plants to confer glyphosate tolerance.

For purposes of the present invention the term "mature EPSP synthase" relates to the EPSPS polypeptide without the N-terminal chloroplast transit peptide. It is now known that the precursor form of the EPSP synthase in plants (with the transit peptide) is expressed and upon delivery to the chloroplast, the transit peptide is cleaved yielding the mature EPSP synthase. All numbering of amino acid positions are given with respect to the mature EPSP synthase (without chloroplast transit peptide leader) to facilitate comparison of EPSPS sequences from sources which have chloroplast transit peptides (i.e., plants and fungi) to sources which do not utilize a chloroplast targeting signal (i.e., bacteria).

In the amino acid sequences which follow, the standard single letter or three letter nomenclature are used. All peptide structures represented in the following description are shown in conventional format in which the amino group at the N-terminus appears to the left and the carboxyl group at the C-terminus at the right. Likewise, amino acid nomenclature for the naturally occurring amino acids found in protein is as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His;H), isoleucine (Ile;I), leucine (Leu;L), lysine (Lys;k), methionine (Met;M), phenylalanine (Phe;F), proline (Pro;P), serine (Ser;S), threonine (Thr;T), tryptophan (Trp;W), tyrosine (Tyr;Y), and valine (Val;V). An "X" is used when the amino acid residue is unknown and parentheses designate that an unambiguous assignment is not possible and the amino acid designation within the parentheses is the most probable estimate based on known information.

The term "nonpolar" amino acids include alanine, valine, leucine, isoleucine, proline, phenylalanine, tryptophan, and methionine. The term "uncharged polar" amino acids include glycine, serine, threonine, cysteine, tyrosine, asparagine and glutamine. The term "charged polar" amino acids includes the "acidic" and "basic" amino acids. The term "acidic" amino acids includes aspartic acid and glutamic acid. The term "basic" amino acid includes lysine, arginine and histidine. The term "polar" amino acids includes both "charged polar" and "uncharged polar" amino acids.

Deoxyribonucleic acid (DNA) is a polymer comprising four mononucleotide units, dAMP (2'-Deoxyadenosine-5-monophosphate), dGMP (2'-Deoxyguanosine-5-monophosphate), dCMP (2'-Deoxycytosine-5-monophosphate) and dTMP (2'-Deoxythymosine-5-monophosphate) linked in various sequences by 3',5'-phosphodiester bridges. The structural DNA consists of multiple nucleotide triplets called "codons" which code for the amino acids. The codons correspond to the various amino acids as follows: Arg (CGA, CGC, CGG, CGT, AGA, AGG); Leu (CTA, CTC, CTG, CTT, TTA, TTG); Ser (TCA, TCC, TCG, TCT, AGC, AGT); Thr (ACA, ACC, ACG, ACT); Pro (CCA, CCC, CCG, CCT); Ala (GCA, GCC, GCG, GCT); Gly (GGA, GGC, GGG, GGT); Ile (ATA, ATC, ATT); Val (GTA, GTC, GTG, GTT); Lys (AAA, AAG); Asn (AAC, AAT); Gla (CAA, CAG); His (CAC, CAT); Glu (GAA, GAG); Asp (GAC, GAT); Tyr (TAC, TAT); Cys (TGC, TGT); Phe (TTC, TTT); Met (ATG); and Trp (UGG). Moreover, due to the redundancy of the genetic code (i.e., more than one codon for all but two amino acids), there are many possible DNA sequences which may code for a particular amino acid sequence.

SUMMARY OF THE INVENTION

DNA molecules comprising DNA encoding kinetically efficient, glyphosate-tolerant EPSP synthases are disclosed. The EPSP synthases of the present invention reduce the amount of overproduction of the EPSPS enzyme in a transgenic plant necessary for the enzyme to maintain catalytic activity while still conferring glyphosate tolerance. The EPSP synthases described herein represent a new class of EPSPS enzymes, referred to hereinafter as Class II EPSPS enzymes. Class II EPSPS enzymes of the present invention usually share only between about 47% and 55% amino acid similarity or between about 22% and 30% amino acid identity to other known bacterial or plant EPSPS enzymes and exhibit tolerance to glyphosate while maintaining suitable $K_m$ (PEP) ranges. Suitable ranges of $K_m$ (PEP) for EPSPS for enzymes of the present invention are between 1–150 μM, with a more preferred range of between 1–35 μM, and a most preferred range between 2–25 μM. These kinetic constants are determined under the assay conditions specified hereinafter. An EPSPS of the present invention preferably has a $K_i$ for glyphosate range of between 15–10000 μM. The $K_i/K_m$ ratio should be between about 2–500, and more preferably between 25–500. The $V_{max}$ of the purified enzyme should preferably be in the range of 2–100 units/mg (μmoles/minute.mg at 25° C.) and the $K_m$ for shikimate-3-phosphate should preferably be in the range of 0.1 to 50 μM.

Genes coding for Class II EPSPS enzymes have been isolated from five (5) different bacteria:Agrobacterium tumefaciens sp. strain CP4, Achromobacter sp. strain LBAA, Pseudomonas sp. strain PG2982, Bacillus subtilis, and Staphylococcus aureus. The LBAA and PG2982 Class II EPSPS genes have been determined to be identical and the proteins encoded by these two genes are very similar to the CP4 protein and share approximately 84% amino acid identity with it. Class II EPSPS enzymes often may be distinguished from Class I EPSPS's by their inability to react with polyclonal antibodies prepared from Class I EPSPS enzymes under conditions where other Class I EPSPS enzymes would readily react with the Class I antibodies as well as the presence of certain unique regions of amino acid homology which are conserved in Class II EPSP synthases as discussed hereinafter.

Other Class II EPSPS enzymes can be readily isolated and identified by utilizing a nucleic acid probe from one of the Class II EPSPS genes disclosed herein using standard hybridization techniques. Such a probe from the CP4 strain has been prepared and utilized to isolate the Class II EPSPS genes from strains LBAA and PG2982. These genes may also optionally be adapted for enhanced expression in plants by known methodology. Such a probe has also been used to identify homologous genes is bacteria isolated de novo from soil.

The Class II EPSPS enzymes are preferably fused to a chloroplast transit peptide (CTP) to target the protein to the chloroplasts of the plant into which it may be introduced. Chimeric genes encoding this CTP-Class II EPSPS fusion protein may be prepared with an appropriate promoter and 3' polyadenylation site for introduction into a desired plant by standard methods.

To obtain the maximal tolerance to glyphosate herbicide it is preferable to transform the desired plant with a plant-expressible Class II EPSPS gene in conjunction with another plant-expressible gene which expresses a protein capable of degrading glyphosate such as a plant-expressible gene encoding a glyphosate oxidoreductase enzyme as described in PCT Application No. WO 92/00377, the disclosure of which is hereby incorporated by reference.

Therefore, in one aspect, the present invention provides a new class of EPSP synthases that exhibit a low $K_m$ for phosphoenolpyruvate (PEP), a high $V_{max}/K_m$ ratio, and a high $K_i$ for glyphosate such that when introduced into a plant, the plant is made glyphosate-tolerant such that the catalytic activity of the enzyme and plant metabolism are maintained in a substantially normal state. For purposes of this discussion, a highly efficient EPSPS refers to its efficiency in the presence of glyphosate.

More particularly, the present invention provides EPSPS enzymes having a $K_m$ for phosphoenolpyruvate (PEP) between 1–150 μM and a $K_i$(glyphosate)/$K_m$ (PEP) ratio between 3–500, said enzymes having the sequence domains:

-R-$X_1$-H-$X_2$-E-(SEQ ID NO:37), in which
  $X_1$ is an uncharged polar or acidic amino acid,
  $X_2$ is serine or threonine; and
-G-D-K-$X_3$-(SEQ ID NO:38), in which
  $X_3$ is serine or threonine; and
-S-A-Q-$X_4$-K-(SEQ ID NO:39), in which
  $X_4$ is any amino acid; and
-N-$X_5$-T-R-(SEQ ID NO:40), in which
  $X_5$ is any amino acid.

Exemplary Class II EPSPS enzyme sequences are disclosed from seven sources: Agrobacterium sp. strain designated CP4, Achromobacter sp. strain LBAA, Pseudomonas sp. strain PG2982, Bacillus subtilis 1A2, Staphylococcus aureus (ATCC 35556), Synechocystis sp. PCC6803 and Dichelobacter nodosus.

In another aspect of the present invention, a double-stranded DNA molecule comprising DNA encoding a Class II EPSPS enzyme is disclosed. Exemplary Class II EPSPS enzyme DNA sequences are disclosed from seven sources: Agrobacterium sp. strain designated CP4, Achromobacter sp. strain LBAA, Pseudomonas sp. strain PG2982, Bacillus subtilis 1A2, Staphylococcus aureus (ATCC 35556), Synechocystis sp. PCC6803 and Dichelobacter nodosus.

In a further aspect of the present invention, nucleic acid probes from EPSPS Class II genes are presented that are suitable for use in screening for Class II EPSPS genes in other sources by assaying for the ability of a DNA sequence from the other source to hybridize to the probe.

In yet another aspect of the present invention, a recombinant, double-stranded DNA molecule comprising in sequence:

a) a promoter which functions in plant cells to cause the production of an RNA sequence;

b) a structural DNA sequence that causes the production of an RNA sequence which encodes a Class II EPSPS enzyme having the sequence domains;

-R-$X_1$-H-$X_2$-E-(SEQ ID NO:37), in which
$X_1$ is an uncharged polar or acidic amino acid,
$X_2$ is serine or threonine; and -G-D-K-$X_3$-(SEQ ID NO:38), in which
$X_3$ is serine or threonine; and -S-A-Q-$X_4$-K-(SEQ ID NO:39), in which
$X_4$ is any amino acid; and -N-$X_5$-T-R-(SEQ ID NO:40), in which
$X_5$ is any amino acid; and c) a 3' nontranslated region which functions in plant cells to cause the addition of a stretch of polyadenyl nucleotides to the 3' end of the RNA sequence where the promoter is heterologous with respect to the structural DNA sequence and adapted to cause sufficient expression of the EPSP synthase polypeptide to enhance the glyphosate tolerance of a plant cell transformed with said DNA molecule.

In still yet another aspect of the present invention, transgenic plants and transformed plant cells are disclosed that are made glyphosate-tolerant by the introduction of the above-described plant-expressible Class II EPSPS DNA molecule into the plant's genome.

In still another aspect of the present invention, a method for selectively controlling weeds in a crop field is presented by planting crop seeds or crop plants transformed with a plant-expressible Class II EPSPS DNA molecule to confer glyphosate tolerance to the plants which allows for glyphosate containing herbicides to be applied to the crop to selectively kill the glyphosate sensitive weeds, but not the crops.

Other and further objects, advantages and aspects of the invention will become apparent from the accompanying drawing figures and the description of the invention.

BRIEF DESCRIPTION OF THE DRAWINGS

FIGS. 1A, 1B, show the DNA sequence (SEQ ID NO:1) for the full-length promoter of figwort mosaic virus (FMV35S).

FIG. 3A, 3B, 3C, 3D and 3E show the structural DNA sequence (SEQ ID NO:2) for the Class II EPSPS gene from bacterial isolate Agrobacterium sp. strain CP4 and the deduced amino acid sequence (SEQ ID NO:3).

FIG. 4A, 4B, 4C, 4D and 4E show the structural DNA sequence (SEQ ID NO:4) for the Class II EPSPS gene from the bacterial isolate Achromobacter sp. strain LBAA and the deduced amino acid sequence (SEQ ID NO:5).

FIG. 5A, 5B, 5C, 5D and 5E show the structural DNA sequence (SEQ ID NO:6) for the Class II EPSPS gene from the bacterial isolate Pseudomonas sp. strain PG2982 and the deduced amino acid sequence (SEQ ID NO:7).

FIG. 6A and 6B show the Bestfit comparison of the CP4 EPSPS amino acid sequence (SEQ ID NO:3) with that for the E. coli EPSPS (SEQ ID NO:8).

FIG. 7A and 7B show the Bestfit comparison of the CP4 EPSPS amino acid sequence (SEQ ID NO:3) with that for the LBAA EPSPS (SEQ ID NO:5).

FIG. 8A and 8B show the structural DNA sequence (SEQ ID NO:9) for the synthetic CP4 Class II EPSPS gene.

FIG. 9 shows the DNA sequence (SEQ ID NO:10) of the chloroplast transit peptide (CTP) and encoded amino acid sequence (SEQ ID NO:11) derived from the Arabidopsis thaliana EPSPS CTP and containing a SphI restriction site at the chloroplast processing site, hereinafter referred to as CTP2.

FIG. 10A and 10B show the DNA sequence (SEQ ID NO:12) of the chloroplast transit peptide and encoded amino acid sequence (SEQ ID NO:13) derived from the Arabidopsis thaliana EPSPS gene and containing an EcoRI restriction site within the mature region of the EPSPS, hereinafter referred to as CTP3.

FIG. 11 shows the DNA sequence (SEQ ID NO:14) of the chloroplast transit peptide and encoded amino acid sequence (SEQ ID NO:15) derived from the Petunia hybrida EPSPS CTP and containing a SphI restriction site at the chloroplast processing site and in which the amino acids at the processing site are changed to -Cys-Met-, hereinafter referred to as CTP4.

FIG. 12A and 12B show the DNA sequence (SEQ ID NO:16) of the chloroplast transit peptide and encoded amino acid sequence (SEQ ID NO:17) derived from the Petunia hybrida EPSPS gene with the naturally occurring EcoRI site in the mature region of the EPSPS gene, hereinafter referred to as CTP5.

FIG. 18A, 18B, 18C and 18D show the structural DNA sequence (SEQ ID NO:41) for the Class II EPSPS gene from the bacterial isolate Bacillus subtilis and the deduced amino acid sequence (SEQ ID NO:42).

FIG. 19A, 19B, 19C and 19D show the structural DNA sequence (SEQ ID NO:43) for the Class II EPSPS gene from the bacterial isolate Staphylococcus aureus and the deduced amino acid sequence (SEQ ID NO:44).

FIG. 20A, 20B, 20C, 20D, 20E, 20F, 20G, 20H, 20I, 20J and 20K show the Bestfit comparison of the representative Class II EPSPS amino acid sequences Pseudomonas sp. stain PG2982 (SEQ ID NO:7), Achromobacter sp. strain LBAA (SEQ ID NO:5), Agrobacterium sp. strain designated CP4 (SEQ ID NO:3), Bacillus subtilis (SEQ ID NO:42), and Staphylococcus aureus (SEQ ID NO:44) with that for representative Class I EPSPS amino acid sequences [Sacchromyces cerevisiae (SEQ ID NO:49), Aspergillus nidulans (SEQ ID NO:50), Brassica napus (SEQ ID NO:51), Arabidopsis thaliana (SEQ ID NO:52), Nicotina tobacum (SEQ ID NO:53), L. esculentum (SEQ ID NO:54), Petunia hybrida (SEQ ID NO:55), Zea mays (SEQ ID NO:56), Solmenella gallinarum (SEQ ID NO:57), Solmenella typhimurium (SEQ ID NO:58), Solmenella typhi (SEQ ID NO:65), E. coli (SEQ ID NO:8), K. pneumoniae (SEQ ID NO:59), Y. enterocolitica (SEQ ID NO:60), H. influenzae (SEQ ID NO:61), P. multocida (SEQ ID NO:62), Aeromonas salmonicida (SEQ ID NO:63), Bacillus pertussis (SEQ ID NO:64)] and illustrates the conserved regions among Class II EPSPS sequences which are unique to Class II EPSPS sequences. To aid in a comparison of the EPSPS sequences, only mature EPSPS sequences were compared. That is, the sequence corresponding to the chloroplast transit peptide, if present in a subject EPSPS, was removed prior to making the sequence alignment.

FIG. 21A, 21B, 21C, 21D and 21E show the structural DNA sequence (SEQ ID NO:66) for the Class II EPSPS gene from the bacterial isolate Synechocystis sp. PCC6803 and the deduced amino acid sequence (SEQ ID NO:67).

FIG. 22A, 22B, 22C, 22D and 22E show the structural DNA sequence (SEQ ID NO:68) for the Class II EPSPS gene from the bacterial isolate Dichelobacter nodosus and the deduced amino acid sequence (SEQ ID NO:69).

FIG. 23A, 23B, 23C and 23D show the Bestfit comparison of the representative Class II EPSPS amino acid sequences Pseudomonas sp. strain PG2982 (SEQ ID NO:7), Achromobacter sp. strain LBAA (SEQ ID NO:5), Agrobacterium sp. strain designated CP4 (SEQ ID NO:3), Synechocystis sp. PCC6803 (SEQ ID NO:67), Bacillus subtilis (SEQ ID NO:42), Dichelobacter nodosus (SEQ ID NO:69) and Staphylococcus aureus (SEQ ID NO:44).

STATEMENT OF THE INVENTION

Figure 2:
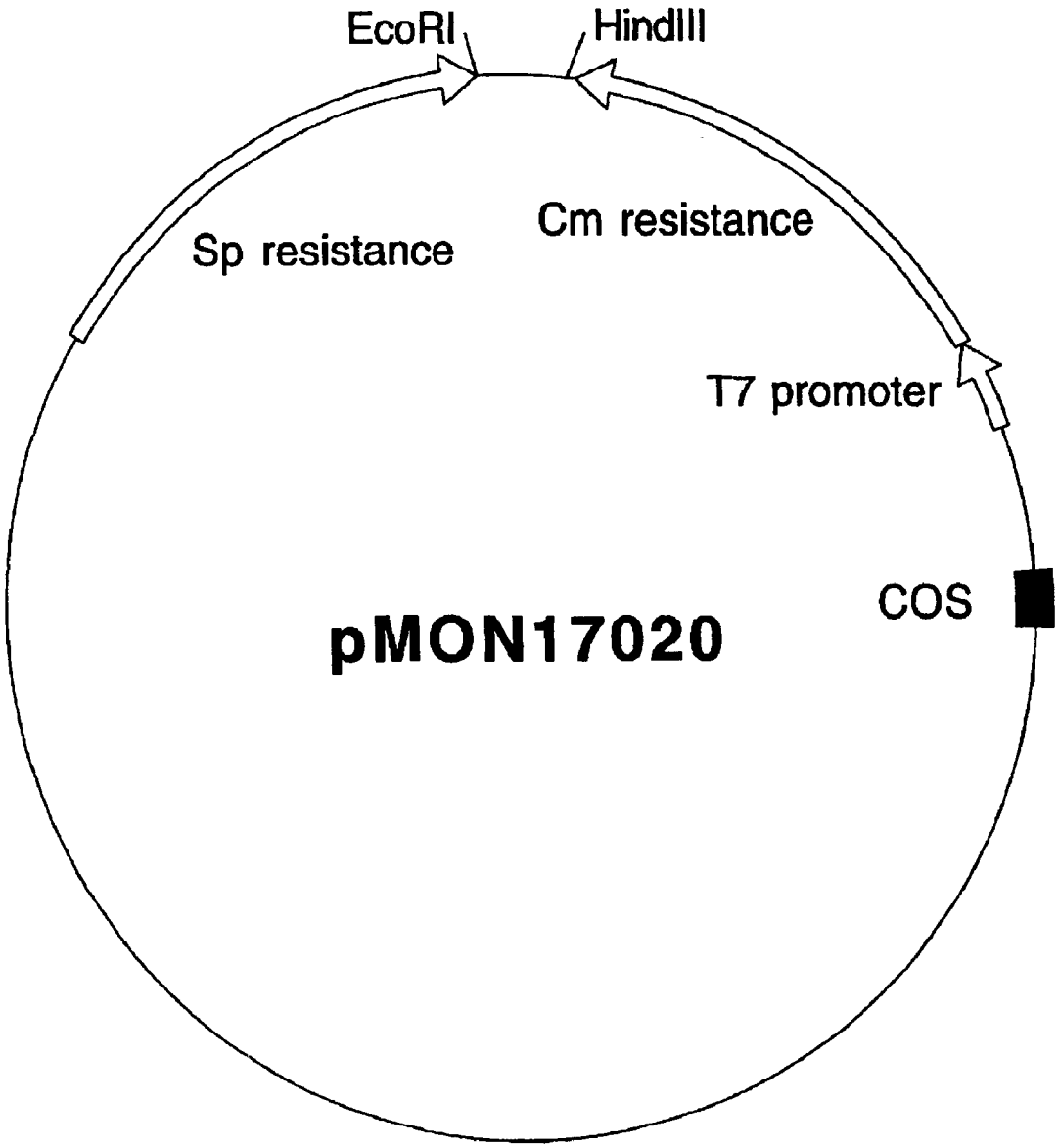
FIG. 2 shows the cosmid cloning vector pMON17020.

The expression of a plant gene which exists in double-stranded DNA form involves synthesis of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA.

Transcription of DNA into mRNA is regulated by a region of DNA usually referred to as the "promoter." The promoter region contains a sequence of bases that signals RNA polymerase to associate with the DNA, and to initiate the transcription into mRNA using one of the DNA strands as a template to make a corresponding complementary strand of RNA. A number of promoters which are active in plant cells have been described in the literature. These include the nopaline synthase (NOS) and octopine synthase (OCS) promoters (which are carried on tumor-inducing plasmids of Agrobacterium tumefaciens), the cauliflower mosaic virus (CaMV) 19S and 35S promoters, the light-inducible promoter from the small subunit of ribulose bis-phosphate carboxylase (ssRUBISCO, a very abundant plant polypeptide) and the full-length transcript promoter from the figwort mosaic virus (FMV35S), promoters from the maize ubiquitin and rice actin genes. All of these promoters have been used to create various types of DNA constructs which have been expressed in plants; see, e.g., PCT publication WO 84/02913 (Rogers et al., Mosanto).

Promoters which are known or found to cause transcription of DNA in plant cells can be used in the present invention. Such promoters may be obtained from a variety of sources such as plants and plant DNA virsues and include, but are not limited to, the CaMV35A and FMV35S promoters and promoters isolated from plant genes such as ssRUBISCO genes and the maize ubiquitin and rice actin genes. As described below, it is preferred that the particular promoter selected should be capable of causing sufficient expression to result in the production of an effective amount of a Class II EPSPS to render the plant substantially tolerant to glyphosate herbicides. The amount of Class II EPSPS needed to induce the desired tolerance may vary with the plant species. It is preferred that the promoters utilized have relatively high expression in all meristematic tissues in addition to other tissues inasmuch as it is now known that glyphosate is translocated and accumulated in this type of plant tissue. Alternatively, a combination of chimeric genes can be used to cumulatively result in the necessary overall expression level of the selected Class II EPSPS enzyme to result in the glyphosate-tolerant phenotype.

The mRNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNAs, from suitable eukaryotic genes, or from a synthetic gene sequence. The present invention is not limited to constructs, as presented in the following examples, wherein the non-translated region is derived from both the 5' non-translated sequence that accompanies the promoter sequence and part of the 5' non-translated region of the virus coat protein gene. Rather, the non-translated leader sequence can be derived from an unrelated promoter or coding sequence as discussed above.

Preferred promoters for use in the present invention the full-length transcript (SEQ ID NO:1) promoter from the figwort mosaic virus (FMV35S) and the full-length transcript (35S) promoter from cauliflower mosaic virus (CaMV), including the enhanced CaMV35S promoter (Kay et al. 1987). The FMV35S promoter functions as strong and uniform promoter with particularly good expression in meristematic tissue for chimeric genes inserted into plants, particularly dicotyledons. The resulting transgenic plant in general expresses the protein encoded by the inserted gene at a higher and more uniform level throughout the tissues and cells of the transformed plant than the same gene driven by an enhanced CaMV35S promoter. Referring to FIG. 1, the DNA sequence (SEQ ID NO:1) of the FMV35S promoter is located between nucleotides 6368 and 6930 of the FMV genome. A 5' non-translated leader sequence is preferably coupled with the promoter. The leader sequence can be from the FMV35S genome itself or can be from a source other than FMV35S.

For expression of heterologous genes in moncotyledonous plants the use of an intron has been found to enhance expression of the heterologous gene. While one may use any of a number of introns which have been isolated from plant genes, the use of the first intron from the maize heat shock 70 gene is preferred.

The 3' non-translated region of the chimeric plant gene contains a polyadenylation signal which functions in plants to cause the addition of polyadenylate nucleotides to the 3' end of the viral RNA. Examples of suitable 3' regions are (1) the 3' transcribed, non-translated regions containing the polyadenylated signal of Agrobacterium tumor-inducing (Ti) plasmid genes, such as the nopaline synthase (NOS) gene, and (2) plant genes like the soybean storage protein genes and the small subunit of the ribulose-1,5-biphosphate carboxylase (ssRUBISCO) gene. An example of a preferred 3' region is that from the ssRUBISCO gene from pea (E9), described in greater detail below.

The DNA constructs of the present invention also contain a structural coding sequence in double-stranded DNA form which encodes a glyphosate-tolerant, highly efficient Class II EPSPS enzyme.

Identification of glyphosate-tolerant, highly efficient EPSPS enzymes

In an attempt to identify and isolate glyphosate-tolerant, highly efficient EPSPS enzymes, kinetic analysis of the EPSPS enzymes from a number of bacteria exhibiting tolerance to glyphosate or that had been isolated from suitable sources was undertaken. It was discovered that in some cases the EPSPS enzymes showed no tolerance to inhibition by glyphosate and it was concluded that the tolerance phenotype of the bacterium was due to an impermeability to glyphosate or other factors. In a number of cases, however, microorganisms were identified whose EPSPS enzyme showed a greater degree of tolerance to inhibition by glyphosate and that displayed a low $K_m$ for PEP when compared to that previously reported for other microbial and plant sources. The EPSPS enzymes from these microorganisms were then subjected to further study and analysis.

Table I displays the data obtained for the EPSPS enzymes identified and isolated as a result of the above described analysis. Table I includes data for three identified Class II EPSPS enzymes that were observed to have a high tolerance to inhibition to glyphosate and a low $K_m$ for PEP as well as data for the native Petunia EPSPS and a glyphosate-tolerant variant of the Petunia EPSPS referred to as GA101. The GA101 variant is so named because it exhibits the substitution of an alanine residue for a glycine residue at position 101 (with respect to Petunia). When the change introduced into the Petunia EPSPS (GA101) was introduced into a number of other EPSPS enzymes, similar changes in a kinetics were observed, an elevation of the $K_i$ for glyphosate and of the $K_m$ for PEP.

TABLE I

Kinetic characterization of EPSPS enzymes

| ENZYME SOURCE | $K_m$ PEP (μM) | $K_I$ Glyphosate (μM) | $K_I/K_m$ |
|---|---|---|---|
| Petunia | 5 | 0.4 | 0.08 |
| Petunia GA101 | 200 | 2000 | 10 |
| PG2982 | 2.1–3.1[1] | 25–82 | ~8–40 |
| LBAA | ~7.3–8[2] | 60 (est)[7] | ~7.9 |
| CP4 | 12[3] | 2720 | 227 |
| *B. subtilis* 1A2 | 13[4] | 440 | 33.8 |
| *S. aureus* | 5[5] | 200 | 40 |

[1]Range of PEP tested = 1–40 μM
[2]Range of PEP tested = 5–80 μM
[3]Range of PEP tested = 1.5–40 μM
[4]Range of PEP tested = 1–60 μM
[5]Range of PEP tested = 1–50 μM
[7](est) = estimated The Agrobacterium sp. strain CP4 was initially identified by its ability to grow on glyphosate as a carbon source (10 mM) in the presence of 1 mM phosphate. The strain CP4 was identified from a collection obtained from a fixed-bed immobilized cell column that employed Mannville R-635 diatomaceous earth beads. The column had been run for three months on a waste-water feed from a glyphosate production plant. The column contained 50 mg/ml glyphosate and $NH_3$ as $NH_4Cl$. Total organic carbon was 300 mg/ml and BOD's (Biological Oxygen Demand—a measure of "soft" carbon availability) were less than 30 mg/ml. This treatment column has been described (Heitkamp et al., 1990). Dworkin-Foster minimal salts medium containing glyphosate at 10 mM and with phosphate at 1 mM was used to select for microbes from a wash of this column that were capable of growing on glyphosate as sole carbon source. Dworkin-Foster minimal medium was made up by combining in I liter (with autoclaved $H_2O$), 1 ml each of A, B and C and 10 ml of D (as per below) and thiamine HCl (5 mg).

| | | |
|---|---|---|
| A. | D–F Salts (1000X stock; per 100 ml; autoclaved): | |
| | $H_2BO_3$ | 1 mg |
| | $MnSO_4.7\ H_2O$ | 1 mg |
| | $ZnSO_4.7\ H_2O$ | 12.5 mg |
| | $CuSO_4.5\ H_2O$ | 8 mg |
| | $NaMoO_3.3\ H_2O$ | 1.7 mg |
| B. | $FeSO_4.7\ H_2O$ (1000X Stock; per 100 ml; autoclaved) | 0.1 g |
| C. | $MgSO_4.7\ H_2O$ (1000X Stock; per 100 ml; autoclaved) | 20 g |
| D. | $(NH_4)_2SO_4$ (100X stock; per 100 ml; autoclaved) | 20 g |

Yeast Extract (YE; Difco) was added to a final concentration of 0.01 or 0.001%. The strain CP4 was also grown on media composed of D–F salts, amended as described above, containing glucose, gluconate and citrate (each at 0.1%) as carbon sources and with inorganic phosphate (0.2–1.0 mM) as the phosphorous source.

Other Class II EPSPS containing microorganisms were identified as Achromobacter sp. strain LBAA (Hallas et al., 1988), Pseudomonas sp. strain PG2982 (Moore et al., 1983; Fitzgibbon 1988), Bacillus subtilis 1A2 (Henner et al., 1984) and Staphylococcus aureus (O'Connell et al., 1993). It had been reported previously, from measurements in crude lysates, that the EPSPS enzyme from strain PG2982 was less sensitive to inhibition to glyphosate than that of E. coli, but there has been no report of the details of this lack of sensitivity and there has been no report on the $K_m$ for PEP for this enzyme or of the DNA sequence for the gene for this enzyme (Fitzgibbon, 1988; Fitzgibbon and Braymer, 1990). Relationship of the Class II EPSPS to those previously studied.

All EPSPS proteins studied to date have shown a remarkable degree of homology. For example, bacterial and plant EPSPS's are about 54% identical and with similarity as high as 80%. Within bacterial EPSPS's and plant EPSPS's themselves the degree of identity and similarity is much greater (see Table II).

TABLE II

Comparison between exemplary Class I EPSPS protein sequences[1]

| | similarity | identity |
|---|---|---|
| *E. coli* vs. *S. typhaurium* | 93 | 88 |
| *P. hybrids* vs. *E. coli* | 72 | 55 |
| *P. hybrids* vs. *L. excalentum* | 93 | 88 |

[1]The EPSPS sequences compared here were obtained from the following reference: *E. coli*, Rogers et al., 1983; *S. typhourium*, Smetzer et al, 1985; *Petanoic hybrids*; Shah et al, 1986; and tomato (*L. escalautum*), Gasper et al, 1988.

When crude extracts of CP4 and LBAA bacteria (50 μg protein) were probed using rabbit anti-EPSPS antibody (Padgette et al., 1987) to the Petunia EPSPS protein in a Western analysis, no positive signal could be detected, even with extended exposure times (Protein A—$^{125}$I development system) and under conditions where the control EPSPS (Petunia EPSPS, 20 ng; a Class I EPSPS) was readily detected. The presence of EPSPS activity in these extracts was confirmed by enzyme assay. This surprising result, indicating a lack of similarity between the EPSPS's from these bacterial isolates and those previously studied, coupled with the combination of a low $K_m$ for PEP and a high $K_i$ for glyphosate, illustrates that these new EPSPS enzymes are different from known EPSPS enzymes (now referred to as Class I EPSPS).

Glyphosate-tolerant Enzymes is Microbial Isolates

For clarity and brevity of disclosure, the following description of the isolation of genes encoding Class II EPSPS enzymes is directed to the isolation of such a gene from a bacterial isolate. Those skilled in the art will recognize that the same or similar strategy can be utilized to isolate such genes from other microbial isolates, plant or fungal sources.

Cloning of the Agrobacterium sp. strain CP4 EPSPS Gene(s) in E. coli

Having established the existence of a suitable EPSPS in Agrobacterium sp. strain CP4, two parallel approaches were undertaken to clone the gene: cloning based on the expected phenotype for a glyphosate-tolerant EPSPS; and purification of the enzyme to provide material to raise antibodies and to obtain amino acid sequences from the protein to facilitate the verification of clones. Cloning and genetic techniques, unless otherwise indicated, are generally those described in Maniatis et al., 1982 or Sambrook et al., 1987. The cloning strategy was as follows: introduction of a cosmid bank of strain Agrobacterium sp. strain CP4 into E. coli and selection for the EPSPS gene by selection for growth on inhibitory concentrations of glyphosate.

Chromosomal DNA was prepared from strain Agrobacterium sp. strain CP4 as follows: The cell pellet from a 200 ml L-Broth (Miller, 1972), late log phase culture of Agrobacterium sp. strain CP4 was resuspended in 10 ml of Solution I; 50 mM Glucose, 10 mM EDTA, 25 mM Tris-CL pH 8.0 (Birnboim and Doly, 1979). SDS was added to a final concentration of 1% and the suspension was subjected to three freeze-thaw cycles, each consisting of immersion in dry ice for 15 minutes and in water at 70° C. for 10 minutes. The lysate was then extracted four times with equal volumes of phenol:chloroform (1:1; phenol saturated with TE; TE=10 mM Tris pH8.0; 1.0 mM EDTA) and the phases separated by centrifugation (15000 g; 10 minutes). The ethanol-precipitable material was pelleted from the supernatant by brief centrifugation (8000 g; 5 minutes) following addition of two volumes of ethanol. The pellet was resuspended in 5 ml TE and dialyzed for 16 hours at 4° C. against 2 liters TE. This preparation yielded a 5 ml DNA solution of 552 μg/ml.

Partially-restricted DNA was prepared as follows. Three 100 μg aliquot samples of CP4 DNA were treated for 1 hour at 37° C. with restriction endonuclease HindIII at rates of 4, 2 and 1 enzyme unit/μg DNA, respectively. The DNA samples were pooled, made 0.25 mM with EDTA and extracted with an equal volume of phenol:chloroform. Following the addition of sodium acetate and ethanol, the DNA was precipitated with two volumes of ethanol and pelleted by centrifugation (12000 g; 10 minutes). The dried DNA pellet was resuspended in 500 μl TE and layered on a 10–40% Sucrose gradient (in 5% increments of 5.5 ml each) in 0.5M NaCl, 50 mM Tris pH8.0, 5 mM EDTA. Following centrifugation for 20 hours at 26,000 rpm in a SW28 rotor, the tubes were punctured and ~1.5 ml fractions collected. Samples (20 μl) of each second fraction were run on 0.7% agarose gel and the size of the DNA determined by comparison with linearized lambda DNA and HindIII-digested lambda DNA standards. Fractions containing DNA of 25–35 kb fragments were pooled, desalted on AMICON10 columns (7000 rpm; 20° C.; 45 minutes) and concentrated by precipitation. This procedure yielded 15 μg of CP4 DNA of the required size. A cosmid bank was constructed using the vector pMON17020. This vector, a map of which is presented in FIG. 2, is based on the pBR327 replicon and contains the spectinomycin/streptomycin ($Sp^r$;spc) resistance gene from Tn7 (Fling et al., 1985), the chloramphenicol resistance gene ($Cm^r$;cat) from Tn9 (Alton et al., 1979), the gene10 promoter region from phage T7 (Dunn et al., 1983), and the 1.6 kb BglII phage lambda cos fragment from pHC79 (Hohn and Collins, 1980). A number of cloning sites are located downstream of the cat gene. Since the predominant block to the expression of genes from other microbial sources in E. coli appears to be at the level of transcription, the use of the T7 promoter and supplying the T7 polymerase in trans from the pGP1-2 plasmid (Tabor and Richardson, 1985), enables the expression of large DNA segments of foreign DNA, even those containing RNA polymerase transcription termination sequences. The expression of the spc gene is impaired by transcription from the T7 promoter such that only Cmr can be selected in strains containing pGP1-2. The use of antibiotic resistances such as Cm resistance which do not employ a membrane component is preferred due to the observation that high level expression of resistance genes that involve a membrane component, i.e. β-lactamase and Amp resistance, give rise to a glyphosate-tolerant phenotype. Presumably, this is due to the exclusion of glyphosate from the cell by the membrane localized resistance protein. It is also preferred that the selectable marker be oriented in the same direction as the T7 promoter.

The vector was then cut with HindIII and treated with calf alkaline phosphatase (CAP) in preparation for cloning. Vector and target sequences were ligated by combining the following:

| | |
|---|---|
| Vector DNA (HindIII/CAP) | 3 μg |
| Size fractionated CP4 HindIII fragments | 1.5 μg |
| 10X ligation buffer | 2.2 μl |
| T4 DNA ligase (New England Biolabs) (400 U/μl) | 1.0 μl |

and adding $H_2O$ to 22.0 μl. This mixture was incubated for 18 hours at 16° C. 10X ligation buffer is 250 mM Tris-HCl, pH 8.0; 100 mM $MgCl_2$; 100 mM Dithiothreitol; 2 mM Spermidine. The ligated DNA (5 μl) was packaged into lambda phage particles (Stratagene; Gigapack Gold) using the manufacturer's procedure.

A sample (200 μl) of E. coli HB101 (Boyer and Rolland-Dussoix, 1973) containing the T7 polymerase expression plasmid pGP1-2 (Tabor and Richardson, 1985) and grown overnight in L-Broth (with maltose at 0.2% and kanamycin at 50/μg/ml) was infected with 50 μl of the packaged DNA. Transformants were selected at 30° C. on M9 (Miller, 1972) agar containing kanamycin (50 μg/ml), chloramphenicol (25 μg/ml), L-proline (50 μg/ml), L-leucine (50 μg/ml) and B1 (5 μg/ml), and with glyphosate at 3.0 mM. Aliquot samples were also plated on the same media lacking glyphosate to titer the packaged cosmids. Cosmid transformants were isolated on this latter medium at a rate of ~$5\times10^5$ per μg CP4 HindIII DNA after 3 days at 30° C. Colonies arose on the glyphosate agar from day 3 until day 15 with a final rate of ~1 per 200 cosmids. DNA was prepared from 14 glyphosate-tolerant clones and, following verification of this phenotype, was transformed into E. coli GB100/pGP1-2 (E. coli GB100 is an aroA derivative of MM294 [Talmadge and Gilbert, 1980]) and tested for complementation for growth in the absence of added aromatic amino acids and aminobenzoic acids. Other aroA strains such as SR481 (Bachman et al., 1980; Padgette et al., 1987), could be used and would be suitable for this experiment. The use of GB100 is merely exemplary and should not be viewed in a limiting sense. This aroA strain usually requires that growth media be supplemented with L-phenylalanine, L-tyrosine and L-tryptophan each at 100 μg/ml and with para-hydroxybenzoic acid, 2,3-dihydroxybenzoic acid and para-aminobenzoic acid each at 5 μg/ml for growth in minimal media. Of the fourteen cosmids tested only one showed complementation of the aroA- phenotype. Transformants of this cosmid, pMON17076, showed weak but uniform growth on the unsupplemented minimal media after 10 days.

The proteins encoded by the cosmids were determined in vivo using a T7 expression system (Tabor and Richardson, 1985). Cultures of E. coli containing pGP1-2 (Tabor and Richardson, 1985) and test and control cosmids were grown at 30° C. in L-broth (2 ml) with chloramphenicol and kanamycin (25 and 50 μg/ml, respectively) to a Klett reading of ~50. An aliquot was removed and the cells collected by centrifugation, washed with M9 salts (Miller, 1972) and resuspended in 1 ml M9 medium containing glucose at 0.2%, thiamine at 20 μg/ml and containing the 18 amino acids at 0.01% (minus cysteine and methionine). Following incubation at 30° C. for 90 minutes, the cultures were transferred to a 42° C. water bath and held there for 15 minutes. Rifampicin (Sigma) was added to 200 μg/ml and the cultures held at 42° C. for 10 additional minutes and then transferred to 30° C. for 20 minutes. Samples were pulsed with 10 μCi of $^{35}$S-methionine for 5 minutes at 30° C. The cells were collected by centrifugation and suspended in 60–120 μl cracking buffer (60 mM Tris-HCl 6.8, 1% SDS, 1% 2-mercaptoethanol, 10% glycerol, 0.01% bromophenol blue). Aliquot samples were electrophoresed on 12.5% SDS-PAGE and following soaking for 60 minutes in 10 volumes of Acetic Acid-Methanol-water (10:30:60), the gel was soaked in ENLIGHTNING™ (DUPONT) following manufacturer's directions, dried, and exposed at −70° C. to X-Ray film. Proteins of about 45 kd in size, labeled with $^{35}$S-methionine, were detected in number of the cosmids, including pMON17076.

Purification of EPSPS from Agrobacterium sp. strain CP4

All protein purification procedures were carried out at 3°–5° C. EPSPS enzyme assays were performed using either the phosphate release or radioactive HPLC method, as previously described in Padgette et al., 1987, using 1 mM phosphoenol pyruvate (PEP, Boehringer) and 2 mM shikimate-3-phosphate (S3P) substrate concentrations. For radioactive HPLC assays, $^{14}$-CPEP (Amersham) was utilized. S3P was synthesized as previously described in Wibbenmeyer et al. 1988. N-terminal amino acid sequencing was performed by loading samples onto a Polybrene precycled filter in aliquots while drying. Automated Edman degradation chemistry was used to determine the N-terminal protein sequence, using an Applied Biosystems Model 470A gas phase sequencer (Hunkapiller et al., 1983) with an Applied Biosystems 120A PTH analyzer.

Five 10-liter fermentations were carried out on a spontaneous "smooth" isolate of strain CP4 that displayed less clumping when grown in liquid culture. This reduced clumping and smooth colony morphology may be due to reduced polysaccharide production by this isolate. In the following section dealing with the purification of the EPSPS enzyme, CP4 refers to the "smooth" isolate—CP4-S1. The cells from the three batches showing the highest specific activities were pooled. Cell paste of Agrobacterium sp. CP4 (300 g) was washed twice with 0.5 L of 0.9% saline and collected by centrifugation (30 minutes, 8000 rpm in a GS3 Sorvall rotor). The cell pellet was suspended in 0.9 L extraction buffer (100 mM TrisCl, 1 mM EDTA, 1 mM BAM (Benzamidine), 5 mM DTT, 10% glycerol, pH 7.5) and lysed by 2 passes through a Manton Gaulin cell. The resulting solution was centrifuged (30 minutes, 8000 rpm) and the supernatant was treated with 0.21 L of 1.5% protamine sulfate (in 100 mM TrisCl, pH 7.5, 0.2% w/v final protamine sulfate concentration). After stirring for 1 hour, the mixture was centrifuged (50 minutes, 8000 rpm) and the resulting supernatant treated with solid ammonium sulfate to 40% saturation and stirred for 1 hour. After centrifugation (50 minutes, 8000 rpm), the resulting supernatant was treated with solid ammonium sulfate to 70% saturation, stirred for 50 minutes, and the insoluble protein was collected by centrifugation (1 hour, 8000 rpm). This 40–70% ammonium sulfate fraction was then dissolved in extraction buffer to give a final volume of 0.2 L, and dialyzed twice (Spectrum 10,000 MW cutoff dialysis tubing) against 2 L of extraction buffer for a total of 12 hours.

To the resulting dialyzed 40–70% ammonium sulfate fraction (0.29 L) was added solid ammonium sulfate to give a final concentration of 1M. This material was loaded (2 ml/min) onto a column (5 cm×15 cm, 295 ml) packed with phenyl Sepharose CL-4B (Pharmacia) resin equilibrated with extraction buffer containing 1M ammonium sulfate, and washed with the same buffer (1.5 L, 2 ml/min). EPSPS was eluted with a linear gradient of extraction buffer going from 1M to 0.00M ammonium sulfate (total volume of 1.5 L, 2 ml/min). Fractions were collected (20 ml) and assayed for EPSPS activity by the phosphate release assay. The fractions with the highest EPSPS activity (fractions 36–50) were pooled and dialyzed against 3×2 L (18 hours) of 10 mM TrisCl, 25 mM KCl, 1 mM EDTA, 5 mM DTT, 10% glycerol, pH 7.8.

The dialyzed EPSPS extract (350 ml) was loaded (5 ml/min) onto a column (2.4 cm×30 cm, 136 ml) packed with Q-Sepharose Fast Flow (Pharmacia) resin equilibrated with 10 mM TrisCl, 25 mM KCl, 5 mM DTT, 10% glycerol, pH 7.8 (Q Sepharose buffer), and washed with 1 L of the same buffer. EPSPS was eluted with a linear gradient of Q Sepharose buffer going from 0.025M to 0.40M KCl (total volume of 1.4 L, 5 ml/min). Fractions were collected (15 ml) and assayed for EPSPS activity by the phosphate release assay. The fractions with the highest EPSPS activity (fractions 47–60) were pooled and the protein was precipitated by adding solid ammonium sulfate to 80% saturation and stirring for 1 hour. The precipitated protein was collected by centrifugation (20 minutes, 12000 rpm in a GSA Sorvall rotor), dissolved in Q Sepharose buffer (total volume of 14 ml), and dialyzed against the same buffer (2×1 L, 18 hours).

The resulting dialyzed partially purified EPSPS extract (19 ml) was loaded (1.7 ml/min) onto a Mono Q 10/10 column (Pharmacia) equilibrated with Q Sepharose buffer, and washed with the same buffer (35 ml). EPSPS was eluted with a linear gradient of 0.025M to 0.35M KCl (total volume of 119 ml, 1.7 ml/min). Fractions were collected (1.7 ml) and assayed for EPSPS activity by the phosphate release assayed. The fractions with the highest EPSPS activity (fractions 30–37) were pooled (6 ml).

The Mono Q pool was made 1M in ammonium sulfate by the addition of solid ammonium sulfate and 2 ml aliquots were chromatographed on a Phenyl Superose 5/5 column (Pharmacia) equilibrated with 100 mM TrisCl, 5 mM DTT, 1M ammonium sulfate, 10% glycerol, pH 7.5 (Phenyl Superose buffer). Samples were loaded (1 ml/min), washed with Phenyl Superose buffer (10 ml), and eluted with a linear gradient of Phenyl Superose buffer going from 1M to 0.00M ammonium sulfate (total volume of 60 ml, 1 ml/min). Fractions were collected (1 ml) and assayed for EPSPS activity by the phosphate release assay. The fractions from each run with the highest EPSPS activity (fractions ~36–40) were pooled together (10 ml, 2.5 mg protein). For N-terminal amino acid sequence determination, a portion of one fraction (#39 from run 1) was dialyzed against 50 mM $NaHCO_3$ (2×1 L). The resulting pure EPSPS sample (0.9 ml, 77 μg protein) was found to exhibit a single N-terminal amino acid sequence of:

XH(G)ASSRPATARKSS(G)LX(G)(T)V(R)IPG(D)(K)(M) (SEQ ID NO:18).

The remaining Phenyl Superose EPSPS pool was dialyzed against 50 mM TrisCl, 2 mM DTT, 10 mM KCl, 10% glycerol, pH 7.5 (2×1 L). An aliquot (0.55 ml, 0.61 mg protein) was loaded (1 ml/min) onto a Mono Q 5/5 column (Pharmacia) equilibrated with Q Sepharose buffer, washed with the same buffer (5 ml), and eluted with a linear gradient of Q Sepharose buffer going from 0–0.14M KCl in 10 minutes, then holding at 0.14M KCl (1 ml/min). Fractions were collected (1 ml) and assayed for EPSPS activity by the phosphate release assay and were subjected to SDS-PAGE (10–15%, Phast System, Pharmacia, with silver staining) to determine protein purity. Fractions exhibiting a single band of protein by SDS-PAGE (22–25, 222 μg) were pooled and dialyzed against 100 mM ammonium bicarbonate, pH 8.1 (2×1 L, 9 hours).

Trypsinolysis and peptide sequencing of Agrobacterium sp strain CP4 EPSPS

To the resulting pure Agrobacterium sp. strain CP4 EPSPS (111 μg) was added 3 μg of trypsin (Calbiochem), and the trypsinolysis reaction was allowed to proceed for 16 hours at 37° C. The tryptic digest was then chromatographed (1 ml/min) on a C18 reverse phase HPLC column (Vydac) as previously described in Padgette et al., 1988 for E. coli EPSPS. For all peptide purifications, 0.1% trifluoroacetic acid (TFA, Pierce) was designated buffer "RP-A" and 0.1% TFA in acetonitrile was buffer "RP-B". The gradient used for elution of the trypsinized Agrobacterium sp. CP4 EPSPS was: 0–8 minutes, 0% RP-B; 8–28 minutes, 0–15% RP-B; 28–40 minutes, 15–21% RP-B; 40–68 minutes, 21–49% RP-B; 68–72 minutes, 49–75% RP-B; 72–74 minutes, 75–100% RP-B. Fractions were collected (1 ml) and, based on the elution profile at 210 nm, at least 70 distinct peptides were produced from the trypsinized EPSPS. Fractions 40–70 were evaporated to dryness and redissolved in 150 μl each of 10% acetonitrile, 0.1% trifluoroacetic acid.

The fraction 61 peptide was further purified on the C18 column by the gradient: 0–5 minutes, 0% RP-B; 5–10 minutes, 0–38% RP-B; 10–30 minutes, 38–45% B. Fractions were collected based on the UV signal at 210 nm. A large peptide peak in fraction 24 eluted at 42% RP-B and was dried down, resuspended as described above, and rechromatographed on the C18 column with the gradient: 0–5 minutes, 0% RP-B; 5–12 min, 0–38% RP-B; 12–15 min, 38–39% RP-B; 15–18 minutes, 39% RP-B; 18–20 minutes, 39–41% RP-B; 20–24 minutes, 41% RP-B; 24–28 minutes, 42% RP-B. The peptide in fraction 25, eluting at 41% RP-B and designated peptide 61–24–25, was subjected to N-terminal amino acid sequencing, and the following sequence was determined:

APSM(I)(D)EYPILAV (SEQ ID NO:19)

The CP4 EPSPS fraction 53 tryptic peptide was further purified by C18 HPLC by the gradient 0% B (5 minutes), 0–30% B (5–17 minutes), 30–40% B (17–37 minutes). The peptide in fraction 28, eluting at 34% B and designated peptide 53–28, was subjected to N-terminal amino acid sequencing, and the following sequence was determined:

ITGLLEGEDVINTGK (SEQ ID NO:20).

In order to verify the CP4 EPSPS cosmid clone, a number of oligonucleotide probes were designed on the basis of the sequence of two of the tryptic sequences from the CP4 enzyme (Table III). The probe identified as MID was very low degeneracy and was used for initial screening. The probes identified as EDV-C and EDV-T were based on the same amino acid sequences and differ in one position (underlined in Table III below) and were used as confirmatory probes, with a positive to be expected only from one of these two probes. In the oligonucleotides below, alternate acceptable nucleotides at a particular position are designated by a "/" such as A/C/T.

TABLE III

Selected CP4 EPSPS peptide sequences and DNA probes

| | |
|---|---|
| PEPTIDE 61-24-25 APSM(I)(D)EYPILAV | (SEQ ID NO:19) |
| Probe MID; 17-mer; mixed probe; 24-fold degenerate ATGATA/C/TGAC/TGAG/ATAC/TCC | (SEQ ID NO:21) |
| PEPTIDE 53-28 ITGLLEGEDVINTGK | (SEQ ID NO:20) |
| Probe EDV-C; 17-mer; mixed probe; 48-fold degenerate GAA/GGAC/TGTA/C/G/TATA/C/TAACAC | (SEQ ID NO:22) |
| Probe EDV-T; 17-mer; mixed probe; 48-fold degenerate GAA/GGAC/TGTA/C/G/TATA/C/TAATAC | (SEQ ID NO:23) |

The probes were labeled using gamma-$^{32}$P-ATP and polynucleotide kinase. DNA from fourteen of the cosmids described above was restricted with EcoRI, transferred to membrane and probed with the oligonucleotide probes. The conditions used were as follows: prehybridization was carried out in 6× SSC, 10× Denhardt's for 2–18 hour periods at 60° C., and hybridization was for 48–72 hours in 6× SSC, 10× Denhardt's, 100 μg/ml tRNA at 10° C. below the $T_d$ for the probe. The $T_d$ of the probe was approximated by the formula 2° C×(A+T)+4° C×(G+C). The filters were then washed three times with 6× SSC for ten minutes each at room temperature, dried and autoradiographed. Using the MID probe, an ~9.9 kb fragment in the pMON17076 cosmid gave the only positive signal. This cosmid DNA was then probed with the EDV-C (SEQ ID NO:22) and EDV-T (SEQ ID NO:23) probes separately and again this ~9.9 kb band gave a signal and only with the EDV-T probe.

The combined data on the glyphosate-tolerant phenotype, the complementation of the E. coli aroA- phenotype, the expression of a ~45 Kd protein, and the hybridization to two probes derived from the CP4 EPSPS amino acid sequence strongly suggested that the pMON17076 cosmid contained the EPSPS gene.

Localization and subcloning of the CP4 EPSPS gene

The CP4 EPSPS gene was further localized as follows: a number of additional Southern analyses were carried out on different restriction digests of pMON17076 using the MID (SEQ ID NO:21) and EDV-T (SEQ ID NO:23) probes separately. Based on these analyses and on subsequent detailed restriction mapping of the pBlueScript (Stratagene) subclones of the ~9.9 kb fragment from pMON17076, a 3.8 kb EcoRI-SalI fragment was identified to which both probes hybridized. This analysis also showed that MID (SEQ ID NO:21) and EDV-T (SEQ ID NO:23) probes hybridized to different sides of BamHI, ClaI, and SacII sites. This 3.8 kb fragment was cloned in both orientations in pBlueScript to form pMON17081 and pMON17082. The phenotypes imparted to E. coli by these clones were then determined. Glyphosate tolerance was determined following transformation into E. coli MM294 containing pGP1-2 (pBlueScript also contains a T7 promoter) on M9 agar media containing glyphosate at 3 mM. Both pMON17081 and pMON17082 showed glyphosate-tolerant colonies at three days at 30° C. at about half the size of the controls on the same media lacking glyphosate. This result suggested that the 3.8 kb fragment contained an intact EPSPS gene. The apparent lack of orientation-dependence of this phenotype could be explained by the presence of the T7 promoter at one side of the cloning sites and the lac promoter at the other. The aroA phenotype was determined in transformants of E. coli GB100 on M9 agar media lacking aromatic supplements. In this experiment, carried out with and without the Plac inducer IPTG, pMON17082 showed much greater growth than pMON17081, suggesting that the EPSPS gene was expressed from the SalI site towards the EcoRI site.

Nucleotide sequencing was begun from a number of restriction site ends, including the BamHI site discussed above. Sequences encoding protein sequences that closely matched the N-terminus protein sequence and that for the tryptic fragment 53-28 (SEQ ID NO:20) (the basis of the EDV-T probe) (SEQ ID NO:23) were localized to the SalI side of this BamHI site. These data provided conclusive evidence for the cloning of the CP4 EPSPS gene and for the direction of transcription of this gene. These data coupled with the restriction mapping data also indicated that the complete gene was located on an ~2.3 kb XhoI fragment and this fragment was subcloned into pBlueScript. The nucleotide sequence of almost 2 kb of this fragment was determined by a combination of sequencing from cloned restriction fragments and by the use of specific primers to extend the sequence. The nucleotide sequence of the CP4 EPSPS gene and flanking regions is shown in FIG. 3 (SEQ ID NO:2). The sequence corresponding to peptide 61-24-25 (SEQ ID NO:19) was also located. The sequence was determined using both the SEQUENASE™ kit from IBI (International Biotechnologies Inc.) and the T7 sequencing/Deaza Kit from Pharmacia.

That the cloned gene encoded the EPSPS activity purified from the Agrobacterium sp. strain CP4 was verified in the following manner: By a series of site directed mutageneses, BglII and NcoI sites were placed at the N-terminus with the fMet contained within the NcoI recognition sequence, the first internal NcoI site was removed (the second internal NcoI site was removed later), and a SacI site was placed after the stop codons. At a later stage the internal NotI site was also removed by site-directed mutagenesis. The following list includes the primers for the site-directed mutagenesis (addition or removal of restriction sites) of the CP4 EPSPS gene. Mutagenesis was carried out by the procedures of Kunkel et al. (1987), essentially as described in Sambrook et al. (1989).

PRIMER BgNc
(addition of BgIII and NcoI sites to N-terminus)
CGTGGATAGATCTAGGAAGACAACCATGGCTCACGGTC
(SEQ ID NO:24)

-continued

PRIMER Sph2
(addition of SphI site to N-terminus)
GGATAGATTAAGGAAGACGCGCATGCTTCACGGTGCAAGCAGCC
(SEQ ID NO:25)

PRIMER S1 (addition of SacI site immediately after stop codons)
GGCTGCCTGATGAGCTCCACAATCGCCATCGATGG
(SEQ ID NO:26)

PRIMER N1
(removal of internal NotI recognition site)
CGTCGCTCGTCGTGCGTGGCCGCCCTGACGGC
(SEQ ID NO:27)

PRIMER NcoI
(removal of first internal NcoI recognition site)
CGGGCAAGGCCATGCAGGCTATGGGCGCC
(SEQ ID NO:28)

PRIMER Nco2
(removal of second internal NcoI recognition site)
CGGGCTGCCGCCTGACTATGGGCCTCGTCGG
(SEQ ID NO:29)

This CP4 EPSPS gene was then cloned as a NcoI-BamHI N-terminal fragment plus a BamHI-SacI C-terminal fragment into a PrecA-gene10L expression vector similar to those described (Wong et al., 1988; Olins et al., 1988) to form pMON17101. The $K_m$ for PEP and the $K_i$ for glyphosate were determined for the EPSPS activity in crude lysates of pMON17101/GB100 transformants following induction with nalidixic acid (Wong et al., 1988) and found to be the same as that determined for the purified and crude enzyme preparations from Agrobacterium sp. strain CP4.

Characterization of the EPSPS gene from Achromobacter sp. strain LBAA and from Pseudomonas sp. strain PG2982

A cosmid bank of partially HindIII-restricted LBAA DNA was constructed in E. coli MM294 in the vector pHC79 (Hohn and Collins, 1980). This bank was probed with a full length CP4 EPSPS gene probe by colony hybridization and positive clones were identified at a rate of ~1 per 400 cosmids. The LBAA EPSPS gene was further localized in these cosmids by Southern analysis. The gene was located on an ~2.8 kb XhoI fragment and by a series of sequencing steps, both from restriction fragment ends and by using the oligonucleotide primers from the sequencing of the CP4 EPSPS gene, the nucleotide sequence of the LBAA EPSPS gene was completed and is presented in FIG. 4 (SEQ ID NO:4).

The EPSPS gene from PG2982 was also cloned. The EPSPS protein was purified, essentially as described for the CP4 enzyme, with the following differences: Following the Sepharose CL-4B column, the fractions with the highest EPSPS activity were pooled and the protein precipitated by adding solid ammonium sulfate to 85% saturation and stirring for 1 hour. The precipitated protein was collected by centrifugation, resuspended in Q Sepharose buffer and following dialysis against the same buffer was loaded onto the column (as for the CP4 enzyme). After purification on the Q Sepharose column, ~40 mg of protein in 100 mM Tris pH 7.8, 10% glycerol, 1 mM EDTA, 1 mM DTT, and 1M ammonium sulfate, was loaded onto a Phenyl Superose (Pharmacia) column. The column was eluted at 1.0 ml/minutes with a 40 ml gradient from 1.0M to 0.00M ammonium sulfate in the above buffer.

Approximately 1.0 mg of protein from the active fractions of the Phenyl Superose 10/10 column was loaded onto a Pharmacia Mono P 5/10 Chromatofocusing column with a flow rate of 0.75 ml/minutes. The starting buffer was 25 mM bis-Tris at pH 6.3, and the column was eluted with 39 ml of Polybuffer 74, pH 4.0. Approximately 50 μg of the peak fraction from the Chromatofocusing column was dialyzed into 25 mM ammonium bicarbonate. This sample was then used to determine the N-terminal amino acid sequence.

The N-terminal sequence obtained was:

XHSASPKPATARRSE (where X=an unidentified residue) (SEQ ID NO:30)

A number of degenerate oligonucleotide probes were designed based on this sequence and used to probe a library of PG2982 partial-HindIII DNA in the cosmid pHC79 (Hohn and Collins, 1980) by colony hybridization under nonstringent conditions. Final washing conditions were 15 minutes with 1× SSC, 0.1% SDS at 55° C. One probe with the sequence GCGGTBGCSGGYTTSGG (where B=C, G, or T; S=C or G, and Y=C or T) (SEQ ID NO:31) identified a set of cosmid clones.

The cosmid set identified in this way was made up of cosmids of diverse HindIII fragments. However, when this set was probed with the CP4 EPSPS gene probe, a cosmid containing the PG2982 EPSPS gene was identified (designated as cosmid 9C1 originally and later as pMON20107). By a series of restriction mappings and Southern analysis this gene was localized to a ~2.8 kb XhoI fragment and the nucleotide sequence of this gene was determined. This DNA sequence (SEQ ID NO:6) is shown in FIG. 5. There are no nucleotide differences between the EPSPS gene sequences from LBAA (SEQ ID NO:4) and PG2982 (SEQ ID NO:6). The kinetic parameters of the two enzymes are within the range of experimental error.

A gene from PG2982 that imparts glyphosate tolerance in E. coli has been sequenced (Fitzgibbon, 1988; Fitzgibbon and Brayruer, 1990). The sequence of the PG2982 EPSPS Class II gene shows no homology to the previously reported sequence suggesting that the glyphosate-tolerant phenotype of the previous work is not related to EPSPS.

Characterization of the EPSPS from Bacillus subtilis

Bacillus subtilis 1A2 (prototroph) was obtained from the Bacillus Genetic Stock Center at Ohio State University. Standard EPSPS assay reactions contained crude bacterial extract with, 1 mM phosphoenolpyruvate (PEP), 2 mM shikimate-3-phosphate (S3P), 0.1 mM ammonium molybdate, 5 mM potassium fluoride, and 50 mM HEPES, pH 7.0 at 25° C. One unit (U) of EPSPS activity is defined as one μmol EPSP formed per minute under these conditions. For kinetic determinations, reactions contained crude bacterial, 2 mM S3P, varying concentrations of PEP, and 50 mM HEPES, pH 7.0 at 25° C. The EPSPS specific activity was found to be 0.003 U/mg. When the assays were performed in the presence of 1 mM glyphosphate, 100% of the EPSPS activity was retained. The $appK_m$(PEP) of the B. subtilis EPSPS was determined by measuring the reaction velocity at varying concentrations of PEP. The results were analyzed graphically by the hyperbolic, Lineweaver-Burk and Eadie-Hofstee plots, which yielded $appK_m$(PEP) values of 15.3 μM, 10.8 μM and 12.2 μM, respectively. These three data treatments are in good agreement, and yield an average value for $appK_m$(PEP) of 13 μM. The $appK_i$(glyphosate) was estimated by determining the reaction rates of B. subtilis 1A2 EPSPS in the presence of several concentrations of glyphosphate, at a PEP concentration of 2 μM. These results were compared to the calculated $V_{max}$ of the EPSPS, and making the assumption that glyphosate is a competitive inhibitor versus PEP for B. subtilis EPSPS, as it is for all other characterized EPSPSs, an $appK_i$(glyphosate) was determined graphically. The $appK_i$(glyphosate) was found to be 0.44 mM.

The EPSPS expressed from the B. subtilis aroE gene described by Henner et al. (1986) was also studied. The source of the B. subtilis aroE (EPSPS) gene was the E. coli plasmid-bearing strain ECE13 (original code=MM294[p trp100]; Henner, et al., 1984; obtained from the Bacillus Genetic Stock Center at Ohio State University; the culture genotype is [pBR322 trp100] Ap [in MM294] [pBR322::6 kb insert with trpFBA-hisH]). Two strategies were taken to express the enzyme in E. coli GB100 (aroA-): 1) the gene was isolated by PCR and cloned into an overexpression vector, and 2) the gene was subcloned into an overexpression vector. For the PCR cloning of the B. subtilis aroE from ECE13, two oligonucleotides were synthesized which incorporated two restriction enzyme recognition sites (NdeI and EcoRI) to the sequences of the following oligonucleotides:

(SEQ ID NO:45)
GGAACATATGAAACGAGATAAGGTGCAG (SEQ ID NO:46)
GGAATTCAAACTTCAGGATCTTGAGATAGAAAATG

The other approach to the isolation of the B. subtilis aroE gene, subcloning from ECE13 into pUC118, was performed as follows:

(i) Cut ECE13 and pUC with XmaI and SphI.

(ii) Isolate 1700bp aroE fragment and 2600bp pUC118 vector fragment.

(iii) Ligate fragments and transform into GB100.

The subclone was designated pMON21133 and the PCR-derived clone was named pMON21132. Clones from both approaches were first confirmed for complementation of the aroA mutation in E. coli GB100. The cultures exhibited EPSPS specific activities of 0.044 U/mg and 0.71 U/mg for the subclone (pMON21133) and PCR-derived clone (pMON21132) enzymes, respectively. These specific activities reflect the expected types of expression levels of the two vectors. The B. subtilis EPSPS was found to be 88% and 100% resistant to inhibition by 1 mM glyphosate under these conditions for the subcloned (pMON21133) and PCR-derived (pMON21132) enzymes, respectively. The $appK_m$ (PEP) and the $appK_i$(glyphosate) of the subcloned B. subtilis EPSPS (pMON21133) were determined as described above. The data were analyzed graphically by the same methods used for the 1A2 isolate, and the results obtained were comparable to those reported above for B. subtilis 1A2 culture.

Characterization of the EPSPS gene from Staphylococcus aureus

The kinetic properties of the S. aureus EPSPS expressed in E. coli were determined, including the specific activity, the $appK_m$(PEP), and the $appK_i$(glyphosate). The S. aureus EPSPS gene has been previously described (O'Connell et al., 1993)

The strategy taken for the cloning of the S. aureus EPSPS was polymerase chain reaction (PCR), utilizing the known nucleotide sequence of the S. aureus aroA gene encoding EPSPS (O'Cormell et al., 1993). The S. aureus culture (ATCC 35556) was fermeated in an M2 facility in three 250 mL shake flasks containing 55 mL of TYE (tryptone 5 g/L, yeast extract 3 g/L, pH 6.8). The three flasks were inoculated with 1.5 mL each of a suspension made from freeze dried ATCC 35556 S. aureus cells in 90 mL of PBS (phosphate-buffered saline) buffer. Flasks were incubated at 30° C. for 5 days while shaking at 250 rpm. The resulting cells were lysed (boiled in TE [tris/EDTA] buffer for 8 minutes) and the DNA utilized for PCR reactions. The EPSPS gene was amplified using PCR and engineered into an E. coli expression vector as follows:

(i) two oligonucleotides were synthesized which incorporated two restriction enzyme recognition sites (NcoI and SacI) to the sequences of the oligonucleotides:

(SEQ ID NO:47)

GGGGCCATGGTAAATGAACAAATCATTG (SEQ ID NO:48)

GGGGGAGCTCATTATCCCTCATTTTGTAAAAGC (ii) The purified, PCR-amplified aroA gene from S. aureus was digested using NcoI and SacI enzymes.

(iii) DNA of pMON 5723, which contains a pRecA bacterial promoter and Gene10 leader sequence (Olins et al., 1988) was digested NcoI and SacI and the 3.5 kb digestion product was purified.

(iv) The S. aureus PCR product and the NcoI/SacI pMON 5723 fragment were ligated and transformed into E. coli JM101 competent cells.

(v) Two spectinomycin-resistant E. coli JM101 clones from above (SA#2 and SA#3) were purified and transformed formed into a competent aroA- E. coli strain, GB100

For complementation experiments SAGB#2 and SAGB#3 were utilized, which correspond to SA#2 and SA#3, respectively, transformed into E. coli GB100. In addition, E. coli GB100 (negative control) and pMON 9563 (wt petunia EPSPS, positive control) were tested for AroA complementation. The organisms were grown in minimal media plus and minus aromatic amino acids. Later analyses showed that the SA#2 and SA#3 clones were identical, and they were assigned the plasmid identifier pMON21139.

SAGB#2 in E. coli GB100 (pMON21139) was also grown in M9 minimal media and induced with nalidixic acid. A negative control, E. coli GB100, was grown under identical conditions except the media was supplemented with aromatic amino acids. The cells were harvested, washed with 0.9% NaCl, and frozen at −80° C., for extraction and EPSPS analysis.

The frozen pMON21139 E. coli GB100 cell pellet from above was extracted and assayed for EPSPS activity as previously described. EPSPS assays were performed using 1 mM phosphoenolpyruvate (PEP), 2 mM shikimate-3-phosphate (S3P), 0. 1 mM ammonium molybdate, 5 mM potassium fluoride, pH 7.0, 25° C. The total assay volume was 50μL, which contained 10 μL of the undiluted desalted extract.

The results indicate that the two clones contain a functional aroA/EPSPS gene since they were able to grow in minimal media which contained no aromatic amino acids. As expected, the GB100 culture did not grow on minimal medium without aromatic amino acids (since no functional EPSPS is present), and the pMON9563 did confer growth in minimal media. These results demonstrated the successful cloning of a functional EPSPS gene from S. aureus. Both clones tested were identical, and the E. coli expression vector was designated pMON21139.

The plasmid pMON21139 in E. coli GB100 was grown in M9 minimal media and was induced with nalidixic acid to induce EPSPS expression driven from the RecA promoter. A desalted extract of the intracellular protein was analyzed for EPSPS activity, yielding an EPSPS specific activity of 0.005 μmol/min mg. Under these assay conditions, the S. aureus EPSPS activity was completely resistant to inhibition by 1 mM glyphosate. Previous analysis had shown that E. coli GB100 is devoid of EPSPS activity.

The $appK_m$(PEP) of the S. aureus EPSPS was determined by measuring the reaction velocity of the enzyme (in crude bacterial extracts) at varying concentrations of PEP. The results were analyzed graphically using several standard kinetic plotting methods. Data analysis using the hyperbolic, Lineweaver-Burke, and Eadie-Hofstee methods yielded $appK_m$(PEP) constants of 7.5, 4.8, and 4.0 μM, respectively. These three data treatments are in good agreement, and yield an average value for $appK_m$(PEP) of 5 μM.

Further information of the glyphosate tolerance of S. aureus EPSPS was obtained by determining the reaction rates of the enzyme in the presence of several concentrations of glyphosate, at a PEP concentration of 2 μM. These results were compared to the calculated maximal velocity of the EPSPS, and making the assumption that glyphosate is a competitive inhibitor versus PEP for S. aureus EPSPS, as it is for all other characterized EPSPSs, an $appK_i$(glyphosate) was determined graphically. The $appK_i$(glyphosate) for S. aureus EPSPS estimated using this method was found to be 0.20 mM.

The EPSPS from S. aureus was found to be glyphosate-tolerant, with an $appK_i$(glyphosate) of approximately 0.2 mM. In addition, the $appK_m$(PEP) for the enzyme is approximately 5 μM, yielding a $appK_i$(glyphosate)/$appK_m$(PEP) of 40.

Alternative Isolation Protocols for Other Class II EPSPS Structural Genes

A number of Class II genes have been isolated and described here. While the cloning of the gene from CP4 was difficult due to the low degree of similarity between the Class I and Class II enzymes and genes, the identification of the other genes were greatly facilitated by the use of this first gene as a probe. In the cloning of the LBAA EPSPS gene, the CP4 gene probe allowed the rapid identification of cosmid clones and the localization of the intact gene to a small restriction fragment and some of the CP4 sequencing primers were also used to sequence the LBAA (and PG2982) EPSPS gene(s). The CP4 gene probe was also used to confirm the PG2982 gene clone. The high degree of similarity of the Class II EPSPS genes may be used to identify and clone additional genes in much the same way that Class I EPSPS gene probes have been used to clone other Class I genes. An example of the latter was in the cloning of the A. thaliana EPSPS gene using the P. hybrida gene as a probe (Klee et al., 1987).

Glyphosate-tolerant EPSPS activity has been reported previously for EPSP synthases from a number of sources. These enzymes have not been characterized to any extent in most cases. The use of Class I and Class II EPSPS gene probes or antibody probes provide a rapid means of initially screening for the nature of the EPSPS and provide tools for the rapid cloning and characterization of the genes for such enzymes.

Two of the three genes described were isolated from bacteria that were isolated from a glyphosate treatment facility (Strains CP4 and LBAA). The third (PG2982) was from a bacterium that had been isolated from a culture collection strain. This latter isolation confirms that exposure to glyphosate is not a prerequisite for the isolation of high glyphosate-tolerant EPSPS enzymes and that the screening of collections of bacteria could yield additional isolates. It is possible to enrich for glyphosate degrading or glyphosate resistant microbial populations (Quinn et al., 1988; Talbot et al., 1984) in cases where it was felt that enrichment for such microorganisms would enhance the isolation frequency of Class II EPSPS microorganisms. Additional bacteria containing class II EPSPS gene have also been identified. A bacterium called C 12, isolated from the same treatment column beads as CP4 (see above) but in a medium in which glyphosate was supplied as both the carbon and phosphorus source, was shown by Southern analysis to hybridize with a probe consisting of the CP4 EPSPS coding sequence. This result, in conjunction with that for strain LBAA, suggests that this enrichment method facilitates the identification of Class II EPSPS isolates. New bacterial isolates containing Class II EPSPS genes have also been identified from environments other than glyphosate waste treatment facilities. An inoculum was prepared by extracting soil (from a recently harvested soybean field in Jerseyville, Ill.) and a population of bacteria selected by growth at 28° C. in Dworkin-Foster medium containing glyphosate at 10 mM as a source of carbon (and with cycloheximide at 100 μg/ml to prevent the growth of fungi). Upon plating on L-agar media, five colony types were identified. Chromosomal DNA was prepared from 2ml L-broth cultures of these isolates and the presence of a Class II EPSPS gene was probed using a the CP4 EPSPS coding sequence probe by Southern analysis under stringent hybridization and washing conditions. One of the soil isolates, S2, was positive by this screen.

Class II EPSPS enzymes are identifiable by an elevated Ki for glyphosate and thus the genes for these will impart a glyphosate tolerance phenotype in heterologous hosts. Expression of the gene from recombinant plasmids or phage may be achieved through the use of a variety of expression promoters and include the T7 promoter and polymerase. The T7 promoter and polymerase system has been shown to work in a wide range of bacterial (and mammalian) hosts and offers the advantage of expression of many proteins that may be present on large cloned fragments. Tolerance to growth on glyphosate may be shown on minimal growth media. In some cases, other genes or conditions that may give glyphosate tolerance have been observed, including over expression of beta-lactamase, the igrA gene (Fitzgibbon and Braymer, 1990), or the gene for glyphosate oxidoreductase (PCT Pub. No. WO92/00377). These are easily distinguished from Class II EPSPS by the absence of EPSPS enzyme activity.

The EPSPS protein is expressed from the aroA gene (also called aroE in some genera, for example, in Bacillus) and mutants in this gene have been produced in a wide variety of bacteria. Determining the identity of the donor organism (bacterium) aids in the isolation of Class II EPSPS gene—such identification may be accomplished by standard microbiological methods and could include Gram stain reaction, growth, color of culture, and gas or acid production on different substrates, gas chromatography analysis of methylesters of the fatty acids in the membranes of the microorganism, and determination of the GC % of the genome. The identity of the donor provides information that may be used to more easily isolate the EPSPS gene. An AroA- host more closely related to the donor organism could be employed to clone the EPSPS gene by complementation but this is not essential since complementation of the E. coli AroA mutant by the CP4 EPSPS gene was observed. In addition, the information on the GC content the genome may be used in choosing nucleotide probes—donor sources with high GC % would preferably use the CP4 EPSPS gene or sequences as probes and those donors with low GC would preferably employ those from Bacillus subtilis, for example.

Relationships between different EPSPS genes

The deduced amino acid sequences of a number of Class I and the Class II EPSPS enzymes were compared using the Bestfit computer program provided in the UWGCG package (Devereux et al. 1984). The degree of similarity and identity as determined using this program is reported. The degree of similarity/identity determined within Class I and Class II protein sequences is remarkably high, for instance, comparing E. coli with S. typhimurium (similarity/identity=93%/88%) and even comparing E. coli with a plant EPSPS (Petunia hybrida; 72%/55%). These data are shown in Table IV. The comparison of sequences between Class I and Class II, however, shows a much lower degree of relatedness between the Classes (similarity/identity=50–53%/23–30%). The display of the Bestfit analysis for the E. coli (SEQ ID NO:8) and CP4 (SEQ ID NO:3) sequences shows the positions of the conserved residues and is presented in FIG. 6. Previous analyses of EPSPS sequences had noted the high degree of conservation of sequences of the enzymes and the almost invariance of sequences in two regions—the "20–35" and "95–107" regions (Gasser et al., 1988; numbered according to the Petunia EPSPS sequence)—and these regions are less conserved in the case of CP4 and LBAA when compared to Class I bacterial and plant EPSPS sequences (see FIG. 6 for a comparison of the E. coli and CP4 EPSPS sequences with the E. coli sequence appearing as the top sequence in the Figure). The corresponding sequences in the CP4 Class II EPSPS are:

```
PGDKSTSHRSFMGGL                    (SEQ ID NO:32)
and
LDFGNAATGCRLT.                     (SEQ ID NO:33)
```

These comparisons show that the overall relatedness of Class I and Class II is EPSPS proteins is low and that sequences in putative conserved regions have also diverged considerably.

In the CP4 EPSPS an alanine residue is present at the "glycine101" position. The replacement of the conserved glycine (from the "95–107" region) by an alanine results in an elevated $K_i$ for glyphosate and in an elevation in the $K_m$ for PEP in Class I EPSPS. In the case of the CP4 EPSPS, which contains an alanine at this position, the $K_m$ for PEP is in the low range, indicating that the Class II enzymes differ in many aspects from the EPSPS enzymes heretofore characterized.

Within the Class II isolates, the degree of similarity/identity is as high as that noted for that within Class I (Table IVA). FIG. 7 displays the Bestfit computer program alignment of the CP4 (SEQ ID NO:3) and LBAA (SEQ ID NO:5) EPSPS deduced amino acid sequences with the CP4 sequence appearing as the top sequence in the Figure. The symbols used in FIGS. 6 and 7 are the standard symbols used in the Bestfit computer program to designate degrees of similarity and identity.

TABLE IVA[1,2]

Comparison of relatedness of EPSPS protein sequences
Comparison between Class I and Class II EPSPS protein sequences

| | similarity | identity |
|---|---|---|
| *S. cerevisiae* vs. CP4 | 54 | 30 |
| *A. nidulans* vs. CP4 | 50 | 25 |
| *B. napus* vs. CP4 | 47 | 22 |
| *A. thaliana* vs. CP4 | 48 | 22 |
| *N. tabacum* vs. CP4 | 50 | 24 |
| *L. esculentum* vs. CP4 | 50 | 24 |
| *P. hybrida* vs. CP4 | 50 | 23 |
| *Z. mays* vs. CP4 | 48 | 24 |
| *S. gallinarum* vs. CP4 | 51 | 25 |
| *S. typhimurium* vs. CP4 | 51 | 25 |

TABLE IVA[1,2]-continued

| | | |
|---|---|---|
| *S. typhi* vs. CP4 | 51 | 25 |
| *K. pneumoniae* vs. CP4 | 56 | 28 |
| *Y. enterocolitica* vs. CP4 | 53 | 25 |
| *H. influenzae* vs. CP4 | 53 | 27 |
| *P. multocida* vs. CP4 | 55 | 30 |
| *A. salmonicida* vs. CP4 | 53 | 23 |
| *B. pertussis* vs. CP4 | 53 | 27 |
| *E. coli* vs. CP4 | 52 | 26 |
| *E. coli* vs. LBAA | 52 | 26 |
| *E. coli* vs. *B. subtilis* | 55 | 29 |
| *E. coli* vs. *D. nodosus* | 55 | 32 |
| *E. coli* vs. *S. aureus* | 55 | 29 |
| *E. coli* vs. *Synechocystis* sp. PCC6803 | 53 | 30 |
| Comparison between Class I EPSPS protein sequences | | |
| | similarity | identity |
| *E. coli* vs. *S. typhimurium* | 93 | 88 |
| *P. hybrids* vs. *E. coli* | 72 | 55 |
| Comparison between Class II EPSPS protein sequences | | |
| | similarity | identity |
| *D. nodosus* vs. CP4 | 62 | 43 |
| LBAA vs. CP4 | 90 | 83 |
| PG2892 vs. CP4 | 90 | 83 |
| *S. aureus* vs. CP4 | 58 | 34 |
| *B. subtills* vs. CP4 | 59 | 41 |
| *Synechocystis* sp. PCC6803 vs. CP4 | 62 | 45 |

[1]The EPSPS sequences compared here were obtained from the following references: *E. coli*, Rogers et al., 1983; *S. typhimurium*, Stalker et al., 1985; *Petunia hybrids*, Shah et al., 1986; *B. pertussis*, Maskell et al., 1988; *S. cerevisiae*, Duncan et al., 1987, *Synechocystis* sp. PCC6803, Dalla Chiesa et al., 1994 and *D. nodosus*, Alm et al., 1994.
[2]"GAP" Program, Genetics Computer Group, (1991), Program Manual for the GCG Package, Version 7, April 1991, 575 Science Drive, Madison, Wisconsin, USA 53711

The relative locations of the major conserved sequences among Class II EPSP sythase which distinguishes this group from the Class I EPSP synthases is listed below in Table IVB.

TABLE IVB

| | Location of Conserved Sequences in Class II EPSP Synthases | | | |
|---|---|---|---|---|
| Source | Seq. 1[1] | Seq. 2[2] | Seq. 3[3] | Seq. 4[4] |
| CP4 | | | | |
| start | 200 | 26 | 173 | 271 |
| end | 204 | 29 | 177 | 274 |
| LBAA | | | | |
| start | 200 | 26 | 173 | 271 |
| end | 204 | 29 | 177 | 274 |
| PG2982 | | | | |
| start | 200 | 26 | 173 | 273 |
| end | 204 | 29 | 177 | 276 |
| *B. subtilis* | | | | |
| start | 190 | 17 | 164 | 257 |
| end | 194 | 20 | 168 | 260 |
| *S. aureus* | | | | |
| start | 193 | 21 | 166 | 261 |
| end | 197 | 24 | 170 | 264 |
| *Synechocystis* sp. PCC6803 | | | | |
| start | 210 | 34 | 183 | 278 |
| end | 214 | 38 | 187 | 281 |

TABLE IVB-continued

| | Location of Conserved Sequences in Class II EPSP Synthases | | | |
|---|---|---|---|---|
| Source | Seq. 1[1] | Seq. 2[2] | Seq. 3[3] | Seq. 4[4] |
| *D. nodosus* | | | | |
| start | 195 | 22 | 168 | 261 |
| end | 199 | 25 | 172 | 264 |
| min. start | 190 | 17 | 164 | 257 |
| max. end | 214 | 38 | 187 | 281 |

[1]-R-$X_1$-H-$X_2$-E-(SEQ ID NO:37)
[2]-G-D-K-$X_3$-(SEQ ID NO:38)
[3]-S-A-Q-$X_4$-K-(SEQ ID NO:39)
[4]-N-$X_5$-T-E-(SEQ ID NO:40)

The domains of EPSP synthase sequence identified in this application were determined to be those important for maintenance of glyphosate resistance and productive binding of PEP. The information used in indentifying these domains included sequence alignments of numerous glyphosate-sensitive EPSPS molecules and the three-dimensional x-ray structures of E. coli EPSPS (Stallings, et al. 1991) and CP4 EPSPS. The structures are representative of a glyphosate-sensitive (i.e., Class I) enzyme, and a naturally-occuring glyphosate-tolerant (i.e., Class II) enzyme of the present invention. These exemplary molecules were superposed three-dimensionally and the results displayed on a computer graphics terminal. Inspection of the display allowed for structure-based fine-tuning of the sequence alignments of glyphosate-sensitive and glyphosate-resistant EPSPS molecules. The new sequence alignments were examined to determine differences between Class I and Class II EPSPS enzymes. Seven regions were identified and these regions were located in the x-ray structure of CP4 EPSPS which also contained a bound analog of the intermediate which forms catalytically between PEP and S3P.

The structure of the CP4 EPSPS with the bound intermediate analog was displayed on a computer graphics terminal and the seven sequence segments were examined. Important residues for glyphosate binding were identified as well as those residues which stabilized the conformations of those important residues; adjoining residues were considered necessary for maintenance of correct three-dimensional structural motifs in the context of glyphosate- sensitive EPSPS molecules. Three of the seven domains were determined not to be important for glyphosate tolerance and maintenance of productive PEP binding. The following four primary domains were determined to be characteristic of Class II EPSPS enzymes of the present invention:

-R-XrH-$X_2$-E(SEQ ID NO:37), in which
$X_1$ is an uncharged polar or acidic amino acid,
$X_2$ is serine or threonine,
The Arginine (R) reside at position 1 is important because the positive charge of its guanidium group destabilizes the binding of glyphosate. The Histidine (H) residue at position 3 stabilizes the Arginine (R) residue at position 4 of SEQ ID NO:40. The Glutamic Acid (E) residue at position 5 stabilizes the Lysine (K) residue at position 5 of SEQ ID NO:39.

-G-D-K-$X_3$(SEQ ID NO:38), in which
$X_3$ is serine or threonine,
The Aspartic acid (D) residue at position 2 stabilizes the Arginine (R) residue at position 4 of SEQ ID NO:40. The Lysine (K) residue at position 3 is important because for productive PEP binding.

-S-A-Q-$X_4$-K(SEQ ID NO:39), in which $X_4$ is any amino acid,

The Alanine (A) residue at position 2 stabilizes the Arginine (R) residue at position 1 of SEQ ID NO:37. The Serine (S) residue at position 1 and the Glutamine (Q) residue at position 3 are important for productive S3P binding.

-N-$X_5$-T-R(SEQ ID NO:40), in which $X_5$ is any amino acid,

The Asparagine (N) residue at position 1 and the Threonine (T) residue at position 3 stabilize residue $X_1$ at position 2 of SEQ ID NO:37. The Arginine (R) residue at position 4 is important because the positive charge of its guanidium group destabilizes the binding of glyphosate.

Since the above sequences are only representative of the Class II EPSPSs which would be included within the generic structure of this group of EPSP synthases, the above sequences may be found within a subject EPSP synthase molecule within slightly more expanded regions. It is believed that the above-described conserved sequences would likely be found in the following regions of the mature EPSP synthases molecule:

-R-$X_1$-H-$X_2$-E-(SEQ ID NO:37) located between amino acids 175 and 230 of the mature EPSP synthase sequence;

-G-D-K-$X_3$-(SEQ ID NO:38) located between amino acids 5 and 55 of the mature EPSP synthase sequence;

-S-A-Q-$X_4$-K-(SEQ ID NO:39) located between amino acids 150 and 200 of the mature EPSP synthase sequence; and -N-$X_5$-T-R-(SEQ ID NO:40) located between amino acids 245 and 295 of the mature EPSPS synthase sequence.

One difference that may be noted between the deduced amino acid sequences of the CP4 and LBAA EPSPS proteins is at position 100 where an Alanine is found in the case of the CP4 enzyme and a Glycine is found in the case of the LBAA enzyme. In the Class I EPSPS enzymes a Glycine is usually found in the equivalent position, i.e Glycine96 in E. coli and K. pneumoniae and Glycine101 in Petunia. In the case of these three enzymes it has been reported that converting that Glycine to an Alanine results in an elevation of the appKi for glyphosate and a concomitant elevation in the appKm for PEP (Kishore et al., 1986; Kishore and Shah, 1988; Sost and Amrhein, 1990), which, as discussed above, makes the enzyme less efficient especially under conditions of lower PEP concentrations. The Glycine100 of the LBAA EPSPS was converted to an Alanine and both the appKm for PEP and the appKi for glyphosate were determined for the variant. The Glycine100Alanine change was introduced by mutagenesis using the following primer:

CGGCAATGCCGCCACCGGCGCGCGCC (SEQ ID NO:34)

and both the wild type and variant genes were expressed in E. coli in a RecA promoter expression vector (pMON17201 and pMON17264, respectively) and the appKm's and appKi's determined in crude lysates. The data indicate that the appKi(glyphosate) for the G100A variant is elevated about 16-fold (Table V). This result is in agreement with the observation of the importance of this G-A change in raising the appKi(glyphosate) in the Class I EPSPS enzymes. However, in contrast to the results in the Class I G-A variants, the appKm(PEP) in the Class II (LBAA) G-A variant is unaltered. This provides yet another distinction between the Class II and Class I EPSPS enzymes.

TABLE V

| | sppKm(PEP) | sppKi (glyphosate) |
|---|---|---|
| Lysato prepared from: | | |
| *E. coli*/pMON17201 (wild type) | 5.3 μM | 28 μM* |
| *E. coli*/pMON17264 (G100A variant) | 5.5 μM | 459 μM# |

@range of PEP; 2–40 μM
*range of glyphosate; 0–310 μM;
#range of glyphosate; 0–5000 μM.

The LBAA G100A variant, by virtue of its superior kinetic properties, should be capable of imparting improved in planta glyphosate tolerance.

Modification and Resynthesis of the Agrobacterium sp. strain CP4 EPSPS Gene Sequence The EPSPS gene from Agrobacterium sp. strain CP4 contains sequences that could be inimical to high expression of the gene in plants. These sequences include potential polyadenylation sites that are often and A+T rich, a higher G+C % than that frequently found in plant genes (63% versus ~50%), concentrated stretches of G and C residues, and codons that are not used frequently in plant genes. The high G+C % in the CP4 EPSPS gene has a number of potential consequences including the following: a higher usage of G or C than that found in plant genes in the third position in codons, and the potential to form strong hair-pin structures that may affect expression or stability of the RNA. The reduction in the G+C content of the CP4 EPSPS gene, the disruption of stretches of G's and C's, the elimination of potential polyadenylation sequences, and improvements in the codon usage to that used more frequently in plant genes, could result in higher expression of the CP4 EPSPS gene in plants.

A synthetic CP4 gene was designed to change as completely as possible those inimical sequences discussed above. In summary, the gene sequence was redesigned to eliminate as much as possible the following sequences or sequence features (while avoiding the introduction of unnecessary restriction sites): stretches of G's and C's of 5 or greater; and A+T rich regions (predominantly) that could function as polyadenylation sites or potential RNA destabilization region. The sequence of this gene is shown in FIG. 8 (SEQ ID NO:9). This coding sequence was expressed in E. coli from the RecA promoter and assayed for EPSPS activity and compared with that from the native CP4 EPSPS gene. The apparent Km for PEP for the native and synthetic genes was 11.8 and 12.7, respectively, indicating that the enzyme expressed from the synthetic gene was unaltered. The N-terminus of the coding sequence was mutagenized to place an SphI site at the ATG to permit the construction of the CTP2-CP4 synthetic fusion for chloroplast import. The following primer was used to accomplish this mutagenesis:

(SEQ ID NO:35)
GGACCGCTGCTTGCACCGTGAAGCATGCTTAAGCTTGGCGTAATCATGG.

Expression of Chloroplast Directed CP4 EPSPS

The glyphosate target in plants, the 5-enolpyruvyl-shikimate-3-phosphate synthase (EPSPS) enzyme, is located in the chloroplast. Many chloroplast-localized proteins, including EPSPS, are expressed from nuclear genes as precursors and are targeted to the chloroplast by a chloroplast transit peptide (CTP) that is removed during the import steps. Examples of other such chloroplast proteins include the small subunit (SSU) of Ribulose-1,5-bisphosphate carboxylase (RUBISCO), Ferredoxia, Ferredoxin oxidoreductase, the Light-harvesting-complex protein I and protein II, and Thioredoxin F. It has been demonstrated in vivo and in vitro that non-chloroplast proteins may be targeted to the chloroplast by use of protein fusions with a CTP and that a CTP sequence is sufficient to target a protein to the chloroplast.

A CTP-CP4 EPSPS fusion was constructed between the Arabidopsis thaliana EPSPS CTP (Klee et al., 1987) and the CP4 EPSPS coding sequences. The Arabidopsis CTP was engineered by site-directed mutagenesis to place a SphI restriction site at the CTP processing site. This mutagenesis replaced the Glu-Lys at this location with Cys-Met. The sequence of this CTP, designated as CTP2 (SEQ ID NO:10), is shown in FIG. 9. The N-terminus of the CP4 EPSPS gene was modified to place a SphI site that spans the Met codon. The second codon was converted to one for leucine in this step also. This change had no apparent effect on the in vivo activity of CP4 EPSPS in E. coli as judged by rate of complementation of the aroA allele. This modified N-terminus was then combined with the SacI C-terminus and cloned downstream of the CTP2 sequences. The CTP2-CP4 EPSPS fusion was cloned into pBlueScript KS(+). This vector may be transcribed in vitro using the T7 polymerase and the RNA translated with $^{35}$S-Methionine to provide material that may be evaluated for import into chloroplasts isolated from Lactuca sativa using the methods described hereinafter (della-Cioppa et al., 1986, 1987). This template was transcribed in vitro using T7 polymerase and the $^{35}$S-methionine-labeled CTP2-CP4 EPSPS material was shown to import into chloroplasts with an efficiency comparable to that for the control Petunia EPSPS (control=$^{35}$S labeled PreEPSPS [pMON6140; della-Cioppa et al., 1986]).

In another example the Arabidopsis EPSPS CTP, designated as CTP3, was fused to the CP4 EPSPS through an EcoRI site. The sequence of this CTP3 (SEQ ID NO:12) is shown in FIG. 10. An EcoRI site was introduced into the Arabidopsis EPSPS mature region around amino acid 27, replacing the sequence -Arg-Ala-Leu-Leu- with -Arg-Ile-Leu-Leu- in the process. The primer of the following sequence was used to modify the N-terminus of the CP4 EPSPS gene to add an EcoRI site to effect the fusion to the

```
CTG3: GGAAGACGCCCAGATTCACGGTGCAAGCAGCCGG
(the EcoRI site is underlined) (SEQ ID NO:36)
```

This CTP3-CP4 EPSPS fusion was also cloned into the pBlueScript vector and the T7 expressed fusion was found to also import into chloroplasts with an efficiency comparable to that for the control Petunia EPSPS (pMON6140).

A related series of CTPs, designated as CTP4 (SphI) and CTP5 (EcoRI), based on the Petunia EPSPS CTP and gene were also fused to the SphI- and EcoRI-modified CP4 EPSPS gene sequences. The SphI site was added by site-directed mutagenesis to place this restriction site (and change the amino acid sequence to -Cys-Met-) at the chloroplast processing site. All of the CTP-CP4 EPSPS fusions were shown to import into chloroplasts with approximately equal efficiency. The CTP4 (SEQ ID NO:14) and CTP5 (SEQ ID NO:16) sequences are shown in FIGS. 11 and 12.

A CTP2-LBAA EPSPS fusion was also constructed following the modification of the N-terminus of the LBAA EPSPS gene by the addition of a SphI site. This fusion was also found to be imported efficiently into chloroplasts.

By similar approaches, the CTP2-CP4 EPSPS and the CTP4-CP4 EPSPS fusion have also been shown to import efficiently into chloroplasts prepared from the leaf sheaths of corn. These results indicate that these CTP-CP4 fusions could also provide useful genes to impart glyphosate tolerance in monocot species.

The use of CTP2 or CTP4 is preferred because these transit peptide constructions yield mature EPSPS enzymes upon import into the chloroplast which are closer in composition to the native EPSPSs not containing a transit peptide signal. Those skilled in the art will recognize that various chimeric constructs can be made which utilize the functionality of a particular CTP to import a Class II EPSPS enzyme into the plant cell chloroplast. The chloroplast import of the Class II EPSPS can be determined using the following assay.

Chloroplast Uptake Assay

Intact chloroplasts are isolated from lettuce (Latuca sativa, var. longifolia) by centrifugation in Percoll/ficoll gradients as modified from Bartlett et al., (1982). The final pellet of intact chloroplasts is suspended in 0.5 ml of sterile 330 mM sorbitol in 50 mM Hepes-KOH, pH 7.7, assayed for chlorophyll (Arnon, 1949), and adjusted to the final chlorophyll concentration of 4 mg/ml (using sorbitol/Hepes). The yield of intact chloroplasts from a single head of lettuce is 3–6 mg chlorophyll.

A typical 300 μl uptake experiment contained 5 mM ATP, 8.3 mM unlabeled methionine, 322 mM sorbitol, 58.3 mM Hepes-KOH (pH 8.0), 50 μl reticulocyte lysate translation products, and intact chloroplasts from L. sativa (200 μg chlorophyll). The uptake mixture is gently rocked at room temperature (in 10×75 mm glass tubes) directly in front of a fiber optic illuminator set at maximum light intensity (150 Watt bulb). Aliquot samples of the uptake mix (about 50 μl) are removed at various times and fractionated over 100 μl silicone-oil gradients (in 150 μl polyethylene tubes) by centrifugation at 11,000× g for 30 seconds. Under these conditions, the intact chloroplasts form a pellet under the silicone-oil layer and the incubation medium (containing the reticulocyte lysate) floats on the surface. After centrifugation, the silicone-oil gradients are immediately frozen in dry ice. The chloroplast pellet is then resuspended in 50–100 μl of lysis buffer (10 mM Hepes-KOH pH 7.5, 1 mM PMSF, 1 mM benzamidine, 5 mM e-amino-n-caproic acid, and 30 μg/ml aprotinin) and centrifuged at 15,000× g for 20 minutes to pellet the thylakoid membranes. The clear supernatant (stromal proteins) from this spin, and an aliquot of the reticulocyte lysate incubation medium from each uptake experiment, are mixed with an equal volume of 2×SDS-PAGE sample buffer for electrophoresis (Laemmli, 1970).

SDS-PAGE is carried out according to Laemmli (1970) in 3–17% (w/v) acrylamide slab gels (60 mm×1.5 mm) with 3% (w/v) acrylamide stacking gels (5 mm×1.5 mm). The gel is fixed for 20–30 rain in a solution with 40% methanol and 10% acetic acid. Then, the gel is soaked in EN$^3$HANCE™ (DuPont) for 20–30 minutes, followed by drying the gel on a gel dryer. The gel is imaged by autoradiography, using an intensifying screen and an overnight exposure to determine whether the CP4 EPSPS is imported into the isolated chloroplasts.

Plant Transformation

Plants which can be made glyphosate-tolerant by practice of the present invention include, but are not limited to, soybean, cotton, corn, canola, oil seed rape, flax, sugarbeet, sunflower, potato, tobacco, tomato, wheat, rice, alfalfa and lettuce as well as various tree, nut and vine species.

A double-stranded DNA molecule of the present invention ("chimeric gene") can be inserted into the genome of a plant by any suitable method. Suitable plant transformation vectors include those derived from a Ti plasmid of Agrobacterium tumefaciens, as well as those disclosed, e.g., by Herrera-Estrella (1983), Beyart (1984), Klee (1985) and EPO publication 120,516 (Schilperoort et al.). In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen.

Class II EPSPS Plant transformation vectors

Figure 13:
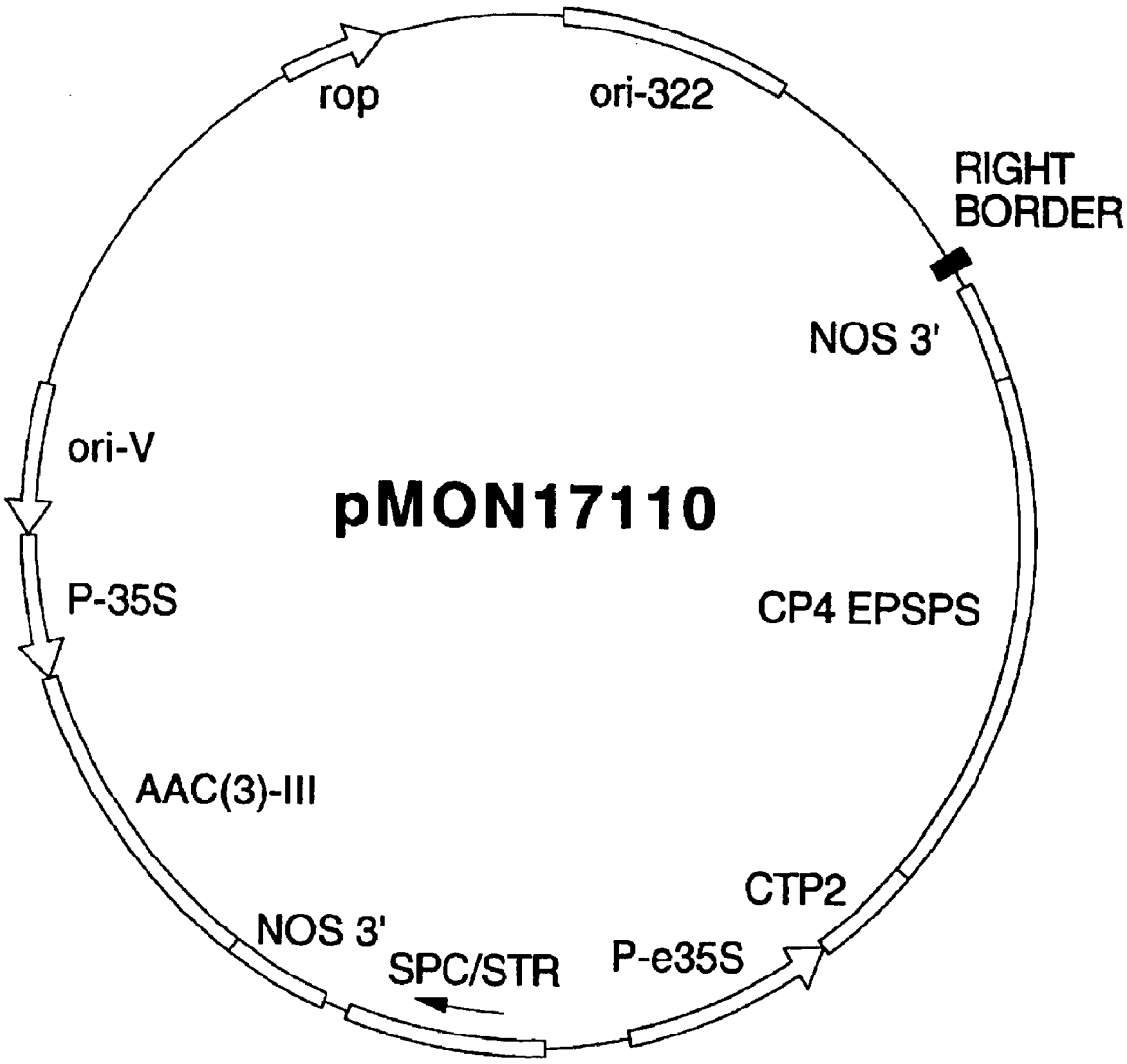
FIG. 13 shows a plasmid map of CP4 plant transformation/expression vector pMON17110.

Class II EPSPS DNA sequences may be engineered into vectors capable of transforming plants by using known techniques. The following description is meant to be illustrative and not to be read in a limiting sense. One of ordinary skill in the art would know that other plasmids, vectors, markers, promoters, etc. would be used with suitable results. The CTP2-CP4 EPSPS fusion was cloned as a BglII-EcoRI fragment into the plant vector pMON979 (described below) to form pMON17110, a map of which is presented in FIG. 13. In this vector the CP4 gene is expressed from the enhanced CaMV35S promoter (E35S; Kay et al. 1987). A FMV35S promoter construct (pMON17116) was completed in the following way: The SalI-NotI and the NotI-BglII fragments from pMON979 containing the Spc/AAC(3)-III/oriV and the pBR322/Right Border/NOS 3'/CP4 EPSPS gene segment from pMON17110 were ligated with the XhoI-BglII FMV35S promoter fragment from pMON981. These vectors were introduced into tobacco, cotton and canola.

A series of vectors was also completed in the vector pMON977 in which the CP4 EPSPS gene, the CTP2-CP4 EPSPS fusion, and the CTP3-CP4 fusion were cloned as BglII-SacI fragments to form pMON17124, pMON17119, and pMON17120, respectively. These plasmids were introduced into tobacco. A pMON977 derivative containing the CTP2-LBAA EPSPS gene was also completed (pMON17206) and introduced into tobacco.

The pMON979 plant transformation/expression vector was derived from pMON886 (described below) by replacing the neomycin phosphotransferase typeII (KAN) gene in pMON886 with the 0.89 kb fragment containing the bacterial gentamicin-3-N-acetyltransferase type III (AAC(3)-III) gene (Hayford et al., 1988). The chimeric P-35S/AA(3)-III/NOS 3' gene encodes gentamicin resistance which permits selection of transformed plant cells. pMON979 also contains a 0.95 kb expression cassette consisting of the enhanced CaMV 35S promoter (Kay et al., 1987), several unique restriction sites, and the NOS 3' end (P-En-CaMV35SfNOS 3'). The rest of the pMON979 DNA segments are exactly the same as in pMON886.

Plasmid pMON886 is made up of the following segments of DNA. The first is a 0.93 kb AvaI to engineered-EcoRV fragment isolated from transposon Tn7 that encodes bacterial spectinomycin/streptomycin resistance (Spc/Str), which is a determinant for selection in E. coli and Agrobacterium tumefaciens. This is joined to the 1.61 kb segment of DNA encoding a chimeric kanamycin resistance which permits selection of transformed plant cells. The chimeric gene (P-35S/KANfNOS 3') consists of the cauliflower mosaic virus (CaMV) 35S promoter, the neomycin phosphotransferase typeII (KAN) gene, and the 3'-nontranslated region of the nopaline synthase gene (NOS 3') (Fraley et al., 1983). The next segment is the 0.75 kb oriV containing the origin of replication from the RK2 plasmid. It is joined to the 3.1 kb SalI to PvuI segment of pBR322 (ori322) which provides the origin of replication for maintenance in E. coli and the bom site for the conjugational transfer into the Agrobacterium tumefaciens cells. The next segment is the 0.36 kb PvuI to BclI from pTiT37 that carries the nopaline-type T-DNA right border (Fraley et al., 1985).

The pMON977 vector is the same as pMON981 except for the presence of the P-En-CaMV35S promoter in place of the FMV35S promoter (see below).

Figure 14:
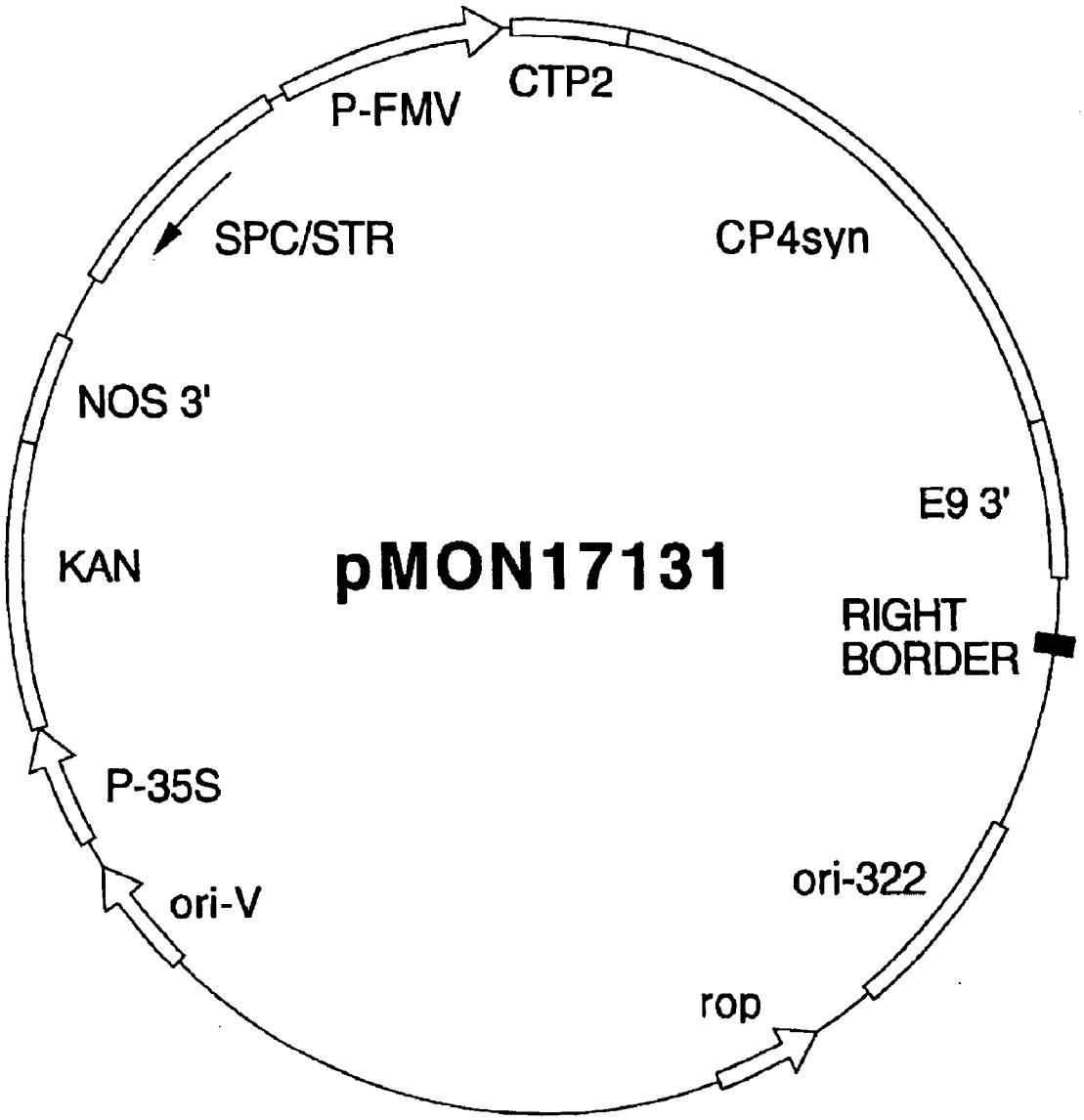
FIG. 14 shows a plasmid map of CP4 synthetic EPSPS gene plant transformation/expression vector pMON17131.

The pMON981 plasmid contains the following DNA segments: the 0.93 kb fragment isolated from transposon Tn7 encoding bacterial spectinomycin/streptomycin resistance [Spc/Str; a determinant for selection in E. coli and Agrobacterium tumefaciens (Fling et al., 1985)]; the chimeric kanamycin resistance gene engineered for plant expression to allow selection of the transformed tissue, consisting of the 0.35 kb cauliflower mosaic virus 35S promoter (P-35S) (Odell et al., 1985), the 0.83 kb neomycin phosphotransferase typeII gene (KAN), and the 0.26 kb 3'-nontranslated region of the nopaline synthase gene (NOS 3') (Fraley et al., 1983); the 0.75 kb origin of replication from the RK2 plasmid (oriV) (Stalker et al., 1981); the 3.1 kb SalI to PvuI segment of pBR322 which provides the origin of replication for maintenance in E. coli (ori-322) and the bom site for the conjugational transfer into the Agrobacterium tumefaciens cells, and the 0.36 kb PvuI to BclI fragment from the pTiT37 plasmid containing the nopaline-type T-DNA right border region (Fraley et al., 1985). The expression cassette consists of the 0.6 kb 35S promoter from the figwort mosaic virus (P-FMV35S) (Gowda et al., 1989) and the 0.7 kb 3' non-translated region of the pea rbcS-E9 gene (E9 3') (Coruzzi et al., 1984, and Morelli et al., 1985). The 0.6 kb SspI fragment containing the FMV35S promoter (FIG. 1) was engineered to place suitable cloning sites downstream of the transcriptional start site. The CTP2-CP4syn gene fusion was introduced into plant expression vectors (including pMON981, to form pMON17131; FIG. 14) and transformed into tobacco, canola, potato, tomato, sugarbeet, cotton, lettuce, cucumber, oil seed rape, poplar, and Arabidopsis.

The plant vector containing the Class II EPSPS gene may be mobilized into any suitable Agrobacterium strain for transformation of the desired plant species. The plant vector may be mobilized into an ABI Agrobacterium strain. A suitable ABI strain is the A208 Agrobacterium tumefaciens carrying the disarmed Ti plasmid pTiC58 (pMP90RK) (Koncz and Schell, 1986). The Ti plasmid does not carry the T-DNA phytohormone genes and the strain is therefore unable to cause the crown gall disease. Mating of the plant vector into ABI was done by the triparental conjugation system using the helper plasmid pRK2013 (Ditta et al., 1980). When the plant tissue is incubated with the ABI-::plant vector conjugate, the vector is transferred to the plant cells by the vir functions encoded by the disarmed pTiC58 plasmid. The vector opens at the T-DNA right border region, and the entire plant vector sequence may be inserted into the host plant chromosome. The pTiC58 Ti plasmid does not transfer to the plant cells but remains in the Agrobacterium.

Class II EPSPS free DNA vectors

Figure 15:
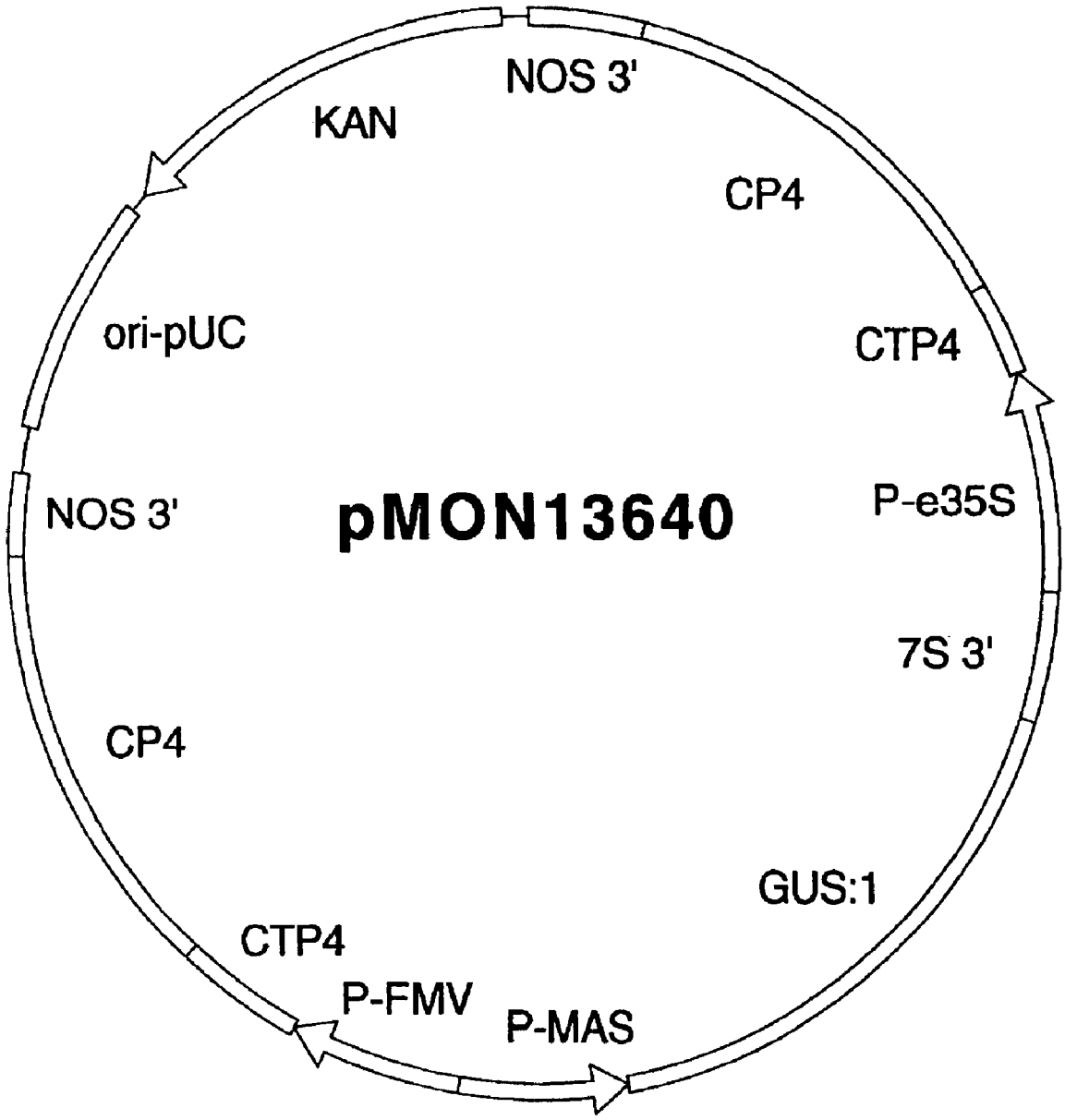
FIG. 15 shows a plasmid map of CP4 EPSPS free DNA plant transformation expression vector pMON13640.

Class II EPSPS genes may also be introduced into plants through direct delivery methods. A number of direct delivery vectors were completed for the CP4 EPSPS gene. The vector pMON13640, a map of which is presented in FIG. 15, is described here. The plasmid vector is based on a pUC plasmid (Vieira and Messing, 1987) containing, in this case, the nptII gene (kanamycin resistance; KAN) from Tn903 to provide a selectable marker in E. coli. The CTP4-EPSPS gene fusion is expressed from the P-FMV35S promoter and contains the NOS 3' polyadenylation sequence fragment and from a second cassette consisting of the E35S promoter, the CTP4-CP4 gene fusion and the NOS 3' sequences. The scoreable GUS marker gene (Jefferson et al., 1987) is expressed from the mannopine synthase promoter (P-MAS; Velten et al., 1984) and the soybean 7S storage protein gene 3' sequences (Schuler et al., 1982). Similar plasmids could also be made in which CTP-CP4 EPSPS fusions are expressed from the enhanced CaMV35S promoter or other plant promoters. Other vectors could be made that are suitable for free DNA delivery into plants and such are within the skill of the art and contemplated to be within the scope of this disclosure.

Plastid transformation:

While transformation of the nuclear genome of plants is much more developed at this time, a rapidly advancing alternative is the transformation of plant organelles. The transformation of plastids of land plants and the regeneration of stable transformants has been demonstrated (Svab et al., 1990; Maliga et al., 1993). Transformants are selected, following double cross-over events into the plastid genome, on the basis of resistance to spectinomycin conferred through rRNA changes or through the introduction of an aminoglycoside 3"-adenyltransferase gene (Svab et al., 1990; Svab and Maliga, 1993), or resistance to kanamycin through the neomycin phosphotransferase NptII (Carrer et al., 1993). DNA is introduced by biolistic means (Svab et al, 1990; Maliga et al., 1993) or by using polyethylene glycol (O'Neill et al., 1993). This transformation route results in the production of 500–10,000 copies of the introduced sequence per cell and high levels of expression of the introduced gene have been reported (Carrer et al., 1993; Maliga et al., 1993). The use of plastid transformation offers the advantages of not requiring the chloroplast transit peptide signal sequence to result in the localization of the heterologous Class II EPSPS in the chloroplast and the potential to have many copies of the heterologous plant-expressible Class II EPSPS gene in each plant cell since at least one copy of the gene would be in each plastid of the cell.

Plant Regeneration

When expression of the Class II EPSPS gene is achieved in transformed cells (or protoplasts), the cells (or protoplasts) are regenerated into whole plants. Choice of methodology for the generation step is not critical, with suitable protocols being available for hosts from Leguminosae (alfalfa, soybean, clover, etc.), Umbelliferae (carrot, celery, parsnip), Cruciferae (cabbage, radish, rapeseed, etc.), Cucurbitaceae (melons and cucumber), Gramineae (wheat, rice, corn, etc.), Solanaceae (potato, tobacco, tomato, peppers), various floral crops as well as various trees such as poplar or apple, nut crops or vine plants such as grapes. See, e.g., Ammirato, 1984; Shimamoto, 1989; Fromm, 1990; Vasil, 1990.

The following examples are provided to better elucidate the practice of the present invention and should not be intrepreted in any way to limit the scope of the present invention. Those skilled in the art will recognize that various modifications, truncations, etc. can be made to the methods and genes described herein while not departing from the spirit and scope of the present invention.

In the examples that follow, EPSPS activity in plants is assayed by the following method. Tissue samples were collected and immediately frozen in liquid nitrogen. One gram of young leaf tissue was frozen in a mortar with liquid nitrogen and ground to a fine powder with a pestle. The powder was then transferred to a second mortar, extraction buffer was added (1 ml/gram), and the sample was ground for an additional 45 seconds. The extraction buffer for canola consists of 100 mM Tris, 1 mM EDTA, 10% glycerol, 5 mM DTT, 1 mM BAM, 5 mM ascorbate, 1.0 mg/ml BSA, pH 7.5 (4° C.). The extraction buffer for tobacco consists of 100 mM Tris, 10 mM EDTA, 35 mM KCl, 20% glycerol, 5 mM DTT, 1 mM BAM, 5 mM ascorbate, 1.0 mg/ml BSA, pH 7.5 (4° C.). The mixture was transferred to a microfuge tube and centrifuged for 5 minutes. The resulting supernatants were desalted on spin G-50 (Pharmacia) columns, previously equilibrated with extraction buffer (without BSA), in 0.25 ml aliquots. The desalted extracts were assayed for EPSP synthase activity by radioactive HPLC assay. Protein concentrations in samples were determined by the BioRad microprotein assay with BSA as the standard.

Protein concentrations were determined using the BioRad Microprotein method, BSA was used to generate a standard curve ranging from 2–24 μg. Either 800 μl of standard or diluted sample was mixed with 200 μl of concentrated BioRad Bradford reagent. The samples were vortexed and read at A(595) after ~5 minutes and compared to the standard curve.

EPSPS enzyme assays contained HEPES (50 mM), shikimate-3-phosphate (2 mM), $NH_4$ molybdate (0.1 mM) and KF (5 mM), with or without glyphosate (0.5 or 1.0 mM). The assay mix (30 μl) and plant extract (10 μl) were preincubated for 1 minute at 25° C. and the reactions were initiated by adding $^{14}$C-PEP (1 mM). The reactions were quenched after 3 minutes with 50 μl of 90% EtOH/0.1M HOAc, pH 4.5. The samples were spun at 6000 rpm and the resulting supernatants were analyzed for $^{14}$C-EPSP production by HPLC. Percent resistant EPSPS is calculated from the EPSPS activities with and without glyphosate.

The percent conversion of $^{14}$C labeled PEP to $^{14}$C EPSP was determined by HPLC radioassay using a C18 guard column (Brownlee) and an $AX_{100}$ HPLC column (0.4×25 cm, Synchropak) with 0.28M isocratic potassium phosphate eluant, pH 6.5, at 1 ml/min. Initial velocities were calculated by multiplying fractional turnover per unit time by the initial concentration of the labeled substrate (1 mM). The assay was linear with time up to ~3 minutes and 30% turnover to EPSPS. Samples were diluted with 10 mM Tris, 10% glycerol, 10 mM DTT, pH 7.5 (4° C.) if necessary to obtain results within the linear range.

In these assays DL-dithiotheitol (DTT), benzamidine (BAM), and bovine serum albumin (BSA, essentially globulin free) were obtained from Sigma. Phosphoenolpyruvate (PEP) was from Boehringer Mannheim and phosphoenol[1-$^{14}$C]pyruvate (28 mCi/mmol) was from Amersham.

EXAMPLES

Example 1

Transformed tobacco plants have been generated with a number of the Class II EPSPS gene vectors containing the CP4 EPSPS DNA sequence as described above with suitable expression of the EPSPS. These transformed plants exhibit glyphosate tolerance imparted by the Class II CP4 EPSPS.

Transformation of tobacco employs the tobacco leaf disc transformation protocol which utilizes healthy leaf tissue about 1 month old. After a 15–20 minutes surface sterilization with 10% Clorox plus a surfactant, the leaves are rinsed 3 times in sterile water. Using a sterile paper punch, leaf discs are punched and placed upside down on MS104 media (MS salts 4.3 g/l, sucrose 30 g/l, B5vitamins 500×2 ml/l, NAA 0.1 mg/l, and BA 1.0 mg/l) for a 1 day preculture.

The discs are then inoculated with an overnight culture of a disarmed Agrobacterium ABI strain containing the subject vector that had been diluted 1/5 (i.e.: about 0.6 OD). The inoculation is done by placing the discs in centrifuge tubes with the culture. After 30 to 60 seconds, the liquid is drained off and the discs were blotted between sterile filter paper. The discs are then placed upside down on MS104 feeder plates with a filter disc to co-culture.

After 2–3 days of co-culture, the discs are transferred, still upside down, to selection plates with MS104 media. After 2–3 weeks, callus tissue formed, and individual clumps are separated from the leaf discs. Shoots are cleanly cut from the callus when they are large enough to be distinguished from stems. The shoots are placed on hormone-free rooting media (MSO: MS salts 4.3 g/l, sucrose 30 g/l, and B5 vitamins 500×2 ml/l) with selection for the appropriate antibiotic resistance. Root formation occurred in 1–2 weeks. Any leaf callus assays are preferably done on rooted shoots while still sterile. Rooted shoots are then placed in soil and kept in a high humidity environment (i.e.: plastic containers or bags). The shoots are hardened off by gradually exposing them to ambient humidity conditions.

Expression of CP4 EPSPS protein in transformed plants

Tobacco cells were transformed with a number of plant vectors containing the native CP4 EPSPS gene, and using different promoters and/or CTP's. Preliminary evidence for expression of the gene was given by the ability of the leaf tissue from antibiotic selected transformed shoots to recallus on glyphosate. In some cases, glyphosate-tolerant callus was selected directly following transformation. The level of expression of the CP4 EPSPS was determined by the level of glyphosate-tolerant EPSPS activity (assayed in the presence of 0.5 mM glyphosate) or by Western blot analysis using a goat anti-CP4 EPSPS antibody. The Western blots were quantitated by densitometer tracing and comparison to a standard curve established using purified CP4 EPSPS. These data are presented as % soluble leaf protein. The data from a number of transformed plant lines and transformation vectors are presented in Table VI below.

TABLE VI

Expression of CP4 EPSPS in transformed tobacco tissue

| Vector | Plant # | CP4 EPSPS** (% leaf protein) |
|---|---|---|
| pMON17110 | 25313 | 0.02 |
| pMON17110 | 25329 | 0.04 |
| pMON17116 | 25095 | 0.02 |
| pMON17119 | 25106 | 0.09 |
| pMON17119 | 25762 | 0.09 |
| pMON17119 | 25767 | 0.03 |

**Glyphosate-tolerant EPSPS activity was also demonstrated in leaf extracts for these plants.

Glyphosate tolerance has also been demonstrated at the whole plant level in transformed tobacco plants. In tobacco, $R_o$ transformants of CTP2-CP4 EPSPS were sprayed at 0.4 lb/acre (0.448 kg/hectare), a rate sufficient to kill control non-transformed tobacco plants corresponding to a rating of 3, 1 and 0 at days 7, 14 and 28, respectively, and were analyzed vegetatively and reproductively (Table VII).

TABLE VII

Glyphosate tolerance in $R_o$ tobacco CP4 transformants*

| | Score** | | | |
|---|---|---|---|---|
| | Vegetative | | | |
| Vector/Plant # | day 7 | day 14 | day 28 | Fertile |
| pMON17110/25313 | 6 | 4 | 2 | no |
| pMON17110/25329 | 9 | 10 | 10 | yes |
| pMON17119/25106 | 9 | 9 | 10 | yes |

*Spray rate = 0.4 lb/acre (0.448 kg/hectare)

**Plants are evaluated on a numerical scoring system of 0–10 where a vegetative score of 10 represents no damage relative to nonsprayed controls and 0 represents a dead plant. Reproductive scores (Fertile) are determined at 28 days after spraying and are evaluated as to whether or not the plant is fertile.

Example 2A

Canola plants were transformed with the pMON17110, pMON17116, and pMON17131 vectors and a number of plant lines of the transformed canola were obtained which exhibit glyphosate tolerance.

Plant Material

Seedlings of Brassica napus cv Westar were established in 2 inch (~5 cm) pots containing Metro Mix 350. They were grown in a growth chabmer at 24° C., 16/8 hour photoperiod, light intensity of 400 $\mu Em^{-2}sec^{-1}$ (HID lamps). They were fertilized with Peters 20-10-20 General Purpose Special. After 2½ weeks they were transplanted to 6 inch (~15 cm) pots and grown in a growth chamber at 15°/10° C. day/night temperature, 16/8 hour photoperiod, light intensity of 800 $uEm^{-2}sec^{-1}$ (HID lamps). They were fertilized with Peters 15-30-15 Hi-Phos Special.

Transformation/Selection/Regeneration

Four terminal internodes from plants just prior to bolting or in the process of bolting but before flowering were removed and surfaced sterilized in 70% v/v ethanol for 1 minute, 2% w/v sodium hypochlorite for 20 minutes and rinsed 3 times with sterile deionized water. Stems with leaves attached could be refrigerated in moist plastic bags for up to 72 hours prior to sterilization. Six to seven stem segments were cut into 5 mm discs with a Redco Vegetable Slicer 200 maintaining orientation of basal end.

The Agrobacterium was grown overnight on a rotator at 24° C. in 2 mls of Luria Broth containing 50 mg/l kanamycin, 24 mg/l chloramphenicol and 100 mg/l spectinomycin. A 1:10 dilution was made in MS (Murashige and Skoog) media giving approximately $9\times10^8$ cells per ml. This was confirmed with optical density readings at 660 mu. The stem discs (explants) were inoculated with 1.0 ml of Agrobacterium and the excess was aspirated from the explants.

The explants were placed basal side down in petri plates containing 1/10× standard MS salts, B5 vitamins, 3% sucrose, 0.8% agar, pH 5.7, 1.0 mg/l 6-benzyladenine (BA). The plates were layered with 1.5 ml of media containing MS salts, B5 vitamins, 3% sucrose, pH 5.7, 4.0 mg/l p-chlorophenoxyacetic acid, 0.005 mg/l kinetin and covered with sterile filter paper.

Following a 2 to 3 day co-culture, the explants were transferred to deep dish petri plates containing MS salts, B5 vitamins, 3% sucrose, 0.8% agar, pH 5.7, 1 mg/l BA, 500 mg/l carbenicillin, 50 mg/l cefotaxime, 200 mg/l kanamycin or 175 mg/l gentamicin for selection. Seven explants were placed on each plate. After 3 weeks they were transferred to fresh media, 5 explants per plate. The explants were cultured in a growth room at 25° C., continuous light (Cool White).

Expression Assay

After 3 weeks shoots were excised from the explants. Leaf recallusing assays were initiated to confirm modification of $R_o$ shoots. Three tiny pieces of leaf tissue were placed on recallusing media containing MS salts, B5 vitamins, 3% sucrose, 0.8% agar, pH 5.7, 5.0 mg/l BA, 0.5 mg/l naphthalene acetic acid (NAA), 500 mg/l carbenicillin, 50 mg/l cefotaxime and 200 mg/l kanamycin or gentamicin or 0.5 mM glyphosate. The leaf assays were incubated in a growth room under the same conditions as explant culture. After 3 weeks the leaf recallusing assays were scored for herbicide tolerance (callus or green leaf tissue) or sensitivity (bleaching).

Transplantation

At the time of excision, the shoot stems were dipped in Rootone® and placed in 2 inch (~5 cm) pots containing Metro-Mix 350 and placed in a closed humid environment. They were placed in a growth chamber at 24° C., 16/8 hour photoperiod, 400 $uEm^{-1}sec^{-2}$(HID lamps) for a hardening-off period of approximately 3 weeks.

The seed harvested from $R_o$ plants is $R_1$ seed which gives rise to $R_1$ plants. To evaluate the glyphosate tolerance of an $R_o$ plant, its progeny are evaluated. Because an $R_o$ plant is assumed to be hemizygous at each insert location, selfing results in maximum genotypic segregation in the $R_1$. Because each insert acts as a dominant allele, in the absence of linkage and assuming only one hemizygous insert is required for tolerance expression, one insert would segregate 3:1, two inserts, 15:1, three inserts 63:1, etc. Therefore, relatively few $R_1$ plants need be grown to find at least one resistant phenotype.

Seed from an $R_o$ plant is harvested, threshed, and dried before planting in a glyphosate spray test. Various techniques have been used to grow the plants for $R_1$ spray evaluations. Tests are conducted in both greenhouses and growth chambers. Two planting systems are used; ~10 cm pots or plant trays containing 32 or 36 cells. Soil used for planting is either Metro 350 plus three types of slow release fertilizer or plant Metro 350. Irrigation is either overhead in greenhouses or sub-irrigation in growth chambers. Fertilizer is applied as required in irrigation water. Temperature regimes appropriate for canola were maintained. A sixteen hour photoperiod was maintained. At the onset of flowering, plants are transplanted to ~15 cm pots for seed production.

A spray "batch" consists of several sets of $R_1$ progenies all sprayed on the same date. Some batches may also include evaluations of other than $R_1$ plants. Each batch also includes sprayed and unsprayed non-transgenic genotypes representing the genotypes in the particular batch which were putatively transformed. Also included in a batch is one or more non-segregating transformed genotypes previously identified as having some resistance.

Two-six plants from each individual $R_o$ progeny are not sprayed and serve as controls to compare and measure the glyphosate tolerance, as well as to assess any variability not induced by the glyphosate. When the other plants reach the 2–4 leaf stage, usually 10 to 20 days after planting, glyphosate is applied at rates varying from 0.28 to 1.12 kg/ha, depending on objectives of the study. Low rate technology using low volumes has been adopted. A laboratory track sprayer has been calibrated to deliver a rate equivalent to field conditions.

A scale of 0 to 10 is used to rate the sprayed plants for vegetative resistance. The scale is relative to the unsprayed plants from the same $R_o$ plant. A 0 is death, while a 10 represents no visible difference from the unsprayed plant. A higher number between 0 and 10 represents progressively less damage as compared to the unsprayed plant. Plants are scored at 7, 14, and 28 days after treatment (DAT), or until bolting, and a line is given the average score of the sprayed plants within an $R_o$ plant family.

Six integers are used to qualitatively describe the degree of reproductive damage from glyphosate:

0: No floral bud development

2: Floral buds present, but aborted prior to opening

4: Flowers open, but no anthers, or anthers fail to extrude past petals

6: Sterile anthers

8: Partially sterile anthers

10: Fully fertile flowers

Plants are scored using this scale at or shortly after initiation of flowering, depending on the rate of floral structure development.

Expression of EPSPS in Canola

After the 3 week period, the transformed canola plants were assayed for the presence of glyphosate-tolerant EPSPS activity (assayed in the presence of glyphosate at 0.5 mM). The results are shown in Table VIII.

TABLE VIII

Expression of CP4 EPSPS in transformed Canola plants

| | Plant # | % resistant EPSPS activity of Leaf extract (at 0.5 mM glyphosate) |
|---|---|---|
| Vector Control | | 0 |
| pMON17110 | 41 | 47 |
| pMON17110 | 52 | 28 |
| pMON17110 | 71 | 82 |
| pMON17110 | 104 | 75 |
| pMON17110 | 172 | 84 |
| pMON17110 | 177 | 85 |
| pMON17110 | 252 | 29* |
| pMON17110 | 350 | 49 |
| pMON17116 | 40 | 25 |
| pMON17116 | 99 | 87 |
| pMON17116 | 175 | 94 |
| pMON17116 | 178 | 43 |
| pMON17116 | 182 | 18 |
| pMON17116 | 252 | 69 |
| pMON17116 | 298 | 44* |
| pMON17116 | 332 | 89 |
| pMON17116 | 383 | 97 |
| pMON17116 | 395 | 52 |

*assayed in the presence of 1.0 mM glyphosate $R_1$ transformants of canola were then grown in a growth chamber and sprayed with glyphosate at 0.56 kg/ha (kilogram/hectare) and rated vegetatively. These results are shown in Table IXA–IXC. It is to be noted that expression of glyphosate resistant EPSPS in all tissues is preferred to observe optimal glyphosate tolerance phenotype in these transgenic plants. In the Tables below, only expression results obtained with leaf tissue are described.

TABLE IXA

Glyphosate tolerance in Class II EPSPS canola $R_1$ transformants (pMON17110 = P-E35S; pMON17116 = P-FMV35S; R1 plants; Spray rate = 0.56 kg/ha)

| | % resistant | Vegetative Score** | |
|---|---|---|---|
| Vector/Plant No. | EPSPS* | day 7 | day 14 |
| Control Westar | 0 | 5 | 3 |
| pMON17110/41 | 47 | 6 | 7 |

TABLE IXA-continued

Glyphosate tolerance in Class II EPSPS canola $R_1$ transformants (pMON17110 = P-E35S; pMON17116 = P-FMV35S; R1 plants; Spray rate = 0.56 kg/ha)

| Vector/Plant No. | % resistant EPSPS* | Vegetative Score** day 7 | Vegetative Score** day 14 |
|---|---|---|---|
| pMON17110/71 | 82 | 6 | 7 |
| pMON17110/177 | 85 | 9 | 10 |
| pMON17116/40 | 25 | 9 | 9 |
| pMON17116/99 | 87 | 9 | 10 |
| pMON17116/175 | 94 | 9 | 10 |
| pMON17116/178 | 43 | 6 | 3 |
| pMON17116/182 | 18 | 9 | 10 |
| pMON17116/383 | 97 | 9 | 10 |

TABLE IXB

Glyphosate tolerance in Class II EPSPS canola $R_1$ transformants (pMON17131 = P-FWV35S; R1 plants; Spray rate = 0.84 kg/ha)

| Vector/Plant No. | Vegetative score** day 14 | Reproductive score day 28 |
|---|---|---|
| 17131/78 | 10 | 10 |
| 17131/102 | 9 | 10 |
| 17131/115 | 9 | 10 |
| 17131/116 | 9 | 10 |
| 17131/157 | 9 | 10 |
| 17131/169 | 10 | 10 |
| 17131/255 | 10 | 10 |
| control Westar | 1 | 0 |

TABLE IXC

Glyphosate tolerance in Class I EPSPS canola transformants (P-E35S; R2 Plants; Spray rate = 0.28 kg/ha)

| Vector/Plant No. | % resistant EPSPS* | Vegetative Score** day 7 | Vegetative Score** day 14 |
|---|---|---|---|
| Control Westar | 0 | 4 | 2 |
| pMON899/715 | 96 | 5 | 6 |
| pMON899/744 | 95 | 8 | 8 |
| pMON899/794 | 86 | 6 | 4 |
| pMON899/818 | 81 | 7 | 8 |
| pMON899/885 | 57 | 7 | 6 |

*% resistant EPSPS activity in the presence of 0.5 mM glyphosate
**A vegetative score of 10 indicates no damage, a score of 0 is given to a dead plant.

The data obtained for the Class II EPSPS transformants may be compared to glyphosate-tolerant Class I EPSP transformants in which the same promoter is used to express the EPSPS genes and in which the level of glyphosate-tolerant EPSPS activity was comparable for the two types of transformants. A comparison of the data of pMON17110 [in Table IXA] and pMON17131 [Table IXB] with that for pMON899 [in Table IXC; the Class I gene in pMON899 is that from A. thaliana {Klee et al., 1987} in which the glycine at position 101 was changed to an alanine] illustrates that the Class II EPSPS is at least as good as that of the Class I EPSPS. An improvement in vegetative tolerance of Class II EPSPS is apparent when one takes into account that the Class II plants were sprayed at twice the rate and were tested as $R_1$ plants.

Example 2B

The construction of two plant transformation vectors and the transformation procedures used to produce glyphosate-tolerant canola plants are described in this example The vectors, pMON17209 and pMON17237, were used to generate transgenic glyphosate-tolerant canola lines. The vectors each contain the gene encoding the 5-enol-pyruvyl-shikimate-3-phosphate synthase (EPSPS) from Agrobacterium sp. strain CP4. The vectors also contain either the gox gene encoding the glyphosate oxidoreductase enzyme (GOX) from Achromobacter sp. strain LBAA (Barry et al., 1992) or the gene encoding a variant of GOX (GOX v.247) which displays improved catalytic properties. These enzymes convert glyphosate to aminomethylphosphonic acid and glyoxylate and protect the plant from damage by the metabolic inactivation of glyphosate. The combined result of providing an alternative, resistant EPSPS enzyme and the metabolism of glyphosate produces transgenic plants with enhanced tolerance to glyphosate Molecular biology techniques. In general, standard molecular biology and microbial genetics approaches were employed (Maniatis et al., 1982). Site-directed mutageneses were carried out as described by Kunkel et al. (1987). Plant-preferred genes were synthesized and the sequence confirmed.

Plant transformation vectors. The following describes the general features of the plant transformation vectors that were modified to form vectors pMON17209 and pMON17237. The Agrobacterium mediated plant transformation vectors contain the following well-characterized DNA segments which are required for replication and function of the plasmids (Rogers and Klee, 1987; Klee and Rogers, 1989). The first segment is the 0.45 kb ClaI-DraI fragment from the pTi15955 octopine Ti plasmid which contains the T-DNA left border region (Barker et al., 1983). It is joined to the 0.75 kb origin of replication (oriV) derived from the broad-host range plasmid RK2 (Stalker et al., 1981). The next segment is the 3.1 kb SalI-PvuI segment of $pBR_{322}$ which provides the origin of replication for maintenance in E. coli and the born site for the conjugational transfer into the Agrobacterium turnefaciens cells (Bolivar et al., 1977). This is fused to the 0.93 kb fragment isolated from transposon Tn7 which encodes bacterial spectinomycin and streptomycin resistance (Fling et al., 1985), a determinant for the selection of the plasmids in E. coli and Agrobacterium. It is fused to the 0.36 kb PvuI-BclI fragment from the pTiT37 plasmid which contains the nopaline-type T-DNA right border region (Fraley et al., 1985). Several chimeric genes engineered for plant expression can be introduced between the Ti right and left border regions of the vector. In addition to the elements described above, this vector also includes the 35S promoter/NPTII/NOS 3' cassette to enable selection of transformed plant tissues on kanamycin (Klee and Rogers, 1989; Fraley et al., 1983; and Odell, et al., 1985) within the borders. An "empty" expression cassette is also present between the borders and consists of the enhanced E35S promoter (Kay et al., 1987), the 3' region from the small subunit of RUBP carboxylase of pea (E9) (Coruzzi et al., 1984; Morelli et al., 1986), and a number of restriction enzyme sites that may be used for the cloning of DNA sequences for expression in plants. The plant transformation system based on Agrobacterium tumefaciens delivery has been reviewed (Klee and Rogers, 1989; Fraley et al., 1986). The Agrobacterium mediated transfer and integration of the vector T-DNA into the plant chromosome results in the expression of the chimeric genes conferring the desired phenotype in plants.

Bacterial Inoculum. The binary vectors are mobilized into Agrobacterium tumefaciens strain ABI by the triparental conjugation system using the helper plasmid pRK2013 (Ditta et al., 1980). The ABI strain contains the disarmed pTiC58 plasmid pMP90RK (Koncz and Schell, 1986) in the chloramphenicol resistant derivative of the Agrobacterium tumefaciens strain A208.

Transformation procedure. Agrobacterium inocula were grown overnight at 28° C. in 2 ml of LBSCK (LBSCK is made as follows: LB liquid medium [1 liter volume]=10 g NaCl; 5 g Yeast Extract; 10 g tryptone; pH 7.0, and autoclave for 22 minutes. After autoclaving, add spectinomycin (50 mg/ml stock)—2 ml, kanamycin (50 mg/ml stock)—1 ml, and chloramphenicol (25 mg/ml stock)—1 ml.). One day prior to inoculation, the Agrobacterium was subcultured by inoculating 200 μl into 2 ml of fresh LBSCK and grown overnight. For inoculation of plant material, the culture was diluted with MSO liquid medium to an $A_{660}$ range of 0.2–0.4.

Seedlings of Brassica napus cv. Westar were grown in Metro Mix 350 (Huminert Seed Co., St. Louis, Mo.) in a growth chamber with a day/night temperature of 15°/10° C., relative humidity of 50%, 16h/8h photoperiod, and at a light intensity of 500 μmol $m^{-2}$ $sec^{-1}$. The plants were watered daily (via sub-irrigation) and fertilized every other day with Peter's 15:30:15 (Fogelsville, Pa.).

In general, all media recipes and the transformation protocol follow those in Fry et al. (1987). Five to six week-old Westar plants were harvested when the plants had bolted (but prior to flowering), the leaves and buds were removed, and the 4–5 inches of stem below the flower buds were used as the explant tissue source. Following sterilization with 70% ethanol for 1 min and 38% Clorox for 20 min, the stems were rinsed three times with sterile water and cut into 5 mm-long segments (the orientation of the basal end of the stem segments was noted). The plant material was incubated for 5 minutes with the diluted Agrobacterium culture at a rate of 5 ml of culture per 5 stems. The suspension of bacteria was removed by aspiration and the explants were placed basal side down—for an optimal shoot regeneration response—onto co-culture plates (1/10 MSO solid medium with a 1.5 ml TXD (tobacco xanthi diploid) liquid medium overlay and covered with a sterile 8.5 cm filter paper). Fifty-to-sixty stem explants were placed onto each co-culture plate.

After a 2 day co-culture period, stem explants were moved onto MS medium containing 750 mg/l carbenicillin, 50 mg/l cefotaxime, and 1 mg/l BAP (benzylaminopurine) for 3 days. The stem explants were then placed for two periods of three weeks each, again basal side down and with 5 explants per plate, onto an MS/0.1 mM glyphosate, selection medium (also containing carbenicillin, cefotaxime, and BAP (The glyphosate stock [0.5M] is prepared as described in the following: 8.45 g glyphosate [analytical grade] is dissolved in 50 ml deionized water, adding KOH pellets to dissolve the glyphosate, and the volume is brought to 100 ml following adjusting the pH to 5.7. The solution is filter-sterilized and stored at 4° C.). After 6 weeks on this glyphosate selection medium, green, normally developing shoots were excised from the stem explants and were placed onto fresh MS medium containing 750 mg/l carbenicillin, 50 mg/l cefotaxime, and 1 mg/l BAP, for further shoot development. When the shoots were 2–3 inches tall, a fresh cut at the end of the stem was made, the cut end was dipped in Root-tone, and the shoot was placed in Metro Mix 350 soil and allowed to harden-off for 2–3 weeks.

Construction of Canola transformation vector pMON17209. The EPSPS gene was isolated originally from Agrobacterium sp. strain CP4 and expresses a highly tolerant enzyme. The original gene contains sequences that could be inimical to high expression of the gene in some plants. These sequences include potential polyadenylation sites that are often A+T rich, a higher G+C % than that frequently found in dicotyledonous plant genes (63% versus ~50%), concentrated stretches of G and C residues, and codons that may not used frequently in dicotyledonous plant genes. The high G+C % in the CP4 EPSPS gene could also result in the formation of strong hairpin structures that may affect expression or stability of the RNA. A plant preferred version of the gene was synthesized and used for these vectors. This coding sequence was expressed in E. coli from a PRecA-gene10L vector (Olins et al., 1988) and the EPSPS activity was compared with that from the native CP4 EPSPS gene. The $appK_m$ for PEP for the native and synthetic genes was 11.8 μM and 12.7 μM, respectively, indicating that the enzyme expressed from the synthetic gene was unaltered. The N-terminus of the coding sequence was then mutagenized to place an SphI site (GCATGC) at the ATG to permit the construction of the CTP2-CP4 synthetic fusion for chloroplast import. This change had no apparent effect on the in vivo activity of CP4 EPSPS in E. coli as judged by complementation of the aroA mutant. A CTP-CP4 EPSPS fusion was constructed between the Arabidopsis thaliana EPSPS CTP (Klee et al., 1987) and the CP4 EPSPS coding sequences. The Arabidopsis CTP was engineered by site-directed mutagenesis to place a SphI restriction site at the CTP processing site. This mutagenesis replaced the Glu-Lys at this location with Cys-Met. The CTP2-CP4 EPSPS fusion was tested for import into chloroplasts isolated from Lactuca sativa using the methods described previously (della-Cioppa et al., 1986; 1987).

The GOX gene that encodes the glyphosate metabolizing enzyme glyphosate oxidoreductase (GOX) was cloned originally from Achromobacter sp. strain LBAA (Hallas et al., 1988; Barry et al., 1992). The gox gene from strain LBAA was also resynthesized in a plant-preferred sequence version and in which many of the restriction sites were removed (PCT Appln. No. WO 92/00377). The GOX protein is targeted to the plastids by a fusion between the C-terminus of a CTP and the N-terminus of GOX. A CTP, derived from the SSU1A gene from Arabidopsis thaliana (Timko et al., 1988) was used. This CTP (CTP1) was constructed by a combination of site-directed mutageneses. The CTP1 is made up of the SSU1A CTP (amino acids 1–55), the first 23 amino acids of the mature SSU1A protein (56–78), a serine residue (amino acid 79), a new segment that repeats amino acids 50 to 56 from the CTP and the first two from the mature protein (amino acids 80–87), and an alanine and methionine residue (amino acid 88 and 89). An NcoI restriction site if located at the 3' end (spans the Met89 codon) to facilitate the construction of precise fusions to the 5' of GOX. At a later stage, a BglII site was introduced upstream of the N-terminus of the SSU1A sequences to facilitate the introduction of the fusions into plant transformation vectors. A fusion was assembled between CTP1 and the synthetic GOX gene.

Figure 24:
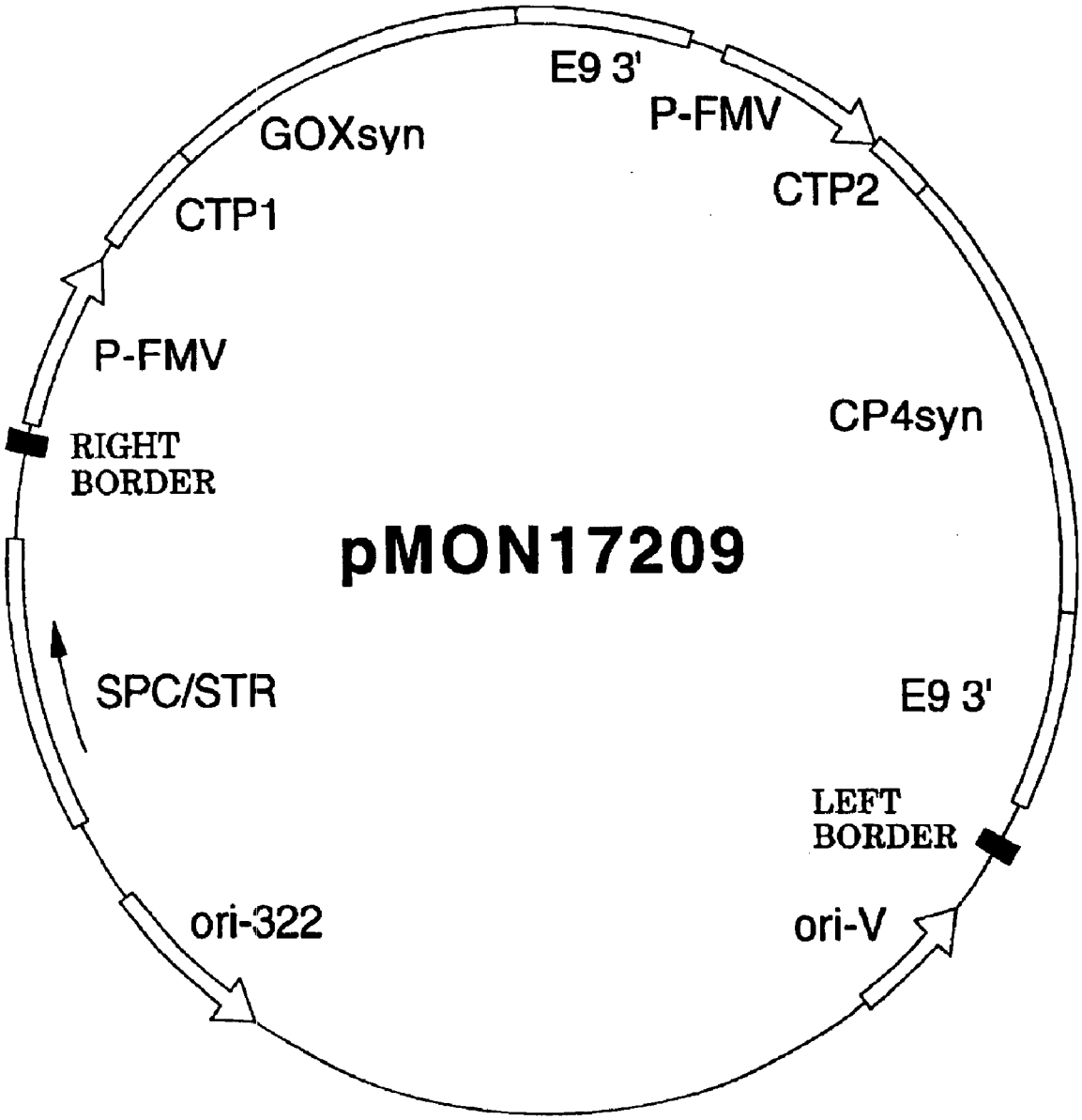
FIG. 24 a plasmid map of canola plant transformation/expression vector pMON17209.

The CP4 EPSPS and GOX genes were combined to form pMON17209 as described in the following. The CTP2-CP4 EPSPS fusion was assembled and inserted between the constitutive FMV35S promoter (Gowda et al., 1989; Richins et al., 1987) and the E9 3' region (Coruzzi et al., 1984; Morelli et al., 1985) in a pUC vector (Yannisch-Perron et al., 1985; Vieira and Messing, 1987) to form pMON17190; this completed element may then be moved easily as a NotI-NotI fragment to other vectors. The CTP1-GOX fusion was also assembled in a pUC vector with the FMV35S promoter. This element was then moved as a HindIII-BamHI fragment into the plant transformation vector pMON10098 and joined to the E9 3' region in the process. The resultant vector pMON17193 has a single NotI site into which the FMV 35S/CTP2-CP4 EPSPS/E9 3' element from pMON17190 was cloned to form pMON17194. The kanamycin plant transformation selection cassette (Fraley et al., 1985) was then deleted from pMON17194, by cutting with XhoI and re-ligating, to form the pMON17209 vector (FIG. 24).

Figure 25:
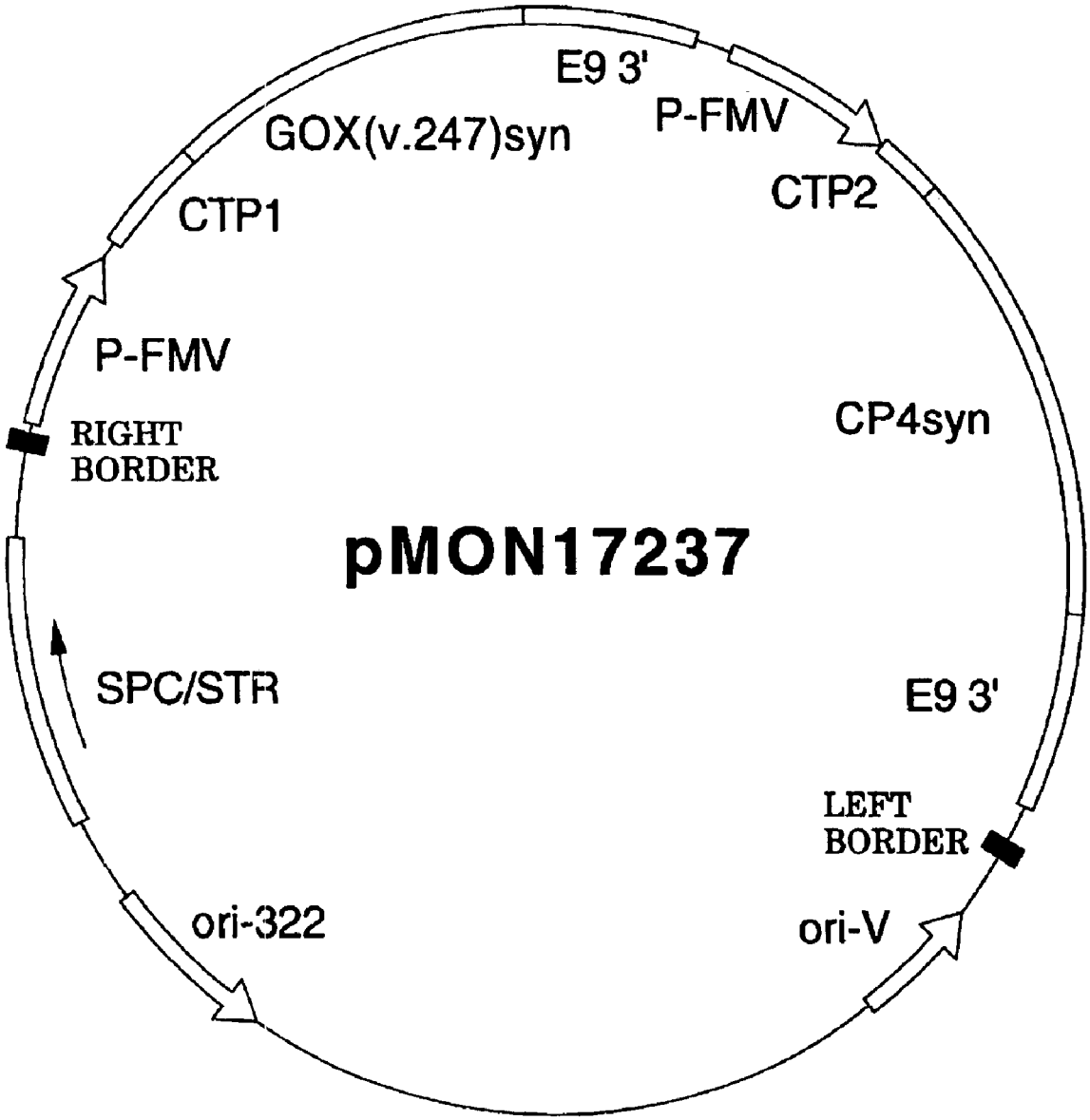
FIG. 25 a plasmid map of canola plant transformation/expression vector pMON17237.

Construction of Canola transformation vector pMON17237. The GOX enzyme has an apparent Km for glyphosate [appK$_m$(glyphosate)] of ~25 mM. In an effort to improve the effectiveness of the glyphosate metabolic rate in plants, a variant of GOX has been identified in which the appK$_m$(glyphosate) has been reduced approximately 10-fold; this variant is referred to as GOX v.247 and the sequence differences between it and the original plant-preferred GOX are illustrated in PCT Appln. No. WO 92/00377. The GOX v.247 coding sequence was combined with CTP1 and assembled with the FMV35S promoter and the E9 3' by cloning into the pMON17227 plant transformation vector to form pMON17241. In this vector, effectively, the CP4 EPSPS was replaced by GOX v.247. The pMON17227 vector had been constructed by replacing the CTP1-GOX sequence in pMON17193 with those for the CTP2-CP4 EPSPS, to form pMON17199 and followed by deleting the kanamycin cassette (as described above for pMON17209). The pMON17237 vector (FIG. 25) was then completed by cloning the FMV35S/CTP2-CP4 EPSPS/E9 3' element as a NotI-NotI fragment into pMON17241.

Example 3

Soybean plants were transformed with the pMON13640 (FIG. 15) vector and a number of plant lines of the transformed soybean were obtained which exhibit glyphosate tolerance.

Soybean plants are transformed with pMON13640 by the method of microprojectile injection using particle gun technology as described in Christou et al. (1988). The seed harvested from $R_o$ plants is $R_1$ seed which gives rise to $R_1$ plants. To evaluate the glyphosate tolerance of an $R_o$ plant, its progeny are evaluated. Because an $R_o$ plant is assumed to be hemizygous at each insert location, selfing results in maximum genotypic segregation in the $R_1$. Because each insert acts as a dominant allele, in the absence of linkage and assuming only one hemizygous insert is required for tolerance expression, one insert would segregate 3:1, two inserts, 15:1, three inserts 63:1, etc. Therefore, relatively few $R_1$ plants need be grown to find at least one resistant phenotype.

Seed from an $R_o$ soybean plant is harvested, and dried before planting in a glyphosate spray test. Seeds are planted into 4 inch (~5 cm) square pots containing Metro 350. Twenty seedlings from each $R_o$ plant is considered adequate for testing. Plants are maintained and grown in a greenhouse environment. A 12.5–14 hour photoperiod and temperatures of 30° C. day and 24° C. night is regulated. Water soluble Peters Pete Lite fertilizer is applied as needed.

A spray "batch" consists of several sets of $R_1$ progenies all sprayed on the same date. Some batches may also include evaluations of other than $R_1$ plants. Each batch also includes sprayed and unsprayed non-transgenic genotypes representing the genotypes in the particular batch which were putatively transformed. Also included in a batch is one or more non-segregating transformed genotypes previously identified as having some resistance.

One to two plants from each individual $R_o$ progeny are not sprayed and serve as controls to compare and measure the glyphosate tolerance, as well as to assess any variability not induced by the glyphosate. When the other plants reach the first trifoliate leaf stage, usually 2–3 weeks after planting, glyphosate is applied at a rate equivalent of 128 oz./acre (8.895 kg/ha) of Roundup®. A laboratory track sprayer has been calibrated to deliver a rate equivalent to those conditions.

A vegetative score of 0 to 10 is used. The score is relative to the unsprayed progenies from the same $R_o$ plant. A 0 is death, while a 10 represents no visible difference from the unsprayed plant. A higher number between 0 and 10 represents progressively less damage as compared to the unsprayed plant. Plants are scored at 7, 14, and 28 days after treatment (DAT). The data from the analysis of one set of transformed and control soybean plants are described on Table X and show that the CP4 EPSPS gene imparts glyphosate tolerance in soybean also.

TABLE X

Glyphosate tolerance in Class II EPSPS soybean transformants
(P-H35S, P-FMV35S; R0 plants; Spray rate = 128 oz./acre)

| | Vegetative score | | |
|---|---|---|---|
| Vector/Plant No. | day 7 | day 14 | day 28 |
| 13640/40-11 | 5 | 6 | 7 |
| 13640/40-3 | 9 | 10 | 10 |
| 13640/40-7 | 4 | 7 | 7 |
| control A5403 2 | 1 | 0 | |
| control A5403 1 | 1 | 0 | |

Example 4

The CP4 EPSPS gene may be used to select transformed plant material directly on media containing glyphosate. The ability to select and to identify transformed plant material depends, in most cases, on the use of a dominant selectable marker gene to enable the preferential and continued growth of the transformed tissues in the presence of a normally inhibitory substance. Antibiotic resistance and herbicide tolerance genes have been used almost exclusively as such dominant selectable marker genes in the presence of the corresponding antibiotic or herbicide. The nptII/kanamycin selection scheme is probably the most frequently used. It has been demonstrated that CP4 EPSPS is also a useful and perhaps superior selectable marker/selection scheme for producing and identifying transformed plants.

Figure 16:
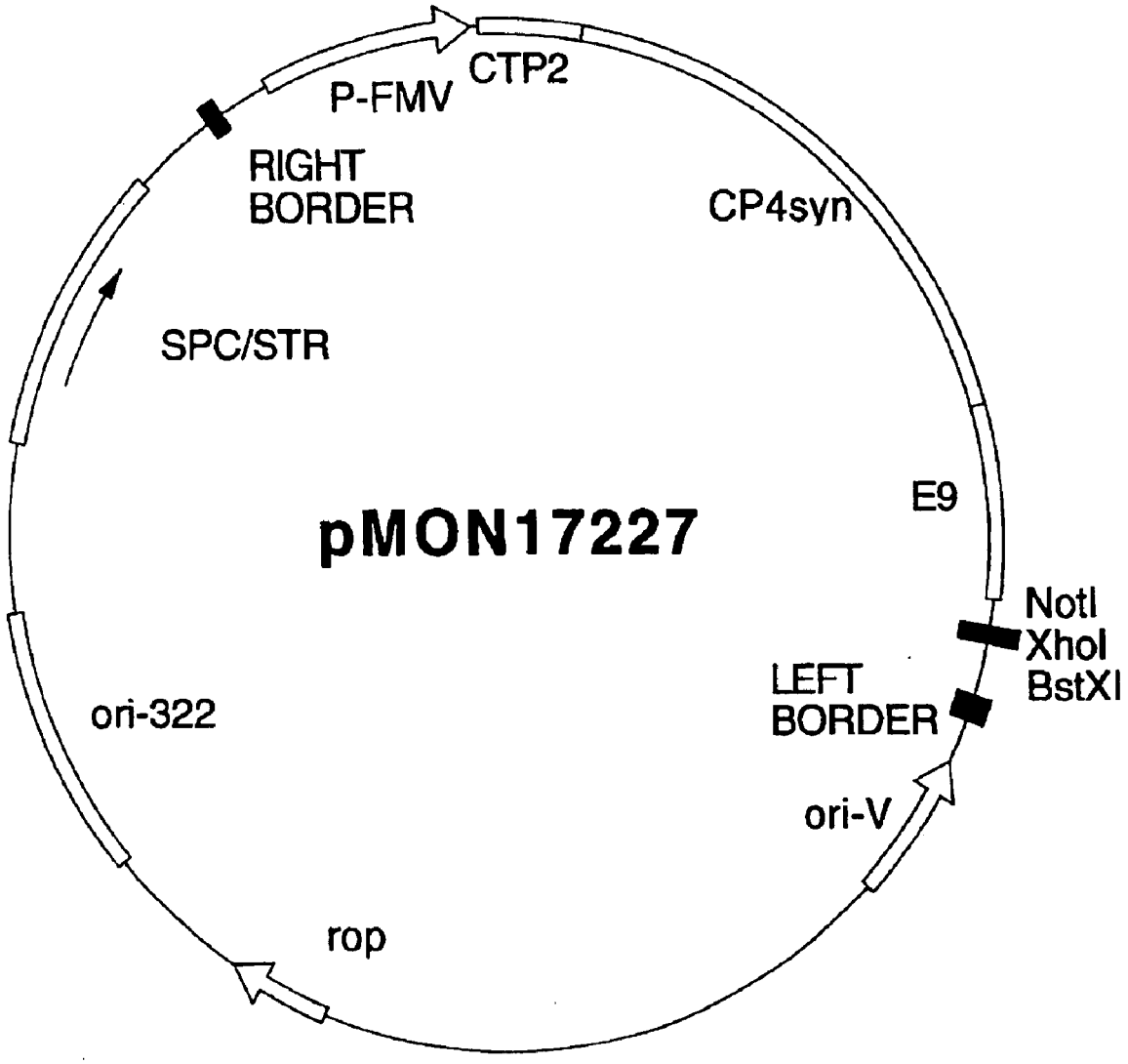
FIG. 16 shows a plasmid map of CP4 plant transformation/direct selection vector pMON17227.

A plant transformation vector that may be used in this scheme is pMON17227 (FIG. 16). This plasmid resembles many of the other plasmids described infra and is essentially composed of the previously described bacterial replicon system that enables this plasmid to replicate in E. coli and to be introduced into and to replicate in Agrobacterium, the bacterial selectable marker gene (Spc/Str), and located between the T-DNA right border and left border is the CTP2-CP4 synthetic gene in the FMV35S promoter-E9 3' cassette. This plasmid also has single sites for a number of restriction enzymes, located within the borders and outside of the expression cassette. This makes it possible to easily add other genes and genetic elements to the vector for introduction into plants.

The protocol for direct selection of transformed plants on glyphosate is outlined for tobacco. Explants are prepared for pre-culture as in the standard procedure as described in Example 1: surface sterilization of leaves from 1 month old tobacco plants (15 minutes in 10% clorox+surfactant; 3×d$H_2O$ washes); explants are cut in 0.5×0.5 cm squares, removing leaf edges, mid-rib, tip, and petiole end for uniform tissue type; explants are placed in single layer, upside down, on MS104 plates+2 ml 4COO5K media to moisten surface; pre-culture 1–2 days. Explants are inoculated using overnight culture of Agrobacterium containing the plant transformation plasmid that is adjusted to a titer of $1.2\times10^9$ bacteria/ml with 4COO5K media. Explants are placed into a centrifuge tube, the Agrobacterium suspension is added and the mixture of bacteria and explants is "Vortexed" on maximum setting for 25 seconds to ensure even penetration of bacteria. The bacteria are poured off and the explants are blotted between layers of dry sterile filter paper to remove excess bacteria. The blotted explants are placed upside down on MS104 plates+2 ml 4COO5K media+filter disc. Co-culture is 2–3 days. The explants are transferred to MS104+Carbenicillin 1000 mg/l+cefotaxime 100 mg/l for 3 days (delayed phase). The explants are then transferred to MS104+glyphosate 0.05 mM+Carbenicillin 1000 mg/l+cefotaxime 100 mg/l for selection phase. At 4–6 weeks shoots are cut from callus and placed on MSO+Carbenicillin 500 mg/l rooting media. Roots form in 3–5 days, at which time leaf pieces can be taken from rooted plates to confirm glyphosate tolerance and that the material is transformed.

The presence of the CP4 EPSPS protein in these transformed tissues has been confirmed by immunoblot analysis of leaf discs. The data from one experiment with pMON17227 is presented in the following: 139 shoots formed on glyphosate from 400 explants inoculated with Agrobacterium ABI/pMON17227; 97 of these were positive on recallusing on glyphosate. These data indicate a transformation rate of 24 per 100 explants, which makes this a highly efficient and time saving transformation procedure for plants. Similar transformation frequencies have been obtained with pMON17131 and direct selection of transformants on glyphosate with the CP4 EPSPS genes has also been shown in other plant species, including, Arabidopsis, soybean, corn, wheat, potato, tomato, cotton, lettuce, and sugarbeet.

The pMON17227 plasmid contains single restriction enzyme recognition cleavage sites (NotI, XhoI, and BstXI) between the CP4 glyphosate selection region and the left border of the vector for the cloning of additional genes and to facilitate the introduction of these genes into plants.

EXAMPLE 5A

The CP4 EPSPS gene has also been introduced into Black Mexican Sweet (BMS) corn cells with expression of the protein and glyphosate resistance detected in callus.

Figure 17:
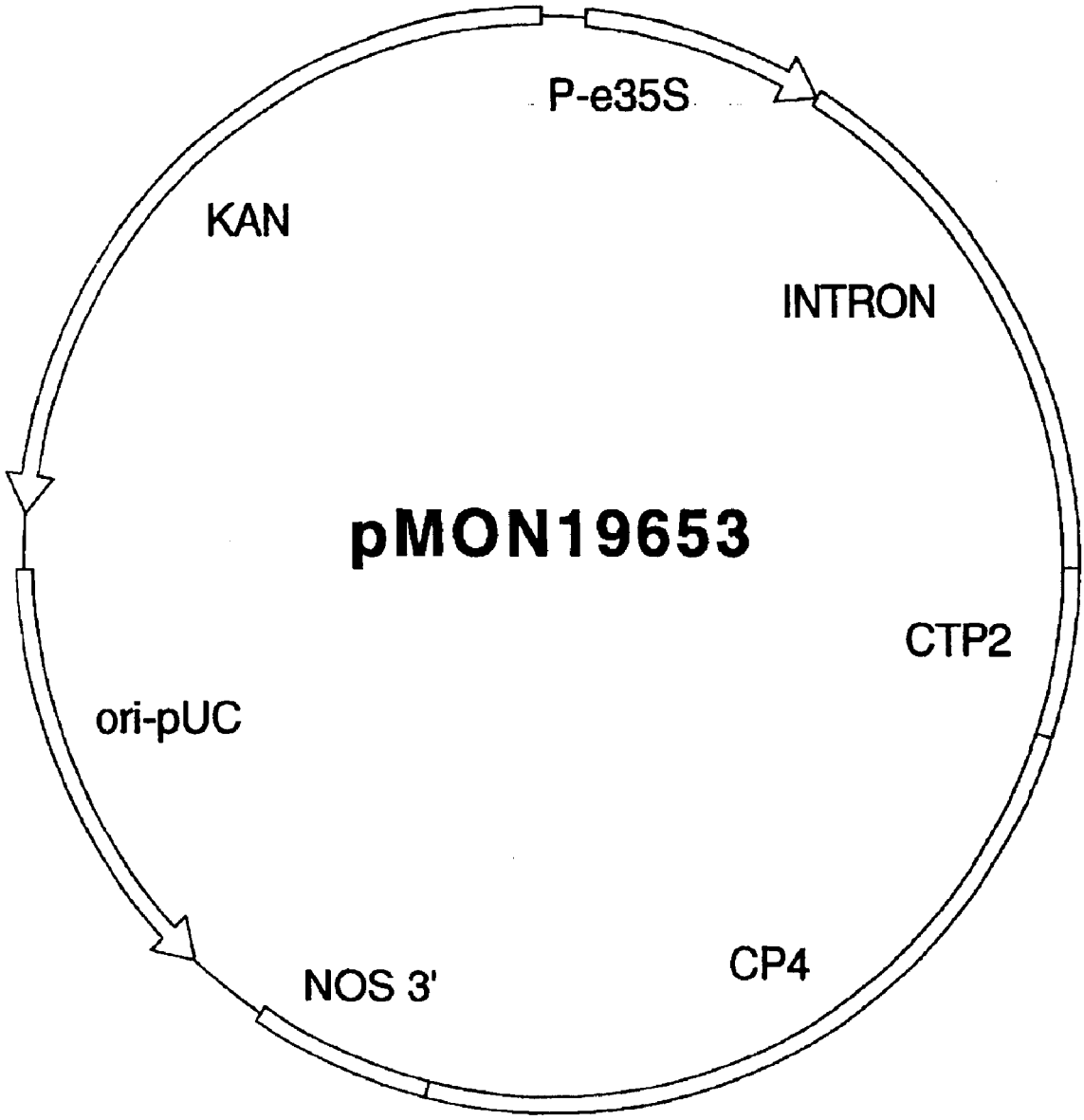
FIG. 17 shows a plasmid map of CP4 plant transformation/expression vector pMON19653.

The backbone for this plasmid was a derivative of the high copy plasmid pUC119 (Viera and Messing, 1987). The 1.3 Kb FspI-DraI pUC119 fragment containing the origin of replication was fused to the 1.3 Kb SmaI-HindIII filled fragment from pKC7 (Rao and Rogers, 1979) which contains the neomycin phosphotransferase type II gene to confer bacterial kanamycin resistance. This plasmid was used to construct a monocot expression cassette vector containing the 0.6 kb cauliflower mosaic virus (CaMV) 35S RNA promoter with a duplication of the −90 to −300 region (Kay et al., 1987), an 0.8 kb fragment containing an intron from a maize gene in the 5' untranslated leader region, followed by a polylinker and the 3' termination sequences from the nopaline synthase (NOS) gene (Fraley et al., 1983). A 1.7 Kb fragment containing the 300 bp chloroplast transit peptide from the Arabidopsis EPSP synthase fused in a frame to the 1.4 Kb coding sequence for the bacterial CP4 EPSP synthase was inserted into the monocot expression cassette in the polylinker between the intron and the NOS termination sequence to form the plasmid pMON19653 (FIG. 17).

pMON19653 DNA was introduced into Black Mexican Sweet (BMS) cells by co-bombardment with EC9, a plasmid containing a sulfonylurea-resistant form of the maize acetolactate synthase gene. 2.5 mg of each plasmid was coated onto tungsten particles and introduced into log-phase BMS cells using a PDS-1000 particle gun essentially as described (Klein et al., 1989). Transformants are selected on MS medium containing 20 ppb chlorsulfuron. After initial selection on chlorsulfuron, the calli can be assayed directly by Western blot. Glyphosate tolerance can be assessed by transferring the calli to medium containing 5mM glyphosate. As shown in Table XI, CP4 EPSPS confers glyphosate tolerance to corn callus.

TABLE XI

Expression of CP4 in BMS Corn Callus-pMON 19653

| Line | CP4 expression (% extract protein) |
|---|---|
| 284 | 0.006% |
| 287 | 0.036 |
| 290 | 0.061 |
| 295 | 0.073 |
| 299 | 0.113 |
| 309 | 0.042 |
| 313 | 0.003 |

To measure CP4 EPSPS expression in corn callus, the following procedure was used: BMS callus (3 g wet weight) was dried on filter paper (Whatman#1) under vacuum, reweighed, and extraction buffer (500 μl/g dry weight; 100 mM Tris, 1 mM EDTA, 10% glycerol) was added. The tissue was homogenized with a Wheaton overhead stirrer for 30 seconds at 2.8 power setting. After centrifugation (3 minutes, Eppendorf microfuge), the supernatant was removed and the protein was quantitated (BioRad Protein Assay). Samples (50 μg/well) were loaded on an SDS PAGE gel (Jule, 3–17%) along with CP4 EPSPS standard (10 ng), electrophoresed, and transferred to nitrocellulose similarly to a previously described method (Padgette, 1987). The nitrocellulose blot was probed with goat anti-CP4 EPSPS IgG, and developed with I-125 Protein G. The radioactive blot was visualized by autoradiography. Results were quantitated by densitometry on an LKB UltraScan XL laser densitomer and are tabulated below in Table X.

TABLE XII

Glyphosate resistance in BMS Corn Callus using pMON 19653

| Vector | Experiment | # chlorosulfuron-resistant lines | # cross-resistant to Glyphosate |
|---|---|---|---|
| 19653 | 253 | 120 | 81/120 = 67.5% |
| 19653 | 254 | 80 | 37/80 = 46% |
| EC9 control | 253/254 | 8 | 0/8 = 0% |

Improvements in the expression of Class II EPSPS could also be achieved by expressing the gene using stronger plant promoters, using better 3' polyadenylation signal sequences, optimizing the sequences around the initiation codon for ribosome loading and translation initiation, or by combination of these or other expression or regulatory sequences or factors.

Example 5B

The plant-expressible genes encoding the CP4 EPSPS and a glyphosate oxidoreductasease enzyme (PCT Pub. No. WO92/00377) were introduced into embryogenic corn callus through particle bombardment. Plasmid DNA was prepared using standard procedures (Ausubel et al., 1987), cesium-chloride purified, and re-suspended at 1 mg/ml in TE buffer. DNA was precipitated onto M10 tungsten or 1.0 μg gold particles (BioRad) using a calcium chloride/spermidine precipitation protocol, essentially as described by Klein et al. (1987). The PDS1000® gunpowder gun (BioRad) was used. Callus tissue was obtained by isolating 1–2 mm long immature embryos from the "Hi-II" genotype (Armstrong et al., 1991), or Hi-II X B73 crosses, onto a modified N6 medium (Armstrong and Green, 1985; Songstad et al., 1991). Embryogenic callus ("type-II"; Armstrong and Green, 1985) initiated from these embryos was maintained by subculturing at two week intervals, and was bombarded when less than two months old. Each plate of callus tissue was bombarded from 1 to 3 times with either tungsten or gold particles coated with the plasmid DNA(s) of interest. Callus was transferred to a modified N6 medium containing an appropriate selective agent (either glyphosate, or one or more of the antibiotics kanamycin, G418, or paromomycin) 1–8 days following bombardment, and then re-transferred to fresh selection media at 2–3 week intervals. Glyphosate-resistant calli first appeared approximately 6–12 weeks post-bombardment. These resistant calli were propagated on selection medium, and samples were taken for assays gene expression. Plant regeneration from resistant calli was accomplished essentially as described by Petersen et al. (1992).

In some cases, both gene(s) were covalently linked together on the same plasmid DNA molecule. In other instances, the genes were present on separate plasmids, but were introduced into the same plant through a process termed "co-transformation". The 1 mg/ml plasmid preparations of interest were mixed together in an equal ratio, by volume, and then precipitated onto the tungsten or gold particles. At a high frequency, as described in the literature (e.g., Schocher et al., 1986), the different plasmid molecules integrate into the genome of the same plant cell. Generally the integration is into the same chromosomal location in the plant cell, presumably due to recombination of the plasmids prior to integration. Less frequently, the different plasmids integrate into separate chromosomal locations. In either case, there is integration of both DNA molecules into the same plant cell, and any plants produced from that cell.

Transgenic corn plants were produced as described above which contained a plant-expressible CP4 gene and a plant-expressible gene encoding a glyphosate oxidoreductase enzyme.

The plant-expressible CP4 gene comprised a structural DNA sequence encoding a CTP2/CP4 EPSPS fusion protein. The CTP2/CP4 EPSPS is a gene fusion composed of the N-terminal 0.23 Kb chloroplast transit peptide sequence from the Arabidopsis thaliana EPSPS gene (Klee et al. 1987, referred to herein as CTP2), and the C-terminal 1.36 Kb 5-enolpyruvylshikimate-3-phosphate synthase gene (CP4) from an Agrobacterium species. Plant expression of the gene fusion produces a pre-protein which is rapidly imported into chloroplasts where the CTP is cleaved and degraded (della-Cioppa et al., 1986) releasing the mature CP4 protein.

The plant-expressible gene expressing a glyphosate oxidoreductase enzyme comprised a structural DNA sequence comprising CTP1/GOXsyn gene fusion composed of the N-terminal 0.26 Kb chloroplast transit peptide sequence derived from the Arabidopsis thaliana SSU 1a gene (Timko et al., 1988 referred to herein as CTP1), and the C-terminal 1.3 Kb synthetic gene sequence encoding a glyphosate oxidoreductase enzyme (GOXsyn, as described in PCT Pub. No. WO92/00377 previously incorporated by reference. The GOXsyn gene encodes the enzyme glyphosate oxidoreductase from an Achromobacter sp. strain LBAA which catalyzes the conversion of glyphosate to herbicidally inactive products, aminomethylphosphonate and glyoxylate. Plant expression of the gene fusion produces a pre-protein which is rapidly imported into chloroplasts where the CTP is cleaved and degraded (della-Cioppa et al., 1986) releasing the mature GOX protein.

Both of the above described genes also include the following regulatory sequences for plant expression: (i) a promoter region comprising a 0.6 Kb 35S cauliflower mosaic virus (CaMV) promoter (Odell et al., 1985) with the duplicated enhancer region (Kay et al., 1987) which also contains a 0.8 Kb fragment containing the first intron from the maize heat shock protein 70 gene (Shah et al., 1985 and PCT Pub. No. WO93/19189, the disclosure of which is hereby incorporated by reference); and (ii) a 3' non-translated region comprising a 0.3 Kb fragment of the 3' non-translated region of the nopaline synthase gene (Fraley et al., 1983 and Depicker, et al., 1982) which functions to direct polyadenylation of the mRNA.

The above described transgenic corn plants exhibit tolerance to glyphosate herbicide in greenhouse and field trials.

Example 6

The LBAA Class II EPSPS gene has been introduced into plants and also imparts glyphosate tolerance. Data on tobacco transformed with pMON17206 (infra) are presented in Table XIII.

TABLE XIII

Tobacco Glyphosate Spray Test
(pMON17206; E35S-CTP2-LBAA EPSPS; 0/4 lbs/ac)

| Line | 7 Day Rating |
|---|---|
| 33358 | 9 |
| 34586 | 9 |
| 33328 | 9 |
| 34606 | 9 |
| 33377 | 9 |
| 34611 | 10 |
| 34607 | 10 |
| 34601 | 9 |
| 34589 | 9 |
| Samsun (Control) | 4 |

From the foregoing, it will be recognized that this invention is one well adapted to attain all the ends and objects hereinabove set forth together with advantages which are obvious and which are inherent to the invention. It will be further understood that certain features and subcombinations are to utility and may be employed without reference to other features and subcombinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

BIBLIOGRAPHY

Alm, R. A., Dalrympie, B. P. and Mattick, J. S. 1994. Sequencing and expression of the aroA gene from Dichelobacter nodosus, Gene, 145: 97–101.

Altos, N. K. and Vapnek, D. (1979) Nature 282:864–869.

Ammirato, P. V., et al. Handbook of Plant Cell Culture—Crop Species. Macmillan Publ. Co. (1984).

Armstrong, C. L., and Green, C. E. 1985. Establishment and maintenance of friable, embryogenic maize callus and the involvement of L-proline. Planta 164:207–214.

Armstrong, C. L., Green, C. E., and Phillips, R. L. 1991. Development and availability of germplasm with high Type II culture formation response. Maize Genetics Cooperation NewsLetter 65:92–93.

Arnon, D. I. Plant Physiol. 24:1–15 (1949).

Ausubel, F. M., Brent, R., Kingston, R. E., Moore, D. D., Seidman, J. G., Smith, J. A., and Struhl, K. 1987. CURRENT PROTOCOLS IN MOLECULAR BIOLOGY, John Wiley and Sons, Inc. New York.

Bachmann, B. J. et al., Microb. Rev., 44:1–56 (1980).

Barker, R., Idler, K., Thompson, D., and Kemp, J. (1983) Nucleotide sequence of the T-DNA region from the Agrobacterium tumefaciens Ti plasmid pTi15955. Plant Mol Biol 2:335–350

Barry, G., Kishore, G., Padgette, S., Taylor, M., Kolacz, K., Weldon, M., Re D., Eichholtz, Fincher, K., and Hallas, L. (1992) Inhibitors of amino acid biosynthesis: Strategies for imparting glyphosate tolerance to crop plants. In: Biosynthesis and Molecular Regulation of Amino Acids in Plants. pp. 139–145. [Edited by Singh, B. K., Flores, H. E., and Shannon, J. C.] American Society of Plant Physiologists, Rockville, Md.

Bartlett, S. G., Grossman, A. R., and Chua, N. H. (1982) in Methods in Chloroplast Molecular Biology, pp. 1081–1091. M. Edelman, R. B., Hallick, and Chua, N. H., eds.

Bevan, M. (1984) Nucleic Acids Res. 12 (22): 8711–8721.

Birnboim, H. C. and Doly, J. (1979) A rapid alkaline extraction procedure for screening recombinant plasmid DNA. Nucl. Acids. Res. 7:1513–1525.

Bolivar, R., Rodriguez, R. L., Greene, P. J., Betlach, M. B., Heynecker, H. L., Boyer, H. W., Crosa, J. H., and Falkow, S. (1977) Construction and characterization of new cloning vehicles, II. A multi-purpose cloning system. Gene 2: 95–113.

Boyer, H. W. and Rolland-Dussolx, D. (1969) A complementation analysis of the restriction and modification of DNA in Escherichia coli, J. Mol. Biol. 41:459.

Carrer, H., Hockenberry, T. N., Svab, Z., and Maliga, P. (1993) Kanamycin resistance as a selectable marker for plastid transformation in tobacco. Mol. Gen. Genet. 241: 49–56.

Criston, P., D. E. McCabe, and W. F. Swain (1988) Stable transformation of Soybean Callus by DNA-Coated Gold Particles. Plant Physiol. 87:671–674.

Coruzzi, G., Broglie, R., Edwards, C., and Chua, N. H. (1984). Tissue-specific and light-regulated expression of a pea nuclear gene encoding the small subunit of ribulose-1,5-bisphosphate carboxylase. EMBO J 3: 1671.

Dalla Chiesa, M., Mayes, S. R., Maskell, D. J., Nixon, P. J. and Barber, J. 1994 An AroA homologue from Synechocystis sp. PCC6803, Gene, 144: 145–146.

della-Cioppa, G., Bauer, S. C., Klein, B. K., Shah, D. M., Fraley, R. T. and Kishore G. K. (1986) Translocation of the precursor of 5-enolpyruvylshikimate-3-phosphate synthase into chloroplasts of higher plants in vitro. Proc. Natl. Acad Sci. USA 83: 6873–6877.

della-Cioppa, G., Bauer, S. C., Taylor, M. T., Rochester, D. E., Klein, B. K., Shah, D. M., Fraley, R. T. and Kishore G. M. (1987) Targeting a herbicide-resistant enzyme from Escherichia coli to chloroplasts of higher plants. Bio/Technology 5: 579–584.

Depicker, A., Stachel, S., Dhaese, P., Zambryski, P., and Goodman, H. M. 1982. Nopaline Synthase: Transcript Mapping and DNA Sequence. J. MOLEC. APPL. GENETICS 1:561–573.

Devereux, J., Haeberli, P. and Smithies, O. (1984) A comprehensive set of sequence analysis programs for the VAX. Nucl. Acids. Res. 12:387–395.

Ditta, G., Stanfield, S., Corbin, D., and Helinski, D. R. (1980) Broad host range DNA cloning system for Gram-Negative bacteria: construction of a gene bank of Rhizobium meliloti. Proc Natl Acad Sci USA 77, 7347–7351.

Duncan, K., Edwards, R. M., Coggins, J. R. (1987) The pentafunctional aroM enzyme of Saccharomyces cerevisiae is a mosaic of monofunctional domains. Biochem. J. 246:375–386.

Dunn, J. J. and Studier, F. W., (1983) J. Mol. Biol. 166:477–535.

Fitzgibbon, J. E. (1988) Pseudomonas sp. strain PG2982: uptake of glyphosate and cloning of a gene which confers increased resistance to glyphosate. Ph.D. Dissertation, Louisiana State University.

Fitzgibbon, E. F. and Braymer, H. D. (1990) Cloning of a gene from Pseudomonas sp. PG2982 conferring increased glyphosate resistance Appl. Environ. Microbiol. 56: 3382–3388.

Fling, M. E., Kopf, J., and Richards, C. (1985). Nucleotide sequence of the transposon Tn7 gene encoding an aminoglycoside-modifying enzyme, 3"(9)-O-nucleotidyltransferase. Nucleic Acids Res. 13 no. 19, 7095–7106.

Fraley, R. T., Rogers, S. G., Horsch, R. B., Sanders, P. R. Flick, J. S., Adams, S. P., Bittner, M. L., Brand, L. A., Fink, C. L., Fry, J. S., Galluppi, G. R., Goldberg, S. B., Hoffman, N. L., and Woo, S. C. 1983. Expression of bacterial genes in plant cells. Proc. Natl. Acad. Sci. USA 80:4803–4807.

Fraley, R. T., Rogers, S. G., Horsch, R. B., Eichholtz D. A., Flick, J. S., Fink, C. L., Hoffmann, N. L. and Sanders, P. R. (1985) The SEV system: a new disarmed Ti plasmid vector system for plant transformation. Bio/Technology 3: 629–635.

Fromm, M., (1990) UCLA Symposium on Molecular Strategies for Crop Improvement, Apr. 16–22, 1990. Keystone, Colo.

Fry J., Barnason A., and Horsch R. (1987) Plant Cell Reports 6: 321–325.

Gasser, C. S., Winter, J. A., Hironaka, C. M. and Shah, D. M. (1988) Structure, expression, and evolution of the 5-enolpyruvylshikimate 3-phosphate synthase genes of petunia and tomato. J. Biol. Chem. 263: 4280–4289.

Gowda, S., Wu, F. C., and Shepard, R. J. (1989). Identification of promoter sequences for the major RNA transcripts of figwort mosaic and peanut chlorotic streak viruses (caulimovirus group). Journal of Cellular Biochemistry supplement 13D, 301 (Abstract).

Hallas, L. E., Hahn, E. M. and Korndorfer, C. (1988) Characterization of microbial traits associated with glyphosate biodegradation in industrial activated sludge. J. Industrial Microbiol. 3: 377–385.

Hayford, M. B., Medford, J. I., Hoffmann, N. L., Rogers, S. G. and Klee, H. J. (1988) Development of a plant transformation selection system based on expression of genes encoding gentamicin acetyltransferases. Plant Physiol. 86: 1216–1222.

Herrera-Estrella, L., et al. (1983) Nature 303:209

Heitkamp, M. A., Hallas, L. and Adams, W. J. (1990) Biotreatment of industrial wastewater with immobilized microorganisms—Presented in Session 11, Paper S40, Society for Industrial Microbiology Annual Meeting, Orlando, Fla. Jul. 29–Aug. 3, 1990.

Henher, J. H., Band, L. and Shimotsu, H. (1984) Nucleotide sequence of the Bacillus subtilis tryptophan operon. Gene., 34: 169–177.

Henner, J. H., Band, L., Flaggs, G. and Chen, E. (1986) The organization and nucleotide sequence of the Bacillus subtilis hisH, tyrA and aroE genes Gene 49: 147–152.

Hohn, B. and Collins J. (1980) A small cosmid for efficient cloning of large DNA fragments. Gene 11: 291–298.

Horsch, R. B. and H. Klee. (1986) Proc. Natl. Acad. Sci. U.S.A. 83:4428–32.

Hunkapiller, M. W., Hewick, R. M., Dreyer, R. J., and Hood, L. (1983) Methods Enzymol. 91, 399–413.

Jefferson, R. A., Kavanaugh, T. A. and Bevan, M. W., 1987, EMBO J., 6:3901–3907.

Kay, R., Chan, A., Daly, M. and McPherson, J. 1987. Duplication of the CaMV 35S promoter sequence creates a strong enhancer for plants. Science 236, 1299–1302.

Kishore, G., Shah, D., Padgette, S., della-Cioppa, G., Gasser, C., Re, D., Hironaka, C., Taylor, M., Wibbenmeyer, J., Eichholtz, D., Hayford, M., Hoffman, N., Delannay, X., Horsch, R., Klee, H., Rogers, S., Rochester, D., Brundage, L., Sanders, P. and Fraley, R. T. (1988) 5-Enolpyruvylshikimate 3-phosphate synthase: From Biochemistry to genetic engineering of glyphosate tolerance, in Biotechnology for Crop Protection ACS Symposium series No. 379. Eds. Hedlin P. A., Menn, J. J. and Hollingsworth, R. M. pp. 37–48.

Kishore, G. and Shah, D. (1988) Ann. Rev. Biochem. 57:627–663.

Kishore, G. M., Brundage, L., Kolk, K., Padgette, S. R., Rochester, D., Huynh, Q. K. and della-Cioppa, G. (1986) Fed. Proc. 45: 1506.

Klee, H. J., et al. (1985) Bio/Technology 3:637–42.

Klee, H. J., Muskopf, Y. M. and Gasser, C. S. (1987) Cloning of an Arabidopsis thaliana gene encoding 5-enolpyruvyl-shikimate-3-phosphate synthase: sequence analysis and manipulation to obtain glyphosate-tolerant plants. Mol. Gen. Genet. 210: 437–442.

Klee, H. J. and Rogers, S. G. (1989) Plant gene vectors and genetic transformation: plant transformation systems based on the use of Agrobacterium tumefaciens in: Cell Culture and Somatic Cell: Genetics of Plants eds. J. Schell and L. K. Vasil. 6: 1–23.

Klein, T. M., Kornstein, L., Sanford, J. C., and Fromm, M. E. 1989. Genetic transformation of maize cells by particle bombardment. Plant Phys. 91:440–444.

Koncz, C. and Schell, J. (1986) The promoter of TL-DNA gene 5 controls the tissue-specific expression of chimeric genes carried by a novel type of Agrobacterium binary vector. Mol. Gen. Genet. 204:383–396.

Kunkel, T. A., Roberts, J. D. and Zakour, R. A. (1987) Rapid and efficient site-specific mutagenesis without phenotypic selection. Methods Enzymol. 154:367.

Laemmli, U.K. (1970), "Cleavage of structural proteins during the assembly of the head of the bacteriophage T4" Nature, 227:680.

Maliga, P., Carrer, H., Kanevski, I., Staub, J., and Svab, Z. (1993) Plastid engineering in land plants: a conservative genome is open to change. Philos. Trans. R. Soc. London B Biol. Sci. 342: 203–208.

Maniatis, T., Fritsch, E. F. and Sambrook, J. (1982) Molecular Cloning: a laboratory manual. Cold Spring Harbor Laboratory, Cold Spring Harbor, N.Y.

Maskell, D. J., Morrissey, P. and Dougan, G. (1988) Cloning and nucleotide sequence of the aroA gene of Bordetella pertussis. J. Bacteriol. 170:2467–2471.

Miller, J. H. (1972). Experiments in Molecular Genetics. Cold Spring Harbor Laboratory, Cold Spring Harbor, N.Y.

Moore, J. K., Braymer, H. D. and Larson, A. D. (1983) Isolation of a Pseudomonas sp. which utilizes the phosphonate herbicide glyphosate. Appl. Environ. Microbiol. 46: 316–320.

Morelli, G., Nagy, F., Fraley, R. T., Rogers, S. G., and Chua, N. H. (1985). A short conserved sequence is involved in the light-inducibility of a gene encoding ribulose 1,5-bisphosphate carboxylase small subunit of pea. Nature 315, 200–204.

O'Connell, C., Pattee, P. A. and Foster, T. J. (1993) Sequence and mapping of the aroA gene of Staphylococcus aureus 8325–4. J. Gen. Micr. 139: 1449–1460.

Odell, J. T., Nagy, F., and Chua, N. H. (1985). Identification of DNA sequences required for activity of the cauliflower mosaic virus 35S promoter. Nature 313, 810–812.

Olins, P. O., Devine, C. S., Rangwala, S. H. and Kavka, K. S. (1988) Gene 73: 227–235.

O'Neill, C., Horvath, G. V., Horvath, E., Dix, P. J. and Medgyesy, P. (1993) Chloroplast transformation in plants: polyethylene glycol (PEG) treatment of protoplasts is an alternative to biolistic delivery systems. Plant J. 3: 729–738.

Padgette, S. R., Huynh, Q. K., Borgmeyer, J., Shah, D. M., Brand, L. A., Re, D. B., Bishop, B. F., Rogers, S. G., Fraley, R. T., and Kishore, G. (1987) Bacterial expression and isolation of Petunia hybrida 5-enol-pyruvylshikimate-3-phosphate synthase. Arch. Biochem. Biophys. 258, 564–573.

Padgette, S. R., Huynh, Q. K., Aykent, S., Sammons, R. D., Sikorski, J. A., and Kishore, G. M. (1988) J. Biol. Chem. 263, 1798–1802.

Petersen, W. L., Sulc, S., and Armstrong, C. L. 1992. Effect of nurse cultures on the production of macro-calli and fertile plants from maize embryogenic suspension protoplasts. Plant Cell Reports 10:591–594.

Quinn, J. P., Peden, J. M. M. and Dick, E. (1988) Glyphosate tolerance and utilization by the microflora of soils treated with the herbicide. Appl. Microbiol. Biotechnol.29: 511–516.

Rao, R. N. and Rogers, S. G. (1979). Plasmid pKC7: A vector containing ten restriction endonuclease sites suitable for cloning DNA segments. Gene 7:79.

Richins, R. D., Scholthof, H. B., and Shepard, R. J. (1987) Sequence of the figwort mosaic virus DNA (caulimovirus group). Nucl. Acids Res. 15: 8451–8466.

Rogers, S. G., Brand, L. A. Holder, S. B. Sharps, E. S. and Brackin, M. J. (1983) Amplification of the aroA gene from E. coli results in tolerance to the herbicide glyphosate. Appl. Environ. Microbiol. 46:37–43.

Rogers, S. G. and Klee, H. J. (1987). "Pathways to genetic manipulation employing Agrobacterium." in Plant Gene Research, Plant DNA Infectious Agents, Vol IV, Hohn, T. and Schell, J., eds. Springer-Verlag, Vienna, pp.179–203.

Sambrook, J., Fritsch, E. F. and Maniatis, T., (1989) Molecular Cloning: A Laboratory Manual, Cold Spring Harbor Laboratory Press, Cold Spring Harbor, N.Y.

Schocher, R. J., Shillito, R. D., Saul, M. W., Paszkowski, J., and Potrykus, I. (1986). Co-transformation of unlinked foreign genes into plants by direct gene transfer. Bio/Technology 4:1093–1097.

Songstad, D. D., Armstrong, C. L., and Petersen, W. L. (1991). $AgNO_3$ increases type II callus production from immature embryos of maize inbred B73 and its derivatives. Plant Cell Reports 9: 699–702.

Schuler, M. A., Schmitt, E. S. and Beachy, R. N. (1982) Nucleic Acids Res. 10:8225–8244.

Schulz, A., Kruper, A. and Amrhein, N. (1985) Differential sensitivity of bacterial 5-enolpyruvylshikimate-3-phosphate synthases to the herbicide glyphosate. FEMS Microbiol. Lett. 28: 297–301.

Schulz, A., Sost, D. and Amrhein, D. (1984) Arch. Microbiol. 137: 121–123.

Shah, D., Horsch, R., Klee, H., Kishore, G., Winter, J., Turner, N., Hironaka, C., Sanders, P., Gasser, C., Aykent, S., Siegal, N., Rogers, S., and Fraley, R. (1986). Engineering herbicide tolerance in transgenic plants. Science 233, 478–481.

Shah, D. M., Rochester, D. E., Krivi, G., Hironaka, C., Mozer, T. J., Fraley, R. T., and D. C. Tiemeier. 1985. Structure and expression of the maize hsp70 gene. Cell. and Mol. Biol. of Plant Stress, Alan R. Liss, Inc. pp. 181–200.

Shimamoto, K. et al. (1989) Nature 338:274–276.

Sost, D., Schulz, A. and Amrhein, N. (1984) FEBS Lett. 173: 238–241.

Sost, D. and Amrhein, N. (1990) Substitution of Gly-96 to Ala in the 5-enolpyruvylshikimate 3-phosphate synthase of Klebsiella pneumoniae results in greatly reduced affinity for the herbicide glyphosate. Arch. Biochem. Biophys. 282: 433–436.

Stalker, D. M., Thomas, C. M., and Helinski, D. R. (1981). Nucleotide sequence of the region of the origin of replication of the broad host range plasmid RK2. Mol Gen Genet 181: 8–12.

Stalker, D. M., Hiatt, W. R. and Comai, L. (1985) A single amino acid substitution in the enzyme 5-enolpyruvylshikimate 3-phosphate synthase confers resistance to glyphosate. J. Biol. Chem. 260: 4724–4728.

Stallings, W. C., Abdel-Meguid, S.S., Lim, L. W., Shieh, Huey-Sheng, Dayringer, H. E., Leimgruber, N. K., Stegeman, R. A., Anderson, K. S., Sikorski, J. A., Padgette S. R., Kishore, G. M. (1991). Structure and Topological Symmetry of the Glyphosate Target 5-enolpyruvylshikimate-3-phosphate synthase, Proc. Natl. Acad. Sci. USA 88, 5046–5050.

Svab, Z., Hajdukiewicz, P., and Maliga, P. (1990) Stable transformation of plastids in higher plants. Proc. Natl. Acad. Sci. USA 87: 8526–8530.

Svab, Z. and Maliga, P. (1993) High frequency plastid transformation in tobacco by selection for a chimeric aadA gene. Proc. Natl. Acad Sci. USA 90:913–917.

Tabor, S. and Richardson, C. C. (1985) A bacteriophage T7 RNA polymerase/promoter system for controlled exclusive expression of specific genes. Proc. Natl. Acad. Sci. USA 82: 1074–1078.

Talbot, H. W., Johnson, L. M. and Munnecke, D. M. (1984) Glyphosate utilization by Pseudomonas sp. and Alcaligenes sp. isolated from environmental sources. Current Microbiol. 10: 255–260.

Talmadge, K., and Gilbert, W., (1980) "Construction of plasmid vectors with unique PstI cloning sites in the signal sequence coding region" Gene, 12: 235–241.

Timko, M. P., Herdies, L., de Almeida, E., Cashmore, A. R., Leemans, J., and Krebbers, E. 1988. Genetic Engineering of Nuclear-Encoded Components of the Photosynthetic Apparatus in Arabidopsis in "The Impact of Chemistry on Biotechnology," ACS Books, 279–295.

Vasil, V., F. Redway and I. Vasil. (1990), Bio/Technology 8:429–434.

Vieira, J. and Messing J. (1987) Production of single-stranded plasmid DNA. Methods Enzymol. 153: 3–11.

Yanisch-Perron, C., Vieira, J. and Messing, J. (1985). Improved M13 phage cloning vectors and host strains: nucleotide sequences of the M13mp18 and pUC19 vectors. Gene 33, 103–119

SEQUENCE LISTING

<160> NUMBER OF SEQ ID NOS: 70

<210> SEQ ID NO 1
<211> LENGTH: 597
<212> TYPE: DNA
<213> ORGANISM: Figwort mosaic virus

<400> SEQUENCE: 1 tcatcaaaat atttagcagc attccagatt gggttcaatc aacaaggtac gagccatatc 60 actttattca aattggtatc gccaaaacca agaaggaact cccatcctca aaggtttgta 120 aggaagaatt ctcagtccaa agcctcaaca aggtcagggt acagagtctc caaaccatta 180 gccaaaagct acaggagatc aatgaagaat cttcaatcaa agtaaactac tgttccagca 240 catgcatcat ggtcagtaag tttcagaaaa agacatccac cgaagactta aagttagtgg 300 gcatctttga aagtaatctt gtcaacatcg agcagctggc ttgtggggac cagacaaaaa 360 aggaatggtg cagaattgtt aggcgcacct accaaaagca tctttgcctt tattgcaaag 420 ataaagcaga ttcctctagt acaagtgggg aacaaaataa cgtggaaaag agctgtcctg 480 acagcccact cactaatgcg tatgacgaac gcagtgacga ccacaaaaga attccctcta 540 tataagaagg cattcattcc catttgaagg atcatcagat actaaccaat atttctc 597

<210> SEQ ID NO 2

-continued

```
<211> LENGTH: 1982
<212> TYPE: DNA
<213> ORGANISM: Agrobacterium sp.
<220> FEATURE:
<221> NAME/KEY: CDS
<222> LOCATION: (62)..(1426)

<400> SEQUENCE: 2

aagcccgcgt tctctccggc gctccgcccg gagagccgtg gatagattaa ggaagacgcc     60

c atg tcg cac ggt gca agc agc cgg ccc gca acc gcc cgc aaa tcc tct    109
  Met Ser His Gly Ala Ser Ser Arg Pro Ala Thr Ala Arg Lys Ser Ser
  1               5                   10                  15

ggc ctt tcc gga acc gtc cgc att ccc ggc gac aag tcg atc tcc cac      157
Gly Leu Ser Gly Thr Val Arg Ile Pro Gly Asp Lys Ser Ile Ser His
            20                  25                  30

cgg tcc ttc atg ttc ggc ggt ctc gcg agc ggt gaa acg cgc atc acc      205
Arg Ser Phe Met Phe Gly Gly Leu Ala Ser Gly Glu Thr Arg Ile Thr
        35                  40                  45

ggc ctt ctg gaa ggc gag gac gtc atc aat acg ggc aag gcc atg cag      253
Gly Leu Leu Glu Gly Glu Asp Val Ile Asn Thr Gly Lys Ala Met Gln
    50                  55                  60

gcc atg ggc gcc agg atc cgt aag gaa ggc gac acc tgg atc atc gat      301
Ala Met Gly Ala Arg Ile Arg Lys Glu Gly Asp Thr Trp Ile Ile Asp
65                  70                  75                  80

ggc gtc ggc aat ggc ggc ctc ctg gcg cct gag gcg ccg ctc gat ttc      349
Gly Val Gly Asn Gly Gly Leu Leu Ala Pro Glu Ala Pro Leu Asp Phe
                85                  90                  95

ggc aat gcc gcc acg ggc tgc cgc ctg acc atg ggc ctc gtc ggg gtc      397
Gly Asn Ala Ala Thr Gly Cys Arg Leu Thr Met Gly Leu Val Gly Val
            100                 105                 110

tac gat ttc gac agc acc ttc atc ggc gac gcc tcg ctc aca aag cgc      445
Tyr Asp Phe Asp Ser Thr Phe Ile Gly Asp Ala Ser Leu Thr Lys Arg
        115                 120                 125

ccg atg ggc cgc gtg ttg aac ccg ctg cgc gaa atg ggc gtg cag gtg      493
Pro Met Gly Arg Val Leu Asn Pro Leu Arg Glu Met Gly Val Gln Val
    130                 135                 140

aaa tcg gaa gac ggt gac cgt ctt ccc gtt acc ttg cgc ggg ccg aag      541
Lys Ser Glu Asp Gly Asp Arg Leu Pro Val Thr Leu Arg Gly Pro Lys
145                 150                 155                 160

acg ccg acg ccg atc acc tac cgc gtg ccg atg gcc tcc gca cag gtg      589
Thr Pro Thr Pro Ile Thr Tyr Arg Val Pro Met Ala Ser Ala Gln Val
                165                 170                 175

aag tcc gcc gtg ctg ctc gcc ggc ctc aac acg ccc ggc atc acg acg      637
Lys Ser Ala Val Leu Leu Ala Gly Leu Asn Thr Pro Gly Ile Thr Thr
            180                 185                 190

gtc atc gag ccg atc atg acg cgc gat cat acg gaa aag atg ctg cag      685
Val Ile Glu Pro Ile Met Thr Arg Asp His Thr Glu Lys Met Leu Gln
        195                 200                 205

ggc ttt ggc gcc aac ctt acc gtc gag acg gat gcg gac ggc gtg cgc      733
Gly Phe Gly Ala Asn Leu Thr Val Glu Thr Asp Ala Asp Gly Val Arg
    210                 215                 220

acc atc cgc ctg gaa ggc cgc ggc aag ctc acc ggc caa gtc atc gac      781
Thr Ile Arg Leu Glu Gly Arg Gly Lys Leu Thr Gly Gln Val Ile Asp
225                 230                 235                 240

gtg ccg ggc gac ccg tcc tcg acg gcc ttc ccg ctg gtt gcg gcc ctg      829
Val Pro Gly Asp Pro Ser Ser Thr Ala Phe Pro Leu Val Ala Ala Leu
                245                 250                 255

ctt gtt ccg ggc tcc gac gtc acc atc ctc aac gtg ctg atg aac ccc      877
Leu Val Pro Gly Ser Asp Val Thr Ile Leu Asn Val Leu Met Asn Pro
            260                 265                 270
```

-continued

```
acc cgc acc ggc ctc atc ctg acg ctg cag gaa atg ggc gcc gac atc      925
Thr Arg Thr Gly Leu Ile Leu Thr Leu Gln Glu Met Gly Ala Asp Ile
        275                 280                 285

gaa gtc atc aac ccg cgc ctt gcc ggc ggc gaa gac gtg gcg gac ctg      973
Glu Val Ile Asn Pro Arg Leu Ala Gly Gly Glu Asp Val Ala Asp Leu
    290                 295                 300

cgc gtt cgc tcc tcc acg ctg aag ggc gtc acg gtg ccg gaa gac cgc     1021
Arg Val Arg Ser Ser Thr Leu Lys Gly Val Thr Val Pro Glu Asp Arg
305                 310                 315                 320

gcg cct tcg atg atc gac gaa tat ccg att ctc gct gtc gcc gcc gcc     1069
Ala Pro Ser Met Ile Asp Glu Tyr Pro Ile Leu Ala Val Ala Ala Ala
                325                 330                 335

ttc gcg gaa ggg gcg acc gtg atg aac ggt ctg gaa gaa ctc cgc gtc     1117
Phe Ala Glu Gly Ala Thr Val Met Asn Gly Leu Glu Glu Leu Arg Val
            340                 345                 350

aag gaa agc gac cgc ctc tcg gcc gtc gcc aat ggc ctc aag ctc aat     1165
Lys Glu Ser Asp Arg Leu Ser Ala Val Ala Asn Gly Leu Lys Leu Asn
        355                 360                 365

ggc gtg gat tgc gat gag ggc gag acg tcg ctc gtc gtg cgc ggc cgc     1213
Gly Val Asp Cys Asp Glu Gly Glu Thr Ser Leu Val Val Arg Gly Arg
    370                 375                 380

cct gac ggc aag ggg ctc ggc aac gcc tcg ggc gcc gcc gtc gcc acc     1261
Pro Asp Gly Lys Gly Leu Gly Asn Ala Ser Gly Ala Ala Val Ala Thr
385                 390                 395                 400

cat ctc gat cac cgc atc gcc atg agc ttc ctc gtc atg ggc ctc gtg     1309
His Leu Asp His Arg Ile Ala Met Ser Phe Leu Val Met Gly Leu Val
                405                 410                 415

tcg gaa aac cct gtc acg gtg gac gat gcc acg atg atc gcc acg agc     1357
Ser Glu Asn Pro Val Thr Val Asp Asp Ala Thr Met Ile Ala Thr Ser
            420                 425                 430

ttc ccg gag ttc atg gac ctg atg gcc ggg ctg ggc gcg aag atc gaa     1405
Phe Pro Glu Phe Met Asp Leu Met Ala Gly Leu Gly Ala Lys Ile Glu
        435                 440                 445

ctc tcc gat acg aag gct gcc tgatgacctt cacaatcgcc atcgatggtc        1456
Leu Ser Asp Thr Lys Ala Ala
    450                 455

ccgctgcggc cggcaagggg acgctctcgc gccgtatcgc ggaggtctat ggctttcatc   1516

atctcgatac gggcctgacc tatcgcgcca cggccaaagc gctgctcgat cgcggcctgt   1576

cgcttgatga cgaggcggtt gcggccgatg tcgcccgcaa tctcgatctt gccgggctcg   1636

accggtcggt gctgtcggcc catgccatcg gcgaggcggc ttcgaagatc gcggtcatgc   1696

cctcggtgcg gcgggcgctg gtcgaggcgc agcgcagctt tgcggcgcgt gagccgggca   1756

cggtgctgga tggacgcgat atcggcacgg tggtctgccc ggatgcgccg gtgaagctct   1816

atgtcaccgc gtcaccggaa gtgcgcgcga aacgccgcta tgacgaaatc ctcggcaatg   1876

gcgggttggc cgattacggg acgatcctcg aggatatccg ccgccgcgac gagcgggaca   1936

tgggtcgggc ggacagtcct ttgaagcccg ccgacgatgc gcactt                  1982
```

<210> SEQ ID NO 3
<211> LENGTH: 455
<212> TYPE: PRT
<213> ORGANISM: Agrobacterium sp.

<400> SEQUENCE: 3

```
Met Ser His Gly Ala Ser Ser Arg Pro Ala Thr Ala Arg Lys Ser Ser
1               5                   10                  15

Gly Leu Ser Gly Thr Val Arg Ile Pro Gly Asp Lys Ser Ile Ser His
            20                  25                  30
```

-continued

```
Arg Ser Phe Met Phe Gly Gly Leu Ala Ser Gly Glu Thr Arg Ile Thr
        35                  40                  45

Gly Leu Leu Glu Gly Glu Asp Val Ile Asn Thr Gly Lys Ala Met Gln
    50                  55                  60

Ala Met Gly Ala Arg Ile Arg Lys Glu Gly Asp Thr Trp Ile Ile Asp
65                  70                  75                  80

Gly Val Gly Asn Gly Gly Leu Leu Ala Pro Glu Ala Pro Leu Asp Phe
                85                  90                  95

Gly Asn Ala Ala Thr Gly Cys Arg Leu Thr Met Gly Leu Val Gly Val
            100                 105                 110

Tyr Asp Phe Asp Ser Thr Phe Ile Gly Asp Ala Ser Leu Thr Lys Arg
        115                 120                 125

Pro Met Gly Arg Val Leu Asn Pro Leu Arg Glu Met Gly Val Gln Val
    130                 135                 140

Lys Ser Glu Asp Gly Asp Arg Leu Pro Val Thr Leu Arg Gly Pro Lys
145                 150                 155                 160

Thr Pro Thr Pro Ile Thr Tyr Arg Val Pro Met Ala Ser Ala Gln Val
                165                 170                 175

Lys Ser Ala Val Leu Leu Ala Gly Leu Asn Thr Pro Gly Ile Thr Thr
            180                 185                 190

Val Ile Glu Pro Ile Met Thr Arg Asp His Thr Glu Lys Met Leu Gln
        195                 200                 205

Gly Phe Gly Ala Asn Leu Thr Val Glu Thr Asp Ala Asp Gly Val Arg
    210                 215                 220

Thr Ile Arg Leu Glu Gly Arg Gly Lys Leu Thr Gly Gln Val Ile Asp
225                 230                 235                 240

Val Pro Gly Asp Pro Ser Ser Thr Ala Phe Pro Leu Val Ala Ala Leu
                245                 250                 255

Leu Val Pro Gly Ser Asp Val Thr Ile Leu Asn Val Leu Met Asn Pro
            260                 265                 270

Thr Arg Thr Gly Leu Ile Leu Thr Leu Gln Glu Met Gly Ala Asp Ile
        275                 280                 285

Glu Val Ile Asn Pro Arg Leu Ala Gly Gly Glu Asp Val Ala Asp Leu
    290                 295                 300

Arg Val Arg Ser Ser Thr Leu Lys Gly Val Thr Val Pro Glu Asp Arg
305                 310                 315                 320

Ala Pro Ser Met Ile Asp Glu Tyr Pro Ile Leu Ala Val Ala Ala Ala
                325                 330                 335

Phe Ala Glu Gly Ala Thr Val Met Asn Gly Leu Glu Glu Leu Arg Val
            340                 345                 350

Lys Glu Ser Asp Arg Leu Ser Ala Val Ala Asn Gly Leu Lys Leu Asn
        355                 360                 365

Gly Val Asp Cys Asp Glu Gly Glu Thr Ser Leu Val Val Arg Gly Arg
    370                 375                 380

Pro Asp Gly Lys Gly Leu Gly Asn Ala Ser Gly Ala Ala Val Ala Thr
385                 390                 395                 400

His Leu Asp His Arg Ile Ala Met Ser Phe Leu Val Met Gly Leu Val
                405                 410                 415

Ser Glu Asn Pro Val Thr Val Asp Asp Ala Thr Met Ile Ala Thr Ser
            420                 425                 430

Phe Pro Glu Phe Met Asp Leu Met Ala Gly Leu Gly Ala Lys Ile Glu
        435                 440                 445
```

-continued

```
Leu Ser Asp Thr Lys Ala Ala
    450                 455


<210> SEQ ID NO 4
<211> LENGTH: 1673
<212> TYPE: DNA
<213> ORGANISM: Agrobacterium sp.
<220> FEATURE:
<221> NAME/KEY: CDS
<222> LOCATION: (86)..(1432)

<400> SEQUENCE: 4

gtagccacac ataattacta tagctaggaa gcccgctatc tctcaatccc gcgtgatcgc     60

gccaaaatgt gactgtgaaa aatcc atg tcc cat tct gca tcc ccg aaa cca      112
                            Met Ser His Ser Ala Ser Pro Lys Pro
                            1               5

gca acc gcc cgc cgc tcg gag gca ctc acg ggc gaa atc cgc att ccg      160
Ala Thr Ala Arg Arg Ser Glu Ala Leu Thr Gly Glu Ile Arg Ile Pro
10                  15                  20                  25

ggc gac aag tcc atc tcg cat cgc tcc ttc atg ttt ggc ggt ctc gca      208
Gly Asp Lys Ser Ile Ser His Arg Ser Phe Met Phe Gly Gly Leu Ala
                30                  35                  40

tcg ggc gaa acc cgc atc acc ggc ctt ctg gaa ggc gag gac gtc atc      256
Ser Gly Glu Thr Arg Ile Thr Gly Leu Leu Glu Gly Glu Asp Val Ile
            45                  50                  55

aat aca ggc cgc gcc atg cag gcc atg ggc gcg aaa atc cgt aaa gag      304
Asn Thr Gly Arg Ala Met Gln Ala Met Gly Ala Lys Ile Arg Lys Glu
        60                  65                  70

ggc gat gtc tgg atc atc aac ggc gtc ggc aat ggc tgc ctg ttg cag      352
Gly Asp Val Trp Ile Ile Asn Gly Val Gly Asn Gly Cys Leu Leu Gln
    75                  80                  85

ccc gaa gct gcg ctc gat ttc ggc aat gcc gga acc ggc gcg cgc ctc      400
Pro Glu Ala Ala Leu Asp Phe Gly Asn Ala Gly Thr Gly Ala Arg Leu
90                  95                  100                 105

acc atg ggc ctt gtc ggc acc tat gac atg aag acc tcc ttt atc ggc      448
Thr Met Gly Leu Val Gly Thr Tyr Asp Met Lys Thr Ser Phe Ile Gly
                110                 115                 120

gac gcc tcg ctg tcg aag cgc ccg atg ggc cgc gtg ctg aac ccg ttg      496
Asp Ala Ser Leu Ser Lys Arg Pro Met Gly Arg Val Leu Asn Pro Leu
            125                 130                 135

cgc gaa atg ggc gtt cag gtg gaa gca gcc gat ggc gac cgc atg ccg      544
Arg Glu Met Gly Val Gln Val Glu Ala Ala Asp Gly Asp Arg Met Pro
        140                 145                 150

ctg acg ctg atc ggc ccg aag acg gcc aat ccg atc acc tat cgc gtg      592
Leu Thr Leu Ile Gly Pro Lys Thr Ala Asn Pro Ile Thr Tyr Arg Val
    155                 160                 165

ccg atg gcc tcc gcg cag gta aaa tcc gcc gtg ctg ctc gcc ggt ctc      640
Pro Met Ala Ser Ala Gln Val Lys Ser Ala Val Leu Leu Ala Gly Leu
170                 175                 180                 185

aac acg ccg ggc gtc acc acc gtc atc gag ccg gtc atg acc cgc gac      688
Asn Thr Pro Gly Val Thr Thr Val Ile Glu Pro Val Met Thr Arg Asp
                190                 195                 200

cac acc gaa aag atg ctg cag ggc ttt ggc gcc gac ctc acg gtc gag      736
His Thr Glu Lys Met Leu Gln Gly Phe Gly Ala Asp Leu Thr Val Glu
            205                 210                 215

acc gac aag gat ggc gtg cgc cat atc cgc atc acc ggc cag ggc aag      784
Thr Asp Lys Asp Gly Val Arg His Ile Arg Ile Thr Gly Gln Gly Lys
        220                 225                 230

ctt gtc ggc cag acc atc gac gtg ccg ggc gat ccg tca tcg acc gcc      832
Leu Val Gly Gln Thr Ile Asp Val Pro Gly Asp Pro Ser Ser Thr Ala
    235                 240                 245
```

-continued

```
ttc ccg ctc gtt gcc gcc ctt ctg gtg gaa ggt tcc gac gtc acc atc      880
Phe Pro Leu Val Ala Ala Leu Leu Val Glu Gly Ser Asp Val Thr Ile
250                 255                 260                 265

cgc aac gtg ctg atg aac ccg acc cgt acc ggc ctc atc ctc acc ttg      928
Arg Asn Val Leu Met Asn Pro Thr Arg Thr Gly Leu Ile Leu Thr Leu
                270                 275                 280

cag gaa atg ggc gcc gat atc gaa gtg ctc aat gcc cgt ctt gca ggc      976
Gln Glu Met Gly Ala Asp Ile Glu Val Leu Asn Ala Arg Leu Ala Gly
            285                 290                 295

ggc gaa gac gtc gcc gat ctg cgc gtc agg gct tcg aag ctc aag ggc     1024
Gly Glu Asp Val Ala Asp Leu Arg Val Arg Ala Ser Lys Leu Lys Gly
        300                 305                 310

gtc gtc gtt ccg ccg gaa cgt gcg ccg tcg atg atc gac gaa tat ccg     1072
Val Val Val Pro Pro Glu Arg Ala Pro Ser Met Ile Asp Glu Tyr Pro
    315                 320                 325

gtc ctg gcg att gcc gcc tcc ttc gcg gaa ggc gaa acc gtg atg gac     1120
Val Leu Ala Ile Ala Ala Ser Phe Ala Glu Gly Glu Thr Val Met Asp
330                 335                 340                 345

ggg ctc gac gaa ctg cgc gtc aag gaa tcg gat cgt ctg gca gcg gtc     1168
Gly Leu Asp Glu Leu Arg Val Lys Glu Ser Asp Arg Leu Ala Ala Val
                350                 355                 360

gca cgc ggc ctt gaa gcc aac ggc gtc gat tgc acc gaa ggc gag atg     1216
Ala Arg Gly Leu Glu Ala Asn Gly Val Asp Cys Thr Glu Gly Glu Met
            365                 370                 375

tcg ctg acg gtt cgc ggc cgc ccc gac ggc aag gga ctg ggc ggc ggc     1264
Ser Leu Thr Val Arg Gly Arg Pro Asp Gly Lys Gly Leu Gly Gly Gly
        380                 385                 390

acg gtt gca acc cat ctc gat cat cgt atc gcg atg agc ttc ctc gtg     1312
Thr Val Ala Thr His Leu Asp His Arg Ile Ala Met Ser Phe Leu Val
    395                 400                 405

atg ggc ctt gcg gcg gaa aag ccg gtg acg gtt gac gac agt aac atg     1360
Met Gly Leu Ala Ala Glu Lys Pro Val Thr Val Asp Asp Ser Asn Met
410                 415                 420                 425

atc gcc acg tcc ttc ccc gaa ttc atg gac atg atg ccg gga ttg ggc     1408
Ile Ala Thr Ser Phe Pro Glu Phe Met Asp Met Met Pro Gly Leu Gly
                430                 435                 440

gca aag atc gag ttg agc ata ctc tagtcactcg acagcgaaaa tattatttgc    1462
Ala Lys Ile Glu Leu Ser Ile Leu
            445

gagattgggc attattaccg gttggtctca gcgggggttt aatgtccaat cttccatacg   1522

taacagcatc aggaaatatc aaaaaagctt tagaaggaat tgctagagca gcgacgccgc   1582

ctaagctttc tcaagacttc gttaaaactg tactgaaatc ccggggggtc cggggatcaa   1642

atgacttcat ttctgagaaa ttggcctcgc a                                  1673
```

<210> SEQ ID NO 5
<211> LENGTH: 449
<212> TYPE: PRT
<213> ORGANISM: Agrobacterium sp.

<400> SEQUENCE: 5

```
Met Ser His Ser Ala Ser Pro Lys Pro Ala Thr Ala Arg Arg Ser Glu
1               5                   10                  15

Ala Leu Thr Gly Glu Ile Arg Ile Pro Gly Asp Lys Ser Ile Ser His
            20                  25                  30

Arg Ser Phe Met Phe Gly Gly Leu Ala Ser Gly Glu Thr Arg Ile Thr
        35                  40                  45

Gly Leu Leu Glu Gly Glu Asp Val Ile Asn Thr Gly Arg Ala Met Gln
```

-continued

```
    50                  55                  60

Ala Met Gly Ala Lys Ile Arg Lys Glu Gly Asp Val Trp Ile Ile Asn
65                  70                  75                  80

Gly Val Gly Asn Gly Cys Leu Leu Gln Pro Glu Ala Ala Leu Asp Phe
                85                  90                  95

Gly Asn Ala Gly Thr Gly Ala Arg Leu Thr Met Gly Leu Val Gly Thr
            100                 105                 110

Tyr Asp Met Lys Thr Ser Phe Ile Gly Asp Ala Ser Leu Ser Lys Arg
        115                 120                 125

Pro Met Gly Arg Val Leu Asn Pro Leu Arg Glu Met Gly Val Gln Val
    130                 135                 140

Glu Ala Ala Asp Gly Asp Arg Met Pro Leu Thr Leu Ile Gly Pro Lys
145                 150                 155                 160

Thr Ala Asn Pro Ile Thr Tyr Arg Val Pro Met Ala Ser Ala Gln Val
                165                 170                 175

Lys Ser Ala Val Leu Leu Ala Gly Leu Asn Thr Pro Gly Val Thr Thr
            180                 185                 190

Val Ile Glu Pro Val Met Thr Arg Asp His Thr Glu Lys Met Leu Gln
        195                 200                 205

Gly Phe Gly Ala Asp Leu Thr Val Glu Thr Asp Lys Asp Gly Val Arg
    210                 215                 220

His Ile Arg Ile Thr Gly Gln Gly Lys Leu Val Gly Gln Thr Ile Asp
225                 230                 235                 240

Val Pro Gly Asp Pro Ser Ser Thr Ala Phe Pro Leu Val Ala Ala Leu
                245                 250                 255

Leu Val Glu Gly Ser Asp Val Thr Ile Arg Asn Val Leu Met Asn Pro
            260                 265                 270

Thr Arg Thr Gly Leu Ile Leu Thr Leu Gln Glu Met Gly Ala Asp Ile
        275                 280                 285

Glu Val Leu Asn Ala Arg Leu Ala Gly Gly Glu Asp Val Ala Asp Leu
    290                 295                 300

Arg Val Arg Ala Ser Lys Leu Lys Gly Val Val Val Pro Pro Glu Arg
305                 310                 315                 320

Ala Pro Ser Met Ile Asp Glu Tyr Pro Val Leu Ala Ile Ala Ala Ser
                325                 330                 335

Phe Ala Glu Gly Glu Thr Val Met Asp Gly Leu Asp Glu Leu Arg Val
            340                 345                 350

Lys Glu Ser Asp Arg Leu Ala Ala Val Ala Arg Gly Leu Glu Ala Asn
        355                 360                 365

Gly Val Asp Cys Thr Glu Gly Glu Met Ser Leu Thr Val Arg Gly Arg
    370                 375                 380

Pro Asp Gly Lys Gly Leu Gly Gly Gly Thr Val Ala Thr His Leu Asp
385                 390                 395                 400

His Arg Ile Ala Met Ser Phe Leu Val Met Gly Leu Ala Ala Glu Lys
                405                 410                 415

Pro Val Thr Val Asp Asp Ser Asn Met Ile Ala Thr Ser Phe Pro Glu
            420                 425                 430

Phe Met Asp Met Met Pro Gly Leu Gly Ala Lys Ile Glu Leu Ser Ile
        435                 440                 445

Leu
```

<210> SEQ ID NO 6
<211> LENGTH: 1500

-continued

```
<212> TYPE: DNA
<213> ORGANISM: Pseudomonas sp.
<220> FEATURE:
<221> NAME/KEY: CDS
<222> LOCATION: (34)..(1380)

<400> SEQUENCE: 6

gtgatcgcgc caaaatgtga ctgtgaaaaa tcc atg tcc cat tct gca tcc ccg      54
                                  Met Ser His Ser Ala Ser Pro
                                  1               5

aaa cca gca acc gcc cgc cgc tcg gag gca ctc acg ggc gaa atc cgc      102
Lys Pro Ala Thr Ala Arg Arg Ser Glu Ala Leu Thr Gly Glu Ile Arg
        10                  15                  20

att ccg ggc gac aag tcc atc tcg cat cgc tcc ttc atg ttt ggc ggt      150
Ile Pro Gly Asp Lys Ser Ile Ser His Arg Ser Phe Met Phe Gly Gly
    25                  30                  35

ctc gca tcg ggc gaa acc cgc atc acc ggc ctt ctg gaa ggc gag gac      198
Leu Ala Ser Gly Glu Thr Arg Ile Thr Gly Leu Leu Glu Gly Glu Asp
40                  45                  50                  55

gtc atc aat aca ggc cgc gcc atg cag gcc atg ggc gcg aaa atc cgt      246
Val Ile Asn Thr Gly Arg Ala Met Gln Ala Met Gly Ala Lys Ile Arg
                60                  65                  70

aaa gag ggc gat gtc tgg atc atc aac ggc gtc ggc aat ggc tgc ctg      294
Lys Glu Gly Asp Val Trp Ile Ile Asn Gly Val Gly Asn Gly Cys Leu
            75                  80                  85

ttg cag ccc gaa gct gcg ctc gat ttc ggc aat gcc gga acc ggc gcg      342
Leu Gln Pro Glu Ala Ala Leu Asp Phe Gly Asn Ala Gly Thr Gly Ala
        90                  95                  100

cgc ctc acc atg ggc ctt gtc ggc acc tat gac atg aag acc tcc ttt      390
Arg Leu Thr Met Gly Leu Val Gly Thr Tyr Asp Met Lys Thr Ser Phe
    105                 110                 115

atc ggc gac gcc tcg ctg tcg aag cgc ccg atg ggc cgc gtg ctg aac      438
Ile Gly Asp Ala Ser Leu Ser Lys Arg Pro Met Gly Arg Val Leu Asn
120                 125                 130                 135

ccg ttg cgc gaa atg ggc gtt cag gtg gaa gca gcc gat ggc gac cgc      486
Pro Leu Arg Glu Met Gly Val Gln Val Glu Ala Ala Asp Gly Asp Arg
                140                 145                 150

atg ccg ctg acg ctg atc ggc ccg aag acg gcc aat ccg atc acc tat      534
Met Pro Leu Thr Leu Ile Gly Pro Lys Thr Ala Asn Pro Ile Thr Tyr
            155                 160                 165

cgc gtg ccg atg gcc tcc gcg cag gta aaa tcc gcc gtg ctg ctc gcc      582
Arg Val Pro Met Ala Ser Ala Gln Val Lys Ser Ala Val Leu Leu Ala
        170                 175                 180

ggt ctc aac acg ccg ggc gtc acc acc gtc atc gag ccg gtc atg acc      630
Gly Leu Asn Thr Pro Gly Val Thr Thr Val Ile Glu Pro Val Met Thr
    185                 190                 195

cgc gac cac acc gaa aag atg ctg cag ggc ttt ggc gcc gac ctc acg      678
Arg Asp His Thr Glu Lys Met Leu Gln Gly Phe Gly Ala Asp Leu Thr
200                 205                 210                 215

gtc gag acc gac aag gat ggc gtg cgc cat atc cgc atc acc ggc cag      726
Val Glu Thr Asp Lys Asp Gly Val Arg His Ile Arg Ile Thr Gly Gln
                220                 225                 230

ggc aag ctt gtc ggc cag acc atc gac gtg ccg ggc gat ccg tca tcg      774
Gly Lys Leu Val Gly Gln Thr Ile Asp Val Pro Gly Asp Pro Ser Ser
            235                 240                 245

acc gcc ttc ccg ctc gtt gcc gcc ctt ctg gtg gaa ggt tcc gac gtc      822
Thr Ala Phe Pro Leu Val Ala Ala Leu Leu Val Glu Gly Ser Asp Val
        250                 255                 260

acc atc cgc aac gtg ctg atg aac ccg acc cgt acc ggc ctc atc ctc      870
Thr Ile Arg Asn Val Leu Met Asn Pro Thr Arg Thr Gly Leu Ile Leu
    265                 270                 275
```

-continued

```
acc ttg cag gaa atg ggc gcc gat atc gaa gtg ctc aat gcc cgt ctt      918
Thr Leu Gln Glu Met Gly Ala Asp Ile Glu Val Leu Asn Ala Arg Leu
280                 285                 290                 295

gca ggc ggc gaa gac gtc gcc gat ctg cgc gtc agg gct tcg aag ctc      966
Ala Gly Gly Glu Asp Val Ala Asp Leu Arg Val Arg Ala Ser Lys Leu
                300                 305                 310

aag ggc gtc gtc gtt ccg ccg gaa cgt gcg ccg tcg atg atc gac gaa     1014
Lys Gly Val Val Val Pro Pro Glu Arg Ala Pro Ser Met Ile Asp Glu
            315                 320                 325

tat ccg gtc ctg gcg att gcc gcc tcc ttc gcg gaa ggc gaa acc gtg     1062
Tyr Pro Val Leu Ala Ile Ala Ala Ser Phe Ala Glu Gly Glu Thr Val
        330                 335                 340

atg gac ggg ctc gac gaa ctg cgc gtc aag gaa tcg gat cgt ctg gca     1110
Met Asp Gly Leu Asp Glu Leu Arg Val Lys Glu Ser Asp Arg Leu Ala
    345                 350                 355

gcg gtc gca cgc ggc ctt gaa gcc aac ggc gtc gat tgc acc gaa ggc     1158
Ala Val Ala Arg Gly Leu Glu Ala Asn Gly Val Asp Cys Thr Glu Gly
360                 365                 370                 375

gag atg tcg ctg acg gtt cgc ggc cgc ccc gac ggc aag gga ctg ggc     1206
Glu Met Ser Leu Thr Val Arg Gly Arg Pro Asp Gly Lys Gly Leu Gly
                380                 385                 390

ggc ggc acg gtt gca acc cat ctc gat cat cgt atc gcg atg agc ttc     1254
Gly Gly Thr Val Ala Thr His Leu Asp His Arg Ile Ala Met Ser Phe
            395                 400                 405

ctc gtg atg ggc ctt gcg gcg gaa aag ccg gtg acg gtt gac gac agt     1302
Leu Val Met Gly Leu Ala Ala Glu Lys Pro Val Thr Val Asp Asp Ser
        410                 415                 420

aac atg atc gcc acg tcc ttc ccc gaa ttc atg gac atg atg ccg gga     1350
Asn Met Ile Ala Thr Ser Phe Pro Glu Phe Met Asp Met Met Pro Gly
    425                 430                 435

ttg ggc gca aag atc gag ttg agc ata ctc tagtcactcg acagcgaaaa       1400
Leu Gly Ala Lys Ile Glu Leu Ser Ile Leu
440                 445

tattatttgc gagattgggc attattaccg gttggtctca gcgggggttt aatgtccaat   1460

cttccatacg taacagcatc aggaaatatc aaaaaagctt                         1500


<210> SEQ ID NO 7
<211> LENGTH: 449
<212> TYPE: PRT
<213> ORGANISM: Pseudomonas sp.

<400> SEQUENCE: 7

Met Ser His Ser Ala Ser Pro Lys Pro Ala Thr Ala Arg Arg Ser Glu
1               5                   10                  15

Ala Leu Thr Gly Glu Ile Arg Ile Pro Gly Asp Lys Ser Ile Ser His
            20                  25                  30

Arg Ser Phe Met Phe Gly Gly Leu Ala Ser Gly Glu Thr Arg Ile Thr
        35                  40                  45

Gly Leu Leu Glu Gly Glu Asp Val Ile Asn Thr Gly Arg Ala Met Gln
    50                  55                  60

Ala Met Gly Ala Lys Ile Arg Lys Glu Gly Asp Val Trp Ile Ile Asn
65                  70                  75                  80

Gly Val Gly Asn Gly Cys Leu Leu Gln Pro Glu Ala Ala Leu Asp Phe
                85                  90                  95

Gly Asn Ala Gly Thr Gly Ala Arg Leu Thr Met Gly Leu Val Gly Thr
            100                 105                 110

Tyr Asp Met Lys Thr Ser Phe Ile Gly Asp Ala Ser Leu Ser Lys Arg
```

-continued

```
        115                 120                 125

Pro Met Gly Arg Val Leu Asn Pro Leu Arg Glu Met Gly Val Gln Val
    130                 135                 140

Glu Ala Ala Asp Gly Asp Arg Met Pro Leu Thr Leu Ile Gly Pro Lys
145                 150                 155                 160

Thr Ala Asn Pro Ile Thr Tyr Arg Val Pro Met Ala Ser Ala Gln Val
                165                 170                 175

Lys Ser Ala Val Leu Leu Ala Gly Leu Asn Thr Pro Gly Val Thr Thr
            180                 185                 190

Val Ile Glu Pro Val Met Thr Arg Asp His Thr Glu Lys Met Leu Gln
        195                 200                 205

Gly Phe Gly Ala Asp Leu Thr Val Glu Thr Asp Lys Asp Gly Val Arg
    210                 215                 220

His Ile Arg Ile Thr Gly Gln Gly Lys Leu Val Gly Gln Thr Ile Asp
225                 230                 235                 240

Val Pro Gly Asp Pro Ser Ser Thr Ala Phe Pro Leu Val Ala Ala Leu
                245                 250                 255

Leu Val Glu Gly Ser Asp Val Thr Ile Arg Asn Val Leu Met Asn Pro
            260                 265                 270

Thr Arg Thr Gly Leu Ile Leu Thr Leu Gln Glu Met Gly Ala Asp Ile
        275                 280                 285

Glu Val Leu Asn Ala Arg Leu Ala Gly Gly Glu Asp Val Ala Asp Leu
    290                 295                 300

Arg Val Arg Ala Ser Lys Leu Lys Gly Val Val Val Pro Pro Glu Arg
305                 310                 315                 320

Ala Pro Ser Met Ile Asp Glu Tyr Pro Val Leu Ala Ile Ala Ala Ser
                325                 330                 335

Phe Ala Glu Gly Glu Thr Val Met Asp Gly Leu Asp Glu Leu Arg Val
            340                 345                 350

Lys Glu Ser Asp Arg Leu Ala Ala Val Ala Arg Gly Leu Glu Ala Asn
        355                 360                 365

Gly Val Asp Cys Thr Glu Gly Glu Met Ser Leu Thr Val Arg Gly Arg
    370                 375                 380

Pro Asp Gly Lys Gly Leu Gly Gly Gly Thr Val Ala Thr His Leu Asp
385                 390                 395                 400

His Arg Ile Ala Met Ser Phe Leu Val Met Gly Leu Ala Ala Glu Lys
                405                 410                 415

Pro Val Thr Val Asp Asp Ser Asn Met Ile Ala Thr Ser Phe Pro Glu
            420                 425                 430

Phe Met Asp Met Met Pro Gly Leu Gly Ala Lys Ile Glu Leu Ser Ile
        435                 440                 445

Leu


<210> SEQ ID NO 8
<211> LENGTH: 423
<212> TYPE: PRT
<213> ORGANISM: Escherichia coli

<400> SEQUENCE: 8

Ser Leu Thr Leu Gln Pro Ile Ala Arg Val Asp Gly Thr Ile Asn Leu
1               5                   10                  15

Pro Gly Ser Lys Thr Val Ser Asn Arg Ala Leu Leu Leu Ala Ala Leu
            20                  25                  30

Ala His Gly Lys Thr Val Leu Thr Asn Leu Leu Asp Ser Asp Asp Val
```

-continued

```
        35                  40                  45

Arg His Met Leu Asn Ala Leu Thr Ala Leu Gly Val Ser Tyr Thr Leu
    50                  55                  60

Ser Ala Asp Arg Thr Arg Cys Glu Ile Ile Gly Asn Gly Gly Pro Leu
65                  70                  75                  80

His Ala Glu Gly Ala Leu Glu Leu Phe Leu Gly Asn Ala Gly Thr Ala
                85                  90                  95

Met Arg Pro Leu Ala Ala Ala Leu Cys Leu Gly Ser Asn Asp Ile Val
            100                 105                 110

Leu Thr Gly Glu Pro Arg Met Lys Glu Arg Pro Ile Gly His Leu Val
        115                 120                 125

Asp Ala Leu Arg Leu Gly Gly Ala Lys Ile Thr Tyr Leu Glu Gln Glu
    130                 135                 140

Asn Tyr Pro Pro Leu Arg Leu Gln Gly Gly Phe Thr Gly Gly Asn Val
145                 150                 155                 160

Asp Val Asp Gly Ser Val Ser Ser Gln Phe Leu Thr Ala Leu Leu Met
                165                 170                 175

Thr Ala Pro Leu Ala Pro Glu Asp Thr Val Ile Arg Ile Lys Gly Asp
            180                 185                 190

Leu Val Ser Lys Pro Tyr Ile Asp Ile Thr Leu Asn Leu Met Lys Thr
        195                 200                 205

Phe Gly Val Glu Ile Glu Asn Gln His Tyr Gln Gln Phe Val Val Lys
    210                 215                 220

Gly Gly Gln Ser Tyr Gln Ser Pro Gly Thr Tyr Leu Val Glu Gly Asp
225                 230                 235                 240

Ala Ser Ser Ala Ser Tyr Phe Leu Ala Ala Ala Ala Ile Lys Gly Gly
                245                 250                 255

Thr Val Lys Val Thr Gly Ile Gly Arg Asn Ser Met Gln Gly Asp Ile
            260                 265                 270

Arg Phe Ala Asp Val Leu Glu Lys Met Gly Ala Thr Ile Cys Trp Gly
        275                 280                 285

Asp Asp Tyr Ile Ser Cys Thr Arg Gly Glu Leu Asn Ala Ile Asp Met
    290                 295                 300

Asp Met Asn His Ile Pro Asp Ala Ala Met Thr Ile Ala Thr Ala Ala
305                 310                 315                 320

Leu Phe Ala Lys Gly Thr Thr Arg Leu Arg Asn Ile Tyr Asn Trp Arg
                325                 330                 335

Val Lys Glu Thr Asp Arg Leu Phe Ala Met Ala Thr Glu Leu Arg Lys
            340                 345                 350

Val Gly Ala Glu Val Glu Glu Gly His Asp Tyr Ile Arg Ile Thr Pro
        355                 360                 365

Pro Glu Lys Leu Asn Phe Ala Glu Ile Ala Thr Tyr Asn Asp His Arg
    370                 375                 380

Met Ala Met Cys Phe Ser Leu Val Ala Leu Ser Asp Thr Pro Val Thr
385                 390                 395                 400

Ile Leu Asp Pro Lys Cys Thr Ala Lys Thr Phe Pro Asp Tyr Phe Glu
                405                 410                 415

Gln Leu Ala Arg Ile Ser Gln
            420
```

<210> SEQ ID NO 9
<211> LENGTH: 1377
<212> TYPE: DNA
<213> ORGANISM: Artificial sequence -continued <220> FEATURE:
<223> OTHER INFORMATION: Synthetic

<400> SEQUENCE: 9 ccatggctca cggtgcaagc agccgtccag caactgctcg taagtcctct ggtctttctg 60 gaaccgtccg tattccaggt gacaagtcta tctcccacag gtccttcatg tttggaggtc 120 tcgctagcgg tgaaactcgt atcaccggtc ttttggaagg tgaagatgtt atcaacactg 180 gtaaggctat gcaagctatg ggtgccagaa tccgtaagga aggtgatact tggatcattg 240 atggtgttgg taacggtgga ctccttgctc ctgaggctcc tctcgatttc ggtaacgctg 300 caactggttg ccgtttgact atgggtcttg ttggtgttta cgatttcgat agcactttca 360 ttggtgacgc ttctctcact aagcgtccaa tgggtcgtgt gttgaaccca cttcgcgaaa 420 tgggtgtgca ggtgaagtct gaagacggtg atcgtcttcc agttaccttg cgtggaccaa 480 agactccaac gccaatcacc tacagggtac ctatggcttc cgctcaagtg aagtccgctg 540 ttctgcttgc tggtctcaac accccaggta tcaccactgt tatcgagcca atcatgactc 600 gtgaccacac tgaaaagatg cttcaaggtt ttggtgctaa ccttaccgtt gagactgatg 660 ctgacggtgt gcgtaccatc cgtcttgaag gtcgtggtaa gctcaccggt caagtgattg 720 atgttccagg tgatccatcc tctactgctt tcccattggt tgctgccttg cttgttccag 780 gttccgacgt caccatcctt aacgttttga tgaacccaac ccgtactggt ctcatcttga 840 ctctgcagga aatgggtgcc gacatcgaag tgatcaaccc acgtcttgct ggtggagaag 900 acgtggctga cttgcgtgtt cgttcttcta ctttgaaggg tgttactgtt ccagaagacc 960 gtgctccttc tatgatcgac gagtatccaa ttctcgctgt tgcagctgca ttcgctgaag 1020 gtgctaccgt tatgaacggt ttggaagaac tccgtgttaa ggaaagcgac cgtctttctg 1080 ctgtcgcaaa cggtctcaag ctcaacggtg ttgattgcga tgaaggtgag acttctctcg 1140 tcgtgcgtgg tcgtcctgac ggtaagggtc tcggtaacgc ttctggagca gctgtcgcta 1200 cccacctcga tcaccgtatc gctatgagct tcctcgttat gggtctcgtt tctgaaaacc 1260 ctgttactgt tgatgatgct actatgatcg ctactagctt cccagagttc atggatttga 1320 tggctggtct tggagctaag atcgaactct ccgacactaa ggctgcttga tgagctc 1377

<210> SEQ ID NO 10
<211> LENGTH: 318
<212> TYPE: DNA
<213> ORGANISM: Arabidopsis thaliana
<220> FEATURE:
<221> NAME/KEY: CDS
<222> LOCATION: (87)..(317)

<400> SEQUENCE: 10 agatctatcg ataagcttga tgtaattgga ggaagatcaa aattttcaat ccccattctt 60 cgattgcttc aattgaagtt tctccg atg gcg caa gtt agc aga atc tgc aat 113
Met Ala Gln Val Ser Arg Ile Cys Asn
1 5 ggt gtg cag aac cca tct ctt atc tcc aat ctc tcg aaa tcc agt caa 161
Gly Val Gln Asn Pro Ser Leu Ile Ser Asn Leu Ser Lys Ser Ser Gln
10 15 20 25 cgc aaa tct ccc tta tcg gtt tct ctg aag acg cag cag cat cca cga 209
Arg Lys Ser Pro Leu Ser Val Ser Leu Lys Thr Gln Gln His Pro Arg
30 35 40 gct tat ccg att tcg tcg tcg tgg gga ttg aag aag agt ggg atg acg 257
Ala Tyr Pro Ile Ser Ser Ser Trp Gly Leu Lys Lys Ser Gly Met Thr
45 50 55

-continued

```
tta att ggc tct gag ctt cgt cct ctt aag gtc atg tct tct gtt tcc      305
Leu Ile Gly Ser Glu Leu Arg Pro Leu Lys Val Met Ser Ser Val Ser
        60                  65                  70

acg gcg tgc atg c                                                    318
Thr Ala Cys Met
    75


<210> SEQ ID NO 11
<211> LENGTH: 77
<212> TYPE: PRT
<213> ORGANISM: Arabidopsis thaliana

<400> SEQUENCE: 11

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys Met
65                  70                  75


<210> SEQ ID NO 12
<211> LENGTH: 402
<212> TYPE: DNA
<213> ORGANISM: Arabidopsis thaliana
<220> FEATURE:
<221> NAME/KEY: CDS
<222> LOCATION: (87)..(401)

<400> SEQUENCE: 12

agatctatcg ataagcttga tgtaattgga ggaagatcaa aattttcaat ccccattctt     60

cgattgcttc aattgaagtt tctccg atg gcg caa gtt agc aga atc tgc aat     113
                             Met Ala Gln Val Ser Arg Ile Cys Asn
                             1               5

ggt gtg cag aac cca tct ctt atc tcc aat ctc tcg aaa tcc agt caa      161
Gly Val Gln Asn Pro Ser Leu Ile Ser Asn Leu Ser Lys Ser Ser Gln
10                  15                  20                  25

cgc aaa tct ccc tta tcg gtt tct ctg aag acg cag cag cat cca cga      209
Arg Lys Ser Pro Leu Ser Val Ser Leu Lys Thr Gln Gln His Pro Arg
                30                  35                  40

gct tat ccg att tcg tcg tcg tgg gga ttg aag aag agt ggg atg acg      257
Ala Tyr Pro Ile Ser Ser Ser Trp Gly Leu Lys Lys Ser Gly Met Thr
            45                  50                  55

tta att ggc tct gag ctt cgt cct ctt aag gtc atg tct tct gtt tcc      305
Leu Ile Gly Ser Glu Leu Arg Pro Leu Lys Val Met Ser Ser Val Ser
        60                  65                  70

acg gcg gag aaa gcg tcg gag att gta ctt caa ccc att aga gaa atc      353
Thr Ala Glu Lys Ala Ser Glu Ile Val Leu Gln Pro Ile Arg Glu Ile
    75                  80                  85

tcc ggt ctt att aag ttg cct ggc tcc aag tct cta tca aat aga att c    402
Ser Gly Leu Ile Lys Leu Pro Gly Ser Lys Ser Leu Ser Asn Arg Ile
90                  95                  100                 105


<210> SEQ ID NO 13
<211> LENGTH: 105
<212> TYPE: PRT
<213> ORGANISM: Arabidopsis thaliana
```

-continued

<400> SEQUENCE: 13

Met Ala Gln Val Ser Arg Ile Cys Asn Gly Val Gln Asn Pro Ser Leu
1 5 10 15

Ile Ser Asn Leu Ser Lys Ser Ser Gln Arg Lys Ser Pro Leu Ser Val
20 25 30

Ser Leu Lys Thr Gln Gln His Pro Arg Ala Tyr Pro Ile Ser Ser Ser
35 40 45

Trp Gly Leu Lys Lys Ser Gly Met Thr Leu Ile Gly Ser Glu Leu Arg
50 55 60

Pro Leu Lys Val Met Ser Ser Val Ser Thr Ala Glu Lys Ala Ser Glu
65 70 75 80

Ile Val Leu Gln Pro Ile Arg Glu Ile Ser Gly Leu Ile Lys Leu Pro
85 90 95

Gly Ser Lys Ser Leu Ser Asn Arg Ile
100 105

<210> SEQ ID NO 14
<211> LENGTH: 233
<212> TYPE: DNA
<213> ORGANISM: Petunia x hybrida
<220> FEATURE:
<221> NAME/KEY: CDS
<222> LOCATION: (14)..(232)

<400> SEQUENCE: 14 agatctttca aga atg gca caa att aac aac atg gct caa ggg ata caa 49
Met Ala Gln Ile Asn Asn Met Ala Gln Gly Ile Gln
1 5 10 acc ctt aat ccc aat tcc aat ttc cat aaa ccc caa gtt cct aaa tct 97
Thr Leu Asn Pro Asn Ser Asn Phe His Lys Pro Gln Val Pro Lys Ser
15 20 25 tca agt ttt ctt gtt ttt gga tct aaa aaa ctg aaa aat tca gca aat 145
Ser Ser Phe Leu Val Phe Gly Ser Lys Lys Leu Lys Asn Ser Ala Asn
30 35 40 tct atg ttg gtt ttg aaa aaa gat tca att ttt atg caa aag ttt tgt 193
Ser Met Leu Val Leu Lys Lys Asp Ser Ile Phe Met Gln Lys Phe Cys
45 50 55 60 tcc ttt agg att tca gca tca gtg gct aca gcc tgc atg c 233
Ser Phe Arg Ile Ser Ala Ser Val Ala Thr Ala Cys Met
65 70

<210> SEQ ID NO 15
<211> LENGTH: 73
<212> TYPE: PRT
<213> ORGANISM: Petunia x hybrida

<400> SEQUENCE: 15

Met Ala Gln Ile Asn Asn Met Ala Gln Gly Ile Gln Thr Leu Asn Pro
1 5 10 15

Asn Ser Asn Phe His Lys Pro Gln Val Pro Lys Ser Ser Ser Phe Leu
20 25 30

Val Phe Gly Ser Lys Lys Leu Lys Asn Ser Ala Asn Ser Met Leu Val
35 40 45

Leu Lys Lys Asp Ser Ile Phe Met Gln Lys Phe Cys Ser Phe Arg Ile
50 55 60

Ser Ala Ser Val Ala Thr Ala Cys Met
65 70

<210> SEQ ID NO 16

-continued

```
<211> LENGTH: 352
<212> TYPE: DNA
<213> ORGANISM: Petunia x hybrida
<220> FEATURE:
<221> NAME/KEY: CDS
<222> LOCATION: (49)..(351)

<400> SEQUENCE: 16

agatctgcta gaaataattt tgtttaactt taagaaggag atatatcc atg gca caa      57
                                                     Met Ala Gln
                                                     1

att aac aac atg gct caa ggg ata caa acc ctt aat ccc aat tcc aat      105
Ile Asn Asn Met Ala Gln Gly Ile Gln Thr Leu Asn Pro Asn Ser Asn
    5                   10                  15

ttc cat aaa ccc caa gtt cct aaa tct tca agt ttt ctt gtt ttt gga      153
Phe His Lys Pro Gln Val Pro Lys Ser Ser Ser Phe Leu Val Phe Gly
20                  25                  30                  35

tct aaa aaa ctg aaa aat tca gca aat tct atg ttg gtt ttg aaa aaa      201
Ser Lys Lys Leu Lys Asn Ser Ala Asn Ser Met Leu Val Leu Lys Lys
                40                  45                  50

gat tca att ttt atg caa aag ttt tgt tcc ttt agg att tca gca tca      249
Asp Ser Ile Phe Met Gln Lys Phe Cys Ser Phe Arg Ile Ser Ala Ser
            55                  60                  65

gtg gct aca gca cag aag cct tct gag ata gtg ttg caa ccc att aaa      297
Val Ala Thr Ala Gln Lys Pro Ser Glu Ile Val Leu Gln Pro Ile Lys
        70                  75                  80

gag att tca ggc act gtt aaa ttg cct ggc tct aaa tca tta tct aat      345
Glu Ile Ser Gly Thr Val Lys Leu Pro Gly Ser Lys Ser Leu Ser Asn
    85                  90                  95

aga att c                                                            352
Arg Ile
100


<210> SEQ ID NO 17
<211> LENGTH: 101
<212> TYPE: PRT
<213> ORGANISM: Petunia x hybrida

<400> SEQUENCE: 17

Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Ser Phe Leu
            20                  25                  30

Val Phe Gly Ser Lys Lys Leu Lys Asn Ser Ala Asn Ser Met Leu Val
        35                  40                  45

Leu Lys Lys Asp Ser Ile Phe Met Gln Lys Phe Cys Ser Phe Arg Ile
    50                  55                  60

Ser Ala Ser Val Ala Thr Ala Gln Lys Pro Ser Glu Ile Val Leu Gln
65                  70                  75                  80

Pro Ile Lys Glu Ile Ser Gly Thr Val Lys Leu Pro Gly Ser Lys Ser
                85                  90                  95

Leu Ser Asn Arg Ile
            100


<210> SEQ ID NO 18
<211> LENGTH: 28
<212> TYPE: PRT
<213> ORGANISM: Agrobacterium sp.
<220> FEATURE:
<221> NAME/KEY: UNSURE
<222> LOCATION: (1)..(18)
<223> OTHER INFORMATION: Xaa = Unknown
```

-continued

<400> SEQUENCE: 18

Xaa His Gly Ala Ser Ser Arg Pro Ala Thr Ala Arg Lys Ser Ser Gly
1 5 10 15

Leu Xaa Gly Thr Val Arg Ile Pro Gly Asp Lys Met
20 25

<210> SEQ ID NO 19
<211> LENGTH: 13
<212> TYPE: PRT
<213> ORGANISM: Agrobacterium sp.

<400> SEQUENCE: 19

Ala Pro Ser Met Ile Asp Glu Tyr Pro Ile Leu Ala Val
1 5 10

<210> SEQ ID NO 20
<211> LENGTH: 15
<212> TYPE: PRT
<213> ORGANISM: Agrobacterium sp.

<400> SEQUENCE: 20

Ile Thr Gly Leu Leu Glu Gly Glu Asp Val Ile Asn Thr Gly Lys
1 5 10 15

<210> SEQ ID NO 21
<211> LENGTH: 17
<212> TYPE: DNA
<213> ORGANISM: Artificial sequence
<220> FEATURE:
<223> OTHER INFORMATION: Synthetic

<400> SEQUENCE: 21 atgathgayg artaycc 17

<210> SEQ ID NO 22
<211> LENGTH: 17
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: R = A or G;
Y = C or T/U;
N = A or C or G or T/U;
H = A or C or T/U

<400> SEQUENCE: 22 gargaygtna thaacac 17

<210> SEQ ID NO 23
<211> LENGTH: 17
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: R = A or G;
Y = C or T/U;
N = A or C or G or T/U;
H = A or C or T/U

<400> SEQUENCE: 23

-continued gargaygtna thaatac 17

<210> SEQ ID NO 24
<211> LENGTH: 38
<212> TYPE: DNA
<213> ORGANISM: Artificial sequence
<220> FEATURE:
<223> OTHER INFORMATION: Oligonucleotide

<400> SEQUENCE: 24 cgtggataga tctaggaaga caaccatggc tcacggtc 38

<210> SEQ ID NO 25
<211> LENGTH: 44
<212> TYPE: DNA
<213> ORGANISM: Artificial sequence
<220> FEATURE:
<223> OTHER INFORMATION: Oligonucleotide

<400> SEQUENCE: 25 ggatagatta aggaagacgc gcatgcttca cggtgcaagc agcc 44

<210> SEQ ID NO 26
<211> LENGTH: 35
<212> TYPE: DNA
<213> ORGANISM: Artificial sequence
<220> FEATURE:
<223> OTHER INFORMATION: Oligonucleotide

<400> SEQUENCE: 26 ggctgcctga tgagctccac aatcgccatc gatgg 35

<210> SEQ ID NO 27
<211> LENGTH: 32
<212> TYPE: DNA
<213> ORGANISM: Artificial sequence
<220> FEATURE:
<223> OTHER INFORMATION: Oligonucleotide

<400> SEQUENCE: 27 cgtcgctcgt cgtgcgtggc cgccctgacg gc 32

<210> SEQ ID NO 28
<211> LENGTH: 29
<212> TYPE: DNA
<213> ORGANISM: Artificial sequence
<220> FEATURE:
<223> OTHER INFORMATION: Oligonucleotide

<400> SEQUENCE: 28 cgggcaaggc catgcaggct atgggcgcc 29

<210> SEQ ID NO 29
<211> LENGTH: 31
<212> TYPE: DNA
<213> ORGANISM: Artificial sequence
<220> FEATURE:
<223> OTHER INFORMATION: Oligonucleotide

<400> SEQUENCE: 29 cgggctgccg cctgactatg ggcctcgtcg g 31

<210> SEQ ID NO 30
<211> LENGTH: 15
<212> TYPE: PRT
<213> ORGANISM: Pseudomonas sp.

-continued

<220> FEATURE:
<221> NAME/KEY: NON_CONS
<222> LOCATION: (1)..(1)
<223> OTHER INFORMATION: Xaa = unknown

<400> SEQUENCE: 30

Xaa His Ser Ala Ser Pro Lys Pro Ala Thr Ala Arg Arg Ser Glu
1 5 10 15

<210> SEQ ID NO 31
<211> LENGTH: 17
<212> TYPE: DNA
<213> ORGANISM: Artificial sequence
<220> FEATURE:
<223> OTHER INFORMATION: Oligonucleotide
<220> FEATURE:
<221> NAME/KEY: misc_feature
<222> LOCATION: (1)..(17)
<223> OTHER INFORMATION: B = C or G or T
S = G or C
Y = C or T

<400> SEQUENCE: 31 gcggtbgcsg gyttsgg 17

<210> SEQ ID NO 32
<211> LENGTH: 16
<212> TYPE: PRT
<213> ORGANISM: Artificial sequence
<220> FEATURE:
<223> OTHER INFORMATION: Synthetic

<400> SEQUENCE: 32

Pro Gly Asp Lys Ser Ile Ser His Arg Ser Phe Met Phe Gly Gly Leu
1 5 10 15

<210> SEQ ID NO 33
<211> LENGTH: 13
<212> TYPE: PRT
<213> ORGANISM: Artificial sequence
<220> FEATURE:
<223> OTHER INFORMATION: Oligonucleotide

<400> SEQUENCE: 33

Leu Asp Phe Gly Asn Ala Ala Thr Gly Cys Arg Leu Thr
1 5 10

<210> SEQ ID NO 34
<211> LENGTH: 26
<212> TYPE: DNA
<213> ORGANISM: Artificial sequence
<220> FEATURE:
<223> OTHER INFORMATION: Oligonucleotide

<400> SEQUENCE: 34 cggcaatgcc gccaccggcg cgcgcc 26

<210> SEQ ID NO 35
<211> LENGTH: 49
<212> TYPE: DNA
<213> ORGANISM: Artificial sequence
<220> FEATURE:
<223> OTHER INFORMATION: Oligonucleotide

<400> SEQUENCE: 35 ggacggctgc ttgcaccgtg aagcatgctt aagcttggcg taatcatgg 49

-continued

<210> SEQ ID NO 36
<211> LENGTH: 35
<212> TYPE: DNA
<213> ORGANISM: Artificial sequence
<220> FEATURE:
<223> OTHER INFORMATION: Oligonucleotide

<400> SEQUENCE: 36 ggaagacgcc cagaattcac ggtgcaagca gccgg 35

<210> SEQ ID NO 37
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: NON_CONS
<222> LOCATION: (2)..(2)
<223> OTHER INFORMATION: Xaa = Gly, Ser, Thr, Cys, Tyr, Asn, Gln, Asp,
or Glu
<220> FEATURE:
<221> NAME/KEY: NON_CONS
<222> LOCATION: (4)..(4)
<223> OTHER INFORMATION: Xaa = Ser or Thr

<400> SEQUENCE: 37

Arg Xaa His Xaa Glu
1 5

<210> SEQ ID NO 38
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: NON_CONS
<222> LOCATION: (4)..(4)
<223> OTHER INFORMATION: Xaa = Ser or Thr

<400> SEQUENCE: 38

Gly Asp Lys Xaa
1

<210> SEQ ID NO 39
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: NON_CONS
<222> LOCATION: (4)..(4)
<223> OTHER INFORMATION: Xaa=Ala, Arg, Asn, Asp, Cys, Gln, Glu, Gly,
His, Ile, Leu, Lys, Met, Phe, Pro, Ser, Thr, Trp, Tyr, or Val

<400> SEQUENCE: 39

Ser Ala Gln Xaa Lys
1 5

<210> SEQ ID NO 40
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: NON_CONS
<222> LOCATION: (2)..(2)
<223> OTHER INFORMATION: Xaa=Ala, Arg, Asn, Asp, Cys, ln, lu, ly, His, -continued

```
      Ile, Leu, Lys, Met, Phe, Pro, Ser, Thr, Trp, Tyr or Val

<400> SEQUENCE: 40

Asn Xaa Thr Arg
1


<210> SEQ ID NO 41
<211> LENGTH: 1287
<212> TYPE: DNA
<213> ORGANISM: Bacillus subtilis
<220> FEATURE:
<221> NAME/KEY: CDS
<222> LOCATION: (1)..(1287)

<400> SEQUENCE: 41

atg aaa cga gat aag gtg cag acc tta cat gga gaa ata cat att ccc       48
Met Lys Arg Asp Lys Val Gln Thr Leu His Gly Glu Ile His Ile Pro
1               5                   10                  15

ggt gat aaa tcc att tct cac cgc tct gtt atg ttt ggc gcg cta gcg       96
Gly Asp Lys Ser Ile Ser His Arg Ser Val Met Phe Gly Ala Leu Ala
            20                  25                  30

gca ggc aca aca aca gtt aaa aac ttt ctg ccg gga gca gat tgt ctg      144
Ala Gly Thr Thr Thr Val Lys Asn Phe Leu Pro Gly Ala Asp Cys Leu
        35                  40                  45

agc acg atc gat tgc ttt aga aaa atg ggt gtt cac att gag caa agc      192
Ser Thr Ile Asp Cys Phe Arg Lys Met Gly Val His Ile Glu Gln Ser
    50                  55                  60

agc agc gat gtc gtg att cac gga aaa gga atc gat gcc ctg aaa gag      240
Ser Ser Asp Val Val Ile His Gly Lys Gly Ile Asp Ala Leu Lys Glu
65                  70                  75                  80

cca gaa agc ctt tta gat gtc gga aat tca ggt aca acg att cgc ctg      288
Pro Glu Ser Leu Leu Asp Val Gly Asn Ser Gly Thr Thr Ile Arg Leu
                85                  90                  95

atg ctc gga ata ttg gcg ggc cgt cct ttt tac agc gcg gta gcc gga      336
Met Leu Gly Ile Leu Ala Gly Arg Pro Phe Tyr Ser Ala Val Ala Gly
            100                 105                 110

gat gag agc att gcg aaa cgc cca atg aag cgt gtg act gag cct ttg      384
Asp Glu Ser Ile Ala Lys Arg Pro Met Lys Arg Val Thr Glu Pro Leu
        115                 120                 125

aaa aaa atg ggg gct aaa atc gac ggc aga gcc ggc gga gag ttt aca      432
Lys Lys Met Gly Ala Lys Ile Asp Gly Arg Ala Gly Gly Glu Phe Thr
    130                 135                 140

ccg ctg tca gtg agc ggc gct tca tta aaa gga att gat tat gta tca      480
Pro Leu Ser Val Ser Gly Ala Ser Leu Lys Gly Ile Asp Tyr Val Ser
145                 150                 155                 160

cct gtt gca agc gcg caa att aaa tct gct gtt ttg ctg gcc gga tta      528
Pro Val Ala Ser Ala Gln Ile Lys Ser Ala Val Leu Leu Ala Gly Leu
                165                 170                 175

cag gct gag ggc aca aca act gta aca gag ccc cat aaa tct cgg gac      576
Gln Ala Glu Gly Thr Thr Thr Val Thr Glu Pro His Lys Ser Arg Asp
            180                 185                 190

cac act gag cgg atg ctt tct gct ttt ggc gtt aag ctt tct gaa gat      624
His Thr Glu Arg Met Leu Ser Ala Phe Gly Val Lys Leu Ser Glu Asp
        195                 200                 205

caa acg agt gtt tcc att gct ggt ggc cag aaa ctg aca gct gct gat      672
Gln Thr Ser Val Ser Ile Ala Gly Gly Gln Lys Leu Thr Ala Ala Asp
    210                 215                 220

att ttt gtt cct gga gac att tct tca gcc gcg ttt ttc ctt gct gct      720
Ile Phe Val Pro Gly Asp Ile Ser Ser Ala Ala Phe Phe Leu Ala Ala
225                 230                 235                 240

ggc gcg atg gtt cca aac agc aga att gta ttg aaa aac gta ggt tta      768
```

-continued

```
Gly Ala Met Val Pro Asn Ser Arg Ile Val Leu Lys Asn Val Gly Leu
                245                 250                 255

aat ccg act cgg aca ggt att att gat gtc ctt caa aac atg ggg gca      816
Asn Pro Thr Arg Thr Gly Ile Ile Asp Val Leu Gln Asn Met Gly Ala
            260                 265                 270

aaa ctt gaa atc aaa cca tct gct gat agc ggt gca gag cct tat gga      864
Lys Leu Glu Ile Lys Pro Ser Ala Asp Ser Gly Ala Glu Pro Tyr Gly
        275                 280                 285

gat ttg att ata gaa acg tca tct cta aag gca gtt gaa atc gga gga      912
Asp Leu Ile Ile Glu Thr Ser Ser Leu Lys Ala Val Glu Ile Gly Gly
    290                 295                 300

gat atc att ccg cgt tta att gat gag atc cct atc atc gcg ctt ctt      960
Asp Ile Ile Pro Arg Leu Ile Asp Glu Ile Pro Ile Ile Ala Leu Leu
305                 310                 315                 320

gcg act cag gcg gaa gga acc acc gtt att aag gac gcg gca gag cta     1008
Ala Thr Gln Ala Glu Gly Thr Thr Val Ile Lys Asp Ala Ala Glu Leu
                325                 330                 335

aaa gtg aaa gaa aca aac cgt att gat act gtt gtt tct gag ctt cgc     1056
Lys Val Lys Glu Thr Asn Arg Ile Asp Thr Val Val Ser Glu Leu Arg
            340                 345                 350

aag ctg ggt gct gaa att gaa ccg aca gca gat gga atg aag gtt tat     1104
Lys Leu Gly Ala Glu Ile Glu Pro Thr Ala Asp Gly Met Lys Val Tyr
        355                 360                 365

ggc aaa caa acg ttg aaa ggc ggc gct gca gtg tcc agc cac gga gat     1152
Gly Lys Gln Thr Leu Lys Gly Gly Ala Ala Val Ser Ser His Gly Asp
    370                 375                 380

cat cga atc gga atg atg ctt ggt att gct tcc tgt ata acg gag gag     1200
His Arg Ile Gly Met Met Leu Gly Ile Ala Ser Cys Ile Thr Glu Glu
385                 390                 395                 400

ccg att gaa atc gag cac acg gat gcc att cac gtt tct tat cca acc     1248
Pro Ile Glu Ile Glu His Thr Asp Ala Ile His Val Ser Tyr Pro Thr
                405                 410                 415

ttc ttc gag cat tta aat aag ctt tcg aaa aaa tcc tga                 1287
Phe Phe Glu His Leu Asn Lys Leu Ser Lys Lys Ser
            420                 425


<210> SEQ ID NO 42
<211> LENGTH: 428
<212> TYPE: PRT
<213> ORGANISM: Bacillus subtilis

<400> SEQUENCE: 42

Met Lys Arg Asp Lys Val Gln Thr Leu His Gly Glu Ile His Ile Pro
1               5                   10                  15

Gly Asp Lys Ser Ile Ser His Arg Ser Val Met Phe Gly Ala Leu Ala
            20                  25                  30

Ala Gly Thr Thr Thr Val Lys Asn Phe Leu Pro Gly Ala Asp Cys Leu
        35                  40                  45

Ser Thr Ile Asp Cys Phe Arg Lys Met Gly Val His Ile Glu Gln Ser
    50                  55                  60

Ser Ser Asp Val Val Ile His Gly Lys Gly Ile Asp Ala Leu Lys Glu
65                  70                  75                  80

Pro Glu Ser Leu Leu Asp Val Gly Asn Ser Gly Thr Thr Ile Arg Leu
                85                  90                  95

Met Leu Gly Ile Leu Ala Gly Arg Pro Phe Tyr Ser Ala Val Ala Gly
            100                 105                 110

Asp Glu Ser Ile Ala Lys Arg Pro Met Lys Arg Val Thr Glu Pro Leu
        115                 120                 125
```

-continued

```
Lys Lys Met Gly Ala Lys Ile Asp Gly Arg Ala Gly Gly Glu Phe Thr
    130                 135                 140

Pro Leu Ser Val Ser Gly Ala Ser Leu Lys Gly Ile Asp Tyr Val Ser
145                 150                 155                 160

Pro Val Ala Ser Ala Gln Ile Lys Ser Ala Val Leu Leu Ala Gly Leu
                165                 170                 175

Gln Ala Glu Gly Thr Thr Thr Val Thr Glu Pro His Lys Ser Arg Asp
            180                 185                 190

His Thr Glu Arg Met Leu Ser Ala Phe Gly Val Lys Leu Ser Glu Asp
        195                 200                 205

Gln Thr Ser Val Ser Ile Ala Gly Gly Gln Lys Leu Thr Ala Ala Asp
    210                 215                 220

Ile Phe Val Pro Gly Asp Ile Ser Ser Ala Ala Phe Phe Leu Ala Ala
225                 230                 235                 240

Gly Ala Met Val Pro Asn Ser Arg Ile Val Leu Lys Asn Val Gly Leu
                245                 250                 255

Asn Pro Thr Arg Thr Gly Ile Ile Asp Val Leu Gln Asn Met Gly Ala
            260                 265                 270

Lys Leu Glu Ile Lys Pro Ser Ala Asp Ser Gly Ala Glu Pro Tyr Gly
        275                 280                 285

Asp Leu Ile Ile Glu Thr Ser Ser Leu Lys Ala Val Glu Ile Gly Gly
    290                 295                 300

Asp Ile Ile Pro Arg Leu Ile Asp Glu Ile Pro Ile Ile Ala Leu Leu
305                 310                 315                 320

Ala Thr Gln Ala Glu Gly Thr Thr Val Ile Lys Asp Ala Ala Glu Leu
                325                 330                 335

Lys Val Lys Glu Thr Asn Arg Ile Asp Thr Val Val Ser Glu Leu Arg
            340                 345                 350

Lys Leu Gly Ala Glu Ile Glu Pro Thr Ala Asp Gly Met Lys Val Tyr
        355                 360                 365

Gly Lys Gln Thr Leu Lys Gly Gly Ala Ala Val Ser Ser His Gly Asp
    370                 375                 380

His Arg Ile Gly Met Met Leu Gly Ile Ala Ser Cys Ile Thr Glu Glu
385                 390                 395                 400

Pro Ile Glu Ile Glu His Thr Asp Ala Ile His Val Ser Tyr Pro Thr
                405                 410                 415

Phe Phe Glu His Leu Asn Lys Leu Ser Lys Lys Ser
            420                 425


<210> SEQ ID NO 43
<211> LENGTH: 1293
<212> TYPE: DNA
<213> ORGANISM: Staphylococcus aureus
<220> FEATURE:
<221> NAME/KEY: CDS
<222> LOCATION: (1)..(1293)

<400> SEQUENCE: 43

atg gta aat gaa caa atc att gat att tca ggt ccg tta aag ggc gaa       48
Met Val Asn Glu Gln Ile Ile Asp Ile Ser Gly Pro Leu Lys Gly Glu
1               5                   10                  15

ata gaa gtg ccg ggc gat aag tca atg aca cac cgt gca atc atg ttg       96
Ile Glu Val Pro Gly Asp Lys Ser Met Thr His Arg Ala Ile Met Leu
            20                  25                  30

gcg tcg cta gct gaa ggt gta tct act ata tat aag cca cta ctt ggc      144
Ala Ser Leu Ala Glu Gly Val Ser Thr Ile Tyr Lys Pro Leu Leu Gly
        35                  40                  45
```

-continued

```
gaa gat tgt cgt cgt acg atg gac att ttc cga cac tta ggt gta gaa      192
Glu Asp Cys Arg Arg Thr Met Asp Ile Phe Arg His Leu Gly Val Glu
    50                  55                  60

atc aaa gaa gat gat gaa aaa tta gtt gtg act tcc cca gga tat caa      240
Ile Lys Glu Asp Asp Glu Lys Leu Val Val Thr Ser Pro Gly Tyr Gln
65                  70                  75                  80

gtt aac acg cca cat caa gta ttg tat aca ggt aat tct ggt acg aca      288
Val Asn Thr Pro His Gln Val Leu Tyr Thr Gly Asn Ser Gly Thr Thr
                85                  90                  95

aca cga tta ttg gca ggt ttg tta agt ggt tta ggt aat gaa agt gtt      336
Thr Arg Leu Leu Ala Gly Leu Leu Ser Gly Leu Gly Asn Glu Ser Val
            100                 105                 110

ttg tct ggc gat gtt tca att ggt aaa agg cca atg gat cgt gtc ttg      384
Leu Ser Gly Asp Val Ser Ile Gly Lys Arg Pro Met Asp Arg Val Leu
        115                 120                 125

aga cca ttg aaa ctt atg gat gcg aat att gaa ggt att gaa gat aat      432
Arg Pro Leu Lys Leu Met Asp Ala Asn Ile Glu Gly Ile Glu Asp Asn
    130                 135                 140

tat aca cca tta att att aag cca tct gtc ata aaa ggt ata aat tat      480
Tyr Thr Pro Leu Ile Ile Lys Pro Ser Val Ile Lys Gly Ile Asn Tyr
145                 150                 155                 160

caa atg gaa gtt gca agt gca caa gta aaa agt gcc att tta ttt gca      528
Gln Met Glu Val Ala Ser Ala Gln Val Lys Ser Ala Ile Leu Phe Ala
                165                 170                 175

agt ttg ttt tct aag gaa ccg acc atc att aaa gaa tta gat gta agt      576
Ser Leu Phe Ser Lys Glu Pro Thr Ile Ile Lys Glu Leu Asp Val Ser
            180                 185                 190

cga aat cat act gag acg atg ttc aaa cat ttt aat att cca att gaa      624
Arg Asn His Thr Glu Thr Met Phe Lys His Phe Asn Ile Pro Ile Glu
        195                 200                 205

gca gaa ggg tta tca att aat aca acc cct gaa gca att cga tac att      672
Ala Glu Gly Leu Ser Ile Asn Thr Thr Pro Glu Ala Ile Arg Tyr Ile
    210                 215                 220

aaa cct gca gat ttt cat gtt cct ggc gat att tca tct gca gcg ttc      720
Lys Pro Ala Asp Phe His Val Pro Gly Asp Ile Ser Ser Ala Ala Phe
225                 230                 235                 240

ttt att gtt gca gca ctt atc aca cca gga agt gat gta aca att cat      768
Phe Ile Val Ala Ala Leu Ile Thr Pro Gly Ser Asp Val Thr Ile His
                245                 250                 255

aat gtt gga atc aat caa aca cgt tca ggt att att gat att gtt gaa      816
Asn Val Gly Ile Asn Gln Thr Arg Ser Gly Ile Ile Asp Ile Val Glu
            260                 265                 270

aaa atg ggc ggt aat atc caa ctt ttc aat caa aca act ggt gct gaa      864
Lys Met Gly Gly Asn Ile Gln Leu Phe Asn Gln Thr Thr Gly Ala Glu
        275                 280                 285

cct act gct tct att cgt att caa tac aca cca atg ctt caa cca ata      912
Pro Thr Ala Ser Ile Arg Ile Gln Tyr Thr Pro Met Leu Gln Pro Ile
    290                 295                 300

aca atc gaa gga gaa tta gtt cca aaa gca att gat gaa ctg cct gta      960
Thr Ile Glu Gly Glu Leu Val Pro Lys Ala Ile Asp Glu Leu Pro Val
305                 310                 315                 320

ata gca tta ctt tgt aca caa gca gtt ggc acg agt aca att aaa gat     1008
Ile Ala Leu Leu Cys Thr Gln Ala Val Gly Thr Ser Thr Ile Lys Asp
                325                 330                 335

gcc gag gaa tta aaa gta aaa gaa aca aat aga att gat aca acg gct     1056
Ala Glu Glu Leu Lys Val Lys Glu Thr Asn Arg Ile Asp Thr Thr Ala
            340                 345                 350

gat atg tta aac ttg tta ggg ttt gaa tta caa cca act aat gat gga     1104
Asp Met Leu Asn Leu Leu Gly Phe Glu Leu Gln Pro Thr Asn Asp Gly
```

-continued

```
        355                 360                 365

ttg att att cat ccg tca gaa ttt aaa aca aat gca aca gat att tta     1152
Leu Ile Ile His Pro Ser Glu Phe Lys Thr Asn Ala Thr Asp Ile Leu
    370                 375                 380

act gat cat cga ata gga atg atg ctt gca gtt gct tgt gta ctt tca     1200
Thr Asp His Arg Ile Gly Met Met Leu Ala Val Ala Cys Val Leu Ser
385                 390                 395                 400

agc gag cct gtc aaa atc aaa caa ttt gat gct gta aat gta tca ttt     1248
Ser Glu Pro Val Lys Ile Lys Gln Phe Asp Ala Val Asn Val Ser Phe
                405                 410                 415

cca gga ttt tta cca aaa cta aag ctt tta caa aat gag gga taa         1293
Pro Gly Phe Leu Pro Lys Leu Lys Leu Leu Gln Asn Glu Gly
            420                 425                 430


<210> SEQ ID NO 44
<211> LENGTH: 430
<212> TYPE: PRT
<213> ORGANISM: Staphylococcus aureus

<400> SEQUENCE: 44

Met Val Asn Glu Gln Ile Ile Asp Ile Ser Gly Pro Leu Lys Gly Glu
1               5                   10                  15

Ile Glu Val Pro Gly Asp Lys Ser Met Thr His Arg Ala Ile Met Leu
            20                  25                  30

Ala Ser Leu Ala Glu Gly Val Ser Thr Ile Tyr Lys Pro Leu Leu Gly
        35                  40                  45

Glu Asp Cys Arg Arg Thr Met Asp Ile Phe Arg His Leu Gly Val Glu
    50                  55                  60

Ile Lys Glu Asp Asp Glu Lys Leu Val Val Thr Ser Pro Gly Tyr Gln
65                  70                  75                  80

Val Asn Thr Pro His Gln Val Leu Tyr Thr Gly Asn Ser Gly Thr Thr
                85                  90                  95

Thr Arg Leu Leu Ala Gly Leu Leu Ser Gly Leu Gly Asn Glu Ser Val
            100                 105                 110

Leu Ser Gly Asp Val Ser Ile Gly Lys Arg Pro Met Asp Arg Val Leu
        115                 120                 125

Arg Pro Leu Lys Leu Met Asp Ala Asn Ile Glu Gly Ile Glu Asp Asn
    130                 135                 140

Tyr Thr Pro Leu Ile Ile Lys Pro Ser Val Ile Lys Gly Ile Asn Tyr
145                 150                 155                 160

Gln Met Glu Val Ala Ser Ala Gln Val Lys Ser Ala Ile Leu Phe Ala
                165                 170                 175

Ser Leu Phe Ser Lys Glu Pro Thr Ile Ile Lys Glu Leu Asp Val Ser
            180                 185                 190

Arg Asn His Thr Glu Thr Met Phe Lys His Phe Asn Ile Pro Ile Glu
        195                 200                 205

Ala Glu Gly Leu Ser Ile Asn Thr Thr Pro Glu Ala Ile Arg Tyr Ile
    210                 215                 220

Lys Pro Ala Asp Phe His Val Pro Gly Asp Ile Ser Ser Ala Ala Phe
225                 230                 235                 240

Phe Ile Val Ala Ala Leu Ile Thr Pro Gly Ser Asp Val Thr Ile His
                245                 250                 255

Asn Val Gly Ile Asn Gln Thr Arg Ser Gly Ile Ile Asp Ile Val Glu
            260                 265                 270

Lys Met Gly Gly Asn Ile Gln Leu Phe Asn Gln Thr Thr Gly Ala Glu
        275                 280                 285
```

```
Pro Thr Ala Ser Ile Arg Ile Gln Tyr Thr Pro Met Leu Gln Pro Ile
    290                 295                 300

Thr Ile Glu Gly Glu Leu Val Pro Lys Ala Ile Asp Glu Leu Pro Val
305                 310                 315                 320

Ile Ala Leu Leu Cys Thr Gln Ala Val Gly Thr Ser Thr Ile Lys Asp
                325                 330                 335

Ala Glu Glu Leu Lys Val Lys Glu Thr Asn Arg Ile Asp Thr Thr Ala
            340                 345                 350

Asp Met Leu Asn Leu Leu Gly Phe Glu Leu Gln Pro Thr Asn Asp Gly
        355                 360                 365

Leu Ile Ile His Pro Ser Glu Phe Lys Thr Asn Ala Thr Asp Ile Leu
    370                 375                 380

Thr Asp His Arg Ile Gly Met Met Leu Ala Val Ala Cys Val Leu Ser
385                 390                 395                 400

Ser Glu Pro Val Lys Ile Lys Gln Phe Asp Ala Val Asn Val Ser Phe
                405                 410                 415

Pro Gly Phe Leu Pro Lys Leu Lys Leu Leu Gln Asn Glu Gly
            420                 425                 430


<210> SEQ ID NO 45
<211> LENGTH: 28
<212> TYPE: DNA
<213> ORGANISM: Artificial sequence
<220> FEATURE:
<223> OTHER INFORMATION: Oligonucleotide

<400> SEQUENCE: 45

ggaacatatg aaacgagata aggtgcag                                        28


<210> SEQ ID NO 46
<211> LENGTH: 35
<212> TYPE: DNA
<213> ORGANISM: Artificial sequence
<220> FEATURE:
<223> OTHER INFORMATION: Oligonucleotide

<400> SEQUENCE: 46

ggaattcaaa cttcaggatc ttgagataga aaatg                                35


<210> SEQ ID NO 47
<211> LENGTH: 28
<212> TYPE: DNA
<213> ORGANISM: Artificial sequence
<220> FEATURE:
<223> OTHER INFORMATION: Oligonucleotide

<400> SEQUENCE: 47

ggggccatgg taaatgaaca aatcattg                                        28


<210> SEQ ID NO 48
<211> LENGTH: 33
<212> TYPE: DNA
<213> ORGANISM: Artificial sequence
<220> FEATURE:
<223> OTHER INFORMATION: Oligonucleotide

<400> SEQUENCE: 48

gggggagctc attatccctc attttgtaaa agc                                  33


<210> SEQ ID NO 49
<211> LENGTH: 480
```

-continued

<212> TYPE: PRT
<213> ORGANISM: Saccharomyces cerevisiae

<400> SEQUENCE: 49

Leu Thr Asp Glu Thr Leu Val Tyr Pro Phe Lys Asp Ile Pro Ala Asp
1 5 10 15

Gln Gln Lys Val Val Ile Pro Pro Gly Ser Lys Ser Ile Ser Asn Arg
20 25 30

Ala Leu Ile Leu Ala Ala Leu Gly Glu Gly Gln Cys Lys Ile Lys Asn
35 40 45

Leu Leu His Ser Asp Asp Thr Lys His Met Leu Thr Ala Val His Glu
50 55 60

Leu Lys Gly Ala Thr Ile Ser Trp Glu Asp Asn Gly Glu Thr Val Val
65 70 75 80

Val Glu Gly His Gly Gly Ser Thr Leu Ser Ala Cys Ala Asp Pro Leu
85 90 95

Tyr Leu Gly Asn Ala Gly Thr Ala Ser Arg Phe Leu Thr Ser Leu Ala
100 105 110

Ala Leu Val Asn Ser Thr Ser Ser Gln Lys Tyr Ile Val Leu Thr Gly
115 120 125

Asn Ala Arg Met Gln Gln Arg Pro Ile Ala Pro Leu Val Asp Ser Leu
130 135 140

Arg Ala Asn Gly Thr Lys Ile Glu Tyr Leu Asn Asn Glu Gly Ser Leu
145 150 155 160

Pro Ile Lys Val Tyr Thr Asp Ser Val Phe Lys Gly Gly Arg Ile Glu
165 170 175

Leu Ala Ala Thr Val Ser Ser Gln Tyr Val Ser Ser Ile Leu Met Cys
180 185 190

Ala Pro Tyr Ala Glu Glu Pro Val Thr Leu Ala Leu Val Gly Gly Lys
195 200 205

Pro Ile Ser Lys Leu Tyr Val Asp Met Thr Ile Lys Met Met Glu Lys
210 215 220

Phe Gly Ile Asn Val Glu Thr Ser Thr Thr Glu Pro Tyr Thr Tyr Tyr
225 230 235 240

Ile Pro Lys Gly His Tyr Ile Asn Pro Ser Glu Tyr Val Ile Glu Ser
245 250 255

Asp Ala Ser Ser Ala Thr Tyr Pro Leu Ala Phe Ala Ala Met Thr Gly
260 265 270

Thr Thr Val Thr Val Pro Asn Ile Gly Phe Glu Ser Leu Gln Gly Asp
275 280 285

Ala Arg Phe Ala Arg Asp Val Leu Lys Pro Met Gly Cys Lys Ile Thr
290 295 300

Gln Thr Ala Thr Ser Thr Thr Val Ser Gly Pro Pro Val Gly Thr Leu
305 310 315 320

Lys Pro Leu Lys His Val Asp Met Glu Pro Met Thr Asp Ala Phe Leu
325 330 335

Thr Ala Cys Val Val Ala Ala Ile Ser His Asp Ser Asp Pro Asn Ser
340 345 350

Ala Asn Thr Thr Thr Ile Glu Gly Ile Ala Asn Gln Arg Val Lys Glu
355 360 365

Cys Asn Arg Ile Leu Ala Met Ala Thr Glu Leu Ala Lys Phe Gly Val
370 375 380

Lys Thr Thr Glu Leu Pro Asp Gly Ile Gln Val His Gly Leu Asn Ser
385 390 395 400

-continued

```
Ile Lys Asp Leu Lys Val Pro Ser Asp Ser Ser Gly Pro Val Gly Val
                405                 410                 415

Cys Thr Tyr Asp Asp His Arg Val Ala Met Ser Phe Ser Leu Leu Ala
            420                 425                 430

Gly Met Val Asn Ser Gln Asn Glu Arg Asp Glu Val Ala Asn Pro Val
        435                 440                 445

Arg Ile Leu Glu Arg His Cys Thr Gly Lys Thr Trp Pro Gly Trp Trp
    450                 455                 460

Asp Val Leu His Ser Glu Leu Gly Ala Lys Leu Asp Gly Ala Glu Pro
465                 470                 475                 480


<210> SEQ ID NO 50
<211> LENGTH: 460
<212> TYPE: PRT
<213> ORGANISM: Aspergillus ridulaus

<400> SEQUENCE: 50

Leu Ala Pro Ser Ile Glu Val His Pro Gly Val Ala His Ser Ser Asn
1               5                   10                  15

Val Ile Cys Ala Pro Pro Gly Ser Lys Ser Ile Ser Asn Arg Ala Leu
            20                  25                  30

Val Leu Ala Ala Leu Gly Ser Gly Thr Cys Arg Ile Lys Asn Leu Leu
        35                  40                  45

His Ser Asp Asp Thr Glu Val Met Leu Asn Ala Leu Glu Arg Leu Gly
    50                  55                  60

Ala Ala Thr Phe Ser Trp Glu Glu Glu Gly Glu Val Leu Val Val Asn
65                  70                  75                  80

Gly Lys Gly Gly Asn Leu Gln Ala Ser Ser Ser Pro Leu Tyr Leu Gly
                85                  90                  95

Asn Ala Gly Thr Ala Ser Arg Phe Leu Thr Thr Val Ala Thr Leu Ala
            100                 105                 110

Asn Ser Ser Thr Val Asp Ser Ser Val Leu Thr Gly Asn Asn Arg Met
        115                 120                 125

Lys Gln Arg Pro Ile Gly Asp Leu Val Asp Ala Leu Thr Ala Asn Val
    130                 135                 140

Leu Pro Leu Asn Thr Ser Lys Gly Arg Ala Ser Leu Pro Leu Lys Ile
145                 150                 155                 160

Ala Ala Ser Gly Gly Phe Ala Gly Gly Asn Ile Asn Leu Ala Ala Lys
                165                 170                 175

Val Ser Ser Gln Tyr Val Ser Ser Leu Leu Met Cys Ala Pro Tyr Ala
            180                 185                 190

Lys Glu Pro Val Thr Leu Arg Leu Val Gly Gly Lys Pro Ile Ser Gln
        195                 200                 205

Pro Tyr Ile Asp Met Thr Thr Ala Met Met Arg Ser Phe Gly Ile Asp
    210                 215                 220

Val Gln Lys Ser Thr Thr Glu Glu His Thr Tyr His Ile Pro Gln Gly
225                 230                 235                 240

Arg Tyr Val Asn Pro Ala Glu Tyr Val Ile Glu Ser Asp Ala Ser Cys
                245                 250                 255

Ala Thr Tyr Pro Leu Ala Val Ala Ala Val Thr Gly Thr Thr Cys Thr
            260                 265                 270

Val Pro Asn Ile Gly Ser Ala Ser Leu Gln Gly Asp Ala Arg Phe Ala
        275                 280                 285

Val Glu Val Leu Arg Pro Met Gly Cys Thr Val Glu Gln Thr Glu Thr
```

-continued

```
    290                 295                 300

Ser Thr Thr Val Thr Gly Pro Ser Asp Gly Ile Leu Arg Ala Thr Ser
305                 310                 315                 320

Lys Arg Gly Tyr Gly Thr Asn Asp Arg Cys Val Pro Arg Cys Phe Arg
                325                 330                 335

Thr Gly Ser His Arg Pro Met Glu Lys Ser Gln Thr Thr Pro Pro Val
            340                 345                 350

Ser Ser Gly Ile Ala Asn Gln Arg Val Lys Glu Cys Asn Arg Ile Lys
        355                 360                 365

Ala Met Lys Asp Glu Leu Ala Lys Phe Gly Val Ile Cys Arg Glu His
    370                 375                 380

Asp Asp Gly Leu Glu Ile Asp Gly Ile Asp Arg Ser Asn Leu Arg Gln
385                 390                 395                 400

Pro Val Gly Gly Val Phe Cys Tyr Asp Asp His Arg Val Ala Phe Ser
                405                 410                 415

Phe Ser Val Leu Ser Leu Val Thr Pro Gln Pro Thr Leu Ile Leu Glu
            420                 425                 430

Lys Glu Cys Val Gly Lys Thr Trp Pro Gly Trp Trp Asp Thr Leu Arg
        435                 440                 445

Gln Leu Phe Lys Val Lys Leu Glu Gly Lys Glu Leu
    450                 455                 460


<210> SEQ ID NO 51
<211> LENGTH: 444
<212> TYPE: PRT
<213> ORGANISM: Brassica napus

<400> SEQUENCE: 51

Lys Ala Ser Glu Ile Val Leu Gln Pro Ile Arg Glu Ile Ser Gly Leu
1               5                   10                  15

Ile Lys Leu Pro Gly Ser Lys Ser Leu Ser Asn Arg Ile Leu Leu Leu
            20                  25                  30

Ala Ala Leu Ser Glu Gly Thr Thr Val Val Asp Asn Leu Leu Asn Ser
        35                  40                  45

Asp Asp Ile Asn Tyr Met Leu Asp Ala Leu Lys Lys Leu Gly Leu Asn
    50                  55                  60

Val Glu Arg Asp Ser Val Asn Asn Arg Ala Val Val Glu Gly Cys Gly
65                  70                  75                  80

Gly Ile Phe Pro Ala Ser Leu Asp Ser Lys Ser Asp Ile Glu Leu Tyr
                85                  90                  95

Leu Gly Asn Ala Gly Thr Ala Met Arg Pro Leu Thr Ala Ala Val Thr
            100                 105                 110

Ala Ala Gly Gly Asn Ala Ser Tyr Val Leu Asp Gly Val Pro Arg Met
        115                 120                 125

Arg Glu Arg Pro Ile Gly Asp Leu Val Val Gly Leu Lys Gln Leu Gly
    130                 135                 140

Ala Asp Val Glu Cys Thr Leu Gly Thr Asn Cys Pro Pro Val Arg Val
145                 150                 155                 160

Asn Ala Asn Gly Gly Leu Pro Gly Gly Lys Val Lys Leu Ser Gly Ser
                165                 170                 175

Ile Ser Ser Gln Tyr Leu Thr Ala Leu Leu Met Ala Ala Pro Leu Ala
            180                 185                 190

Leu Gly Asp Val Glu Ile Glu Ile Ile Asp Lys Leu Ile Ser Val Pro
        195                 200                 205
```

-continued

```
Tyr Val Glu Met Thr Leu Lys Leu Met Glu Arg Phe Gly Val Ser Ala
    210                 215                 220

Glu His Ser Asp Ser Trp Asp Arg Phe Phe Val Lys Gly Gly Gln Lys
225                 230                 235                 240

Tyr Lys Ser Pro Gly Asn Ala Tyr Val Glu Gly Asp Ala Ser Ser Ala
                245                 250                 255

Ser Tyr Phe Leu Ala Gly Ala Ala Ile Thr Gly Glu Thr Val Thr Val
            260                 265                 270

Glu Gly Cys Gly Thr Thr Ser Leu Gln Gly Asp Val Lys Phe Ala Glu
        275                 280                 285

Val Leu Glu Lys Met Gly Cys Lys Val Ser Trp Thr Glu Asn Ser Val
    290                 295                 300

Thr Val Thr Gly Pro Ser Arg Asp Ala Phe Gly Met Arg His Leu Arg
305                 310                 315                 320

Ala Val Asp Val Asn Met Asn Lys Met Pro Asp Val Ala Met Thr Leu
                325                 330                 335

Ala Val Val Ala Leu Phe Ala Asp Gly Pro Thr Thr Ile Arg Asp Val
            340                 345                 350

Ala Ser Trp Arg Val Lys Glu Thr Glu Arg Met Ile Ala Ile Cys Thr
        355                 360                 365

Glu Leu Arg Lys Leu Gly Ala Thr Val Glu Glu Gly Ser Asp Tyr Cys
    370                 375                 380

Val Ile Thr Pro Pro Ala Lys Val Lys Pro Ala Glu Ile Asp Thr Tyr
385                 390                 395                 400

Asp Asp His Arg Met Ala Met Ala Phe Ser Leu Ala Ala Cys Ala Asp
                405                 410                 415

Val Pro Val Thr Ile Lys Asp Pro Gly Cys Thr Arg Lys Thr Phe Pro
            420                 425                 430

Asp Tyr Phe Gln Val Leu Glu Ser Ile Thr Lys His
        435                 440


<210> SEQ ID NO 52
<211> LENGTH: 444
<212> TYPE: PRT
<213> ORGANISM: Arabidopsis thaliana

<400> SEQUENCE: 52

Lys Ala Ser Glu Ile Val Leu Gln Pro Ile Arg Glu Ile Ser Gly Leu
1               5                   10                  15

Ile Lys Leu Pro Gly Ser Lys Ser Leu Ser Asn Arg Ile Leu Leu Leu
            20                  25                  30

Ala Ala Leu Ser Glu Gly Thr Thr Val Val Asp Asn Leu Leu Asn Ser
        35                  40                  45

Asp Asp Ile Asn Tyr Met Leu Asp Ala Leu Lys Arg Leu Gly Leu Asn
    50                  55                  60

Val Glu Thr Asp Ser Glu Asn Asn Arg Ala Val Val Glu Gly Cys Gly
65                  70                  75                  80

Gly Ile Phe Pro Ala Ser Ile Asp Ser Lys Ser Asp Ile Glu Leu Tyr
                85                  90                  95

Leu Gly Asn Ala Gly Thr Ala Met Arg Pro Leu Thr Ala Ala Val Thr
            100                 105                 110

Ala Ala Gly Gly Asn Ala Ser Tyr Val Leu Asp Gly Val Pro Arg Met
        115                 120                 125

Arg Glu Arg Pro Ile Gly Asp Leu Val Val Gly Leu Lys Gln Leu Gly
    130                 135                 140
```

-continued

```
Ala Asp Val Glu Cys Thr Leu Gly Thr Asn Cys Pro Pro Val Arg Val
145                 150                 155                 160

Asn Ala Asn Gly Gly Leu Pro Gly Gly Lys Val Lys Leu Ser Gly Ser
                165                 170                 175

Ile Ser Ser Gln Tyr Leu Thr Ala Leu Leu Met Ser Ala Pro Leu Ala
            180                 185                 190

Leu Gly Asp Val Glu Ile Glu Ile Val Asp Lys Leu Ile Ser Val Pro
        195                 200                 205

Tyr Val Glu Met Thr Leu Lys Leu Met Glu Arg Phe Gly Val Ser Val
    210                 215                 220

Glu His Ser Asp Ser Trp Asp Arg Phe Phe Val Lys Gly Gly Gln Lys
225                 230                 235                 240

Tyr Lys Ser Pro Gly Asn Ala Tyr Val Glu Gly Asp Ala Ser Ser Ala
                245                 250                 255

Cys Tyr Phe Leu Ala Gly Ala Ala Ile Thr Gly Glu Thr Val Thr Val
            260                 265                 270

Glu Gly Cys Gly Thr Thr Ser Leu Gln Gly Asp Val Lys Phe Ala Glu
        275                 280                 285

Val Leu Glu Lys Met Gly Cys Lys Val Ser Trp Thr Glu Asn Ser Val
    290                 295                 300

Thr Val Thr Gly Pro Pro Arg Asp Ala Phe Gly Met Arg His Leu Arg
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Thr Ile Arg Asp Val
            340                 345                 350

Ala Ser Trp Arg Val Lys Glu Thr Glu Arg Met Ile Ala Ile Cys Thr
        355                 360                 365

Glu Leu Arg Lys Leu Gly Ala Thr Val Glu Glu Gly Ser Asp Tyr Cys
    370                 375                 380

Val Ile Thr Pro Pro Lys Lys Val Lys Thr Ala Glu Ile Asp Thr Tyr
385                 390                 395                 400

Asp Asp His Arg Met Ala Met Ala Phe Ser Leu Ala Ala Cys Ala Asp
                405                 410                 415

Val Pro Ile Thr Ile Asn Asp Ser Gly Cys Thr Arg Lys Thr Phe Pro
            420                 425                 430

Asp Tyr Phe Gln Val Leu Glu Arg Ile Thr Lys His
        435                 440


<210> SEQ ID NO 53
<211> LENGTH: 444
<212> TYPE: PRT
<213> ORGANISM: Nicotiana tabacum

<400> SEQUENCE: 53

Lys Pro Asn Glu Ile Val Leu Gln Pro Ile Lys Asp Ile Ser Gly Thr
1               5                   10                  15

Val Lys Leu Pro Gly Ser Lys Ser Leu Ser Asn Arg Ile Leu Leu Leu
            20                  25                  30

Ala Ala Leu Ser Lys Gly Arg Thr Val Val Asp Asn Leu Leu Ser Ser
        35                  40                  45

Asp Asp Ile His Tyr Met Leu Gly Ala Leu Lys Thr Leu Gly Leu His
    50                  55                  60

Val Glu Asp Asp Asn Glu Asn Gln Arg Ala Ile Val Glu Gly Cys Gly
```

-continued

```
65                  70                  75                  80

Gly Gln Phe Pro Val Gly Lys Lys Ser Glu Glu Glu Ile Gln Leu Phe
                85                  90                  95

Leu Gly Asn Ala Gly Thr Ala Met Arg Pro Leu Thr Ala Ala Val Thr
            100                 105                 110

Val Ala Gly Gly His Ser Arg Tyr Val Leu Asp Gly Val Pro Arg Met
        115                 120                 125

Arg Glu Arg Pro Ile Gly Asp Leu Val Asp Gly Leu Lys Gln Leu Gly
    130                 135                 140

Ala Glu Val Asp Cys Phe Leu Gly Thr Asn Cys Pro Pro Val Arg Ile
145                 150                 155                 160

Val Ser Lys Gly Gly Leu Pro Gly Gly Lys Val Lys Leu Ser Gly Ser
                165                 170                 175

Ile Ser Ser Gln Tyr Leu Thr Ala Leu Leu Met Ala Ala Pro Leu Ala
            180                 185                 190

Leu Gly Asp Val Glu Ile Glu Ile Ile Asp Lys Leu Ile Ser Val Pro
        195                 200                 205

Tyr Val Glu Met Thr Leu Lys Leu Met Glu Arg Phe Gly Val Ser Val
    210                 215                 220

Glu His Thr Ser Ser Trp Asp Lys Phe Leu Val Arg Gly Gly Gln Lys
225                 230                 235                 240

Tyr Lys Ser Pro Gly Lys Ala Tyr Val Glu Gly Asp Ala Ser Ser Ala
                245                 250                 255

Ser Tyr Phe Leu Ala Gly Ala Ala Val Thr Gly Gly Thr Val Thr Val
            260                 265                 270

Glu Gly Cys Gly Thr Ser Ser Leu Gln Gly Asp Val Lys Phe Ala Glu
        275                 280                 285

Val Leu Glu Lys Met Gly Ala Glu Val Thr Trp Thr Glu Asn Ser Val
    290                 295                 300

Thr Val Lys Gly Pro Pro Arg Asn Ser Ser Gly Met Lys His Leu Arg
305                 310                 315                 320

Ala Val Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Ile Ala Ile Cys Thr
        355                 360                 365

Glu Leu Arg Lys Leu Gly Ala Thr Val Val Glu Gly Ser Asp Tyr Cys
    370                 375                 380

Ile Ile Thr Pro Pro Glu Lys Leu Asn Val Thr Glu Ile Asp Thr Tyr
385                 390                 395                 400

Asp Asp His Arg Met Ala Met Ala Phe Ser Leu Ala Ala Cys Ala Asp
                405                 410                 415

Val Pro Val Thr Ile Lys Asp Pro Gly Cys Thr Arg Lys Thr Phe Pro
            420                 425                 430

Asn Tyr Phe Asp Val Leu Gln Gln Tyr Ser Lys His
        435                 440
```

<210> SEQ ID NO 54
<211> LENGTH: 444
<212> TYPE: PRT
<213> ORGANISM: Lycopersicon esculentum
<220> FEATURE:
<221> NAME/KEY: UNSURE
<222> LOCATION: (1)..(444)

-continued

<223> OTHER INFORMATION: Xaa = any

<400> SEQUENCE: 54

```
Lys Pro His Glu Ile Val Leu Xaa Pro Ile Lys Asp Ile Ser Gly Thr
1               5                   10                  15

Val Lys Leu Pro Gly Ser Lys Ser Leu Ser Asn Arg Ile Leu Leu Leu
            20                  25                  30

Ala Ala Leu Ser Glu Gly Arg Thr Val Val Asp Asn Leu Leu Ser Ser
        35                  40                  45

Asp Asp Ile His Tyr Met Leu Gly Ala Leu Lys Thr Leu Gly Leu His
    50                  55                  60

Val Glu Asp Asp Asn Glu Asn Gln Arg Ala Ile Val Glu Gly Cys Gly
65                  70                  75                  80

Gly Gln Phe Pro Val Gly Lys Lys Ser Glu Glu Glu Ile Gln Leu Phe
                85                  90                  95

Leu Gly Asn Ala Gly Thr Ala Met Arg Pro Leu Thr Ala Ala Val Thr
            100                 105                 110

Val Ala Gly Gly His Ser Arg Tyr Val Leu Asp Gly Val Pro Arg Met
        115                 120                 125

Arg Glu Arg Pro Ile Gly Asp Leu Val Asp Gly Leu Lys Gln Leu Gly
    130                 135                 140

Ala Glu Val Asp Cys Ser Leu Gly Thr Asn Cys Pro Pro Val Arg Ile
145                 150                 155                 160

Val Ser Lys Gly Gly Leu Pro Gly Gly Lys Val Lys Leu Ser Gly Ser
                165                 170                 175

Ile Ser Ser Gln Tyr Leu Thr Ala Leu Leu Met Ala Ala Pro Leu Ala
            180                 185                 190

Leu Gly Asp Val Glu Ile Glu Ile Ile Asp Lys Leu Ile Ser Val Pro
        195                 200                 205

Tyr Val Glu Met Thr Leu Lys Leu Met Glu Arg Phe Gly Val Phe Val
    210                 215                 220

Glu His Ser Ser Gly Trp Asp Arg Phe Leu Val Lys Gly Gly Gln Lys
225                 230                 235                 240

Tyr Lys Ser Pro Gly Lys Ala Phe Val Glu Gly Asp Ala Ser Ser Ala
                245                 250                 255

Ser Tyr Phe Leu Ala Gly Ala Ala Val Thr Gly Gly Thr Val Thr Val
            260                 265                 270

Glu Gly Cys Gly Thr Ser Ser Leu Gln Gly Asp Val Lys Phe Ala Glu
        275                 280                 285

Val Leu Glu Lys Met Gly Ala Glu Val Thr Trp Thr Glu Asn Ser Val
    290                 295                 300

Thr Val Lys Gly Pro Pro Arg Asn Ser Ser Gly Met Lys His Leu Arg
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Thr Ile Arg Asp Val
            340                 345                 350

Ala Ser Trp Arg Val Lys Glu Thr Glu Arg Met Ile Ala Ile Cys Thr
        355                 360                 365

Glu Leu Arg Lys Leu Gly Ala Thr Val Val Glu Gly Ser Asp Tyr Cys
    370                 375                 380

Ile Ile Thr Pro Pro Glu Lys Leu Asn Val Thr Glu Ile Asp Thr Tyr
385                 390                 395                 400
```

-continued

```
Asp Asp His Arg Met Ala Met Ala Phe Ser Leu Ala Ala Cys Ala Asp
                405                 410                 415

Val Pro Val Thr Ile Lys Asn Pro Gly Cys Thr Arg Lys Thr Phe Pro
            420                 425                 430

Asp Tyr Phe Glu Val Leu Gln Lys Tyr Ser Lys His
        435                 440


<210> SEQ ID NO 55
<211> LENGTH: 444
<212> TYPE: PRT
<213> ORGANISM: Petunia x hybrida

<400> SEQUENCE: 55

Lys Pro Ser Glu Ile Val Leu Gln Pro Ile Lys Glu Ile Ser Gly Thr
1               5                   10                  15

Val Lys Leu Pro Gly Ser Lys Ser Leu Ser Asn Arg Ile Leu Leu Leu
            20                  25                  30

Ala Ala Leu Ser Glu Gly Thr Thr Val Val Asp Asn Leu Leu Ser Ser
        35                  40                  45

Asp Asp Ile His Tyr Met Leu Gly Ala Leu Lys Thr Leu Gly Leu His
    50                  55                  60

Val Glu Glu Asp Ser Ala Asn Gln Arg Ala Val Val Glu Gly Cys Gly
65                  70                  75                  80

Gly Leu Phe Pro Val Gly Lys Glu Ser Lys Glu Glu Ile Gln Leu Phe
                85                  90                  95

Leu Gly Asn Ala Gly Thr Ala Met Arg Pro Leu Thr Ala Ala Val Thr
            100                 105                 110

Val Ala Gly Gly Asn Ser Arg Tyr Val Leu Asp Gly Val Pro Arg Met
        115                 120                 125

Arg Glu Arg Pro Ile Ser Asp Leu Val Asp Gly Leu Lys Gln Leu Gly
    130                 135                 140

Ala Glu Val Asp Cys Phe Leu Gly Thr Lys Cys Pro Pro Val Arg Ile
145                 150                 155                 160

Val Ser Lys Gly Gly Leu Pro Gly Gly Lys Val Lys Leu Ser Gly Ser
                165                 170                 175

Ile Ser Ser Gln Tyr Leu Thr Ala Leu Leu Met Ala Ala Pro Leu Ala
            180                 185                 190

Leu Gly Asp Val Glu Ile Glu Ile Ile Asp Lys Leu Ile Ser Val Pro
        195                 200                 205

Tyr Val Glu Met Thr Leu Lys Leu Met Glu Arg Phe Gly Ile Ser Val
    210                 215                 220

Glu His Ser Ser Ser Trp Asp Arg Phe Phe Val Arg Gly Gly Gln Lys
225                 230                 235                 240

Tyr Lys Ser Pro Gly Lys Ala Phe Val Glu Gly Asp Ala Ser Ser Ala
                245                 250                 255

Ser Tyr Phe Leu Ala Gly Ala Ala Val Thr Gly Gly Thr Ile Thr Val
            260                 265                 270

Glu Gly Cys Gly Thr Asn Ser Leu Gln Gly Asp Val Lys Phe Ala Glu
        275                 280                 285

Val Leu Glu Lys Met Gly Ala Glu Val Thr Trp Thr Glu Asn Ser Val
    290                 295                 300

Thr Val Lys Gly Pro Pro Arg Ser Ser Ser Gly Arg Lys His Leu Arg
305                 310                 315                 320

Ala Ile Asp Val Asn Met Asn Lys Met Pro Asp Val Ala Met Thr Leu
                325                 330                 335
```

-continued

```
Ala Val Val Ala Leu Tyr Ala Asp Gly Pro Thr Ala Ile Arg Asp Val
            340                 345                 350

Ala Ser Trp Arg Val Lys Glu Thr Glu Arg Met Ile Ala Ile Cys Thr
        355                 360                 365

Glu Leu Arg Lys Leu Gly Ala Thr Val Glu Glu Gly Pro Asp Tyr Cys
    370                 375                 380

Ile Ile Thr Pro Pro Glu Lys Leu Asn Val Thr Asp Ile Asp Thr Tyr
385                 390                 395                 400

Asp Asp His Arg Met Ala Met Ala Phe Ser Leu Ala Ala Cys Ala Asp
                405                 410                 415

Val Pro Val Thr Ile Asn Asp Pro Gly Cys Thr Arg Lys Thr Phe Pro
            420                 425                 430

Asn Tyr Phe Asp Val Leu Gln Gln Tyr Ser Lys His
        435                 440


<210> SEQ ID NO 56
<211> LENGTH: 444
<212> TYPE: PRT
<213> ORGANISM: Zea mays

<400> SEQUENCE: 56

Ala Gly Ala Glu Glu Ile Val Leu Gln Pro Ile Lys Glu Ile Ser Gly
1               5                   10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Ala Asp Lys Ala Ala Lys Arg Ala Val Val Val Gly Cys
65                  70                  75                  80

Gly Gly Lys Phe Pro Val Glu Asp Ala Lys Glu Glu Val Gln Leu Phe
                85                  90                  95

Leu Gly Asn Ala Gly Thr Ala Met Arg Pro Leu Thr Ala Ala Val Thr
            100                 105                 110

Ala Ala Gly Gly Asn Ala Thr Tyr Val Leu Asp Gly Val Pro Arg Met
        115                 120                 125

Arg Glu Arg Pro Ile Gly Asp Leu Val Val Gly Leu Lys Gln Leu Gly
    130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Pro
            180                 185                 190

Leu Gly Asp Val Glu Ile Glu Ile Ile Asp Lys Leu Ile Ser Ile Pro
        195                 200                 205

Tyr Val Glu Met Thr Leu Arg Leu Met Glu Arg Phe Gly Val Lys Ala
    210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ala Ile Thr Gly Gly Thr Val Thr Val
```

-continued

```
            260                 265                 270

Glu Gly Cys Gly Thr Thr Ser Leu Gln Gly Asp Val Lys Phe Ala Glu
        275                 280                 285

Val Leu Glu Met Met Gly Ala Lys Val Thr Trp Thr Glu Thr Ser Val
    290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
        355                 360                 365

Glu Leu Thr Lys Leu Gly Ala Ser Val Glu Glu Gly Pro Asp Tyr Cys
    370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
        435                 440


<210> SEQ ID NO 57
<211> LENGTH: 427
<212> TYPE: PRT
<213> ORGANISM: Salmonella gallinarum

<400> SEQUENCE: 57

Met Glu Ser Leu Thr Leu Gln Pro Ile Ala Arg Val Asp Gly Ala Ile
1               5                   10                  15

Asn Leu Pro Gly Ser Lys Ser Val Ser Asn Arg Ala Leu Leu Leu Ala
            20                  25                  30

Ala Leu Ala Cys Gly Lys Thr Val Leu Thr Asn Leu Leu Asp Ser Asp
        35                  40                  45

Asp Val Arg His Met Leu Asn Ala Leu Ser Ala Leu Gly Ile Asn Tyr
    50                  55                  60

Thr Leu Ser Ala Asp Arg Thr Arg Cys Asp Ile Thr Gly Asn Gly Gly
65                  70                  75                  80

Pro Leu Arg Ala Pro Gly Ala Leu Glu Leu Phe Leu Gly Asn Ala Gly
                85                  90                  95

Thr Ala Met Arg Pro Leu Ala Ala Ala Leu Cys Leu Gly Gln Asn Glu
            100                 105                 110

Ile Val Leu Thr Gly Glu Pro Arg Met Lys Glu Arg Pro Ile Gly His
        115                 120                 125

Leu Val Asp Ser Leu Arg Gln Gly Gly Ala Asn Ile Asp Tyr Leu Glu
    130                 135                 140

Gln Glu Asn Tyr Pro Pro Leu Arg Leu Arg Gly Gly Phe Ile Gly Gly
145                 150                 155                 160

Asp Ile Glu Val Asp Gly Ser Val Ser Ser Gln Phe Leu Thr Ala Leu
                165                 170                 175

Leu Met Thr Ala Pro Leu Ala Pro Lys Asp Thr Ile Ile Arg Val Lys
            180                 185                 190
```

-continued

```
Gly Glu Leu Val Ser Lys Pro Tyr Ile Asp Ile Thr Leu Asn Leu Met
        195                 200                 205

Lys Thr Phe Gly Val Glu Ile Ala Asn His His Tyr Gln Gln Phe Val
    210                 215                 220

Val Lys Gly Gly Gln Gln Tyr His Ser Pro Gly Arg Tyr Leu Val Glu
225                 230                 235                 240

Gly Asp Ala Ser Ser Ala Ser Tyr Phe Leu Ala Ala Gly Ala Ile Lys
                245                 250                 255

Gly Gly Thr Val Lys Val Thr Gly Ile Gly Arg Lys Ser Met Gln Gly
            260                 265                 270

Asp Ile Arg Phe Ala Asp Val Leu Glu Lys Met Gly Ala Thr Ile Thr
        275                 280                 285

Trp Gly Asp Asp Phe Ile Ala Cys Thr Arg Gly Glu Leu His Ala Ile
    290                 295                 300

Asp Met Asp Met Asn His Ile Pro Asp Ala Ala Met Thr Ile Ala Thr
305                 310                 315                 320

Thr Ala Leu Phe Ala Lys Gly Thr Thr Thr Leu Arg Asn Ile Tyr Asn
                325                 330                 335

Trp Arg Val Lys Glu Thr Asp Arg Leu Phe Ala Met Ala Thr Glu Leu
            340                 345                 350

Arg Lys Val Gly Ala Glu Val Glu Glu Gly His Asp Tyr Ile Arg Ile
        355                 360                 365

Thr Pro Pro Ala Lys Leu Gln His Ala Asp Ile Gly Thr Tyr Asn Asp
    370                 375                 380

His Arg Met Ala Met Cys Phe Ser Leu Val Ala Leu Ser Asp Thr Pro
385                 390                 395                 400

Val Thr Ile Leu Asp Pro Lys Cys Thr Ala Lys Thr Phe Pro Asp Tyr
                405                 410                 415

Phe Glu Gln Leu Ala Arg Met Ser Thr Pro Ala
            420                 425


<210> SEQ ID NO 58
<211> LENGTH: 427
<212> TYPE: PRT
<213> ORGANISM: Salmonella typhimurium

<400> SEQUENCE: 58

Met Glu Ser Leu Thr Leu Gln Pro Ile Ala Arg Val Asp Gly Ala Ile
1               5                   10                  15

Asn Leu Pro Gly Ser Lys Ser Val Ser Asn Arg Ala Leu Leu Leu Ala
            20                  25                  30

Ala Leu Ala Cys Gly Lys Thr Val Leu Thr Asn Leu Leu Asp Ser Asp
        35                  40                  45

Asp Val Arg His Met Leu Asn Ala Leu Ser Ala Leu Gly Ile Asn Tyr
    50                  55                  60

Thr Leu Ser Ala Asp Arg Thr Arg Cys Asp Ile Thr Gly Asn Gly Gly
65                  70                  75                  80

Pro Leu Arg Ala Ser Gly Thr Leu Glu Leu Phe Leu Gly Asn Ala Gly
                85                  90                  95

Thr Ala Met Arg Pro Leu Ala Ala Ala Leu Cys Leu Gly Gln Asn Glu
            100                 105                 110

Ile Val Leu Thr Gly Glu Pro Arg Met Lys Glu Arg Pro Ile Gly His
        115                 120                 125

Leu Val Asp Ser Leu Arg Gln Gly Gly Ala Asn Ile Asp Tyr Leu Glu
    130                 135                 140
```

-continued

```
Gln Glu Asn Tyr Pro Pro Leu Arg Leu Arg Gly Gly Phe Ile Gly Gly
145                 150                 155                 160

Asp Ile Glu Val Asp Gly Ser Val Ser Ser Gln Phe Leu Thr Ala Leu
                165                 170                 175

Leu Met Thr Ala Pro Leu Ala Pro Glu Asp Thr Ile Ile Arg Val Lys
            180                 185                 190

Gly Glu Leu Val Ser Lys Pro Tyr Ile Asp Ile Thr Leu Asn Leu Met
        195                 200                 205

Lys Thr Phe Gly Val Glu Ile Ala Asn His His Tyr Gln Gln Phe Val
    210                 215                 220

Val Lys Gly Gly Gln Gln Tyr His Ser Pro Gly Arg Tyr Leu Val Glu
225                 230                 235                 240

Gly Asp Ala Ser Ser Ala Ser Tyr Phe Leu Ala Ala Gly Gly Ile Lys
                245                 250                 255

Gly Gly Thr Val Lys Val Thr Gly Ile Gly Gly Lys Ser Met Gln Gly
            260                 265                 270

Asp Ile Arg Phe Ala Asp Val Leu His Lys Met Gly Ala Thr Ile Thr
        275                 280                 285

Trp Gly Asp Asp Phe Ile Ala Cys Thr Arg Gly Glu Leu His Ala Ile
    290                 295                 300

Asp Met Asp Met Asn His Ile Pro Asp Ala Ala Met Thr Ile Ala Thr
305                 310                 315                 320

Thr Ala Leu Phe Ala Lys Gly Thr Thr Thr Leu Arg Asn Ile Tyr Asn
                325                 330                 335

Trp Arg Val Lys Glu Thr Asp Arg Leu Phe Ala Met Ala Thr Glu Leu
            340                 345                 350

Arg Lys Val Gly Ala Glu Val Glu Glu Gly His Asp Tyr Ile Arg Ile
        355                 360                 365

Thr Pro Pro Ala Lys Leu Gln His Ala Asp Ile Gly Thr Tyr Asn Asp
    370                 375                 380

His Arg Met Ala Met Cys Phe Ser Leu Val Ala Leu Ser Asp Thr Pro
385                 390                 395                 400

Val Thr Ile Leu Asp Pro Lys Cys Thr Ala Lys Thr Phe Pro Asp Tyr
                405                 410                 415

Phe Glu Gln Leu Ala Arg Met Ser Thr Pro Ala
            420                 425


<210> SEQ ID NO 59
<211> LENGTH: 427
<212> TYPE: PRT
<213> ORGANISM: Klebsiella pneumoniae

<400> SEQUENCE: 59

Met Glu Ser Leu Thr Leu Gln Pro Ile Ala Arg Val Asp Gly Thr Val
1               5                   10                  15

Asn Leu Pro Gly Ser Lys Ser Val Ser Asn Arg Ala Leu Leu Leu Ala
            20                  25                  30

Ala Leu Ala Arg Gly Thr Thr Val Leu Thr Asn Leu Leu Asp Ser Asp
        35                  40                  45

Asp Val Arg His Met Leu Asn Ala Leu Ser Ala Leu Gly Val His Tyr
    50                  55                  60

Val Leu Ser Ser Asp Arg Thr Arg Cys Glu Val Thr Gly Thr Gly Gly
65                  70                  75                  80

Pro Leu Gln Ala Gly Ser Ala Leu Glu Leu Phe Leu Gly Asn Ala Gly
```

-continued

```
                85                  90                  95

Thr Ala Met Arg Pro Leu Ala Ala Ala Leu Cys Leu Gly Ser Asn Asp
            100                 105                 110

Ile Val Leu Thr Gly Glu Pro Arg Met Lys Glu Arg Pro Ile Gly His
        115                 120                 125

Leu Val Asp Ala Leu Arg Gln Gly Gly Ala Gln Ile Asp Tyr Leu Glu
    130                 135                 140

Gln Glu Asn Tyr Pro Pro Leu Arg Leu Arg Gly Gly Phe Thr Gly Gly
145                 150                 155                 160

Asp Val Glu Val Asp Gly Ser Val Ser Ser Gln Phe Leu Thr Ala Leu
                165                 170                 175

Leu Met Ala Ser Pro Leu Ala Pro Gln Asp Thr Val Ile Ala Ile Lys
            180                 185                 190

Gly Glu Leu Val Ser Arg Pro Tyr Ile Asp Ile Thr Leu His Leu Met
        195                 200                 205

Lys Thr Phe Gly Val Glu Val Glu Asn Gln Ala Tyr Gln Arg Phe Ile
    210                 215                 220

Val Arg Gly Asn Gln Gln Tyr Gln Ser Pro Gly Asp Tyr Leu Val Glu
225                 230                 235                 240

Gly Asp Ala Ser Ser Ala Ser Tyr Phe Leu Ala Ala Gly Ala Ile Lys
                245                 250                 255

Gly Gly Thr Val Lys Val Thr Gly Ile Gly Arg Asn Ser Val Gln Gly
            260                 265                 270

Asp Ile Arg Phe Ala Asp Val Leu Glu Lys Met Gly Ala Thr Val Thr
        275                 280                 285

Trp Gly Glu Asp Tyr Ile Ala Cys Thr Arg Gly Glu Leu Asn Ala Ile
    290                 295                 300

Asp Met Asp Met Asn His Ile Pro Asp Ala Ala Met Thr Ile Ala Thr
305                 310                 315                 320

Ala Ala Leu Phe Ala Arg Gly Thr Thr Thr Leu Arg Asn Ile Tyr Asn
                325                 330                 335

Trp Arg Val Lys Glu Thr Asp Arg Leu Phe Ala Met Ala Thr Glu Leu
            340                 345                 350

Arg Lys Val Gly Ala Glu Val Glu Glu Gly Glu Asp Tyr Ile Arg Ile
        355                 360                 365

Thr Pro Pro Leu Thr Leu Gln Phe Ala Glu Ile Gly Thr Tyr Asn Asp
    370                 375                 380

His Arg Met Ala Met Cys Phe Ser Leu Val Ala Leu Ser Asp Thr Pro
385                 390                 395                 400

Val Thr Ile Leu Asp Pro Lys Cys Thr Ala Lys Thr Phe Pro Asp Tyr
                405                 410                 415

Phe Gly Gln Leu Ala Arg Ile Ser Thr Leu Ala
            420                 425


<210> SEQ ID NO 60
<211> LENGTH: 427
<212> TYPE: PRT
<213> ORGANISM: Yersinia enterocolitica

<400> SEQUENCE: 60

Met Leu Glu Ser Leu Thr Leu His Pro Ile Ala Leu Ile Asn Gly Thr
1               5                   10                  15

Val Asn Leu Pro Gly Ser Lys Ser Val Ser Asn Arg Ala Leu Leu Leu
            20                  25                  30
```

-continued

```
Ala Ala Leu Ala Glu Gly Thr Thr Gln Leu Asn Asn Leu Leu Asp Ser
        35                  40                  45

Asp Asp Ile Arg His Met Leu Asn Ala Leu Gln Ala Leu Gly Val Lys
    50                  55                  60

Tyr Arg Leu Ser Ala Asp Arg Thr Arg Cys Glu Val Asp Gly Leu Gly
65                  70                  75                  80

Gly Lys Leu Val Ala Glu Gln Pro Leu Glu Leu Phe Leu Gly Asn Ala
                85                  90                  95

Gly Thr Ala Met Arg Pro Leu Ala Ala Ala Leu Cys Leu Gly Lys Asn
            100                 105                 110

Asp Ile Val Leu Thr Gly Glu Pro Arg Met Lys Glu Arg Pro Ile Gly
        115                 120                 125

His Leu Val Asp Ala Leu Arg Gln Gly Gly Ala Gln Ile Asp Tyr Leu
    130                 135                 140

Glu Gln Glu Asn Tyr Arg Arg Cys Ile Ala Gly Gly Phe Arg Gly Gly
145                 150                 155                 160

Lys Leu Thr Val Asp Gly Ser Val Ser Ser Gln Phe Leu Thr Ala Leu
                165                 170                 175

Leu Met Thr Ala Pro Leu Ala Glu Gln Asp Thr Glu Ile Gln Ile Gln
            180                 185                 190

Gly Glu Leu Val Ser Lys Pro Tyr Ile Asp Ile Thr Leu His Leu Met
        195                 200                 205

Lys Ala Phe Gly Val Asp Val Val His Glu Asn Tyr Gln Ile Phe His
    210                 215                 220

Ile Lys Gly Gly Gln Thr Tyr Arg Ser Pro Gly Ile Tyr Leu Val Glu
225                 230                 235                 240

Gly Asp Ala Ser Ser Ala Ser Tyr Phe Leu Ala Ala Ala Ala Ile Lys
                245                 250                 255

Gly Gly Thr Val Arg Val Thr Gly Ile Gly Lys Gln Ser Val Gln Gly
            260                 265                 270

Asp Thr Lys Phe Ala Asp Val Leu Glu Lys Met Gly Ala Lys Ile Ser
        275                 280                 285

Trp Gly Asp Asp Tyr Ile Glu Cys Ser Arg Gly Glu Leu Gln Gly Ile
    290                 295                 300

Asp Met Asp Met Asn His Ile Pro Asp Ala Ala Met Thr Ile Ala Thr
305                 310                 315                 320

Thr Ala Leu Phe Ala Asp Gly Pro Thr Val Ile Arg Asn Ile Tyr Asn
                325                 330                 335

Trp Arg Val Lys Glu Thr Asp Arg Leu Ser Ala Met Ala Thr Glu Leu
            340                 345                 350

Arg Lys Val Gly Ala Glu Val Glu Glu Gly Gln Asp Tyr Ile Arg Val
        355                 360                 365

Val Pro Pro Ala Gln Leu Ile Ala Ala Glu Ile Gly Thr Tyr Asn Asp
    370                 375                 380

His Arg Met Ala Met Cys Phe Ser Leu Val Ala Leu Ser Asp Thr Pro
385                 390                 395                 400

Val Thr Ile Leu Asp Pro Lys Cys Thr Ala Lys Thr Phe Pro Asp Tyr
                405                 410                 415

Phe Glu Gln Leu Ala Arg Leu Ser Gln Ile Ala
            420                 425
```

<210> SEQ ID NO 61
<211> LENGTH: 432
<212> TYPE: PRT

-continued

<213> ORGANISM: Haemophilus influenzae

<400> SEQUENCE: 61

Met Glu Lys Ile Thr Leu Ala Pro Ile Ser Ala Val Glu Gly Thr Ile
1 5 10 15

Asn Leu Pro Gly Ser Lys Ser Leu Ser Asn Arg Ala Leu Leu Leu Ala
20 25 30

Ala Leu Ala Lys Gly Thr Thr Lys Val Thr Asn Leu Leu Asp Ser Asp
35 40 45

Asp Ile Arg His Met Leu Asn Ala Leu Lys Ala Leu Gly Val Arg Tyr
50 55 60

Gln Leu Ser Asp Asp Lys Thr Ile Cys Glu Ile Glu Gly Leu Gly Gly
65 70 75 80

Ala Phe Asn Ile Gln Asp Asn Leu Ser Leu Phe Leu Gly Asn Ala Gly
85 90 95

Thr Ala Met Arg Pro Leu Thr Ala Ala Leu Cys Leu Lys Gly Asn His
100 105 110

Glu Val Glu Ile Ile Leu Thr Gly Glu Pro Arg Met Lys Glu Arg Pro
115 120 125

Ile Leu His Leu Val Asp Ala Leu Arg Gln Ala Gly Ala Asp Ile Arg
130 135 140

Tyr Leu Glu Asn Glu Gly Tyr Pro Pro Leu Ala Ile Arg Asn Lys Gly
145 150 155 160

Ile Lys Gly Gly Lys Val Lys Ile Asp Gly Ser Ile Ser Ser Gln Phe
165 170 175

Leu Thr Ala Leu Leu Met Ser Ala Pro Leu Ala Glu Asn Asp Thr Glu
180 185 190

Ile Glu Ile Ile Gly Glu Leu Val Ser Lys Pro Tyr Ile Asp Ile Thr
195 200 205

Leu Ala Met Met Arg Asp Phe Gly Val Lys Val Glu Asn His His Tyr
210 215 220

Gln Lys Phe Gln Val Lys Gly Asn Gln Ser Tyr Ile Ser Pro Asn Lys
225 230 235 240

Tyr Leu Val Glu Gly Asp Ala Ser Ser Ala Ser Tyr Phe Leu Ala Ala
245 250 255

Gly Ala Ile Lys Gly Lys Val Lys Val Thr Gly Ile Gly Lys Asn Ser
260 265 270

Ile Gln Gly Asp Arg Leu Phe Ala Asp Val Leu Glu Lys Met Gly Ala
275 280 285

Lys Ile Thr Trp Gly Glu Asp Phe Ile Gln Ala Glu His Ala Glu Leu
290 295 300

Asn Gly Ile Asp Met Asp Met Asn His Ile Pro Asp Ala Ala Met Thr
305 310 315 320

Ile Ala Thr Thr Ala Leu Phe Ser Asn Gly Glu Thr Val Ile Arg Asn
325 330 335

Ile Tyr Asn Trp Arg Val Lys Glu Thr Asp Arg Leu Thr Ala Met Ala
340 345 350

Thr Glu Leu Arg Lys Val Gly Ala Glu Val Glu Glu Gly Glu Asp Phe
355 360 365

Ile Arg Ile Gln Pro Leu Ala Leu Asn Gln Phe Lys His Ala Asn Ile
370 375 380

Glu Thr Tyr Asn Asp His Arg Met Ala Met Cys Phe Ser Leu Ile Ala
385 390 395 400

-continued

```
Leu Ser Asn Thr Pro Val Thr Ile Leu Asp Pro Lys Cys Thr Ala Lys
                405                 410                 415

Thr Phe Pro Thr Phe Phe Asn Glu Phe Glu Lys Ile Cys Leu Lys Asn
            420                 425                 430


<210> SEQ ID NO 62
<211> LENGTH: 441
<212> TYPE: PRT
<213> ORGANISM: Pasteurella multocida

<400> SEQUENCE: 62

Val Ile Lys Asp Ala Thr Ala Ile Thr Leu Asn Pro Ile Ser Tyr Ile
1               5                   10                  15

Glu Gly Glu Val Arg Leu Pro Gly Ser Lys Ser Leu Ser Asn Arg Ala
            20                  25                  30

Leu Leu Leu Ser Ala Leu Ala Lys Gly Lys Thr Thr Leu Thr Asn Leu
        35                  40                  45

Leu Asp Ser Asp Asp Val Arg His Met Leu Asn Ala Leu Lys Glu Leu
    50                  55                  60

Gly Val Thr Tyr Gln Leu Ser Glu Asp Lys Ser Val Cys Glu Ile Glu
65                  70                  75                  80

Gly Leu Gly Arg Ala Phe Glu Trp Gln Ser Gly Leu Ala Leu Phe Leu
                85                  90                  95

Gly Asn Ala Gly Thr Ala Met Arg Pro Leu Thr Ala Ala Leu Cys Leu
            100                 105                 110

Ser Thr Pro Asn Arg Glu Gly Lys Asn Glu Ile Val Leu Thr Gly Glu
        115                 120                 125

Pro Arg Met Lys Glu Arg Pro Ile Gln His Leu Val Asp Ala Leu Cys
    130                 135                 140

Gln Ala Gly Ala Glu Ile Gln Tyr Leu Glu Gln Glu Gly Tyr Pro Pro
145                 150                 155                 160

Ile Ala Ile Arg Asn Thr Gly Leu Lys Gly Gly Arg Ile Gln Ile Asp
                165                 170                 175

Gly Ser Val Ser Ser Gln Phe Leu Thr Ala Leu Leu Met Ala Ala Pro
            180                 185                 190

Met Ala Glu Ala Asp Thr Glu Ile Glu Ile Ile Gly Glu Leu Val Ser
        195                 200                 205

Lys Pro Tyr Ile Asp Ile Thr Leu Lys Met Met Gln Thr Phe Gly Val
    210                 215                 220

Glu Val Glu Asn Gln Ala Tyr Gln Arg Phe Leu Val Lys Gly His Gln
225                 230                 235                 240

Gln Tyr Gln Ser Pro His Arg Phe Leu Val Glu Gly Asp Ala Ser Ser
                245                 250                 255

Ala Ser Tyr Phe Leu Ala Ala Ala Ala Ile Lys Gly Lys Val Lys Val
            260                 265                 270

Thr Gly Val Gly Lys Asn Ser Ile Gln Gly Asp Arg Leu Phe Ala Asp
        275                 280                 285

Val Leu Glu Lys Met Gly Ala His Ile Thr Trp Gly Asp Asp Phe Ile
    290                 295                 300

Gln Val Glu Lys Gly Asn Leu Lys Gly Ile Asp Met Asp Met Asn His
305                 310                 315                 320

Ile Pro Asp Ala Ala Met Thr Ile Ala Thr Thr Ala Leu Phe Ala Glu
                325                 330                 335

Gly Glu Thr Val Ile Arg Asn Ile Tyr Asn Trp Arg Val Lys Glu Thr
            340                 345                 350
```

-continued

```
Asp Arg Leu Thr Ala Met Ala Thr Glu Leu Arg Lys Val Gly Ala Glu
        355                 360                 365

Val Glu Glu Gly Glu Asp Phe Ile Arg Ile Gln Pro Leu Asn Leu Ala
    370                 375                 380

Gln Phe Gln His Ala Glu Leu Asn Ile His Asp His Arg Met Ala Met
385                 390                 395                 400

Cys Phe Ala Leu Ile Ala Leu Ser Lys Thr Ser Val Thr Ile Leu Asp
                405                 410                 415

Pro Ser Cys Thr Ala Lys Thr Phe Pro Thr Phe Leu Ile Leu Phe Thr
            420                 425                 430

Leu Asn Thr Arg Glu Val Ala Tyr Arg
        435                 440


<210> SEQ ID NO 63
<211> LENGTH: 426
<212> TYPE: PRT
<213> ORGANISM: Aeromonas salmonicida

<400> SEQUENCE: 63

Asn Ser Leu Arg Leu Glu Pro Ile Ser Arg Val Ala Gly Glu Val Asn
1               5                   10                  15

Leu Pro Gly Ser Lys Ser Val Ser Asn Arg Ala Leu Leu Leu Ala Ala
            20                  25                  30

Leu Ala Arg Gly Thr Thr Arg Leu Thr Asn Leu Leu Asp Ser Asp Asp
        35                  40                  45

Ile Arg His Met Leu Ala Ala Leu Thr Gln Leu Gly Val Lys Tyr Lys
    50                  55                  60

Leu Ser Ala Asp Lys Thr Glu Cys Thr Val His Gly Leu Gly Arg Ser
65                  70                  75                  80

Phe Ala Val Ser Ala Pro Val Asn Leu Phe Leu Gly Asn Ala Gly Thr
                85                  90                  95

Ala Met Arg Pro Leu Cys Ala Ala Leu Cys Leu Gly Ser Gly Glu Tyr
            100                 105                 110

Met Leu Gly Gly Glu Pro Arg Met Glu Glu Arg Pro Ile Gly His Leu
        115                 120                 125

Val Asp Cys Leu Ala Leu Lys Gly Ala His Ile Gln Tyr Leu Lys Lys
    130                 135                 140

Asp Gly Tyr Pro Pro Leu Val Val Asp Ala Lys Gly Leu Trp Gly Gly
145                 150                 155                 160

Asp Val His Val Asp Gly Ser Val Ser Ser Gln Phe Leu Thr Ala Phe
                165                 170                 175

Leu Met Ala Ala Pro Ala Met Ala Pro Val Ile Pro Arg Ile His Ile
            180                 185                 190

Lys Gly Glu Leu Val Ser Lys Pro Tyr Ile Asp Ile Thr Leu His Ile
        195                 200                 205

Met Asn Ser Ser Gly Val Val Ile Glu His Asp Asn Tyr Lys Leu Phe
    210                 215                 220

Tyr Ile Lys Gly Asn Gln Ser Ile Val Ser Pro Gly Asp Phe Leu Val
225                 230                 235                 240

Glu Gly Asp Ala Ser Ser Ala Ser Tyr Phe Leu Ala Ala Gly Ala Ile
                245                 250                 255

Lys Gly Lys Val Arg Val Thr Gly Ile Gly Lys His Ser Ile Gly Asp
            260                 265                 270

Ile His Phe Ala Asp Val Leu Glu Arg Met Gly Ala Arg Ile Thr Trp
```

-continued

```
        275                 280                 285

Gly Asp Asp Phe Ile Glu Ala Glu Gln Gly Pro Leu His Gly Val Asp
    290                 295                 300

Met Asp Met Asn His Ile Pro Asp Val Gly His Asp His Ser Gly Gln
305                 310                 315                 320

Ser His Cys Leu Pro Arg Val Pro Pro His Ser Gln His Leu Gln Leu
                325                 330                 335

Ala Val Arg Asp Asp Arg Cys Thr Pro Cys Thr His Gly His Arg Arg
            340                 345                 350

Ala Gln Ala Gly Val Ser Glu Glu Gly Thr Thr Phe Ile Thr Arg Asp
        355                 360                 365

Ala Ala Asp Pro Ala Gln Ala Arg Arg Asp Arg His Leu Gln Arg Ser
    370                 375                 380

Arg Ile Ala Met Cys Phe Ser Leu Val Ala Leu Ser Asp Ile Ala Val
385                 390                 395                 400

Thr Ile Asn Asp Pro Gly Cys Thr Ser Lys Thr Phe Pro Asp Tyr Phe
                405                 410                 415

Asp Lys Leu Ala Ser Val Ser Gln Ala Val
            420                 425


<210> SEQ ID NO 64
<211> LENGTH: 442
<212> TYPE: PRT
<213> ORGANISM: Bacillus pertussis

<400> SEQUENCE: 64

Met Ser Gly Leu Ala Tyr Leu Asp Leu Pro Ala Ala Arg Leu Ala Arg
1               5                   10                  15

Gly Glu Val Ala Leu Pro Gly Ser Lys Ser Ile Ser Asn Arg Val Leu
            20                  25                  30

Leu Leu Ala Ala Leu Ala Glu Gly Ser Thr Glu Ile Thr Gly Leu Leu
        35                  40                  45

Asp Ser Asp Asp Thr Arg Val Met Leu Ala Ala Leu Arg Gln Leu Gly
    50                  55                  60

Val Ser Val Gly Glu Val Ala Asp Gly Cys Val Thr Ile Glu Gly Val
65                  70                  75                  80

Ala Arg Phe Pro Thr Glu Gln Ala Glu Leu Phe Leu Gly Asn Ala Gly
                85                  90                  95

Thr Ala Phe Arg Pro Leu Thr Ala Ala Leu Ala Leu Met Gly Gly Asp
            100                 105                 110

Tyr Arg Leu Ser Gly Val Pro Arg Met His Glu Arg Pro Ile Gly Asp
        115                 120                 125

Leu Val Asp Ala Leu Arg Gln Phe Gly Ala Gly Ile Glu Tyr Leu Gly
    130                 135                 140

Gln Ala Gly Tyr Pro Pro Leu Arg Ile Gly Gly Gly Ser Ile Arg Val
145                 150                 155                 160

Asp Gly Pro Val Arg Val Glu Gly Ser Val Ser Ser Gln Phe Leu Thr
                165                 170                 175

Ala Leu Leu Met Ala Ala Pro Val Leu Ala Arg Arg Ser Gly Gln Asp
            180                 185                 190

Ile Thr Ile Glu Val Val Gly Glu Leu Ile Ser Lys Pro Tyr Ile Glu
        195                 200                 205

Ile Thr Leu Asn Leu Met Ala Arg Phe Gly Val Ser Val Arg Arg Asp
    210                 215                 220
```

-continued

```
Gly Trp Arg Ala Phe Thr Ile Ala Arg Asp Ala Val Tyr Arg Gly Pro
225                 230                 235                 240

Gly Arg Met Ala Ile Glu Gly Asp Ala Ser Thr Ala Ser Tyr Phe Leu
                245                 250                 255

Ala Leu Gly Ala Ile Gly Gly Gly Pro Val Arg Val Thr Gly Val Gly
            260                 265                 270

Glu Asp Ser Ile Gln Gly Asp Val Ala Phe Ala Ala Thr Leu Ala Ala
        275                 280                 285

Met Gly Ala Asp Val Arg Tyr Gly Pro Gly Trp Ile Glu Thr Arg Gly
    290                 295                 300

Val Arg Val Ala Glu Gly Gly Arg Leu Lys Ala Phe Asp Ala Asp Phe
305                 310                 315                 320

Asn Leu Ile Pro Asp Ala Ala Met Thr Ala Ala Thr Leu Ala Leu Tyr
                325                 330                 335

Ala Asp Gly Pro Cys Arg Leu Arg Asn Ile Gly Ser Trp Arg Val Lys
            340                 345                 350

Glu Thr Asp Arg Ile His Ala Met His Thr Glu Leu Glu Lys Leu Gly
        355                 360                 365

Ala Gly Val Gln Ser Gly Ala Asp Trp Leu Glu Val Ala Pro Pro Glu
    370                 375                 380

Pro Gly Gly Trp Arg Asp Ala His Ile Gly Thr Trp Asp Asp His Arg
385                 390                 395                 400

Met Ala Met Cys Phe Leu Leu Ala Ala Phe Gly Pro Ala Ala Val Arg
                405                 410                 415

Ile Leu Asp Pro Gly Cys Val Ser Lys Thr Phe Pro Asp Tyr Phe Asp
            420                 425                 430

Val Tyr Ala Gly Leu Leu Ala Ala Arg Asp
        435                 440


<210> SEQ ID NO 65
<211> LENGTH: 427
<212> TYPE: PRT
<213> ORGANISM: Salmonella typhimurium

<400> SEQUENCE: 65

Met Glu Ser Leu Thr Leu Gln Pro Ile Ala Arg Val Asp Gly Ala Ile
1               5                   10                  15

Asn Leu Pro Gly Ser Lys Ser Val Ser Asn Arg Ala Leu Leu Leu Ala
            20                  25                  30

Ala Leu Ala Cys Gly Lys Thr Val Leu Thr Asn Leu Leu Asp Ser Asp
        35                  40                  45

Asp Val Arg His Met Leu Asn Ala Leu Ser Ala Leu Gly Ile Asn Tyr
    50                  55                  60

Thr Leu Ser Ala Asp Arg Thr Arg Cys Asp Ile Thr Gly Asn Gly Gly
65                  70                  75                  80

Pro Leu Arg Ala Ser Gly Thr Leu Glu Leu Phe Leu Gly Asn Ala Gly
                85                  90                  95

Thr Ala Met Arg Pro Leu Ala Ala Ala Leu Cys Leu Gly Gln Asn Glu
            100                 105                 110

Ile Val Leu Thr Gly Glu Pro Arg Met Lys Glu Arg Pro Ile Gly His
        115                 120                 125

Leu Val Asp Ser Leu Arg Gln Gly Gly Ala Asn Ile Asp Tyr Leu Glu
    130                 135                 140

Gln Glu Asn Tyr Pro Pro Leu Arg Leu Arg Gly Gly Phe Ile Gly Gly
145                 150                 155                 160
```

-continued

```
Asp Ile Glu Val Asp Gly Ser Val Ser Ser Gln Phe Leu Thr Ala Leu
                165                 170                 175

Leu Met Thr Ala Pro Leu Ala Pro Glu Asp Thr Ile Ile Arg Val Lys
            180                 185                 190

Gly Glu Leu Val Ser Lys Pro Tyr Ile Asp Ile Thr Leu Asn Leu Met
        195                 200                 205

Lys Thr Phe Gly Val Glu Ile Ala Asn His His Tyr Gln Gln Phe Val
    210                 215                 220

Val Lys Gly Gly Gln Gln Tyr His Ser Pro Gly Arg Tyr Leu Val Glu
225                 230                 235                 240

Gly Asp Ala Ser Ser Ala Ser Tyr Phe Leu Ala Ala Gly Gly Ile Lys
                245                 250                 255

Gly Gly Thr Val Lys Val Thr Gly Ile Gly Gly Lys Ser Met Gln Gly
            260                 265                 270

Asp Ile Arg Phe Ala Asp Val Leu His Lys Met Gly Ala Thr Ile Thr
        275                 280                 285

Trp Gly Asp Asp Phe Ile Ala Cys Thr Arg Gly Glu Leu His Ala Ile
    290                 295                 300

Asp Met Asp Met Asn His Ile Pro Asp Ala Ala Met Thr Ile Ala Thr
305                 310                 315                 320

Thr Ala Leu Phe Ala Lys Gly Thr Thr Thr Leu Arg Asn Ile Tyr Asn
                325                 330                 335

Trp Arg Val Lys Glu Thr Asp Arg Leu Phe Ala Met Ala Thr Glu Leu
            340                 345                 350

Arg Lys Val Gly Ala Glu Val Glu Glu Gly His Asp Tyr Ile Arg Ile
        355                 360                 365

Thr Pro Pro Ala Lys Leu Gln His Ala Asp Ile Gly Thr Tyr Asn Asp
    370                 375                 380

His Arg Met Ala Met Cys Phe Ser Leu Val Ala Leu Ser Asp Thr Pro
385                 390                 395                 400

Val Thr Ile Leu Asp Pro Lys Cys Thr Ala Lys Thr Phe Pro Asp Tyr
                405                 410                 415

Phe Glu Gln Leu Ala Arg Met Ser Thr Pro Ala
            420                 425


<210> SEQ ID NO 66
<211> LENGTH: 1894
<212> TYPE: DNA
<213> ORGANISM: Synechocystis sp.
<220> FEATURE:
<221> NAME/KEY: CDS
<222> LOCATION: (275)..(1618)

<400> SEQUENCE: 66

acgggctgta acggtagtag gggtcccgag cacaaaagcg gtgccggcaa gcagaactaa      60

tttccatggg gaataatggt atttcattgg tttggcctct ggtctggcaa tggttgctag     120

gcgatcgcct gttgaaatta acaaactgtc gcccttccac tgaccatggt aacgatgttt     180

tttacttcct tgactaaccg aggaaaattt ggcgggggc agaaatgcca atacaattta     240

gcttggtctt ccctgcccct aatttgtccc ctcc atg gcc ttg ctt tcc ctc aac     295
                                      Met Ala Leu Leu Ser Leu Asn
                                      1               5

aat cat caa tcc cat caa cgc tta act gtt aat ccc cct gcc caa ggg       343
Asn His Gln Ser His Gln Arg Leu Thr Val Asn Pro Pro Ala Gln Gly
        10                  15                  20
```

-continued

```
gtc gct ttg act ggc cgc cta agg gtg ccg ggg gat aaa tcc att tcc      391
Val Ala Leu Thr Gly Arg Leu Arg Val Pro Gly Asp Lys Ser Ile Ser
    25                  30                  35

cat cgg gcc ttg atg ttg ggg gcg atc gcc acc ggg gaa acc att atc      439
His Arg Ala Leu Met Leu Gly Ala Ile Ala Thr Gly Glu Thr Ile Ile
40                  45                  50                  55

gaa ggg cta ctg ttg ggg gaa gat ccc cgt agt acg gcc cat tgc ttt      487
Glu Gly Leu Leu Leu Gly Glu Asp Pro Arg Ser Thr Ala His Cys Phe
                60                  65                  70

cgg gcc atg gga gca gaa atc agc gaa cta aat tca gaa aaa atc atc      535
Arg Ala Met Gly Ala Glu Ile Ser Glu Leu Asn Ser Glu Lys Ile Ile
            75                  80                  85

gtt cag ggt cgg ggt ctg gga cag ttg cag gaa ccc agt acc gtt ttg      583
Val Gln Gly Arg Gly Leu Gly Gln Leu Gln Glu Pro Ser Thr Val Leu
        90                  95                  100

gat gcg ggg aac tct ggc acc acc atg cgc tta atg ttg ggc ttg cta      631
Asp Ala Gly Asn Ser Gly Thr Thr Met Arg Leu Met Leu Gly Leu Leu
    105                 110                 115

gcc ggg caa aaa gat tgt tta ttc acc gtc acc ggc gat gat tcc ctc      679
Ala Gly Gln Lys Asp Cys Leu Phe Thr Val Thr Gly Asp Asp Ser Leu
120                 125                 130                 135

cgt cac cgc ccc atg tcc cgg gta att caa ccc ttg caa caa atg ggg      727
Arg His Arg Pro Met Ser Arg Val Ile Gln Pro Leu Gln Gln Met Gly
                140                 145                 150

gca aaa att tgg gcc cgg agt aac ggc aag ttt gcg ccg ctg gca gtc      775
Ala Lys Ile Trp Ala Arg Ser Asn Gly Lys Phe Ala Pro Leu Ala Val
            155                 160                 165

cag ggt agc caa tta aaa ccg atc cat tac cat tcc ccc att gct tca      823
Gln Gly Ser Gln Leu Lys Pro Ile His Tyr His Ser Pro Ile Ala Ser
        170                 175                 180

gcc cag gta aag tcc tgc ctg ttg cta gcg ggg tta acc acc gag ggg      871
Ala Gln Val Lys Ser Cys Leu Leu Leu Ala Gly Leu Thr Thr Glu Gly
    185                 190                 195

gac acc acg gtt aca gaa cca gct cta tcc cgg gat cat agc gaa cgc      919
Asp Thr Thr Val Thr Glu Pro Ala Leu Ser Arg Asp His Ser Glu Arg
200                 205                 210                 215

atg ttg cag gcc ttt gga gcc aaa tta acc att gat cca gta acc cat      967
Met Leu Gln Ala Phe Gly Ala Lys Leu Thr Ile Asp Pro Val Thr His
                220                 225                 230

agc gtc act gtc cat ggc ccg gcc cat tta acg ggg caa cgg gtg gtg     1015
Ser Val Thr Val His Gly Pro Ala His Leu Thr Gly Gln Arg Val Val
            235                 240                 245

gtg cca ggg gac atc agc tcg gcg gcc ttt tgg tta gtg gcg gca tcc     1063
Val Pro Gly Asp Ile Ser Ser Ala Ala Phe Trp Leu Val Ala Ala Ser
        250                 255                 260

att ttg cct gga tca gaa ttg ttg gtg gaa aat gta ggc att aac ccc     1111
Ile Leu Pro Gly Ser Glu Leu Leu Val Glu Asn Val Gly Ile Asn Pro
    265                 270                 275

acc agg aca ggg gtg ttg gaa gtg ttg gcc cag atg ggg gcg gac att     1159
Thr Arg Thr Gly Val Leu Glu Val Leu Ala Gln Met Gly Ala Asp Ile
280                 285                 290                 295

acc ccg gag aat gaa cga ttg gta acg ggg gaa ccg gta gca gat ctg     1207
Thr Pro Glu Asn Glu Arg Leu Val Thr Gly Glu Pro Val Ala Asp Leu
                300                 305                 310

cgg gtt agg gca agc cat ctc cag ggt tgc acc ttc ggc ggc gaa att     1255
Arg Val Arg Ala Ser His Leu Gln Gly Cys Thr Phe Gly Gly Glu Ile
            315                 320                 325

att ccc cga ctg att gat gaa att ccc att ttg gca gtg gcg gcg gcc     1303
Ile Pro Arg Leu Ile Asp Glu Ile Pro Ile Leu Ala Val Ala Ala Ala
        330                 335                 340
```

-continued

```
ttt gca gag ggc act acc cgc att gaa gat gcc gca gaa ctg agg gtt     1351
Phe Ala Glu Gly Thr Thr Arg Ile Glu Asp Ala Ala Glu Leu Arg Val
    345                 350                 355

aaa gaa agc gat cgc ctg gcg gcc att gct tcg gag ttg ggc aaa atg     1399
Lys Glu Ser Asp Arg Leu Ala Ala Ile Ala Ser Glu Leu Gly Lys Met
360                 365                 370                 375

ggg gcc aaa gtc acc gaa ttt gat gat ggc ctg gaa att caa ggg gga     1447
Gly Ala Lys Val Thr Glu Phe Asp Asp Gly Leu Glu Ile Gln Gly Gly
                380                 385                 390

agc ccg tta caa ggg gcc gag gtg gat agc ttg acg gat cat cgc att     1495
Ser Pro Leu Gln Gly Ala Glu Val Asp Ser Leu Thr Asp His Arg Ile
            395                 400                 405

gcc atg gcg ttg gcg atc gcc gct tta ggt agt ggg ggg caa aca att     1543
Ala Met Ala Leu Ala Ile Ala Ala Leu Gly Ser Gly Gly Gln Thr Ile
        410                 415                 420

att aac cgg gcg gaa gcg gcc gcc att tcc tat cca gaa ttt ttt ggc     1591
Ile Asn Arg Ala Glu Ala Ala Ala Ile Ser Tyr Pro Glu Phe Phe Gly
    425                 430                 435

acg cta ggg caa gtt gcc caa gga taa agttagaaaa actcctgggc           1638
Thr Leu Gly Gln Val Ala Gln Gly
440                 445

ggtttgtaaa tgttttacca aggtagtttg gggtaaaggc cccagcaagt gctgccaggg   1698

taatttatcc gcaattgacc aatcggcatg gaccgtatcg ttcaaactgg gtaattctcc   1758

ctttaattcc ttaaaagctc gcttaaaact gcccaacgta tctccgtaat ggcgagtgag   1818

tagaagtaat ggggccaaac ggcgatcgcc acgggaaatt aaagcctgca tcactgacca   1878

cttataactt tcggga                                                   1894
```

<210> SEQ ID NO 67
<211> LENGTH: 447
<212> TYPE: PRT
<213> ORGANISM: Synechocystis sp.

<400> SEQUENCE: 67

```
Met Ala Leu Leu Ser Leu Asn Asn His Gln Ser His Gln Arg Leu Thr
1               5                   10                  15

Val Asn Pro Pro Ala Gln Gly Val Ala Leu Thr Gly Arg Leu Arg Val
            20                  25                  30

Pro Gly Asp Lys Ser Ile Ser His Arg Ala Leu Met Leu Gly Ala Ile
        35                  40                  45

Ala Thr Gly Glu Thr Ile Ile Glu Gly Leu Leu Leu Gly Glu Asp Pro
    50                  55                  60

Arg Ser Thr Ala His Cys Phe Arg Ala Met Gly Ala Glu Ile Ser Glu
65                  70                  75                  80

Leu Asn Ser Glu Lys Ile Ile Val Gln Gly Arg Gly Leu Gly Gln Leu
                85                  90                  95

Gln Glu Pro Ser Thr Val Leu Asp Ala Gly Asn Ser Gly Thr Thr Met
            100                 105                 110

Arg Leu Met Leu Gly Leu Leu Ala Gly Gln Lys Asp Cys Leu Phe Thr
        115                 120                 125

Val Thr Gly Asp Asp Ser Leu Arg His Arg Pro Met Ser Arg Val Ile
    130                 135                 140

Gln Pro Leu Gln Gln Met Gly Ala Lys Ile Trp Ala Arg Ser Asn Gly
145                 150                 155                 160

Lys Phe Ala Pro Leu Ala Val Gln Gly Ser Gln Leu Lys Pro Ile His
                165                 170                 175
```

-continued

```
Tyr His Ser Pro Ile Ala Ser Ala Gln Val Lys Ser Cys Leu Leu Leu
            180                 185                 190

Ala Gly Leu Thr Thr Glu Gly Asp Thr Thr Val Thr Glu Pro Ala Leu
        195                 200                 205

Ser Arg Asp His Ser Glu Arg Met Leu Gln Ala Phe Gly Ala Lys Leu
    210                 215                 220

Thr Ile Asp Pro Val Thr His Ser Val Thr Val His Gly Pro Ala His
225                 230                 235                 240

Leu Thr Gly Gln Arg Val Val Val Pro Gly Asp Ile Ser Ser Ala Ala
                245                 250                 255

Phe Trp Leu Val Ala Ala Ser Ile Leu Pro Gly Ser Glu Leu Leu Val
            260                 265                 270

Glu Asn Val Gly Ile Asn Pro Thr Arg Thr Gly Val Leu Glu Val Leu
        275                 280                 285

Ala Gln Met Gly Ala Asp Ile Thr Pro Glu Asn Glu Arg Leu Val Thr
    290                 295                 300

Gly Glu Pro Val Ala Asp Leu Arg Val Arg Ala Ser His Leu Gln Gly
305                 310                 315                 320

Cys Thr Phe Gly Gly Glu Ile Ile Pro Arg Leu Ile Asp Glu Ile Pro
                325                 330                 335

Ile Leu Ala Val Ala Ala Ala Phe Ala Glu Gly Thr Thr Arg Ile Glu
            340                 345                 350

Asp Ala Ala Glu Leu Arg Val Lys Glu Ser Asp Arg Leu Ala Ala Ile
        355                 360                 365

Ala Ser Glu Leu Gly Lys Met Gly Ala Lys Val Thr Glu Phe Asp Asp
    370                 375                 380

Gly Leu Glu Ile Gln Gly Gly Ser Pro Leu Gln Gly Ala Glu Val Asp
385                 390                 395                 400

Ser Leu Thr Asp His Arg Ile Ala Met Ala Leu Ala Ile Ala Ala Leu
                405                 410                 415

Gly Ser Gly Gly Gln Thr Ile Ile Asn Arg Ala Glu Ala Ala Ala Ile
            420                 425                 430

Ser Tyr Pro Glu Phe Phe Gly Thr Leu Gly Gln Val Ala Gln Gly
        435                 440                 445


<210> SEQ ID NO 68
<211> LENGTH: 1479
<212> TYPE: DNA
<213> ORGANISM: Dichelobacter nodosus
<220> FEATURE:
<221> NAME/KEY: CDS
<222> LOCATION: (107)..(1438)

<400> SEQUENCE: 68

tttaaaaaca atgagttaaa aaattatttt tctggcacac gcgctttttt tgcatttttt     60

ctcccatttt tccggcacaa taacgttggt tttataaaag gaaatg atg atg acg       115
                                                   Met Met Thr
                                                   1

aat ata tgg cac acc gcg ccc gtc tct gcg ctt tcc ggc gaa ata acg      163
Asn Ile Trp His Thr Ala Pro Val Ser Ala Leu Ser Gly Glu Ile Thr
    5                   10                  15

ata tgc ggc gat aaa tca atg tcg cat cgc gcc tta tta tta gca gcg      211
Ile Cys Gly Asp Lys Ser Met Ser His Arg Ala Leu Leu Leu Ala Ala
20                  25                  30                  35

tta gca gaa gga caa acg gaa atc cgc ggc ttt tta gcg tgc gcg gat      259
Leu Ala Glu Gly Gln Thr Glu Ile Arg Gly Phe Leu Ala Cys Ala Asp
```

-continued

```
                40                  45                  50

tgt ttg gcg acg cgg caa gca ttg cgc gca tta ggc gtt gat att caa      307
Cys Leu Ala Thr Arg Gln Ala Leu Arg Ala Leu Gly Val Asp Ile Gln
            55                  60                  65

aga gaa aaa gaa ata gtg acg att cgc ggt gtg gga ttt ctg ggt ttg      355
Arg Glu Lys Glu Ile Val Thr Ile Arg Gly Val Gly Phe Leu Gly Leu
        70                  75                  80

cag ccg ccg aaa gca ccg tta aat atg caa aac agt ggc act agc atg      403
Gln Pro Pro Lys Ala Pro Leu Asn Met Gln Asn Ser Gly Thr Ser Met
    85                  90                  95

cgt tta ttg gca gga att ttg gca gcg cag cgc ttt gag agc gtg tta      451
Arg Leu Leu Ala Gly Ile Leu Ala Ala Gln Arg Phe Glu Ser Val Leu
100                 105                 110                 115

tgc ggc gat gaa tca tta gaa aaa cgt ccg atg cag cgc att att acg      499
Cys Gly Asp Glu Ser Leu Glu Lys Arg Pro Met Gln Arg Ile Ile Thr
                120                 125                 130

ccg ctt gtg caa atg ggg gca aaa att gtc agt cac agc aat ttt acg      547
Pro Leu Val Gln Met Gly Ala Lys Ile Val Ser His Ser Asn Phe Thr
            135                 140                 145

gcg ccg tta cat att tca gga cgc ccg ctg acc ggc att gat tac gcg      595
Ala Pro Leu His Ile Ser Gly Arg Pro Leu Thr Gly Ile Asp Tyr Ala
        150                 155                 160

tta ccg ctt ccc agc gcg caa tta aaa agt tgc ctt att ttg gca gga      643
Leu Pro Leu Pro Ser Ala Gln Leu Lys Ser Cys Leu Ile Leu Ala Gly
    165                 170                 175

tta ttg gct gac ggt acc acg cgg ctg cat act tgc ggc atc agt cgc      691
Leu Leu Ala Asp Gly Thr Thr Arg Leu His Thr Cys Gly Ile Ser Arg
180                 185                 190                 195

gac cac acg gaa cgc atg ttg ccg ctt ttt ggt ggc gca ctt gag atc      739
Asp His Thr Glu Arg Met Leu Pro Leu Phe Gly Gly Ala Leu Glu Ile
                200                 205                 210

aag aaa gag caa ata atc gtc acc ggt gga caa aaa ttg cac ggt tgc      787
Lys Lys Glu Gln Ile Ile Val Thr Gly Gly Gln Lys Leu His Gly Cys
            215                 220                 225

gtg ctt gat att gtc ggc gat ttg tcg gcg gcg gcg ttt ttt atg gtt      835
Val Leu Asp Ile Val Gly Asp Leu Ser Ala Ala Ala Phe Phe Met Val
        230                 235                 240

gcg gct ttg att gcg ccg cgc gcg gaa gtc gtt att cgt aat gtc ggc      883
Ala Ala Leu Ile Ala Pro Arg Ala Glu Val Val Ile Arg Asn Val Gly
    245                 250                 255

att aat ccg acg cgg gcg gca atc att act ttg ttg caa aaa atg ggc      931
Ile Asn Pro Thr Arg Ala Ala Ile Ile Thr Leu Leu Gln Lys Met Gly
260                 265                 270                 275

gga cgg att gaa ttg cat cat cag cgc ttt tgg ggc gcc gaa ccg gtg      979
Gly Arg Ile Glu Leu His His Gln Arg Phe Trp Gly Ala Glu Pro Val
                280                 285                 290

gca gat att gtt gtt tat cat tca aaa ttg cgc ggc att acg gtg gcg     1027
Ala Asp Ile Val Val Tyr His Ser Lys Leu Arg Gly Ile Thr Val Ala
            295                 300                 305

ccg gaa tgg att gcc aac gcg att gat gaa ttg ccg att ttt ttt att     1075
Pro Glu Trp Ile Ala Asn Ala Ile Asp Glu Leu Pro Ile Phe Phe Ile
        310                 315                 320

gcg gca gct tgc gcg gaa ggg acg act ttt gtg ggc aat ttg tca gaa     1123
Ala Ala Ala Cys Ala Glu Gly Thr Thr Phe Val Gly Asn Leu Ser Glu
    325                 330                 335

ttg cgt gtg aaa gaa tcg gat cgt tta gcg gcg atg gcg caa aat tta     1171
Leu Arg Val Lys Glu Ser Asp Arg Leu Ala Ala Met Ala Gln Asn Leu
340                 345                 350                 355

caa act ttg ggc gtg gcg tgc gac gtt ggc gcc gat ttt att cat ata     1219
```

-continued

```
Gln Thr Leu Gly Val Ala Cys Asp Val Gly Ala Asp Phe Ile His Ile
                360                 365                 370

tat gga aga agc gat cgg caa ttt tta ccg gcg cgg gtg aac agt ttt     1267
Tyr Gly Arg Ser Asp Arg Gln Phe Leu Pro Ala Arg Val Asn Ser Phe
            375                 380                 385

ggc gat cat cgg att gcg atg agt ttg gcg gtg gca ggt gtg cgc gcg     1315
Gly Asp His Arg Ile Ala Met Ser Leu Ala Val Ala Gly Val Arg Ala
        390                 395                 400

gca ggt gaa tta ttg att gat gac ggc gcg gtg gcg gcg gtt tct atg     1363
Ala Gly Glu Leu Leu Ile Asp Asp Gly Ala Val Ala Ala Val Ser Met
    405                 410                 415

ccg caa ttt cgc gat ttt gcc gcc gca att ggt atg aat gta gga gaa     1411
Pro Gln Phe Arg Asp Phe Ala Ala Ala Ile Gly Met Asn Val Gly Glu
420                 425                 430                 435

aaa gat gcg aaa aat tgt cac gat tga tggtcctagc ggtgttggaa           1458
Lys Asp Ala Lys Asn Cys His Asp
                440

aaggcacggt ggcgcaagct t                                             1479


<210> SEQ ID NO 69
<211> LENGTH: 443
<212> TYPE: PRT
<213> ORGANISM: Dichelobacter nodosus

<400> SEQUENCE: 69

Met Met Thr Asn Ile Trp His Thr Ala Pro Val Ser Ala Leu Ser Gly
1               5                   10                  15

Glu Ile Thr Ile Cys Gly Asp Lys Ser Met Ser His Arg Ala Leu Leu
            20                  25                  30

Leu Ala Ala Leu Ala Glu Gly Gln Thr Glu Ile Arg Gly Phe Leu Ala
        35                  40                  45

Cys Ala Asp Cys Leu Ala Thr Arg Gln Ala Leu Arg Ala Leu Gly Val
    50                  55                  60

Asp Ile Gln Arg Glu Lys Glu Ile Val Thr Ile Arg Gly Val Gly Phe
65                  70                  75                  80

Leu Gly Leu Gln Pro Pro Lys Ala Pro Leu Asn Met Gln Asn Ser Gly
                85                  90                  95

Thr Ser Met Arg Leu Leu Ala Gly Ile Leu Ala Ala Gln Arg Phe Glu
            100                 105                 110

Ser Val Leu Cys Gly Asp Glu Ser Leu Glu Lys Arg Pro Met Gln Arg
        115                 120                 125

Ile Ile Thr Pro Leu Val Gln Met Gly Ala Lys Ile Val Ser His Ser
    130                 135                 140

Asn Phe Thr Ala Pro Leu His Ile Ser Gly Arg Pro Leu Thr Gly Ile
145                 150                 155                 160

Asp Tyr Ala Leu Pro Leu Pro Ser Ala Gln Leu Lys Ser Cys Leu Ile
                165                 170                 175

Leu Ala Gly Leu Leu Ala Asp Gly Thr Thr Arg Leu His Thr Cys Gly
            180                 185                 190

Ile Ser Arg Asp His Thr Glu Arg Met Leu Pro Leu Phe Gly Gly Ala
        195                 200                 205

Leu Glu Ile Lys Lys Glu Gln Ile Ile Val Thr Gly Gly Gln Lys Leu
    210                 215                 220

His Gly Cys Val Leu Asp Ile Val Gly Asp Leu Ser Ala Ala Ala Phe
225                 230                 235                 240

Phe Met Val Ala Ala Leu Ile Ala Pro Arg Ala Glu Val Val Ile Arg
```

-continued

```
                245                 250                 255

Asn Val Gly Ile Asn Pro Thr Arg Ala Ala Ile Ile Thr Leu Leu Gln
            260                 265                 270

Lys Met Gly Gly Arg Ile Glu Leu His His Gln Arg Phe Trp Gly Ala
        275                 280                 285

Glu Pro Val Ala Asp Ile Val Val Tyr His Ser Lys Leu Arg Gly Ile
    290                 295                 300

Thr Val Ala Pro Glu Trp Ile Ala Asn Ala Ile Asp Glu Leu Pro Ile
305                 310                 315                 320

Phe Phe Ile Ala Ala Ala Cys Ala Glu Gly Thr Thr Phe Val Gly Asn
                325                 330                 335

Leu Ser Glu Leu Arg Val Lys Glu Ser Asp Arg Leu Ala Ala Met Ala
            340                 345                 350

Gln Asn Leu Gln Thr Leu Gly Val Ala Cys Asp Val Gly Ala Asp Phe
        355                 360                 365

Ile His Ile Tyr Gly Arg Ser Asp Arg Gln Phe Leu Pro Ala Arg Val
    370                 375                 380

Asn Ser Phe Gly Asp His Arg Ile Ala Met Ser Leu Ala Val Ala Gly
385                 390                 395                 400

Val Arg Ala Ala Gly Glu Leu Leu Ile Asp Asp Gly Ala Val Ala Ala
                405                 410                 415

Val Ser Met Pro Gln Phe Arg Asp Phe Ala Ala Ala Ile Gly Met Asn
            420                 425                 430

Val Gly Glu Lys Asp Ala Lys Asn Cys His Asp
        435                 440


<210> SEQ ID NO 70
<211> LENGTH: 455
<212> TYPE: PRT
<213> ORGANISM: Artificial sequence
<220> FEATURE:
<223> OTHER INFORMATION: Synthetic

<400> SEQUENCE: 70

Met Leu His Gly Ala Ser Ser Arg Pro Ala Thr Ala Arg Lys Ser Ser
1               5                   10                  15

Gly Leu Ser Gly Thr Val Arg Ile Pro Gly Asp Lys Ser Ile Ser His
            20                  25                  30

Arg Ser Phe Met Phe Gly Gly Leu Ala Ser Gly Glu Thr Arg Ile Thr
        35                  40                  45

Gly Leu Leu Glu Gly Glu Asp Val Ile Asn Thr Gly Lys Ala Met Gln
    50                  55                  60

Ala Met Gly Ala Arg Ile Arg Lys Glu Gly Asp Thr Trp Ile Ile Asp
65                  70                  75                  80

Gly Val Gly Asn Gly Gly Leu Leu Ala Pro Glu Ala Pro Leu Asp Phe
                85                  90                  95

Gly Asn Ala Ala Thr Gly Cys Arg Leu Thr Met Gly Leu Val Gly Val
            100                 105                 110

Tyr Asp Phe Asp Ser Thr Phe Ile Gly Asp Ala Ser Leu Thr Lys Arg
        115                 120                 125

Pro Met Gly Arg Val Leu Asn Pro Leu Arg Glu Met Gly Val Gln Val
    130                 135                 140

Lys Ser Glu Asp Gly Asp Arg Leu Pro Val Thr Leu Arg Gly Pro Lys
145                 150                 155                 160

Thr Pro Thr Pro Ile Thr Tyr Arg Val Pro Met Ala Ser Ala Gln Val
```

-continued

```
                165                 170                 175

Lys Ser Ala Val Leu Leu Ala Gly Leu Asn Thr Pro Gly Ile Thr Thr
            180                 185                 190

Val Ile Glu Pro Ile Met Thr Arg Asp His Thr Glu Lys Met Leu Gln
        195                 200                 205

Gly Phe Gly Ala Asn Leu Thr Val Glu Thr Asp Ala Asp Gly Val Arg
    210                 215                 220

Thr Ile Arg Leu Glu Gly Arg Gly Lys Leu Thr Gly Gln Val Ile Asp
225                 230                 235                 240

Val Pro Gly Asp Pro Ser Ser Thr Ala Phe Pro Leu Val Ala Ala Leu
                245                 250                 255

Leu Val Pro Gly Ser Asp Val Thr Ile Leu Asn Val Leu Met Asn Pro
            260                 265                 270

Thr Arg Thr Gly Leu Ile Leu Thr Leu Gln Glu Met Gly Ala Asp Ile
        275                 280                 285

Glu Val Ile Asn Pro Arg Leu Ala Gly Gly Glu Asp Val Ala Asp Leu
    290                 295                 300

Arg Val Arg Ser Ser Thr Leu Lys Gly Val Thr Val Pro Glu Asp Arg
305                 310                 315                 320

Ala Pro Ser Met Ile Asp Glu Tyr Pro Ile Leu Ala Val Ala Ala Ala
                325                 330                 335

Phe Ala Glu Gly Ala Thr Val Met Asn Gly Leu Glu Glu Leu Arg Val
            340                 345                 350

Lys Glu Ser Asp Arg Leu Ser Ala Val Ala Asn Gly Leu Lys Leu Asn
        355                 360                 365

Gly Val Asp Cys Asp Glu Gly Glu Thr Ser Leu Val Val Arg Gly Arg
    370                 375                 380

Pro Asp Gly Lys Gly Leu Gly Asn Ala Ser Gly Ala Ala Val Ala Thr
385                 390                 395                 400

His Leu Asp His Arg Ile Ala Met Ser Phe Leu Val Met Gly Leu Val
                405                 410                 415

Ser Glu Asn Pro Val Thr Val Asp Asp Ala Thr Met Ile Ala Thr Ser
            420                 425                 430

Phe Pro Glu Phe Met Asp Leu Met Ala Gly Leu Gly Ala Lys Ile Glu
        435                 440                 445

Leu Ser Asp Thr Lys Ala Ala
    450                 455
```

We claim:

1. An isolated DNA molecule which encodes an EPSPS enzyme having the sequence of SEQ ID NO:3.

2. [A] *The* DNA molecule of claim 1 having the sequence of SEQ ID NO:2.

3. [A] *The* DNA molecule of claim 1 having the sequence of SEQ ID NO:9.

4. A recombinant, double-stranded DNA molecule comprising in sequence:

a) a promoter which functions in plant cells to cause the production of an RNA sequence;

b) a structural DNA sequence that causes the production of an RNA sequence which encodes a EPSPS enzyme having the sequence domains:

-R-$X_1$-H-$X_2$-E-(SEQ ID NO:37), in which
$X_1$ is G, S, T, C, Y, N, Q, D or E;
$X_2$ is S or T; and -G-D-K-$X_3$-(SEQ ID NO:38), in which
$X_3$ is S or T; and -S-A-Q-$X_4$-K-(SEQ ID NO:39), in which
$X_4$ is A, R, N, D, C, Q, E, G, H, I, L, K, M, F, P, S, T, W, Y or V; and -N-$X_5$-T-R-(SEQ ID NO:40), in which
$X_5$ is A, R, N, D, C, Q, E, G, H, I, L, K, M, F, P, S, T, W, Y or V,

*provided that when $X_1$ is D, $X_2$ is T, $X_3$ is S, and $X_4$ is V, then $X_5$ is A, R, N, D, C, Q, E, G, H, I, L, K, M, F, S, T, W, Y, or V*; and c) a 3' non-translated region which functions in plant cells to cause the addition of a stretch of polyadenyl nucleotides to the 3' end of the RNA sequence;

where the promoter is heterologous with respect to the structural DNA sequence and adapted to cause sufficient expression of the encoded EPSPS enzyme to enhance the glyphosate tolerance of a plant cell transformed with the DNA molecule.

5. [A] *The* DNA molecule of claim 4 in which the structural DNA sequence encodes a fusion polypeptide comprising an amino-terminal chloroplast transit peptide and the EPSPS enzyme.

6. [A] *The* DNA molecule of claim 4 in which $X_1$ is D or N; $X_2$ is S or T; $X_3$ is S or T; $X_4$ is V, I or L; and $X_5$ is P or Q, *provided that when $X_1$ is D, $X_2$ is T, $X_3$ is S, and $X_4$ is V, then $X_5$ is Q.*

[7. A DNA molecule of claim 6 in which the structural DNA sequence encodes an EPSPS enzyme selected from the group consisting of SEQ ID NO:2, SEQ ID NO:4, SEQ ID NO:6, SEQ ID NO:41 and SEQ ID NO:43.]

8. [A] *The* DNA molecule of claim 5 in which $X_1$ is D or N; $X_2$ is S or T; $X_3$ is S or T; $X_4$ is V, I or L; and $X_5$ is P or Q, *provided that when $X_1$ is D, $X_2$ is T, $X_3$ is S, and $X_4$ is V, then $X_5$ is Q.*

[9. A DNA molecule of claim 8 in which the structural DNA sequence encodes an EPSPS enzyme selected from the group consisting of SEQ ID NO:2, SEQ ID NO:4, SEQ ID NO:6, SEQ ID NO:41 and SEQ ID NO:43.]

10. [A] *The* DNA molecule of claim [8] *137* in which the EPSPS [sequence is] *enzyme has the sequence set forth in* SEQ ID NO:3.

11. [A] *The* DNA molecule of claim [10] *4* in which the promoter is a plant DNA virus promoter.

12. [A] *The* DNA molecule of claim 11 in which the promoter is selected from the group consisting of CaMV35S and FMV35S promoters.

13. [A] *The* DNA molecule of claim [10] *5* in which the structural DNA sequence encodes a chloroplast transit peptide selected from the group consisting of SEQ ID NO:11 and SEQ ID NO:15.

14. [A] *The* DNA molecule of claim 13 in which the 3' non-translated region is selected from the group consisting of the NOS 3' and the E9 3' non-translated regions.

15. A method of producing genetically transformed plants which are tolerant toward glyphosate herbicide, comprising the steps of:

a) inserting into the genome of a plant cell a recombinant, double-stranded DNA molecule comprising:

i) a promoter which functions in plant cells to cause the production of an RNA sequence, ii) a structural DNA sequence that causes the production of an RNA sequence which encodes an EPSPS enzyme having the sequence domains:

-R-$X_1$-H-$X_2$-E-(SEQ ID NO:37), in which
$X_1$ is G, S, T, C, Y, N, Q, D or E;
$X_2$ is S or T; and -G-D-K-$X_3$-(SEQ ID NO:38), in which
$X_3$ is S or T; and -S-A-Q-$X_4$-K-(SEQ ID NO:39), in which
$X_4$ is A, R, N, D, C, Q, E, G, H, I, L, K, M, F, P, S, T, W, Y or V; and -N-$X_5$-T-R-(SEQ ID NO:40), in which
$X_5$ is A, R, N, D, C, Q, E, G, H, I, L, K, M, F, P, S, T, W, Y or V, *provided that when $X_1$ is D, $X_2$ is T, $X_3$ is S, and $X_4$ is V, then $X_5$ is A, R, N, D, C, Q, E, G, H, I, L, K, M, F, S, T, W, Y or V*; and iii) a 3' non-translated DNA sequence which functions in plant cells to cause the addition of a stretch of polyadenyl nucleotides to the 3' end of the RNA sequence;

where the promoter is heterologous with respect to the structural DNA sequence and adapted to cause sufficient expression of the polypeptide to enhance the glyphosate tolerance of a plant cell transformed with the DNA molecule;

b) obtaining a transformed plant cell; and c) regenerating from the transformed plant cell a genetically transformed plant which has increased tolerance to glyphosate herbicide.

16. [A] *The* method of claim 15 in which $X_1$ is D or N; $X_2$ is S or T; $X_3$ is S or T; $X_4$ is V, I or L; and $X_5$ is P or Q, *provided that when $X_1$ is D, $X_2$ is T, $X_3$ is S, and $X_4$ is V, then $X_5$ is Q.*

[17. A method of claim 16 in which the structural DNA sequence encodes an EPSPS enzyme selected from the group consisting of SEQ ID NO:2, SEQ ID NO:4, SEQ ID NO:6, SEQ ID NO:41 and SEQ ID NO:43.]

18. [A] *The* method of claim 15 in which the structural DNA sequence encodes a fusion polypeptide comprising an amino-terminal chloroplast transit peptide and the EPSPS enzyme.

19. [A] *The* method of claim 18 in which $X_1$ is D or N; $X_2$ is S or T; $X_3$ is S or T; $X_4$ is V, I or L; and $X_5$ is P or Q, *provided that when $X_1$ is D, $X_2$ is T, $X_3$ is S, and $X_4$ is V, then $X_5$ is Q.*

[20. A method of claim 19 in which the structural DNA sequence encodes an EPSPS enzyme selected from the group consisting of SEQ ID NO:2, SEQ ID NO:4, SEQ ID NO:6, SEQ ID NO:42 and SEQ ID NO:44.]

21. [A] *The* method of claim [19] *143* in which the EPSPS enzyme is that set forth in SEQ ID NO:3.

22. [A] *The* method of claim [21] *15* in which the promoter is from a plant DNA virus.

23. [A] *The* method of claim 22 in which the promoter is selected from the group consisting of CaMV35S and FMV35S promoters.

24. A glyphosate-tolerant plant cell comprising [a] *the* DNA molecule of [claims] *claim 4,* 5 *or* 8[or 10].

25. [A] *The* glyphosate-tolerant plant cell of claim 24 in which the promoter is a plant DNA virus promoter.

26. [A] *The* glyphosate-tolerant plant cell of claim 25 in which the promoter is selected from the group consisting of CaMV35S and FMV35S promoters.

27. [A] *The* glyphosate-tolerant plant cell of claim 24 selected from the group consisting of corn, wheat, rice, barley, soybean, cotton, sugarbeet, oilseed rape, canola, flax, sunflower, potato, tobacco, tomato, alfalfa, poplar, pine, [eukalyptus] *eucalyptus*, apple, lettuce, peas, lentils, grape and turf grasses.

28. A glyphosate-tolerant plant comprising *the* plant [cells] *cell* of claim 27.

29. [A] *The* glyphosate-tolerant plant of claim 28 in which the promoter is from a DNA plant virus promoter.

30. [A] *The* glyphosate-tolerant plant of claim 29 in which the promoter is selected from the group consisting of CaMV35S and FMV35S promoters.

31. [A] *The* glyphosate-tolerant plant of claim 30 selected from the group consisting of corn, wheat, rice, barley, soybean, cotton, sugarbeet, oilseed rape, canola, flax, sunflower, potato, tobacco, tomato, alfalfa, poplar, pine, [eukalyptus] *eucalyptus*, apple, lettuce, peas, lentils, grape and turf grasses.

32. A method for selectively controlling weeds in a field containing a crop having plant crop seeds or plants comprising the steps of:

a) planting the crop seeds or plants which are glyphosate-tolerant as a result of a recombinant double-stranded DNA molecule being inserted into the crop seed or plant, the DNA molecule having:

i) a promoter which functions in plant cells to cause the production of an RNA sequence, ii) a structural DNA sequence that causes the production of an RNA sequence which encodes an EPSPS enzyme having the sequence domains:

-R-$X_1$-H-$X_2$-E-(SEQ ID NO:37), in which
$X_1$ is G, S, T, C, Y, N, Q, D or E;
$X_2$ is S or T; and
-G-D-K-$X_3$-(SEQ ID NO:38), in which
$X_3$ is S or T; and
-S-A-Q-$X_4$-K-(SEQ ID NO:39), in which
$X_4$ is A, R, N, D, C, Q, E, G, H, I, L, K, M, F, P, S, T, W, Y or V; and
-N-$X_5$-T-R-(SEQ ID NO:40), in which
$X_5$ is A, R, N, D, C, Q, E, G, H, I, L, K, M, F, P, S, T, W, Y or V, *provided that when $X_1$ is D, $X_2$ is T, $X_3$ is S, and $X_4$ is V, then $X_5$ is A, R, N, D, C, Q, E, G, H, I, L, K, M, F, S, T, W, Y or V*; and iii) a 3' non-translated DNA sequence which functions in plant cells to cause the addition of a stretch of polyadenyl nucleotides to the 3' end of the RNA sequence where the promoter is heterologous with respect to the structural DNA sequence and adapted to cause sufficient expression of the EPSPS enzyme to enhance the glyphosate tolerance of the crop plant transformed with the DNA molecule; and b) applying to the crop and weeds in the field a sufficient amount of glyphosate herbicide to control the weeds without significantly affecting the crop.

33. [A] *The* method of claim 32 in which $X_1$ is D or N; $X_2$ is S or T; $X_3$ is S or T; $X_4$ is V, I or L; and $X_5$ is P or Q, *provided that when $X_1$ is D, $X_2$ is T, $X_3$ is S, and $X_4$ is V, then $X_5$ is Q*.

[34. A method of claim 33 in which the structural DNA sequence encodes an EPSPS enzyme selected from the group consisting of SEQ ID NO:2, SEQ ID NO:4, SEQ ID NO:6, SEQ ID NO:42 and SEQ ID NO:44.]

35. [A] *The* method of claim 32 in which the structural DNA sequence encodes a fusion polypeptide comprising an amino-terminal chloroplast transit peptide and the EPSPS enzyme.

36. [A] *The* method of claim 35 in which $X_1$ is D or N; $X_2$ is S or T; $X_3$ is S or T; $X_4$ is V, I or L; and $X_5$ is P or Q, *provided that when $X_1$ is D, $X_2$ is T, $X_3$ is S, and $X_4$ is V, then $X_5$ is Q*.

[37. A method of claim 36 in which the structural DNA sequence encodes an EPSPS enzyme selected from the group consisting of SEQ ID NO:2, SEQ ID NO:4, SEQ ID NO:6, SEQ ID NO:41 and SEQ ID NO:43.]

38. [A] *The* method of claim [36] *155* in which the DNA molecule encodes an EPSPS enzyme as set forth in SEQ ID NO:3.

39. [A] *The* method of claim [38] *32* in which the DNA molecule further comprises a promoter selected from the group consisting of the CAMV35S and FMV35S promoters.

40. [A] *The* method of claim 39 in which the crop plant is selected from the group consisting of corn, wheat, rice, barley, soybean, cotton, sugarbeet, oilseed rape, canola, flax, sunflower, potato, tobacco, tomato, alfalfa, poplar, pine, [eukalyptus] *eucalyptus*, apple, lettuce, peas, lentils, grape and turf grasses.

41. [A] *The* DNA molecule of claim 5 in which the structural DNA sequence encodes a chloroplast transit peptide selected from the group consisting of SEQ ID NO:11, SEQ ID NO:13, SEQ ID NO:15 and SEQ ID NO:17.

42. [A] *The* DNA molecule of claim 41 in which the chloroplast transit peptide is encoded by a DNA sequence selected from the group consisting of SEQ ID NO:10, SEQ ID NO:12, SEQ ID NO:14 and SEQ ID NO:16.

43. [A] *The* DNA molecule of claim 5 in which the structural DNA sequence encodes a chloroplast transit peptide selected from the group consisting of SEQ ID NO:11 and SEQ ID NO:15.

44. [A] *The* DNA molecule of claim 43 in which the chloroplast transit peptide is encoded by a DNA sequence selected from the group consisting of SEQ ID NO:10 and SEQ ID NO:14.

45. [A] *The* DNA molecule of claim 41 in which the promoter is selected from the group consisting of CaMV 35S and FMV 35S promoters.

46. [A] *The* DNA molecule of claim 42 in which the promoter is selected from the group consisting of CaMV 35S and FMV 35S promoters.

47. [A] *The* DNA molecule of claim 43 in which the promoter is selected from the group consisting of CaMV 35S and FMV 35S promoters.

48. [A] *The* DNA molecule of claim 44 in which the promoter is selected from the group consisting of CaMV 35S and FMV 35S promoters.

49. [A] *The* DNA molecule of claim 45 in which the 3' non-translated region is selected from the group consisting of the NOS 3' and the E9 3' non-translated regions.

50. [A] *The* DNA molecule of claim 46 in which the 3' non-translated region is selected from the group consisting of the NOS 3' and the E9 3' non-translated regions.

51. [A] *The* DNA molecule of claim 47 in which the 3' non-translated region is selected from the group consisting of the NOS 3' and the E9 3' non-translated regions.

52. [A] *The* DNA molecule of claim 48 in which the 3' non-translated region is selected from the group consisting of the NOS 3' and the E9 3' non-translated regions.

[53. A DNA molecule of claim 49 in which the structural DNA sequence encodes an EPSPS enzyme selected from the group consisting of SEQ ID NO:3, SEQ ID NO:5, SEQ ID NO:7, SEQ ID NO:42 and SEQ ID NO:44.]

[54. A DNA molecule of claim 50 in which the structural DNA sequence encodes an EPSPS enzyme selected from the group consisting of SEQ ID NO:3, SEQ ID NO:5, SEQ ID NO:7, SEQ ID NO:42 and SEQ ID NO:44.]

[55. A DNA molecule of claim 51 in which the structural DNA sequence encodes an EPSPS enzyme selected from the group consisting of SEQ ID NO:3, SEQ ID NO:5, SEQ ID NO:7, SEQ ID NO:42 and SEQ ID NO:44.]

[56. A DNA molecule of claim 52 in which the structural DNA sequence encodes an EPSPS enzyme selected from the group consisting of SEQ ID NO:3, SEQ ID NO:5, SEQ ID NO:7, SEQ ID NO:42 and SEQ ID NO:44.]

57. [A] *The* DNA molecule of claim [53] *137* in which the structural DNA sequence contains an EPSPS encoding sequence selected from the group consisting of SEQ ID NO:2, SEQ ID NO:4, *and* SEQ ID NO:6[, SEQ ID NO:41 and SEQ ID NO:43].

58. [A] *The* DNA molecule of claim [54] *137* in which the structural DNA sequence contains an EPSPS encoding sequence [selected from the group consisting of SEQ ID NO:2, SEQ ID NO:4, SEQ ID NO:6, SEQ ID NO:41 and SEQ ID NO:43] *as set forth in SEQ ID NO:9*.

[59. A DNA molecule of claim 55 in which the structural DNA sequence contains an EPSPS encoding sequence selected from the group consisting of SEQ ID NO:2, SEQ ID NO:4, SEQ ID NO:6, SEQ ID NO:41 and SEQ ID NO:43.]

[60. A DNA molecule of claim 56 in which the structural DNA sequence contains an EPSPS coding sequence selected from the group consisting of SEQ ID NO:2, SEQ ID NO:4, SEQ ID NO:6, SEQ ID NO:41 and SEQ ID NO:43.]

[61. A DNA molecule of claim 49 in which the structural DNA sequence encodes an EPSPS enzyme having the sequence of SEQ ID NO:3.]

[62. A DNA molecule of claim 50 in which the structural DNA sequence encodes an EPSPS enzyme having the sequence of SEQ ID NO:3.]

[63. A DNA molecule of claim 51 in which the structural DNA sequence encodes an EPSPS enzyme having the sequence of SEQ ID NO:3.]

[64. A DNA molecule of claim 52 in which the structural DNA sequence encodes an EPSPS enzyme having the sequence of SEQ ID NO:3.]

[65. A DNA molecule of claim 61 in which the structural DNA sequence contains an EPSPS encoding sequence selected from the group consisting of SEQ ID NO:2 and SEQ ID NO:9.]

[66. A DNA molecule of claim 62 in which the structural DNA sequence contains an EPSPS encoding sequence selected from the group consisting of SEQ ID NO:2 and SEQ ID NO:9.]

[67. A DNA molecule of claim 63 in which the structural DNA sequence contains an EPSPS encoding sequence selected from the group consisting of SEQ ID NO:2 and SEQ ID NO:9.]

[68. A DNA molecule of claim 64 in which the structural DNA sequence contains an EPSPS encoding sequence selected from the group consisting of SEQ ID NO:2 and SEQ ID NO:9.]

69. [A] *The* glyphosate-tolerant plant cell of claim [25] *149* in which:

(a) the promoter is selected from the group consisting of CaMV 35S and FMV 35S promoters;

(b) the structural DNA sequence encodes:

(i) a chloroplast transit peptide selected from the group consisting of SEQ ID NO:11, SEQ ID NO:13, SEQ ID NO:15 and SEQ ID NO:17; and (ii) an EPSPS enzyme selected from the group consisting of SEQ ID NO:3, SEQ ID NO:5, *and* SEQ ID NO:7[, SEQ ID NO:42 and SEQ ID NO:44]; and (c) the 3' non-translated region is selected from the group consisting of the NOS 3' and the E9 3' non-translated regions.

70. [A] *The* glyphosate-tolerant plant cell of claim 69 in which the structural DNA sequence comprises:

(a) a chloroplast transit peptide encoding DNA sequence selected from the group consisting of SEQ ID NO:10, SEQ ID NO:12, SEQ ID NO:14 and SEQ ID NO:16; and (b) an EPSPS encoding sequence selected from the group consisting of SEQ ID NO:2, SEQ ID NO:4, *and* SEQ ID NO:6[, SEQ ID NO:41 and SEQ ID NO:43].

71. [A] *The* glyphosate-tolerant plant cell of claim 69 in which the structural DNA sequence comprises:

(a) a chloroplast transist peptide encoding DNA sequence selected from the group consisting of SEQ ID NO:10 and SEQ ID NO:14; and (b) a DNA sequence encoding an EPSPS enzyme having the sequence of SEQ ID NO:3.

72. [A] *The* glyphosate-tolerant plant cell of claim 71 in which the structural DNA sequence comprises an EPSPS encoding sequence [selected from the group consisting of SEQ ID NO:2 and] *as set forth in* SEQ ID NO:9.

73. [A] *The* glyphosate-tolerant plant cell of claim 71 selected from the group consisting of corn, wheat, rice, barley, soybean, cotton, sugarbeet, oilseed rape, canola, flax, sunflower, potato, tobacco, tomato, alfalfa, poplar, pine, [eukalyptus] *eucalyptus*, apple, lettuce, peas, lentils, grape and turf grasses.

74. A glyphosate-tolerant plant comprising [a] *the* DNA molecule of [claims 5, 8 or 10] *claim 131* in which:

(a) the promoter is selected from the group consisting of CaMV 35S and FMV 35S promoters;

(b) the structural DNA sequence encodes[:];

(i) a chloroplast transit peptide selected from the group consisting of SEQ ID NO:11, SEQ ID NO:13, SEQ ID NO:15 and SEQ ID NO:17; and (ii) an EPSPS enzyme selected from the group consisting of SEQ ID NO:3, SEQ ID NO:5, *and* SEQ ID NO:7[, SEQ ID NO:42 and SEQ ID NO:44]; and (c) the 3' non-translated region is selected from the group consisting of the NOS 3' and the E9 3' non-translated regions.

75. [A] *The* glyphosate-tolerant plant of claim 74 in which the structural DNA sequence comprises:

(a) a chloroplast transit peptide encoding DNA sequence selected from the group consisting of SEQ ID NO:10, SEQ ID NO:12, SEQ ID NO:14 and SEQ ID NO:16; and (b) an EPSPS encoding sequence selected from the group consisting of SEQ ID NO:2, SEQ ID NO:4, *and* SEQ ID NO:6[, SEQ ID NO:41 and SEQ ID NO:43].

76. [A] *The* glyphosate-tolerant plant of claim 75 in which the structural DNA sequence comprises:

(a) a chloroplast transit peptide encoding DNA sequence selected from the group consisting of SEQ ID NO:10 and SEQ ID NO:14; and (b) a DNA sequence encoding an EPSPS enzyme having the sequence of SEQ ID NO:3.

77. [A] *The* glyphosate-tolerant plant of claim [76] *74* in which the structural DNA sequence comprises an EPSPS encoding sequence [selected from the group consisting of SEQ ID NO:2 and] *as set forth in* SEQ ID NO:9.

78. [A] *The* glyphosate-tolerant plant of claim [77] *74* selected from the group consisting of corn, wheat, rice, barley, soybean, cotton, sugarbeet, oilseed rape, canola, flax, sunflower, potato, tobacco, tomato, alfalfa, poplar, pine, [eukalyptus] *eucalyptus*, apple, lettuce, peas, lentils, grape and turf grasses.

79. A seed of [a] *the* glyphosate-tolerant plant of claim 28, *wherein the seed comprises the recombinant DNA molecule*.

80. A seed of [a] *the* glyphosate-tolerant plant of claim 31, *wherein the seed comprises the recombinant DNA molecule*.

81. A seed of [a] *the* glyphosate-tolerant plant of claim 75, *wherein the seed comprises the recombinant DNA molecule*.

82. A seed of [a] *the* glyphosate-tolerant plant of claim 76, *wherein the seed comprises the recombinant DNA molecule*.

83. A seed of [a] *the* glyphosate-tolerant plant of claim 77, *wherein the seed comprises the recombinant DNA molecule*.

84. A seed of [a] *the* glyphosate-tolerant plant of claim [78] *129, wherein the seed comprises the recombinant DNA molecule*.

85. A seed of [a] *the* glyphosate-tolerant plant of claim [79] *144, wherein the seed comprises the recombinant DNA molecule*.

[86. A transgenic soybean plant which contains a heterologous gene which encodes an EPSPS enzyme having a $K_m$ for phosphoenolpyruvate (PEP) between 1 and 150 μM and a $K_i$(glyphosate)/$K_m$(PEP) ratio between about 2 and 500, said plant exhibiting tolerance to N-phosphonomethylglycine herbicide at a rate of 1 lb/acre without significant yield reduction due to herbicide application.]

[87. Seed of a soybean plant of claim 86.]

*88. The DNA molecule of claim 6 in which the structural DNA sequence contains an EPSPS encoding sequence selected from the group consisting of SEQ ID NO:41 and SEQ ID NO:43.*

*89. The DNA molecule of claim 8 in which the structural DNA sequence contains an EPSPS encoding sequence selected from the group consisting of SEQ ID NO:41 and SEQ ID NO:43.*

*90. The method of claim 16 in which the structural DNA sequence contains an EPSPS encoding sequence selected from the group consisting of SEQ ID NO:41 and SEQ ID NO: 43.*

*91. The method of claim 19 in which the structural DNA sequence encodes an EPSPS enzyme having a sequence selected from the group consisting of SEQ ID NO:42 and SEQ ID NO:44.*

*92. The method of claim 33 in which the structural DNA sequence encodes an EPSPS enzyme having a sequence selected from the group consisting of SEQ ID NO:42 and SEQ ID NO:44.*

*93. The method of claim 36 in which the structural DNA sequence contains an EPSPS encoding sequence selected from the group consisting of SEQ ID NO:41 and SEQ ID NO:43.*

*94. The DNA molecule of claim 49 in which the structural DNA sequence encodes an EPSPS enzyme having a sequence selected from the group consisting of SEQ ID NO: 42 and SEQ ID NO: 44.*

*95. The DNA molecule of claim 50 in which the structural DNA sequence encodes an EPSPS enzyme having a sequence selected from the group consisting of SEQ ID NO: 42 and SEQ ID NO: 44.*

*96. The DNA molecule of claim 51 in which the structural DNA sequence encodes an EPSPS enzyme having a sequence selected from the group consisting of SEQ ID NO: 42 and SEQ ID NO: 44.*

*97. The DNA molecule of claim 52 in which the structural DNA sequence encodes an EPSPS enzyme having a sequence selected from the group consisting of SEQ ID NO: 42 and SEQ ID NO: 44.*

*98. The glyphosate-tolerant plant cell of claim 25 in which:*

*a) the promoter is selected from the group consisting of CaMV 35S and FMV 35S promoters;*

*b) the structural DNA sequence encodes:*

*i) a chloroplast transit peptide selected from the group consisting of SEQ ID NO:11, SEQ ID NO:13, SEQ ID NO:15 and SEQ ID NO:17; and*

*ii) an EPSPS enzyme selected from the group consisting of SEQ ID NO:42 and SEQ ID NO:44; and*

*c) the 3' non-translated region is selected from the group consisting of the NOS 3' and the E9 3' non-translated regions.*

*99. The glyphosate-tolerant plant cell of claim 26 in which the structural DNA sequence comprises:*

*a) a chloroplast transit peptide encoding DNA sequence selected from the group consisting of SEQ ID NO:10, SEQ ID NO:12, SEQ ID NO:14 and SEQ ID NO:16; and*

*b) an EPSPS encoding sequence selected from the group consisting of SEQ ID NO:41 and SEQ ID NO:43.*

*100. The glyphosate-tolerant plant comprising the DNA molecule of claim 4, 5 or 8 in which:*

*a) the promoter is selected from the group consisting of CaMV 35S and FMV 35S promoters;*

*b) the structural DNA sequence encodes:*

*i) a chloroplast transit peptide selected from the group consisting of SEQ ID NO:11, SEQ ID NO:13, SEQ ID NO:15 and SEQ ID NO:17; and*

*ii) an EPSPS enzyme selected from the group consisting of SEQ ID NO:42 and SEQ ID NO:44; and*

*c) the 3' non-translated region is selected from the group consisting of the NOS 3' and the E9 3' non-translated regions.*

*101. The glyphosate-tolerant plant of claim 28 in which the structural DNA sequence comprises:*

*a) a chloroplast transit peptide encoding DNA sequence selected from the group consisting of SEQ ID NO:10, SEQ ID NO:12, SEQ ID NO:14 and SEQ ID NO:16; and*

*b) an EPSPS encoding sequence selected from the group consisting of SEQ ID NO:41 and SEQ ID NO:43.*

*102. An isolated DNA molecule that encodes a 5-enolpyruvylshikimate-3-phosphate synthase (EPSPS) enzyme having the sequence of SEQ ID NO:70.*

*103. A recombinant, double-stranded DNA molecule comprising in sequence:*

*a) a promoter which functions in plant cells to cause the production of an RNA sequence;*

*b) a structural DNA sequence that causes the production of an RNA sequence which encodes an EPSPS enzyme having the sequence of SEQ ID NO:70; and*

*c) a 3' non-translated region that functions in plant cells to cause the addition of a stretch of polyadenyl nucleotides to the 3' end of the RNA sequence;*

*where the promoter is heterologous with respect to the structural DNA sequence and adapted to cause sufficient expression of the encoded EPSPS enzyme to enhance the glyphosate tolerance of a plant cell transformed with the DNA molecule.*

*104. The DNA molecule of claim 103, wherein the structural DNA sequence further causes the production of an RNA sequence that encodes an amino-terminal chloroplast transit peptide that is fused to the EPSPS enzyme.*

*105. The DNA molecule of claim 104, wherein the chloroplast transit peptide has the sequence of SEQ ID NO:11 or SEQ ID NO:15.*

*106. The DNA molecule of claim 103, wherein the promoter is a plant DNA virus promoter.*

*107. The DNA molecule of claim 106, wherein the promoter is a CaMV35S promoter or an FMV35S promoter.*

*108. The DNA molecule of claim 103, wherein the 3' non-translated region is a NOS 3' or an E9 3' non-translated region.*

*109. A method of producing a genetically transformed plant which is tolerant toward glyphosate herbicide, comprising the steps of:*

*a) inserting into the genome of a plant cell a recombinant double-stranded DNA molecule comprising:*

*i) a promoter that functions in plant cells to cause the production of an RNS sequence;*

*ii) a structural DNA sequence that causes the production of an RNS sequence which encodes an EPSPS enzyme having the sequence of SEQ ID NO: 70; and*

*iii) a 3' non-translated DNA sequence that functions in plant cells to cause the addition of a stretch of polyadenyl nucleotides to the* 3' end of the RNS sequence;

*wherein the promoter is heterologous with respect to the structural DNA sequence and adapted to cause sufficient expression of the polypeptide to enhance the glyphosate tolerance of a plant cell transformed with the DNA molecule;*

*b) obtaining a transformed plant cell; and*

*c) regenerating from the transformed plant cell a genetically transformed plant which has increased tolerance to glyphosate herbicide.*

*110. The method of claim 109, wherein the structural DNA further causes the production of an RNA sequence that encodes an amino-terminal chloroplast transit peptide that is fused to the EPSPS enzyme.*

*111. The method of claim 110, wherein the chloroplast transit peptide has the sequence of SEQ ID NO:11 or SEQ ID NO:15.*

*112. The method of claim 109, in which the promoter is a plant DNA virus promoter.*

*113. The method of claim 112, in which the promoter is a CaMV35S promoter or an FMV35S promoter.*

*114. The method of claim 109, wherein the 3' non-translated DNA sequence is a NOS 3' or an E9 3' non-translated sequence.*

*115. A glyphosate-tolerant plant cell comprising a DNA sequence encoding an EPSPS enzyme having the sequence of SEQ ID NO: 70.*

*116. A glyphosate-tolerant plant comprising a DNA sequence encoding an EPSPS enzyme having the sequence of SEQ ID NO: 70.*

*117. The plant of claim 116, wherein the plant is corn, wheat, rice, barley, soybean, cotton, sugarbeet, oilseed rape, canola, flax, sunflower, potato, tobacco, tomato, alfalfa, poplar, pine, eucalyptus, apple, lettuce, peas, lentils, grape or turf grasses.*

*118. The plant of claim 117, wherein the plant is corn.*

*119. The plant of claim 117, wherein the plant is soybean.*

*120. The plant of claim 117, wherein the plant is canola.*

*121. The plant of claim 117, wherein the plant is cotton.*

*122. A seed of the plant of claim 116, wherein the seed comprises the DNA sequence encoding an EPSPS enzyme having the sequence of SEQ ID NO: 70.*

*123. The seed of claim 122, wherein the seed is corn, wheat, rice, barley, soybean, cotton, sugarbeet, oilseed rape, canola, flax, sunflower, potato, tobacco, tomato, alfalfa, poplar, pine, eucalyptus, apple, lettuce, peas, lentils, grape or turf grass seed.*

*124. The seed of claim 123, wherein the seed is corn seed.*

*125. The seed of claim 123, wherein the seed is soybean seed.*

*126. The seed of claim 123, wherein the seed is canola seed.*

*127. The seed of claim 123, wherein the seed is cotton seed.*

*128. A glyphosate tolerant plant cell comprising the recombinant DNA molecule of claim 103.*

*129. A plant comprising the glyphosate tolerant plant cell of claim 128.*

*130. A method for selectively controlling weeds in a field containing a crop having planted crop seeds or plants comprising the steps of:*

*a) planting the crop seeds or plants which are glyphosate-tolerant as a result of a recombinant double-stranded DNA molecule being inserted into the crop seed or plant, the DNA molecule having:*

*i) a promoter which functions in plant cells to cause the production of an RNA sequence,*

*ii) a structural DNA sequence that causes the production of an RNA sequence which encodes an EPSPS enzyme having the sequence of SEQ ID NO:70; and*

*iii) a 3' non-translated DNA sequence which functions in plant cells to cause the addition of a stretch of polyadenyl nucleotides to the 3' end of the RNA sequence,*

*where the promoter is heterologous with respect to the structural DNA sequence and adapted to cause sufficient expression of the EPSPS enzyme to enhance the glyphosate tolerance of the crop plant transformed with the DNA molecule; and*

*b) applying to the crop and weeds in the field a sufficient amount of glyphosate herbicide to control the weeds without significantly affecting the crop.*

*131. A recombinant, double-stranded DNA molecule comprising in sequence:*

*a) a promoter which functions in plant cells to cause the production of an RNA sequence;*

*b) a structural DNA sequence that causes the production of an RNA sequence which encodes an EPSPS enzyme having the sequence of SEQ ID NO:3, SEQ ID NO:5 or SEQ ID NO: 7;*

*c) a 3' non-translated region which functions in plant cells to cause the addition of a stretch of polyadenyl nucleotides to the 3' end of the RNA sequence;*

*where the promoter is heterologous with respect to the structural DNA sequence and adapted to cause sufficient expression of the encoded EPSPS enzyme to enhance the glyphosate tolerance of a plant cell transformed with the DNA molecule.*

*132. The DNA molecule of claim 131 in which the structural DNA sequence encodes a fusion polypeptide comprising an amino-terminal chloroplast transit peptide and the EPSPS enzyme.*

*133. The DNA molecule of claim 131 in which the promoter is a plant DNA virus promoter.*

*134. The DNA molecule of claim 133 in which the promoter is selected from the group consisting of CaMV35S and FMV35S promoters.*

*135. The DNA molecule of claim 132 in which the structural DNA sequence encodes a chloroplast transit peptide selected from the group consisting of SEQ ID NO: 11 and SEQ ID NO: 15.*

*136. The DNA molecule of claim 131 in which the 3' non-translated region is selected from the group consisting of the NOS 3' and the E9 3' non-translated regions.*

*137. A method of producing genetically transformed plants which are tolerant toward glyphosate herbicide, comprising the steps of:*

*a) inserting into the genome of a plant cell a recombinant, double-stranded DNA molecule comprising:*

*i) a promoter which functions in plant cells to cause the production of an RNA sequence,*

*ii) a structural DNA sequence that causes the production of an RNA sequence which encodes an EPSPS enzyme having the sequence of SEQ ID NO:3, SEQ ID NO:5 or SEQ ID NO:7; and*

*iii) a 3' non-translated DNA sequence which functions in plant cells to cause the addition of a stretch of polyadenyl nucleotides to the 3' end of the RNA sequence;*

*where the promoter is heterologous with respect to the structural DNA sequence and adapted to cause sufficient expression of the polypeptide to enhance the glyphosate tolerance of a plant cell transformed with the DNA molecule;*

*b) obtaining a transformed plant cell; and*

*c) regenerating from the transformed plant cell a genetically transformed plant which has increased tolerance to glyphosate herbicide.*

*138. The method of claim 137 in which the structural DNA sequence encodes a fusion polypeptide comprising an amino-terminal chloroplast transit peptide and the EPSPS enzyme.*

*139. The method of claim 130, wherein the chloroplast transit peptide has the sequence of SEQ ID NO: 11 or SEQ ID NO: 15.*

*140. The method of claim 137 in which the promoter is a plant DNA virus.*

*141. The method of claim 140 in which the promoter is a CaMV35S promoter or a FMV35S promoter.*

*142. The method of claim 137, wherein the 3' non-translated DNA sequence is a NOS 3' or an e9 3' non-translated sequence.*

*143. A glyphosate-tolerant plant cell comprising the DNA molecule of claim 131.*

*144. A plant comprising the glyphosate-tolerant plant cell of claim 143.*

*145. A glyphosate-tolerant plant cell comprising an EPSPS enzyme having the sequence of SEQ ID NO:3, SEQ ID NO:5 or SEQ ID NO:7.*

*146. A glyphosate-tolerant plant comprising an EPSPS enzyme having the sequence of SEQ ID NO: 3, SEQ ID NO: 5 or SEQ ID NO: 7.*

*147. The glyphosate-tolerant plant cell of claim 143 or 145 selected from the group consisting of corn, wheat, rice, barley, soybean, cotton, sugarbeet, oilseed rape, canola, flax, sunflower, potato, tobacco, tomato, alfalfa, poplar, pine, eucalyptus, apple, lettuce, peas, lentils, grape, and turf grasses.*

*148. The glyphosate-tolerant plant of claim 144 or 146 selected from the group consisting of corn, wheat, rice, barley, soybean, cotton, sugarbeet, oilseed rape, canola, flax, sunflower, potato, tobacco, tomato, alfalfa, poplar, pine, eucalyptus, apple, lettuce, peas, lentils, grapes, and turf grasses.*

*149. A method for selectively controlling weeds in a field containing a crop having planted crop seeds or plants comprising the steps of:*

*a) planting the crop seeds or plants which are glyphosate-tolerant as a result of a recombinant double-stranded DNA molecule being inserted into the crop seed or plant, the DNA molecule having:*

*i) a promoter which functions in plant cells to cause the production of an RNA sequence,*

*ii) a structural DNA sequence that causes the production of an RNA sequence which encodes an EPSPS enzyme having the sequence of SEQ ID NO:3, SEQ ID NO:5, or SEQ ID NO:7; and*

*iii) a 3' non-translated DNA sequence which functions in plant cells to cause the addition of a stretch of polyadenyl nucleotides to the 3' end of the RNA sequence,*

*wherein the promoter is heterologous with respect to the structural DNA sequence and adapted to cause sufficient expression of the EPSPS enzyme to enhance the glyphosate tolerance of the crop plant transformed with the DNA molecule; and*

*b) applying to the crop and weeds in the field a sufficient amount of glyphosate herbicide to control the weeds without significantly affecting the crop.*

* * * * *

UNITED STATES PATENT AND TRADEMARK OFFICE

CERTIFICATE OF CORRECTION

PATENT NO. : RE 39,247 E
APPLICATION NO. : 10/622201
DATED : August 22, 2006
INVENTOR(S) : Gerard F. Barry et al.

It is certified that error appears in the above-identified patent and that said Letters Patent is hereby corrected as shown below:

Col. 157, in claim 10, line 1, replace “137” with --131--.

Col. 158, in claim 21, line 1, replace “143” with --137--.

Col. 158, in claim 32, line 2, replace “plant” with --planted--.

Col. 159, in claim 38, line 1, replace “155” with --149--.

Col. 160, in claim 57, line 1, replace “137” with --131--.

Col. 160, in claim 58, line 1, replace “137” with --131--.

Col. 161, in claim 69, line 2, replace “149” with --143--.

Col. 164, in claim 109, lines 7, 9 and 13, replace “RNS” with --RNA--.

Col. 166, in claim 139, line 1, replace “130” with --138--.

Signed and Sealed this

Third Day of July, 2007

JON W. DUDAS
*Director of the United States Patent and Trademark Office*